US009212209B2

(12) United States Patent
Androphy et al.

(10) Patent No.: US 9,212,209 B2
(45) Date of Patent: Dec. 15, 2015

(54) SCREENING METHODS FOR SPINAL MUSCULAR ATROPHY

(71) Applicants: Indiana University Research and Technology Corporation, Indianapolis, IN (US); The Brigham Women's Hospital, Inc., Boston, MA (US); The University of Massachusetts, Boston, MA (US)

(72) Inventors: Elliot Androphy, Indianapolis, IN (US); Gregory D. Cuny, Houston, TX (US); Jonathan Cherry, Carmel, IN (US); Marcie A. Glicksman, Winchester, MA (US)

(73) Assignee: Indiana University Research and Technology Corporation, Indianapolis, IN (US)

( * ) Notice: Subject to any disclaimer, the term of this patent is extended or adjusted under 35 U.S.C. 154(b) by 273 days.

(21) Appl. No.: 13/941,099

(22) Filed: Jul. 12, 2013

(65) Prior Publication Data

US 2014/0193906 A1 Jul. 10, 2014

Related U.S. Application Data

(60) Provisional application No. 61/671,425, filed on Jul. 13, 2012.

(51) Int. Cl.

| | |
|---|---|
| *C12N 15/12* | (2006.01) |
| *C12N 5/00* | (2006.01) |
| *C07K 14/47* | (2006.01) |
| *C07C 311/37* | (2006.01) |
| *C07D 261/06* | (2006.01) |
| *C07D 213/75* | (2006.01) |
| *C07D 215/227* | (2006.01) |
| *C07D 401/04* | (2006.01) |
| *C07D 405/12* | (2006.01) |
| *C07D 239/82* | (2006.01) |
| *C07D 413/12* | (2006.01) |
| *C07D 417/12* | (2006.01) |
| *C07D 471/04* | (2006.01) |
| *C07D 487/04* | (2006.01) |
| *C07D 493/04* | (2006.01) |
| *C07D 277/46* | (2006.01) |

(52) U.S. Cl.
CPC .............. *C07K 14/47* (2013.01); *C07C 311/37* (2013.01); *C07D 213/75* (2013.01); *C07D 215/227* (2013.01); *C07D 239/82* (2013.01); *C07D 261/06* (2013.01); *C07D 277/46* (2013.01); *C07D 401/04* (2013.01); *C07D 405/12* (2013.01); *C07D 413/12* (2013.01); *C07D 417/12* (2013.01); *C07D 471/04* (2013.01); *C07D 487/04* (2013.01); *C07D 493/04* (2013.01); *C07C 2101/08* (2013.01); *C07C 2103/20* (2013.01)

(58) Field of Classification Search
None
See application file for complete search history.

(56) References Cited

U.S. PATENT DOCUMENTS

| | | | |
|---|---|---|---|
| 2006/0223873 A1 | 10/2006 | Shaw et al. | |
| 2014/0193906 A1* | 7/2014 | Androphy | C07K 14/47 435/369 |

FOREIGN PATENT DOCUMENTS

| | | |
|---|---|---|
| WO | 2007019417 A1 | 2/2007 |
| WO | 2009010454 A2 | 1/2009 |
| WO | 2009011850 A2 | 1/2009 |
| WO | 2009049180 A2 | 4/2009 |

OTHER PUBLICATIONS

International Search Report & Written Opinion for PCT/US2013/050361 mailed Jan. 27, 2014.
Crawford, et al., Pardo, C.A., The neurobiology of childhood spinal muscular atrophy. Neurobiol Dis., 1996, 3(2), pp. 97-110.
Lefebvre, et al., Identification and characterization of a spinal muscular atrophy determining gene. Cell 1995, 80, pp. 155-165.
Burglen, et al., Structure and organization of the human survival motor neuron (SMN) gene. Genomics 1996, 32, pp. 479-482.
Melki, J., Spinal muscular atrophy. Curr. Opin. Neurol. 1997, 10, pp. 381-385.
Jablonka, et al., Molecular and cellular basis of spinal muscular atrophy. Amyotroph Lateral Scler Other Motor Neuron Disord 2003, 4 (3), pp. 144-149.
Didonato, et al., Deletion and conversion in spinal muscular atrophy patients: is there a relationship to severity? Ann. Neurol. 1997, 41, pp. 230-237.
Wirth, et al., De novo rearrangements found in 2% of index patients with spinal muscular atrophy: Mutational mechanisms, parental origin, mutation rate, and implications for genetic counseling. Am J Hum Genet 1997, 61 (5), pp. 1102-1111.
Lorson, et al., A single nucleotide in the SMN gene regulates splicing and is responsible for spinal muscular atrophy. Proc Natl Acad Sci USA 1999, 96 (11), pp. 6307-6311.
Lorson, et al., An exonic enhancer is required for inclusion of an essential exon in the SMA-determining gene SMN. Hum Mol Genet 2000, 9 (2), pp. 259-265.
Zhang, et al., An in vivo reporter system for measuring increased inclusion of exon 7 in SMN2 mRNA: potential therapy of SMA. Gene Ther 2001, 8 (20), pp. 1532-1538.

(Continued)

*Primary Examiner* — Michael Burkhart
(74) *Attorney, Agent, or Firm* — Stinson Leonard Street LLP

(57) ABSTRACT

Disclosed herein are compositions and methods for treatment of spinal muscular atrophy (SMA). In certain embodiments, compounds are provided that increase full-length survival of motor neuron (SMN) protein production by an SMN2 gene.

15 Claims, 41 Drawing Sheets

(56) References Cited

OTHER PUBLICATIONS

Hofmann, et al., Htra2-beta 1 stimulates an exonic splicing enhancer and can restore full-length SMN expression to survival motor neuron 2 (SMN2). Proc Natl Acad Sci U S A 2000, 97 (17), pp. 9618-9623.
Andreassi, et al., Aclarubicin treatment restores SMN levels to cells derived from type I spinal muscular atrophy patients. Hum Mol Genet 2001, 10 (24), pp. 2841-2849.
Lunn, et al., Indoprofen upregulates the survival motor neuron protein through a cyclooxygenase-independent mechanism. Chem Biol 2004, 11 (11), pp. 1489-1493.
Jarecki, et al., Diverse small-molecule modulators of SMN expression found by high-throughput compound screening: Early leads towards a therapeutic for Spinal Muscular Atrophy. Hum Mol Genet 2005.
Chang, et al., Treatment of spinal muscular atrophy by sodium butyrate. Proc Natl Acad Sci U S A 2001, 98 (17), pp. 9808-9813.
Avila, et al., Trichostatin A increases SMN expression and survival in a mouse model of spinal muscular atrophy. J Clin Invest 2007, 117 (3), pp. 659-671.
Sumner, et al., Valproic acid increases SMN levels in spinal muscular atrophy patient cells. Ann Neurol 2003, 54 (5), pp. 647-654.
Hahnen, et al., ., In vitro and ex vivo evaluation of second-generation histone deacetylase inhibitors for the treatment of spinal muscular atrophy. J Neurochem 2006, 98 (1), pp. 193-202.
Garbes, et al., LBH589 induces up to 10-fold SMN protein levels by several independent mechanisms and is effective even in cells from SMA patients non-responsive to valproate. Hum Mol Genet 2009, 18 (19), pp. 3645-3658.
Monani, et al., Promoter analysis of the human centromeric and telomeric survival motor neuron genes (SMNC and SMNT). Biochim Biophys Acta 1999, 1445 (3), pp. 330-336.
Mattis, et al., Detection of human survival motor neuron (SMN) protein in mice containing the SMN2 transgene: Applicability to preclinical therapy development for spinal muscular atrophy. J Neurosci Methods 2008.

Pfaffl, M. W., A new mathematical model for relative quantification in real-time RT-PCR. Nucleic Acids Res 2001, 29 (9), e45.
Lipinski, et al., Experimental and computational approaches to estimate solubility and permeability in drug discovery and development settings. Adv Drug Deliv Rev 2001, 46 (1-3), pp. 3-26.
Burnett, et al., Regulation of SMN protein stability. Mol Cell Biol 2009, 29 (5), pp. 1107-1115.
Nlend, et al., Repair of pre-mRNA splicing: prospects for a therapy for spinal muscular atrophy. RNA Biol 2010, 7 (4), pp. 430-440.
Andreassi, et al., Phenylbutyrate increases SMN expression in vitro: relevance for treatment of spinal muscular atrophy. Eur J Hum Genet 2004, 12 (1), pp. 59-65.
Echaniz-Laguna, et al., The promoters of the survival motor neuron gene (SMN) and its copy (SMNc) share common regulatory elements. Am J Hum Genet 1999, 64 (5), pp. 1365-1370.
Coovert, et al., The survival motor neuron protein in spinal muscular atrophy. Hum Mol Gen 1997, 6, pp. 1205-1214.
Lorson, et al., Spinal muscular atrophy: mechanisms and therapeutic strategies. Hum Mol Genet 2010, 19 (R1), R111-8.
Wirth, et al., Spinal muscular atrophy and therapeutic prospects. Prog Mol Subcell Biol 2006, 44, pp. 109-132.
Sumner, C. J., Therapeutics development for spinal muscular atrophy. NeuroRx 2006, 3 (2), pp. 235-245.
Singh, et al., Modulating role of RNA structure in alternative splicing of a critical exon in the spinal muscular atrophy genes. Nucleic Acids Res 2006b.
Heier, et al., ., Translational readthrough by the aminoglycoside geneticin (G418) modulates SMN stability in vitro and improves motor function in SMA mice in vivo. Hum Mol Genet 2009, 18 (7), pp. 1310-1322.
Singh, et al., DcpS as a Therapeutic Target for Spinal Muscular Atrophy. ACS Chem Biol 2008.
Xiao, et al., Discovery, Synthesis and Biological Evaluation of Novel SMN Protein Modulators. J Med Chem 2011.
Cherry, et al., J. Biomolecular Screening, Identification of Novel Compounds That Increase SMN Protein Levels Using an Improved SMN2 Reporter Cell Assay, 2012, 17(4), pp. 481-495.

\* cited by examiner

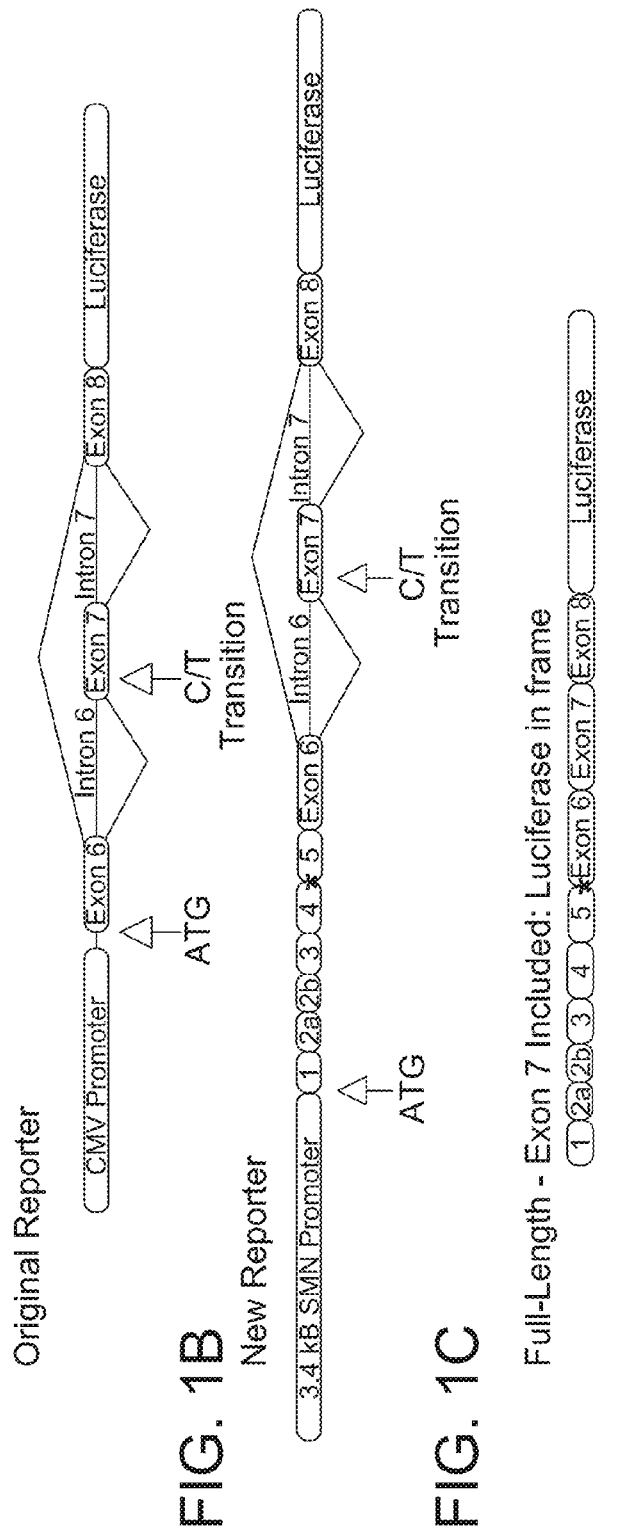

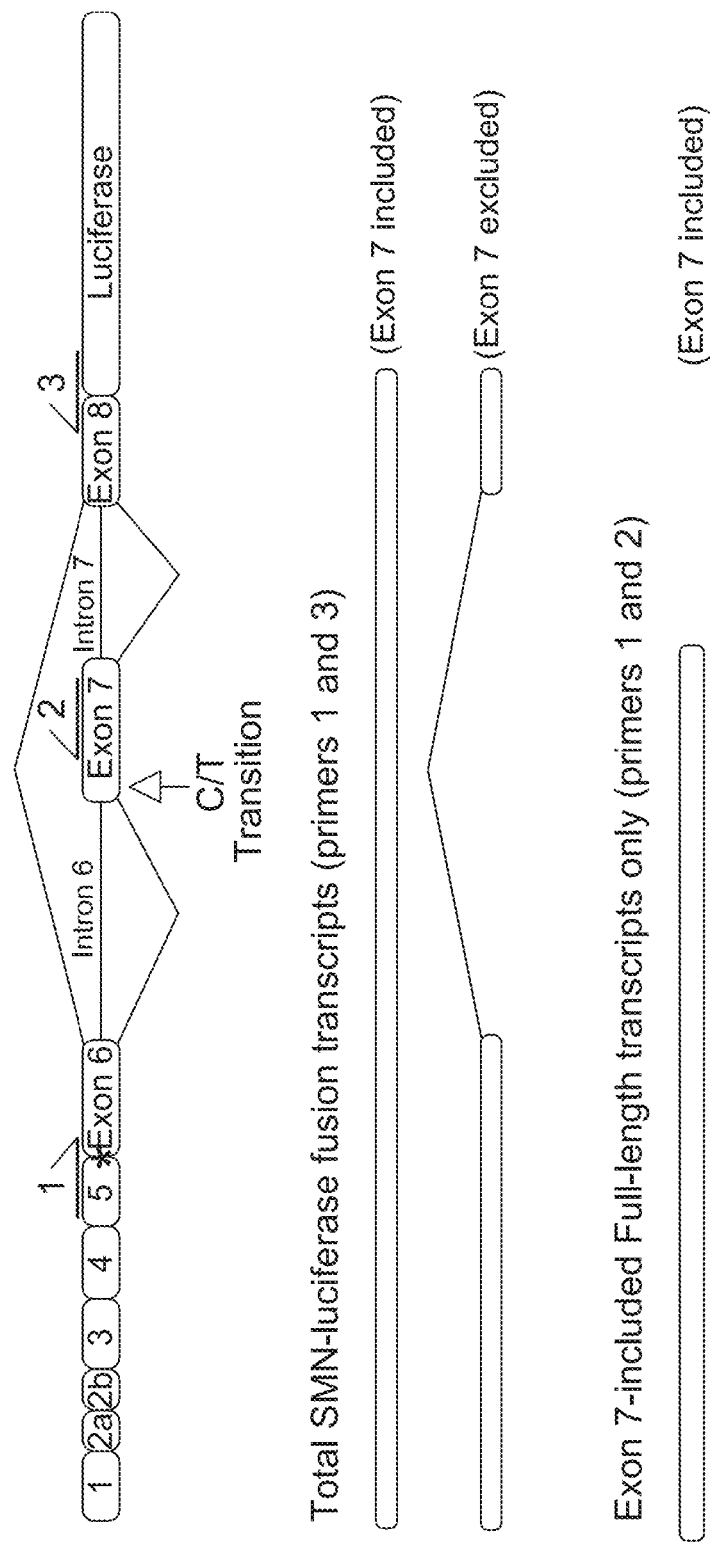

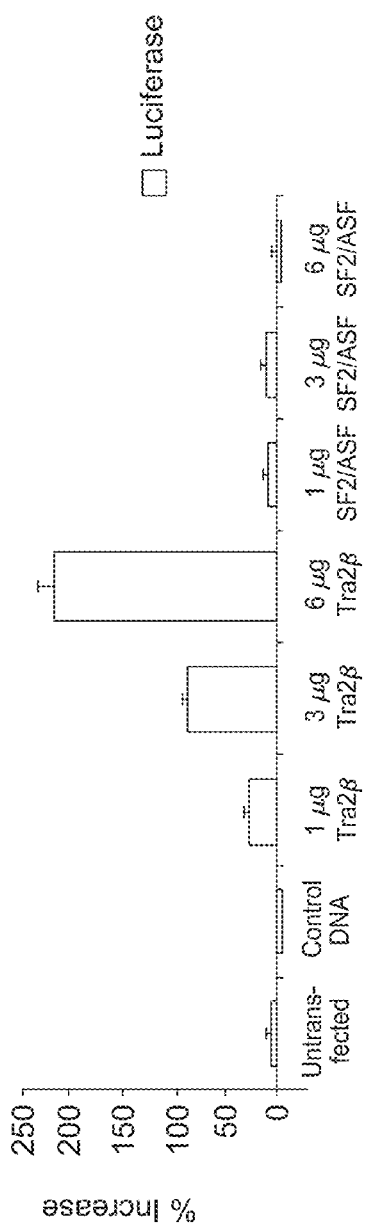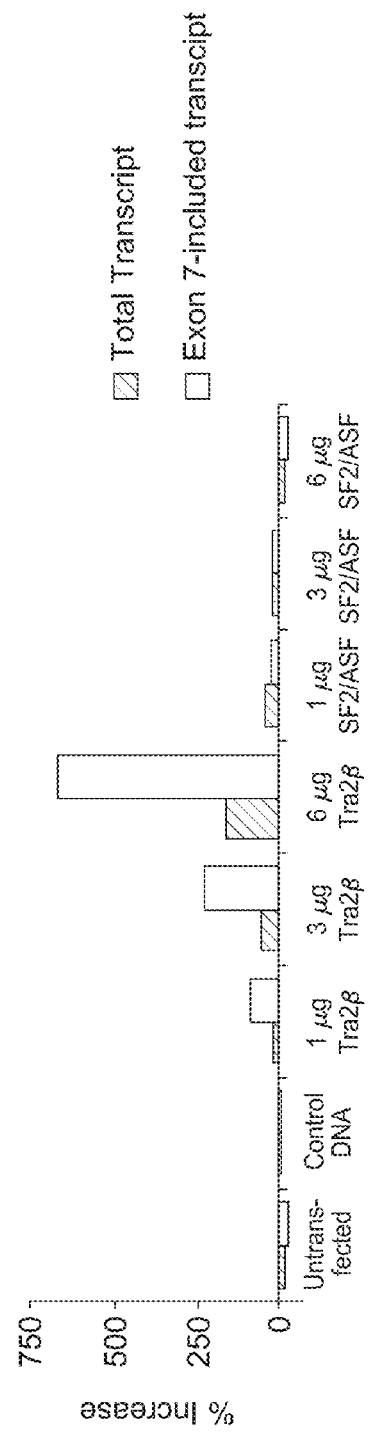
FIG. 5A
FIG. 5C

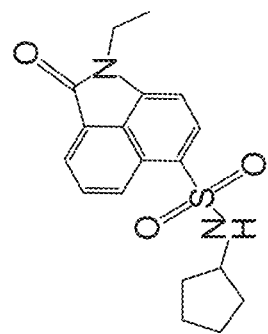
LDN-109657
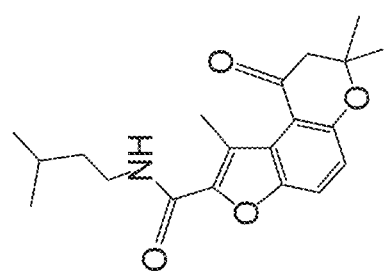
LDN-79199
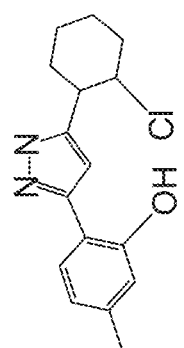
LDN-72939
FIG. 6A

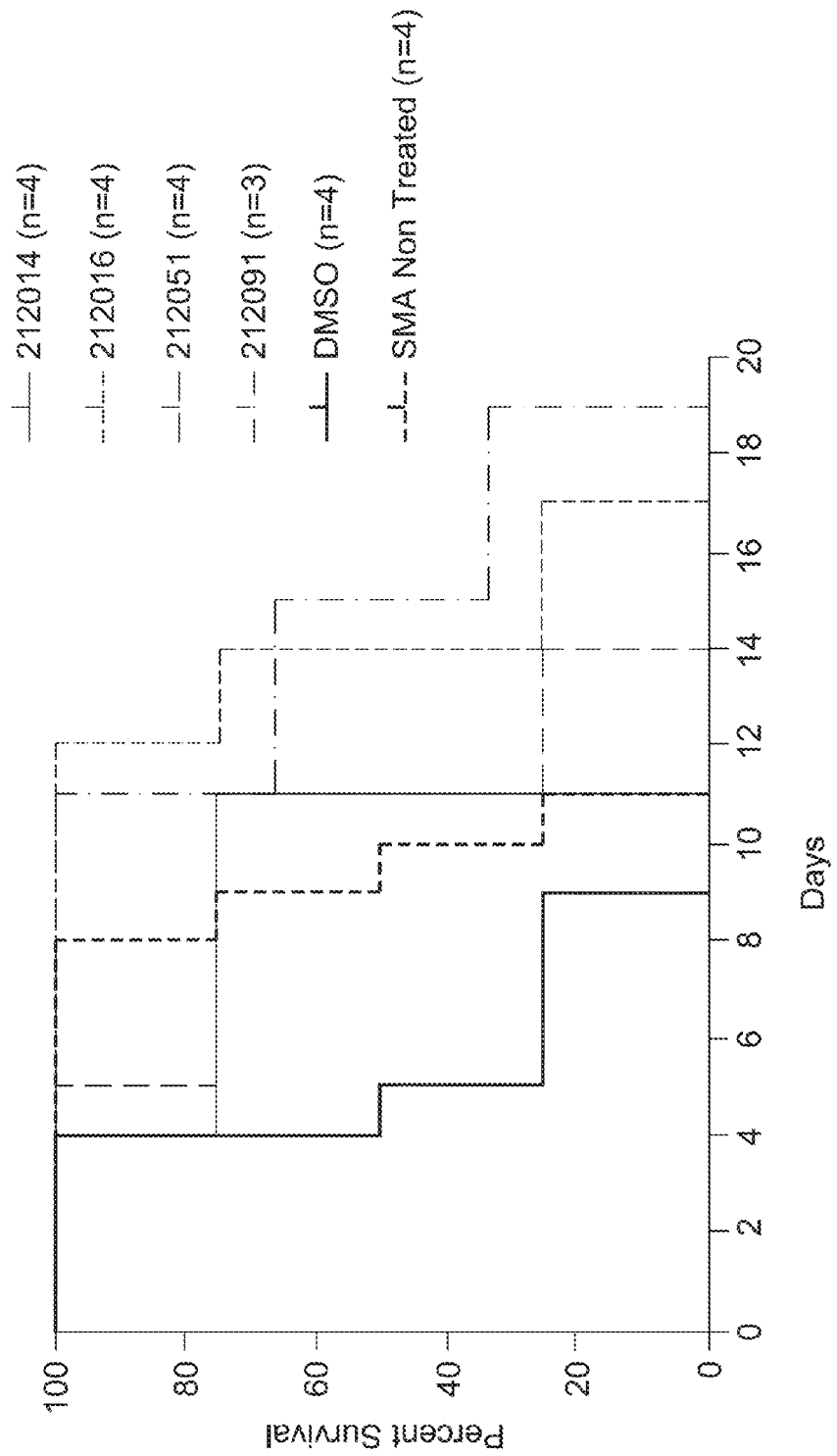

SCREENING METHODS FOR SPINAL MUSCULAR ATROPHY

CROSS REFERENCE TO RELATED APPLICATIONS

This application claims priority to U.S. Provisional Patent Application No. 61/671,425 filed on Jul. 13, 2012, which is hereby incorporated by reference in its entirety.

STATEMENT OF GOVERNMENT SUPPORT

This invention was made with government support under grant numbers HD064850 and NS064349 awarded by the National Institutes of Health. The U.S. Government has certain rights in the invention.

INCORPORATION OF SEQUENCE LISTING

A paper copy of the Sequence Listing and a computer readable form of the sequence containing the file named "31377-18 (IURTC 12111)_ST25.txt", which is 54,433 bytes in size (as measured in MS-DOS), are provided herein and are herein incorporated by reference. This Sequence Listing consists of SEQ ID NOS: 1-9.

FIELD OF DISCLOSURE

The present disclosure relates to pharmaceutically active compounds useful for treating, or lessening the severity of, spinal muscular atrophy.

BACKGROUND OF DISCLOSURE

Spinal muscular atrophy (SMA) is a neurological disorder that results from loss of function of the anterior horn cells in the spinal cord, manifesting as progressive motor weakness, muscle wasting, and paralysis. SMA is caused by insufficient levels of the survival motor neuron (SMN) protein. The SMN locus on chromosome 5q13 contains two inverted copies of SMN called SMN1 and SMN2. Most cases of SMA harbor homozygous deletions of the SMN1 gene and retain at least one copy of SMN2. With a carrier rate of about 1 in 40, SMA is estimated to be the most frequent genetic cause of infant mortality.

SMN2 is a gene duplication of SMN1 with the same predicted amino acid coding capacity. The nucleotide sequences of SMN1 and SMN2 are nearly identical. A critical difference is a C to T transition at the +6 position in exon 7, which dramatically influences the splicing pattern in these genes. Greater than 90% of SMN1 transcripts include exon 7, while there is less than 15% exon 7 inclusion in SMN2 transcripts. This alternatively spliced product produces a truncated and unstable form of the SMN protein. Any increase in the inclusion of exon 7 in SMN2 transcripts would result in higher levels of full length SMN protein. A treatment that increases the amount of full length SMN2 mRNA should result in increased levels of SMN protein. Based on this premise, an in vivo screen that can detect increases in full-length exon 7 included SMN2 transcripts was developed.

A splicing reporter that fused SMN exons 6, 7, and 8 and their introns in frame with firefly luciferase and was expressed from a CMV promoter in C33a cells has previously been constructed. It was found that this reporter could recapitulate changes in splicing observed with over-expression of the splicing factor Tra2β. This assay was used successfully to identify compounds that increase the amount of full-length transcript produced by the SMN2 gene and SMN protein in fibroblasts isolated from an SMA patient. Another study used a SMN2 promoter based reporter to screen a library of small molecules for ability to increase SMN expression levels in NSC34 cells. This reporter measured only SMN2 specific transcription and lacked any SMN gene sequence.

It has been reported that histone deacetylase (HDAC) inhibitors such as sodium butyrate, trichostatin A (TSA), valproic acid, suberoylanilide hydroxamic acid (SAHA) and LBH589 increase SMN transcription and inclusion of exon 7. For many of these HDACs, relatively high (micromolar or millimolar) concentrations of these compounds are necessary. These activators are non-specific and will alter transcription of many genes so long-term safety has been questioned. However, type I severe SMA is fatal and short-term administration of such compounds may provide limited benefits.

A first generation splicing assay had low signal intensity, high basal expression of SMN-luciferase, and became less responsive with serial cell passage. These cells were determined to be unsuitable for high-throughput screening (HTS). The reporter system was redesigned and a more stable and reproducible assay has now been built that may be used for HTS.

Particularly, described herein is a clonal second generation SMN-luciferase reporter cell line that combines the strengths of both the promoter-based assay and a previous splicing reporter. This assay is much more robust, has lower well-to-well variation, and displays more stable luciferase expression that does not change with serial passage. It also faithfully reproduces the reported activity of an array of drug-like compounds that have been shown to increase SMN expression levels. This reporter can detect changes in SMN2 levels in response to overexpression of splicing factors such as Tra2β. This assay is a vast improvement on the previous generation of reporters and represents a valuable tool for further identification and characterization of compounds that increase expression of full-length SMN protein from the SMN2 gene.

Additionally, there is a need for new drugs to treat spinal muscular atrophy. SMN reporters can be used as tools for identifying and characterizing protein factors and chemical compounds that increase expression of full-length SMN2 transcripts. Results from HTSs to identify novel compounds that increase SMN2 expression using this cell based SMN-luciferase reporter assay are also described herein.

As described herein, the present disclosure provides compounds useful for treating or lessening the severity of spinal muscular atrophy. The present disclosure also provides methods of treating or lessening the severity of spinal muscular atrophy comprising administering to a patient susceptible to or having spinal muscular atrophy a compound or composition of the present disclosure.

BRIEF DESCRIPTION

The present disclosure is generally related to compounds and methods for treatment of spinal muscular atrophy (SMA) utilizing the compounds. In certain embodiments, compounds are provided that increase full-length survival of motor neuron (SMN) protein production by an SMN2 gene.

Accordingly, in one aspect, the present disclosure is directed to a compound of formula I:

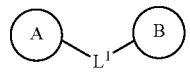

or a pharmaceutically acceptable salt thereof, wherein
each of Ring A and Ring B is independently an optionally substituted group selected from phenyl, a 3-7 membered saturated or partially unsaturated carbocyclic ring, an 8-10 membered bicyclic saturated, partially unsaturated or aryl carbocyclic ring, a 5-6 membered monocyclic heteroaryl ring having 1-3 heteroatoms independently selected from nitrogen, oxygen, or sulfur, a 3-7 membered saturated or partially unsaturated heterocyclic ring having 1-2 heteroatoms independently selected from nitrogen, oxygen, or sulfur, an 8-10 membered bicyclic saturated or partially unsaturated heterocyclic ring having 1-4 heteroatoms independently selected from nitrogen, oxygen, or sulfur, or an 8-10 membered bicyclic heteroaryl ring having 1-4 heteroatoms independently selected from nitrogen, oxygen, or sulfur;

$L^1$ is independently a covalent bond or an optionally substituted bivalent $C_{1-6}$ hydrocarbon chain, wherein one or more methylene units of $L^1$ are optionally and independently replaced by —O—, —S—, —N(R')—, —C(O)—, —C(S)—, —C(NR')—, —C(O)N(R')—, —N(R')C(O)N(R')—, —N(R')C(O)—, —N(R')C(O)O—, —OC(O)N(R')—, —S(O)—, —S(O)$_2$—, —S(O)$_2$N(R')—, —N(R')S(O)$_2$—, —OC(O)—, or —C(O)O—;

each R' is independently —R, —C(O)R, —CO$_2$R, or —SO$_2$R, or:

two R' on the same nitrogen are taken together with their intervening atoms to form a 3-7 membered heterocyclic ring having 1-2 heteroatoms independently selected from nitrogen, oxygen, and sulfur; and each R is hydrogen, or an optionally substituted group selected from $C_{1-6}$ aliphatic, phenyl, a 3-7 membered saturated or partially unsaturated carbocyclic ring, an 8-10 membered bicyclic saturated, partially unsaturated or aryl carbocyclic ring, a 5-6 membered monocyclic heteroaryl ring having 1-3 heteroatoms independently selected from nitrogen, oxygen, or sulfur, a 3-7 membered saturated or partially unsaturated heterocyclic ring having 1-2 heteroatoms independently selected from nitrogen, oxygen, or sulfur, an 8-10 membered bicyclic saturated or partially unsaturated heterocyclic ring having 1-4 heteroatoms independently selected from nitrogen, oxygen, or sulfur, or an 8-10 membered bicyclic heteroaryl ring having 1-4 heteroatoms independently selected from nitrogen, oxygen, or sulfur.

In another aspect, the present disclosure is directed to a composition comprising a compound and a pharmaceutically acceptable carrier, adjuvant or vehicle. The compound has the formula of formula I:

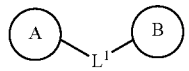

or a pharmaceutically acceptable salt thereof, wherein each of Ring A and Ring B is independently an optionally substituted group selected from phenyl, a 3-7 membered saturated or partially unsaturated carbocyclic ring, an 8-10 membered bicyclic saturated, partially unsaturated or aryl carbocyclic ring, a 5-6 membered monocyclic heteroaryl ring having 1-3 heteroatoms independently selected from nitrogen, oxygen, or sulfur, a 3-7 membered saturated or partially unsaturated heterocyclic ring having 1-2 heteroatoms independently selected from nitrogen, oxygen, or sulfur, an 8-10 membered bicyclic saturated or partially unsaturated heterocyclic ring having 1-4 heteroatoms independently selected from nitrogen, oxygen, or sulfur, or an 8-10 membered bicyclic heteroaryl ring having 1-4 heteroatoms independently selected from nitrogen, oxygen, or sulfur;

$L^1$ is independently a covalent bond or an optionally substituted bivalent $C_{1-6}$ hydrocarbon chain, wherein one or more methylene units of $L^1$ are optionally and independently replaced by —O—, —S—, —N(R')—, —C(O)—, —C(S)—, —C(NR')—, —C(O)N(R')—, —N(R')C(O)N(R')—, —N(R')C(O)—, —N(R')C(O)O—, —OC(O)N(R')—, —S(O)—, —S(O)$_2$—, —S(O)$_2$N(R')—, —N(R')S(O)$_2$—, —OC(O)—, or —C(O)O—;

each R' is independently —R, —C(O)R, —CO$_2$R, or —SO$_2$R, or:

two R' on the same nitrogen are taken together with their intervening atoms to form a 3-7 membered heterocyclic ring having 1-2 heteroatoms independently selected from nitrogen, oxygen, and sulfur; and each R is hydrogen, or an optionally substituted group selected from $C_{1-6}$ aliphatic, phenyl, a 3-7 membered saturated or partially unsaturated carbocyclic ring, an 8-10 membered bicyclic saturated, partially unsaturated or aryl carbocyclic ring, a 5-6 membered monocyclic heteroaryl ring having 1-3 heteroatoms independently selected from nitrogen, oxygen, or sulfur, a 3-7 membered saturated or partially unsaturated heterocyclic ring having 1-2 heteroatoms independently selected from nitrogen, oxygen, or sulfur, an 8-10 membered bicyclic saturated or partially unsaturated heterocyclic ring having 1-4 heteroatoms independently selected from nitrogen, oxygen, or sulfur, or an 8-10 membered bicyclic heteroaryl ring having 1-4 heteroatoms independently selected from nitrogen, oxygen, or sulfur.

In yet another aspect, the present disclosure is directed to a method for increasing the production of full-length SMN protein in a cell having an SMN2 gene. The method comprises contacting the cell with a compound or composition. In some embodiments, the compound has the formula of formula I:

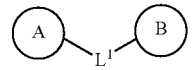

or a pharmaceutically acceptable salt thereof, wherein each of Ring A and Ring B is independently an optionally substituted group selected from phenyl, a 3-7 membered saturated or partially unsaturated carbocyclic ring, an 8-10 membered bicyclic saturated, partially unsaturated or aryl carbocyclic ring, a 5-6 membered monocyclic heteroaryl ring having 1-3 heteroatoms independently selected from nitrogen, oxygen, or sulfur, a 3-7 membered saturated or partially unsaturated heterocyclic ring having 1-2 heteroatoms independently selected from nitrogen, oxygen, or sulfur, an 8-10 membered bicyclic saturated or partially unsaturated heterocyclic ring having 1-4 heteroatoms independently selected from nitrogen, oxygen, or sulfur, or an 8-10 membered bicyclic heteroaryl ring having 1-4 heteroatoms independently selected from nitrogen, oxygen, or sulfur;

$L^1$ is independently a covalent bond or an optionally substituted bivalent $C_{1-6}$ hydrocarbon chain, wherein one or more methylene units of $L^1$ are optionally and independently replaced by —O—, —S—, —N(R')—, —C(O)—, —C(S)—, —C(NR')—, —C(O)N(R')—, —N(R')C(O)N(R')—, —N(R')C(O)—, —N(R')C(O)O—, —OC(O)N(R')—, —S(O)—, —S(O)$_2$—, —S(O)$_2$N(R')—, —N(RDS(O)$_2$—, —OC(O)—, or —C(O)O—;

each R' is independently —R, —C(O)R, —CO$_2$R, or —SO$_2$R, or:

two R' on the same nitrogen are taken together with their intervening atoms to form a 3-7 membered heterocyclic ring having 1-2 heteroatoms independently selected from nitrogen, oxygen, and sulfur; and each R is hydrogen, or an optionally substituted group selected from C$_{1-6}$ aliphatic, phenyl, a 3-7 membered saturated or partially unsaturated carbocyclic ring, an 8-10 membered bicyclic saturated, partially unsaturated or aryl carbocyclic ring, a 5-6 membered monocyclic heteroaryl ring having 1-3 heteroatoms independently selected from nitrogen, oxygen, or sulfur, a 3-7 membered saturated or partially unsaturated heterocyclic ring having 1-2 heteroatoms independently selected from nitrogen, oxygen, or sulfur, an 8-10 membered bicyclic saturated or partially unsaturated heterocyclic ring having 1-4 heteroatoms independently selected from nitrogen, oxygen, or sulfur, or an 8-10 membered bicyclic heteroaryl ring having 1-4 heteroatoms independently selected from nitrogen, oxygen, or sulfur. In other embodiments, a composition is administered, the composition includes the compound described above and a pharmaceutically acceptable carrier, adjuvant or vehicle.

In some embodiments, the full-length SMN protein is produced by upregulation of SMN2 activity. In one embodiment, the upregulation of SMN2 activity includes increased expression of full-length SMN2 transcripts.

In another aspect, the present disclosure is directed to a method of treating a patient susceptible to or having spinal muscular atrophy. The method comprises administering to the patient a therapeutically effective amount of the compound or composition described above.

In another aspect, the present disclosure is directed to a vector. The vector comprises a survival motor neuron (SMN) promoter selected from the group consisting of a survival motor neuron 1 (SMN1) promoter and a survival motor neuron 2 (SMN2) promoter; a transcription start site; a nucleic acid encoding exons 1-8 of the SMN gene and encoding introns 6-8 of the SMN gene; and a reporter gene. In yet another aspect, the present disclosure is directed to a host cell comprising the vector.

In another aspect, the present disclosure is directed to a vector. The vector comprises a survival motor neuron 1 (SMN1) promoter; a transcription start site; a nucleic acid encoding exons 1-8 of the SMN1 gene and encoding introns 6-8 of the SMN1 gene; and a reporter gene. In yet another aspect, the present disclosure is directed to a host cell comprising the vector.

In yet another aspect, the present disclosure is directed to a vector. The vector comprises a survival motor neuron 2 (SMN2) promoter; a transcription start site; a nucleic acid encoding exons 1-8 of the SMN2 gene and encoding introns 6-8 of the SMN2 gene; and a reporter gene. In yet another aspect, the present disclosure is directed to a host cell comprising the vector.

BRIEF DESCRIPTION OF THE DRAWINGS

FIGS. 1A-1D show SMN-reporter mini-genes. FIGS. 1A and 1B illustrate the changes made to the new reporter (see text). The asterisk denotes a restriction site included during cloning that is unique to the SMN reporter gene. These reporters produce a SMN-luciferase fusion protein when exon 7 is included (FIG. 1C) but not when exon 7 is skipped (FIG. 1D). ~90% of mRNA from the SMN2-reporter mini-gene skips exon 7.

FIG. 2A illustrates a comparison of luciferase activity for equivalent numbers of mixed population SMN1-luc, mixed population SMN2-luc, clonal SMN1-luc and clonal SMN2-luc cells. Luciferase activity, scored as relative light units (RLU). FIG. 2B illustrates the detection of SMN-luciferase fusion protein in HEK parent, SMN1-luc, and SMN2-luc reporter cells. Lysates were blotted for the fusion protein with an anti-luciferase antibody and endogenous SMN and compared to actin and tubulin. FIG. 2C illustrates the end point RT-PCR used to compare mRNA species of SMN1-luc and SMN2-luc cells. Primer pairs were designed to amplify both full-length and exon 7 excluded SMN-luciferase mRNA. Percent inclusion was determined by comparing band intensities using QUANTITY ONE software. FIG. 2D illustrates that SMN-luciferase fusion stability was determined by treating cells with 10 µM cycloheximide and measuring luciferase activity at various time points. Data were plotted using PRISM4 (Graphpad Software Inc.) and non-linear regression was used to determine protein half-life.

FIG. 3A depicts results of sodium butyrate, SAHA, TSA, aclarubicin, indoprofen, valproic acid, and tobramycin tested in 6-point dose response experiments. Each compound was tested at concentrations previously reported to increase SMN protein levels. Black square with solid line SMN2-luc cells; gray triangle—SMN1-luc cells; black circle with dotted line—SV40 control. Y-axis represents % activation relative to DMSO control. All points were tested in quadruplicate and plotted as mean±SEM. Curves were created by linear regression using PRISM4 (Graphpad Software Inc.). FIGS. 3B and 3C illustrate SMN1-luc cells treated for 24 hours at increasing concentrations of SAHA. The amount of SMN-luciferase fusion protein detected by anti-luciferase antibody (FIG. 3B) is similar to the % increase in luciferase activity in the same samples (FIG. 3C). FIGS. 3D and 3E illustrate SMN2-luc cells treated for 24 hours with increasing amounts of SAHA or sodium butyrate. The increase in SMN-luciferase fusion protein (FIG. 3D) correlates with luciferase activity (FIG. 3E). Experiments were performed 3 times with similar results. Blots shown are representative.

FIGS. 4A and 4B show analysis of SMN-luciferase fusion transcripts by qRT-PCR. FIG. 4A is a schematic of the primer design for qRT-PCR. Primer pairs were chosen to amplify only the SMN-luciferase fusion transcripts but not endogenous SMN. Primer 1 overlaps a unique Xho I site (*). Primers 1 and 2 can only amplify full-length SMN-luc transcripts that contain exon 7. Primers 1 and 3 amplify SMN-luc reporter transcripts (both exon 7 included and excluded). FIG. 4B illustrates the comparison of increases in amount of total reporter transcripts (lined bars) and amount of exon 7 included reporter transcripts (white bars). Cells were treated at increasing concentrations of compound for 24 hours. Percent increase was calculated in relation to treatment with DMSO and normalized to GAPDH.

FIGS. 5A-5C show over-expression of the splicing factors hTra2β and SF2/ASF. SMN2-luciferase reporter cells were transfected with increasing amounts of HA-tagged hTra2β or SF2/ASF. Cells were incubated for 48 hours and assayed for luciferase activity. FIG. 5A shows the percent increase calculated in relation to treatment with control DNA transfection and normalized to internal renilla control. FIG. 5B illustrates that transfected protein expression was confirmed using anti-HA antibody. The asterisk denotes a background HA band. Actin was used as a loading control. FIG. 5C illustrates the comparison of increases in amount of total reporter transcripts (gray bars), and amount of exon 7 included reporter transcripts (white bars). Percent increase was calculated in relation to treatment with DMSO and normalized to GAPDH.

FIGS. 6A-6C show hit confirmation in the reporter cells. FIG. 6A depicts structures of three hits from the high-throughput screen. FIG. 6B illustrates 12-point dose response experiments. Each compound was tested with the reporter cell lines at 12 concentrations (0.17, 0.5, 1.5, 4.5, 13.7, 41, 123, 370, 1111, 3333, 10,000, 30,000 nM) Black-SMN2-luc cells; grey—SMN1-luc cells; dotted line-SV40 control. Y-axis represents % activation over DMSO control. All points were tested in quadruplicate and plotted as mean±SEM. Curves were created by linear regression using Prism4 (GraphPad Software Inc.). FIG. 6C illustrates primary human fibroblast lysates from carrier (3814; SMN1$^{+/-}$; SMN2$^{+/+}$) and depicts SMA (3813; SMN1$^{-/-}$; SMN2$^{+/+}$) cells that were blotted with antibodies to SMN and a-tubulin. Cells were treated for 48 hours with increasing concentrations of compound. Fold increase was calculated in relation to DMSO treated 3813 and normalized to tubulin levels. Experiments were performed 3 times. Blots shown are representative.

FIG. 26A shows survival proportions of animals in a mouse model of spinal muscular atrophy treated with compounds.

DETAILED DESCRIPTION

Figure 2A:
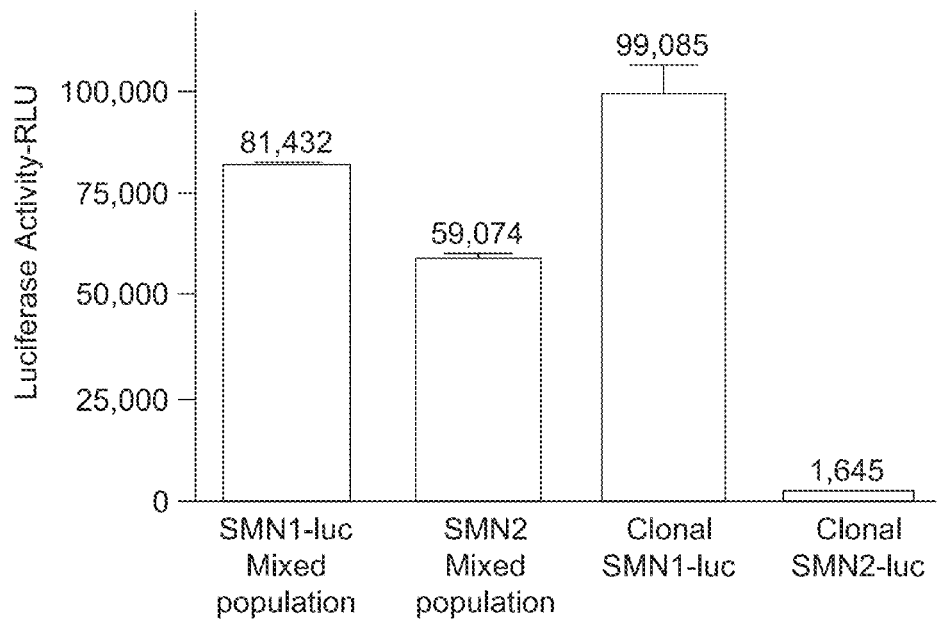
FIGS. 2A-2D show reporter assay validation.

1. General Description of Compounds of the Disclosure

According to one embodiment, the present disclosure provides a compound of formula I:

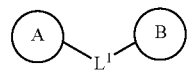

or a pharmaceutically acceptable salt thereof, wherein:
each of Ring A and Ring B is independently an optionally substituted group selected from phenyl, a 3-7 membered saturated or partially unsaturated carbocyclic ring, an 8-10 membered bicyclic saturated, partially unsaturated or aryl carbocyclic ring, a 5-6 membered monocyclic heteroaryl ring having 1-3 heteroatoms independently selected from nitrogen, oxygen, or sulfur, a 3-7 membered saturated or partially unsaturated heterocyclic ring having 1-2 heteroatoms independently selected from nitrogen, oxygen, or sulfur, an 8-10 membered bicyclic saturated or partially unsaturated heterocyclic ring having 1-4 heteroatoms independently selected from nitrogen, oxygen, or sulfur, or an 8-10 membered bicyclic heteroaryl ring having 1-4 heteroatoms independently selected from nitrogen, oxygen, or sulfur;

$L^1$ is independently a covalent bond or an optionally substituted bivalent $C_{1-6}$ hydrocarbon chain, wherein one or more methylene units of $L^1$ are optionally and independently replaced by —O—, —S—, —N(R')—, —C(O)—, —C(S)—, —C(NR')—, —C(O)N(R')—, —N(R')C(O)N(R')—, —N(R')C(O)—, —N(R')C(O)O—, —OC(O)N(R')—, —S(O)—, —S(O)2-, —S(O)$_2$N(R')—, —N(R')S(O)2-, —OC(O)—, or —C(O)O—;

each R' is independently —R, —C(O)R, —CO$_2$R, or —SO$_2$R, or:
  two R' on the same nitrogen are taken together with their intervening atoms to form a 3-7 membered heterocyclic ring having 1-2 heteroatoms independently selected from nitrogen, oxygen, and sulfur; and each R is hydrogen, or an optionally substituted group selected from $C_{1-6}$ aliphatic, phenyl, a 3-7 membered saturated or partially unsaturated carbocyclic ring, an 8-10 membered bicyclic saturated, partially unsaturated or aryl carbocyclic ring, a 5-6 membered monocyclic heteroaryl ring having 1-3 heteroatoms independently selected from nitrogen, oxygen, or sulfur, a 3-7 membered saturated or partially unsaturated heterocyclic ring having 1-2 heteroatoms independently selected from nitrogen, oxygen, or sulfur, an 8-10 membered bicyclic saturated or partially unsaturated heterocyclic ring having 1-4 heteroatoms independently selected from nitrogen, oxygen, or sulfur, or an 8-10 membered bicyclic heteroaryl ring having 1-4 heteroatoms independently selected from nitrogen, oxygen, or sulfur.

According to one embodiment, the present disclosure provides a compound of formula II:

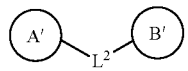

or a pharmaceutically acceptable salt thereof, wherein:
each of Ring A' and Ring B' is independently an optionally substituted group selected from phenyl, an 8-10 membered bicyclic aryl ring, a 5-6 membered monocyclic heteroaryl ring having 1-3 heteroatoms independently selected from nitrogen, oxygen, or sulfur, or an 8-10 membered bicyclic heteroaryl ring having 1-4 heteroatoms independently selected from nitrogen, oxygen, or sulfur;
$L^2$ is —C(O)N(R')—;
R' is —R, —C(O)R, —CO$_2$R, or —SO$_2$R, or:
  two R' on the same nitrogen are taken together with their intervening atoms to form a 3-7 membered heterocyclic ring having 1-2 heteroatoms independently selected from nitrogen, oxygen, and sulfur; and each R is hydrogen, or an optionally substituted group selected from $C_{1-6}$ aliphatic, phenyl, a 3-7 membered saturated or partially unsaturated carbocyclic ring, an 8-10 membered bicyclic saturated, partially unsaturated or aryl carbocyclic ring, a 5-6 membered monocyclic heteroaryl ring having 1-3 heteroatoms independently selected from nitrogen, oxygen, or sulfur, a 3-7 membered saturated or partially unsaturated heterocyclic ring having 1-2 heteroatoms independently selected from nitrogen, oxygen, or sulfur, an 8-10 membered bicyclic saturated or partially unsaturated heterocyclic ring having 1-4 heteroatoms independently selected from nitrogen, oxygen, or sulfur, or an 8-10 membered bicyclic heteroaryl ring having 1-4 heteroatoms independently selected from nitrogen, oxygen, or sulfur.

According to one embodiment, the present disclosure provides a compound of formula III:

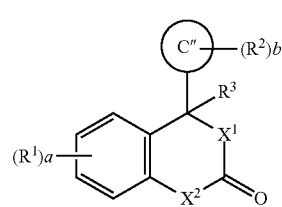

or a pharmaceutically acceptable salt thereof, wherein:
Ring C" is independently an optionally substituted group selected from phenyl, an 8-10 membered bicyclic aryl ring, a 5-6 membered monocyclic heteroaryl ring having 1-3 heteroatoms independently selected from nitrogen, oxygen, or sulfur, or an 8-10 membered bicyclic heteroaryl ring having 1-4 heteroatoms independently selected from nitrogen, oxygen, or sulfur;
each of $R^1$, $R^2$ and $R^3$ is independently halogen, R', —C(O)R', —C(S)R', —CO$_2$R', —C(O)N(R')$_2$, —C(S)N(R')$_2$, —S(O)R', —SO$_2$R', —SO$_2$N(R')$_2$, —OR', —O—($C_{1-6}$ aliphatic)-N(R')$_2$, —O—($C_{1-6}$ aliphatic)-OR', —OC(O)R', —SR', —NO$_2$, —N(R')$_2$, —NR'C(O)R', —NR'C(O)OR', —NR'C(O)N(R')$_2$, —NR'SO$_2$R', —NR'SO$_2$N(R')$_2$, or —NR'OR';
a is 1-4;
b is 1-5;
$X^1$ is —C(R$^x$)$_2$—, —NR—, —NR$^x$C(R$^x$)$_2$— or —OC(R$^x$)$_2$—; $X^2$ is —C(R$^x$)$_2$— or —NR$^x$—;
each R$^x$ is R', —($C_{1-6}$ aliphatic)-N(R')$_2$, or —($C_{1-6}$ aliphatic)-OR';
each R' is —R, —C(O)R, —CO$_2$R, or —SO$_2$R, or:
  two R' on the same nitrogen are taken together with their intervening atoms to form a 3-7 membered heterocyclic ring having 1-2 heteroatoms independently selected from nitrogen, oxygen, and sulfur; and
each R is hydrogen, or an optionally substituted group selected from $C_{1-6}$ aliphatic, phenyl, a 3-7 membered saturated or partially unsaturated carbocyclic ring, an 8-10 membered bicyclic saturated, partially unsaturated or aryl carbocyclic ring, a 5-6 membered monocyclic heteroaryl ring having 1-3 heteroatoms independently selected from nitrogen, oxygen, or sulfur, a 3-7 membered saturated or partially unsaturated heterocyclic ring having 1-2 heteroatoms independently selected from nitrogen, oxygen, or sulfur, an 8-10 membered bicyclic saturated or partially unsaturated heterocyclic ring having 1-4 heteroatoms independently selected from nitrogen, oxygen, or sulfur, or an 8-10 membered bicyclic heteroaryl ring having 1-4 heteroatoms independently selected from nitrogen, oxygen, or sulfur.

2. Definitions

Compounds of this disclosure include those described generally above, and are further illustrated by the embodiments, sub-embodiments, and species disclosed herein. As used herein, the following definitions shall apply unless otherwise indicated. For purposes of this disclosure, the chemical elements are identified in accordance with the Periodic Table of the Elements, CAS version, Handbook of Chemistry and Physics, 75$^{th}$ Ed. Additionally, general principles of organic chemistry are described in "Organic Chemistry," Thomas Sorrell, University Science Books, Sausalito: 1999, and "March's Advanced Organic Chemistry," 5$^{th}$ Ed., Ed.: Smith, M. B. and March, J., John Wiley & Sons, New York: 2001, the entire contents of which are hereby incorporated by reference to the extent they are consistent herewith.

As described herein, compounds of the disclosure may optionally be substituted with one or more substituents, such as are illustrated generally above, or as exemplified by particular classes, subclasses, and species of the disclosure. It will be appreciated that the phrase "optionally substituted" is used interchangeably with the phrase "substituted or unsubstituted." In general, the term "substituted," whether preceded by the term "optionally" or not, refers to the replacement of hydrogen radicals in a given structure with the radical of a specified substituent. Unless otherwise indicated, an optionally substituted group may have a substituent at each substitutable position of the group, and when more than one position in any given structure may be substituted with more than one substituent selected from a specified group, the substituent may be either the same or different at every position. Combinations of substituents envisioned by this disclosure are preferably those that result in the formation of stable or chemically feasible compounds.

The term "stable," as used herein, refers to compounds that are not substantially altered when subjected to conditions to allow for their production, detection, and preferably their recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week.

The term "aliphatic" or "aliphatic group," as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle" "cycloaliphatic" or "cycloalkyl"), that has a single point of attachment to the rest of the molecule. Unless otherwise specified, aliphatic groups contain 1-20 aliphatic carbon atoms. In some embodiments, aliphatic groups contain 1-6 aliphatic carbon atoms. In yet other embodiments aliphatic groups contain 1-4 aliphatic carbon atoms. In some embodiments, "cycloaliphatic" (or "carbocycle" or "cycloalkyl") refers to a monocyclic $C_3$-$C_8$ hydrocarbon or bicyclic $C_8$-$C_{12}$ hydrocarbon that is completely saturated or that contains one or more units of unsaturation, but which is not aromatic, that has a single point of attachment to the rest of the molecule wherein any individual ring in said bicyclic ring system has 3-7 members. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl. In other embodiments, an aliphatic group may have two geminal hydrogen atoms replaced with oxo (a bivalent carbonyl oxygen atom=O), or a ring-forming substituent, such as —O— (straight or branched alkylene or alkylene) —O— to form an acetal or ketal.

In certain embodiments, exemplary aliphatic groups include, but are not limited to, ethynyl, 2-propynyl, 1-propenyl, 2-butenyl, 1,3-butadienyl, 2-pentenyl, vinyl (ethenyl), allyl, isopropenyl, methyl, ethyl, propyl, isopropyl, butyl, isobutyl, sec-butyl, tert-butyl, pentyl, isopentyl, sec-pentyl, neo-pentyl, tert-pentyl, cyclopentyl, hexyl, isohexyl, sec-hexyl, cyclohexyl, 2-methylpentyl, tert-hexyl, 2,3-dimethylbutyl, 3,3-dimethylbutyl, 1,3-dimethylbutyl, and 2,3-dimethyl but-2-yl.

The term "heterocycle," "heterocyclyl," "heterocycloaliphatic," or "heterocyclic" as used herein means non-aromatic, monocyclic, bicyclic, or tricyclic ring systems in which one or more ring members is an independently selected heteroatom. In some embodiments, the "heterocycle," "heterocyclyl," "heterocycloaliphatic," or "heterocyclic" group has three to fourteen ring members in which one or more ring members is a heteroatom independently selected from oxygen, sulfur, nitrogen, or phosphorus, and each ring in the system contains 3 to 7 ring members.

A heterocyclic ring can be attached to its pendant group at any heteroatom or carbon atom that results in a stable structure and, when specified, any of the ring atoms can be optionally substituted. Examples of such saturated or partially unsaturated heterocyclic radicals include, without limitation, tetrahydrofuranyl, tetrahydrothiophenyl pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or $NR^+$ (as in N-substituted pyrrolidinyl).

The term "unsaturated," as used herein, means that a moiety has one or more units of unsaturation.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

The term "aryl" used alone or as part of a larger moiety as in "aralkyl," "aralkoxy," or "aryloxyalkyl," refers to monocyclic, bicyclic, and tricyclic ring systems having a total of five to fourteen ring members, wherein one or more ring in the system is aromatic and wherein each ring in the system contains 3 to 7 ring members. The term "aryl" may be used interchangeably with the term "aryl ring". The term "aryl" also refers to heteroaryl ring systems as defined herein below. In certain embodiments of the present disclosure, "aryl" refers to an aromatic ring system which includes, but not limited to, phenyl, biphenyl, naphthyl, anthracyl and the like, which may bear one or more substituents. Also included within the scope of the term "aryl," as it is used herein, is a group in which an aromatic ring is fused to one or more non-aromatic rings, such as indanyl, phthalimidyl, naphthimidyl, phenanthridinyl, or tetrahydronaphthyl, and the like.

The term "heteroaryl," used alone or as part of a larger moiety as in "heteroaralkyl" or "heteroarylalkoxy," refers to monocyclic, bicyclic, and tricyclic ring systems having a total of five to fourteen ring members, wherein one or more ring in the system is aromatic, one or more ring in the system contains one or more heteroatoms, and wherein each ring in the system contains 3 to 7 ring members. The term "heteroaryl" may be used interchangeably with the term "heteroaryl ring" or the term "heteroaromatic". Heteroaryl groups include thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl.

The terms "heteroaryl" and "heteroar-," as used herein, also include groups in which a heteroaromatic ring is fused to one or more aryl, cycloaliphatic, or heterocyclyl rings. Exemplary heteroaryl rings include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one.

As described herein, compounds of the disclosure may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this disclosure are preferably those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently halogen; $-(CH_2)_{0-4}R^\circ$; $-(CH_2)_{0-4}OR^\circ$; $-O(CH_2)_{0-4}R^\circ$, $-O-(CH_2)_{0-4}C(O)OR^\circ$; $-(CH_2)_{0-4}CH(OR^\circ)_2$; $-(CH_2)_{0-4}SR^\circ$; $-(CH_2)_{0-4}Ph$, which may be substituted with $R^\circ$; $-(CH_2)_{0-4}O(CH_2)_{0-1}Ph$ which may be substituted with $R^\circ$; $-CH=CHPh$, which may be substituted with $R^\circ$; $-(CH_2)_{0-4}O(CH_2)_{0-1}$-pyridyl which may be substituted with $R^\circ$; $-NO_2$; $-CN$; $-N_3$; $-(CH_2)_{0-4}N(R^\circ)_2$; $-(CH_2)_{0-4}N(R^\circ)C(O)R^\circ$; $-N(R^\circ)C(S)R^\circ$; $-(CH_2)_{0-4}N(R^\circ)C(O)NR^\circ_2$; $-N(R^\circ)C(S)NR^\circ_2$; $-(CH_2)_{0-4}N(R^\circ)C(O)OR^\circ$; $-N(R^\circ)N(R^\circ)C(O)R^\circ$; $-N(R^\circ)N(R^\circ)C(O)NR^\circ_2$; $-N(R^\circ)N(R^\circ)C(O)OR^\circ$; $-(CH_2)_{0-4}C(O)R^\circ$; $-C(S)R^\circ$; $-(CH_2)_{0-4}C(O)OR^\circ$; $-(CH_2)_{0-4}C(O)SR^\circ$; $-(CH_2)_{0-4}C(O)OSiR^\circ_3$; $-(CH_2)_{0-4}OC(O)R^\circ$; $-OC(O)(CH_2)_{0-4}SR^\circ$, $SC(S)SR^\circ$; $-(CH_2)_{0-4}SC(O)R^\circ$; $-(CH_2)_{0-4}C(O)NR^\circ_2$; $-C(S)NR^\circ_2$; $-C(S)SR^\circ$; $-SC(S)SR^\circ$, $-(CH_2)_{0-4}OC(O)NR^\circ_2$; $-C(O)N(OR^\circ)R^\circ$; $-C(O)C(O)R^\circ$; $-C(O)CH_2C(O)R^\circ$; $-C(NOR^\circ)R^\circ$; $-(CH_2)_{0-4}SSR^\circ$; $-(CH_2)_{0-4}S(O)_2R^\circ$; $-(CH_2)_{0-4}S(O)_2OR^\circ$; $-(CH_2)_{0-4}S(O)_2R^\circ$; $-S(O)_2NR^\circ_2$; $-(CH_2)_{0-4}S(O)R^\circ$; $-N(R^\circ)S(O)_2NR^\circ_2$; $-N(R^\circ)S(O)_2R^\circ$; $-N(OR^\circ)R^\circ$; $-C(NH)NR^\circ_2$; $-P(O)_2R^\circ$; $-P(O)R^\circ_2$; $-OP(O)R^\circ_2$; $-OP(O)(OR^\circ)_2$; $SiR^\circ_3$; $-(C_{1-4}$ straight or branched alkylene)O—N(R^\circ)_2$; or $-(C_{1-4}$ straight or branched alkylene)C(O)O—N(R^\circ)_2$, wherein each $R^\circ$ may be substituted as defined below and is independently hydrogen, $C_{1-6}$ aliphatic, $-CH_2Ph$, $-O(CH_2)_{0-1}Ph$, $-CH_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of $R^\circ$, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on $R^\circ$ (or the ring formed by taking two independent occurrences of $R^\circ$ together with their intervening atoms), are independently halogen, $-(CH_2)_{0-2}R^\bullet$, -(haloR$^\bullet$), $-(CH_2)_{0-2}OH$, $-(CH_2)_{0-2}OR^\bullet$, $-(CH_2)_{0-2}CH(OR^\bullet)_2$; $-O(haloR^\bullet)$, $-CN$, $-N_3$, $-(CH_2)_{0-2}C(O)R^\bullet$, $-(CH_2)_{0-2}C(O)OH$, $-(CH_2)_{0-2}C(O)OR^\bullet$, $-(CH_2)_{0-2}SR^\bullet$, $-(CH_2)_{0-2}SH$, $-(CH_2)_{0-2}NH_2$, $-(CH_2)_{0-2}NHR^\bullet$, $-(CH_2)_{0-2}NR^\bullet_2$, $-NO$, $-SiR^\bullet_3$, $-OSiR^\bullet_3$, $-C(O)SR^\bullet$—$(C_{1-4}$ straight or branched alkylene)$C(O)OR^\bullet$, or $-SSR^\bullet$ wherein each $R^\bullet$ is unsubstituted or where preceded by "halo" is substituted only with one or more halogens, and is independently selected from $C_{1-4}$ aliphatic, $-CH_2Ph$, $-O(CH_2)_{0-1}Ph$, or a 5-6-membered saturated, partially unsaturated, or aryl ring having 0-4 heteroatoms independently selected from nitrogen, oxygen, or sulfur. Suitable divalent substituents on a saturated carbon atom of $R^\circ$ include =O and =S.

Suitable divalent substituents on a saturated carbon atom of an "optionally substituted" group include the following: =O, =S, =NNR*$_2$, =NNHC(O)R*, =NNHC(O)OR*, =NNHS(O)$_2$R*, =NR*, =NOR*, $-O(C(R^*)_2)_{2-3}O-$, or $-S(C(R^*)_2)_{2-3}S-$, and =C(R*)$_2$, wherein each independent occurrence of R* is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: $-O(CR^*_2)_{2-3}O-$, wherein each independent occurrence of R* is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, $-R^*$, -(haloR*), $-OH$, $-OR^*$, $-O(haloR^*)$, $-CN$, $-C(O)OH$, $-C(O)OR^*$, $-NH_2$, $-NHR^*$, $-NR^*$, or $-NO$, wherein each R* is unsubstituted or where preceded by "halo" is substituted only with one or more halogens, and is independently $C_{1-4}$ aliphatic, $-CH_2Ph$, $-O(CH_2)_{0-1}Ph$, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include $-R^\dagger$, $-NR^\dagger_2$, $-C(O)R^\dagger$, $-C(O)OR^\dagger$, $-C(O)C(O)R^\dagger$, $-C(O)CH_2C(O)R^\dagger$, $-S(O)_2R^\dagger$, $-S(O)_2NR^\dagger_2$, $-C(S)NR^\dagger_2$, $-C(NH)NR^\dagger_2$, or $-N(R^\dagger)S(O)_2R^\dagger$; wherein each $R^\dagger$ is independently hydrogen, $C_{1-6}$ aliphatic which may be substituted as defined below, unsubstituted $-OPh$, or an unsubstituted 5-6-membered saturated, partially unsaturated, or aryl ring having 0-4 heteroatoms independently selected from nitrogen, oxygen, or sulfur, or, notwithstanding the definition above, two independent occurrences of $R^\dagger$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of R⁺ are independently halogen, —R˙, -(haloR˙), —OH, —OR˙, —O(haloR˙), —CN, —C(O)OH, —C(O)OR˙, —NH², —NHR˙, —NR˙, or —NO₂, wherein each R˙ is unsubstituted or where preceded by "halo" is substituted only with one or more halogens, and is independently C$_{1-4}$ aliphatic, —CH₂Ph, —O(CH₂)$_{0-1}$Ph, or a 5-6-membered saturated, partially unsaturated, or aryl ring having 0-4 heteroatoms independently selected from nitrogen, oxygen, or sulfur.

Unless otherwise stated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the disclosure.

Unless otherwise stated, all tautomeric forms of the compounds of the disclosure are within the scope of the disclosure.

Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a ¹¹C- or ¹³C- or ¹⁴C-enriched carbon are within the scope of this disclosure. Such compounds are useful, for example, as analytical tools or probes in biological assays.

3. Description of Exemplary Compounds

According to one embodiment, the present disclosure provides a compound of formula I:

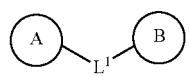

I or a pharmaceutically acceptable salt thereof, wherein:
each of Ring A and Ring B is independently an optionally substituted group selected from phenyl, a 3-7 membered saturated or partially unsaturated carbocyclic ring, an 8-10 membered bicyclic saturated, partially unsaturated or aryl carbocyclic ring, a 5-6 membered monocyclic heteroaryl ring having 1-3 heteroatoms independently selected from nitrogen, oxygen, or sulfur, a 3-7 membered saturated or partially unsaturated heterocyclic ring having 1-2 heteroatoms independently selected from nitrogen, oxygen, or sulfur, an 8-10 membered bicyclic saturated or partially unsaturated heterocyclic ring having 1-4 heteroatoms independently selected from nitrogen, oxygen, or sulfur, or an 8-10 membered bicyclic heteroaryl ring having 1-4 heteroatoms independently selected from nitrogen, oxygen, or sulfur;
L¹ is independently a covalent bond or an optionally substituted bivalent C$_{1-6}$ hydrocarbon chain, wherein one or more methylene units of L¹ are optionally and independently replaced by —O—, —S—, —N(R')—, —C(O)—, —C(S)—, —C(NR')—, —C(O)N(R')—, —N(R')C(O)N(R')—, —N(R')C(O)—, —N(R')C(O)O—, —OC(O)N(R')—, —S(O)—, —S(O)₂—, —S(O)₂N(R')—, —N(R')S(O)₂—, —OC(O)—, or —C(O)O—;
R' is —R, —C(O)R, —CO₂R, or —SO₂R, or:
  two R' on the same nitrogen are taken together with their intervening atoms to form a 3-7 membered heterocyclic ring having 1-2 heteroatoms independently selected from nitrogen, oxygen, and sulfur; and
R is hydrogen, or an optionally substituted group selected from C$_{1-6}$ aliphatic, phenyl, a 3-7 membered saturated or partially unsaturated carbocyclic ring, an 8-10 membered bicyclic saturated, partially unsaturated or aryl carbocyclic ring, a 5-6 membered monocyclic heteroaryl ring having 1-3 heteroatoms independently selected from nitrogen, oxygen, or sulfur, a 3-7 membered saturated or partially unsaturated heterocyclic ring having 1-2 heteroatoms independently selected from nitrogen, oxygen, or sulfur, an 8-10 membered bicyclic saturated or partially unsaturated heterocyclic ring having 1-4 heteroatoms independently selected from nitrogen, oxygen, or sulfur, or an 8-10 membered bicyclic heteroaryl ring having 1-4 heteroatoms independently selected from nitrogen, oxygen, or sulfur.

According to one embodiment, the present disclosure provides a compound of formula II:

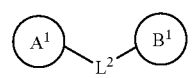

II or a pharmaceutically acceptable salt thereof, wherein:
each of Ring A' and Ring B' is independently an optionally substituted group selected from phenyl, an 8-10 membered bicyclic aryl ring, a 5-6 membered monocyclic heteroaryl ring having 1-3 heteroatoms independently selected from nitrogen, oxygen, or sulfur, or an 8-10 membered bicyclic heteroaryl ring having 1-4 heteroatoms independently selected from nitrogen, oxygen, or sulfur;
L² is —C(O)N(R')—;
each R' is independently —R, —C(O)R, —CO₂R, or —SO₂R, or:
  two R' on the same nitrogen are taken together with their intervening atoms to form a 3-7 membered heterocyclic ring having 1-2 heteroatoms independently selected from nitrogen, oxygen, and sulfur; and
each R is hydrogen, or an optionally substituted group selected from C$_{1-6}$ aliphatic, phenyl, a 3-7 membered saturated or partially unsaturated carbocyclic ring, an 8-10 membered bicyclic saturated, partially unsaturated or aryl carbocyclic ring, a 5-6 membered monocyclic heteroaryl ring having 1-3 heteroatoms independently selected from nitrogen, oxygen, or sulfur, a 3-7 membered saturated or partially unsaturated heterocyclic ring having 1-2 heteroatoms independently selected from nitrogen, oxygen, or sulfur, an 8-10 membered bicyclic saturated or partially unsaturated heterocyclic ring having 1-4 heteroatoms independently selected from nitrogen, oxygen, or sulfur, or an 8-10 membered bicyclic heteroaryl ring having 1-4 heteroatoms independently selected from nitrogen, oxygen, or sulfur.

According to one embodiment, the present disclosure provides a compound of formula III:

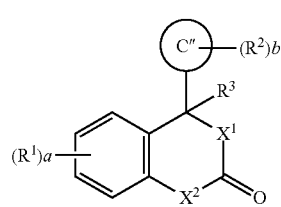

III or a pharmaceutically acceptable salt thereof, wherein:
Ring C" is independently an optionally substituted group selected from phenyl, an 8-10 membered bicyclic aryl ring, a 5-6 membered monocyclic heteroaryl ring having 1-3 heteroatoms independently selected from nitrogen, oxygen, or sulfur, or an 8-10 membered bicyclic heteroaryl ring having 1-4 heteroatoms independently selected from nitrogen, oxygen, or sulfur;

each of $R^1$, $R^2$ and $R^3$ is independently halogen, R', —C(O)R', —C(S)R', —CO$_2$R', —C(O)N(R')$_2$, —C(S)N(R')$_2$, —S(O)R', —SO$_2$R', —SO$_2$N(R')$_2$, —OR', —O—(C$_{1-6}$ aliphatic)-N(R')$_2$, —O—(C$_{1-6}$ aliphatic)-OR', —OC(O)R', —SR', —NO$_2$, —N(R')$_2$, —NR'C(O)R', —NR'C(O)OR', —NR'C(O)N(R')$_2$, —NR'SO$_2$R', —NR'SO$_2$N(R')$_2$, or —NR'OR';

a is 1-4;

b is 1-5;

$X^1$ is —C(R$^x$)$_2$—, —NR$^x$—, —NR$^x$C(R$^x$)$_2$— or —OC(R$^x$)$_2$;

$X^2$ is —C(R$^x$)$_2$— or —NR$^x$—;

each R$^x$ is independently R', —(C$_{1-6}$ aliphatic)-N(R')$_2$, or —(C$_{1-6}$ aliphatic)-OR';

each R' is independently —R, —C(O)R, —CO$_2$R, or —SO$_2$R, or:

two R' on the same nitrogen are taken together with their intervening atoms to form a 3-7 membered heterocyclic ring having 1-2 heteroatoms independently selected from nitrogen, oxygen, and sulfur; and each R is hydrogen, or an optionally substituted group selected from C$_{1-6}$ aliphatic, phenyl, a 3-7 membered saturated or partially unsaturated carbocyclic ring, an 8-10 membered bicyclic saturated, partially unsaturated or aryl carbocyclic ring, a 5-6 membered monocyclic heteroaryl ring having 1-3 heteroatoms independently selected from nitrogen, oxygen, or sulfur, a 3-7 membered saturated or partially unsaturated heterocyclic ring having 1-2 heteroatoms independently selected from nitrogen, oxygen, or sulfur, an 8-10 membered bicyclic saturated or partially unsaturated heterocyclic ring having 1-4 heteroatoms independently selected from nitrogen, oxygen, or sulfur, or an 8-10 membered bicyclic heteroaryl ring having 1-4 heteroatoms independently selected from nitrogen, oxygen, or sulfur.

As generally defined above, Ring A is an optionally substituted group selected from phenyl, a 3-7 membered saturated or partially unsaturated carbocyclic ring, an 8-10 membered bicyclic saturated, partially unsaturated or aryl carbocyclic ring, a 5-6 membered monocyclic heteroaryl ring having 1-3 heteroatoms independently selected from nitrogen, oxygen, or sulfur, a 3-7 membered saturated or partially unsaturated heterocyclic ring having 1-2 heteroatoms independently selected from nitrogen, oxygen, or sulfur, an 8-10 membered bicyclic saturated or partially unsaturated heterocyclic ring having 1-4 heteroatoms independently selected from nitrogen, oxygen, or sulfur, or an 8-10 membered bicyclic heteroaryl ring having 1-4 heteroatoms independently selected from nitrogen, oxygen, or sulfur;

In some embodiments, Ring A is optionally substituted phenyl. In some embodiments, Ring A is substituted phenyl. In some embodiments, Ring A is phenyl. In some embodiments, Ring A is phenyl substituted with one or more halogen atoms. In some embodiments, Ring A is phenyl substituted with two halogen atoms. In some embodiments, Ring A is 2-fluoro-5-chlorophenyl. In some embodiments, Ring A is 2-fluoro-5-bromophenyl. In some embodiments, Ring A is 3-chloro-4-flluorophenyl.

In some embodiments, Ring A is an optionally substituted 3-7 membered saturated or partially unsaturated carbocyclic ring. In some embodiments, Ring A is an optionally substituted 3-7 membered saturated carbocyclic ring. In some embodiments, Ring A is a substituted 3-7 membered saturated carbocyclic ring. In some embodiments, Ring A is an unsubstituted 3-7 membered saturated carbocyclic ring. In some embodiments, Ring A is an optionally substituted 3-7 membered unsaturated carbocyclic ring. In some embodiments, Ring A is a substituted 3-7 membered unsaturated carbocyclic ring. In some embodiments, Ring A is an unsubstituted 3-7 membered unsaturated carbocyclic ring.

In some embodiments, Ring A is an optionally substituted cycloheptyl. In some embodiments, Ring A is an optionally substituted cyclohexyl. In some embodiments, Ring A is an optionally substituted cyclopentyl. In some embodiments, Ring A is an optionally substituted cyclobutyl. In some embodiments, Ring A is an optionally substituted cyclopropyl.

In some embodiments, Ring A is an optionally substituted 8-10 membered bicyclic saturated, partially unsaturated or aryl carbocyclic ring. In some embodiments, Ring A is an optionally substituted 8-10 membered bicyclic saturated carbocyclic ring. In some embodiments, Ring A is an optionally substituted 8-10 membered bicyclic partially unsaturated carbocyclic ring. In some embodiments, Ring A is an optionally substituted 8-10 membered bicyclic aryl ring.

In some embodiments, Ring A is an optionally substituted 5-6 membered monocyclic heteroaryl ring having 1-3 heteroatoms independently selected from nitrogen, oxygen, or sulfur. In some embodiments, Ring A is a substituted 5-6 membered monocyclic heteroaryl ring having 1-3 heteroatoms independently selected from nitrogen, oxygen, or sulfur. In some embodiments, Ring A is an unsubstituted 5-6 membered monocyclic heteroaryl ring having 1-3 heteroatoms independently selected from nitrogen, oxygen, or sulfur.

In some embodiments, Ring A is an optionally substituted 5 membered monocyclic heteroaryl ring having 1-3 heteroatoms independently selected from nitrogen, oxygen or sulfur. In some embodiments, Ring A is an optionally substituted 6 membered monocyclic heteroaryl ring having 1-3 heteroatoms independently selected from nitrogen, oxygen, or sulfur.

In some embodiments, Ring A is an optionally substituted 5-membered monocyclic heteroaryl ring having 1 heteroatom selected from nitrogen, oxygen, or sulfur. In some embodiments, Ring A is selected from pyrrolyl, furanyl, or thienyl.

In some embodiments, Ring A is an optionally substituted 5-membered heteroaryl ring having 2 heteroatoms independently selected from nitrogen, oxygen, or sulfur. In certain embodiments, Ring A is an optionally substituted 5-membered heteroaryl ring having 1 nitrogen atom, and an additional heteroatom selected from sulfur or oxygen. Exemplary Ring A groups include optionally substituted pyrazolyl, imidazolyl, thiazolyl, isothiazolyl, oxazolyl or isoxazolyl.

In some embodiments, Ring A is a 6-membered heteroaryl ring having 1-3 nitrogen atoms. In other embodiments, Ring A is an optionally substituted 6-membered heteroaryl ring having 1-2 nitrogen atoms. In some embodiments, Ring A is an optionally substituted 6-membered heteroaryl ring having 2 nitrogen atoms. In certain embodiments, Ring A is an optionally substituted 6-membered heteroaryl ring having 1 nitrogen. Exemplary Ring A groups include optionally substituted pyridinyl, pyrimidinyl, pyrazinyl, pyridazinyl, triazinyl, or tetrazinyl.

In some embodiments, Ring A is an optionally substituted 3-7 membered saturated or partially unsaturated heterocyclic ring having 1-2 heteroatoms independently selected from nitrogen, oxygen, or sulfur. In some embodiments, Ring A is a substituted 3-7 membered saturated or partially unsaturated heterocyclic ring having 1-2 heteroatoms independently selected from nitrogen, oxygen, or sulfur. In some embodiments, Ring A is an unsubstituted 3-7 membered saturated or partially unsaturated heterocyclic ring having 1-2 heteroatoms independently selected from nitrogen, oxygen, or sulfur.

In some embodiments, Ring A is an optionally substituted 6 membered saturated or partially unsaturated heterocyclic ring having 1-2 heteroatoms independently selected from nitrogen, oxygen, or sulfur. In some embodiments, Ring A is an optionally substituted 6 membered partially unsaturated heterocyclic ring having 2 heteroatoms independently selected from nitrogen, oxygen, or sulfur. In some embodiments, Ring A is an optionally substituted 6 membered partially unsaturated heterocyclic ring having 2 oxygen atom. In some embodiments, Ring A is an optionally substituted 6 membered partially unsaturated heterocyclic ring having 2 oxygen atom having the structure

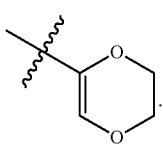 [SMILES: *C1=COCCO1]

In certain embodiments, Ring A is a 3-7 membered saturated or partially unsaturated heterocyclic ring having 1-2 heteroatoms independently selected from nitrogen, oxygen, or sulfur. In certain embodiments, Ring A is oxiranyl, oxetanyl, tetrahydrofuranyl, tetrahydropyranyl, oxepaneyl, aziridineyl, azetidineyl, pyrrolidinyl, piperidinyl, azepanyl, thiiranyl, thietanyl, tetrahydrothiophenyl, tetrahydrothiopyranyl, thiepanyl, dioxolanyl, oxathiolanyl, oxazolidinyl, imidazolidinyl, thiazolidinyl, dithiolanyl, dioxanyl, morpholinyl, oxathianyl, piperazinyl, thiomorpholinyl, dithianyl, dioxepanyl, oxazepanyl, oxathiepanyl, dithiepanyl, diazepanyl, dihydrofuranonyl, tetrahydropyranonyl, oxepanonyl, pyrolidinonyl, piperidinonyl, azepanonyl, dihydrothiophenonyl, tetrahydrothiopyranonyl, thiepanonyl, oxazolidinonyl, oxazinanonyl, oxazepanonyl, dioxolanonyl, dioxanonyl, dioxepanonyl, oxathiolinonyl, oxathianonyl, oxathiepanonyl, thiazolidinonyl, thiazinanonyl, thiazepanonyl, imidazolidinonyl, tetrahydropyrimidinonyl, diazepanonyl, imidazolidinedionyl, oxazolidinedionyl, thiazolidinedionyl, dioxolanedionyl, oxathiolanedionyl, piperazinedionyl, morpholinedionyl, thiomorpholinedionyl, tetrahydropyranyl, tetrahydrofuranyl, morpholinyl, thiomorpholinyl, piperidinyl, piperazinyl, pyrrolidinyl, tetrahydrothiophenyl, or tetrahydrothiopyranyl. In some embodiments, Ring A is an optionally substituted 5 membered saturated or partially unsaturated heterocyclic ring having 1-2 heteroatoms independently selected from nitrogen, oxygen, or sulfur. In some embodiments, two optional substituents are taken together with their intervening atom(s) to form a 3-12-membered saturated, partially unsaturated, or aryl mono- or bicyclic ring having 0-4 heteroatoms independently selected from nitrogen, oxygen, or sulfur, which may be substituted. In some embodiments, Ring A is an optionally substituted group selected from

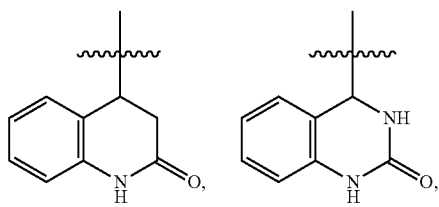

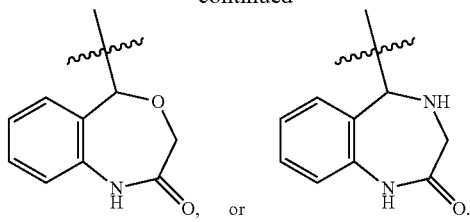

In certain embodiments, Ring A is an optionally substituted 5-6 membered partially unsaturated monocyclic ring having 1-2 heteroatoms independently selected from nitrogen, oxygen, or sulfur. In certain embodiments, Ring A is an optionally substituted tetrahydropyridinyl, dihydrothiazolyl, dihydrooxazolyl, or oxazolinyl group.

In some embodiments, Ring A is an optionally substituted 8-10 membered bicyclic saturated or partially unsaturated heterocyclic ring having 1-4 heteroatoms independently selected from nitrogen, oxygen, or sulfur. In some embodiments, Ring A is an optionally substituted indolinyl. In some embodiments, Ring A is an optionally substituted isoindolinyl. In some embodiments, Ring A is an optionally substituted 1,2,3,4-tetrahydroquinoline. In some embodiments, Ring A is an optionally substituted 1,2,3,4-tetrahydroisoquinoline.

In some embodiments, Ring A is an optionally substituted group selected from or

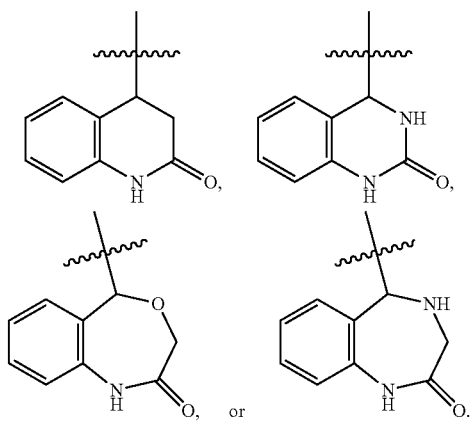

In certain embodiments, Ring A is an optionally substituted 8-10 membered bicyclic heteroaryl ring having 1-4 heteroatoms independently selected from nitrogen, oxygen, or sulfur. In some embodiments, Ring A is an optionally substituted 5,6-fused heteroaryl ring having 1-4 heteroatoms independently selected from nitrogen, oxygen, or sulfur. In other embodiments, Ring A is an optionally substituted 5,6-fused heteroaryl ring having 1-2 heteroatoms independently selected from nitrogen, oxygen, or sulfur. In certain embodiments, Ring A is an optionally substituted 5,6-fused heteroaryl ring having 1 heteroatom independently selected from nitrogen, oxygen, or sulfur. In some embodiments, Ring A is an optionally substituted indolyl. In some embodiments, Ring A is an optionally substituted azabicyclo[3.2.1]octanyl. In certain embodiments, Ring A is an optionally substituted 5,6-fused heteroaryl ring having 2 heteroatoms independently selected from nitrogen, oxygen, or sulfur. In some embodiments, Ring A is an optionally substituted azaindolyl. In some embodiments, Ring A is an optionally substituted benzimidazolyl. In some embodiments, Ring A is an optionally substituted benzothiazolyl. In some embodiments, Ring A is an optionally substituted benzoxazolyl. In some embodiments, Ring A is an optionally substituted indazolyl. In certain embodiments, Ring A is an optionally substituted 5,6-fused heteroaryl ring having 3 heteroatoms independently selected from nitrogen, oxygen, or sulfur.

In certain embodiments, Ring A is an optionally substituted 6,6-fused heteroaryl ring having 1-4 heteroatoms independently selected from nitrogen, oxygen, or sulfur. In some embodiments, Ring A is an optionally substituted 6,6-fused heteroaryl ring having 1-2 heteroatoms independently selected from nitrogen, oxygen, or sulfur. In other embodiments, Ring A is an optionally substituted 6,6-fused heteroaryl ring having 1 heteroatom independently selected from nitrogen, oxygen, or sulfur. In some embodiments, Ring A is an optionally substituted quinolinyl. In some embodiments, Ring A is an optionally substituted isoquinolinyl. According to one aspect, Ring A is an optionally substituted 6,6-fused heteroaryl ring having 2 heteroatoms independently selected from nitrogen, oxygen, or sulfur. In some embodiments, Ring A is a quinazoline or a quinoxaline.

In some embodiments, two substituents on Ring A are optionally taken together with their intervening atoms to form an optionally substituted, 3-7 membered saturated, partially unsaturated or aryl ring having 0-4 heteroatoms independently selected from nitrogen, oxygen or sulfur. In some embodiments, two substituents on Ring A are optionally taken together with their intervening atoms to form an optionally substituted phenyl. In some embodiments, two substituents on Ring A are optionally taken together with their intervening atoms to form an optionally substituted 3-7 membered saturated or partially unsaturated carbocyclic ring. In some embodiments, two substituents on Ring A are optionally taken together with their intervening atoms to form an optionally substituted 3-7 membered saturated or partially unsaturated heterocyclic ring having 1-4 heteroatoms independently selected from nitrogen, oxygen or sulfur. In some embodiments, two substituents on Ring A are optionally taken together with their intervening atoms to form an optionally substituted 5-6 membered heteroaryl ring having 1-4 heteroatoms independently selected from nitrogen, oxygen or sulfur.

As generally defined above, Ring B is an optionally substituted group selected from phenyl, a 3-7 membered saturated or partially unsaturated carbocyclic ring, an 8-10 membered bicyclic saturated, partially unsaturated or aryl carbocyclic ring, a 5-6 membered monocyclic heteroaryl ring having 1-3 heteroatoms independently selected from nitrogen, oxygen, or sulfur, a 3-7 membered saturated or partially unsaturated heterocyclic ring having 1-2 heteroatoms independently selected from nitrogen, oxygen, or sulfur, an 8-10 membered bicyclic saturated or partially unsaturated heterocyclic ring having 1-4 heteroatoms independently selected from nitrogen, oxygen, or sulfur, or an 8-10 membered bicyclic heteroaryl ring having 1-4 heteroatoms independently selected from nitrogen, oxygen, or sulfur;

In some embodiments, Ring B is an optionally substituted phenyl. In some embodiments, Ring B is a substituted phenyl. In some embodiments, Ring B is phenyl. In some embodiments, Ring B is a phenyl substituted with one or more halogen atoms. In some embodiments, Ring B is a phenyl substituted with two halogen atoms. In some embodiments, Ring B is 2-fluoro-5-chlorophenyl. In some embodiments, Ring B is 2-fluoro-5-bromophenyl. In some embodiments, Ring B is 3-chloro-4-fluorophenyl.

In some embodiments, Ring B is an optionally substituted 3-7 membered saturated or partially unsaturated carbocyclic ring. In some embodiments, Ring B is an optionally substituted 3-7 membered saturated carbocyclic ring. In some embodiments, Ring B is a substituted 3-7 membered saturated carbocyclic ring. In some embodiments, Ring B is an unsubstituted 3-7 membered saturated carbocyclic ring. In some embodiments, Ring B is an optionally substituted 3-7 membered unsaturated carbocyclic ring. In some embodiments, Ring B is a substituted 3-7 membered unsaturated carbocyclic ring. In some embodiments, Ring B is an unsubstituted 3-7 membered unsaturated carbocyclic ring.

In some embodiments, Ring B is an optionally substituted cycloheptyl. In some embodiments, Ring B is an optionally substituted cyclohexyl. In some embodiments, Ring B is an optionally substituted cyclopentyl. In some embodiments, Ring B is an optionally substituted cyclobutyl. In some embodiments, Ring B is an optionally substituted cyclopropyl.

In some embodiments, Ring B is an optionally substituted 8-10 membered bicyclic saturated, partially unsaturated or aryl carbocyclic ring. In some embodiments, Ring B is an optionally substituted 8-10 membered bicyclic saturated carbocyclic ring. In some embodiments, Ring B is an optionally substituted 8-10 membered bicyclic partially unsaturated carbocyclic ring. In some embodiments, Ring B is an optionally substituted 8-10 membered bicyclic aryl ring.

In some embodiments, Ring B is an optionally substituted 5-6 membered monocyclic heteroaryl ring having 1-3 heteroatoms independently selected from nitrogen, oxygen, or sulfur. In some embodiments, Ring B is a substituted 5-6 membered monocyclic heteroaryl ring having 1-3 heteroatoms independently selected from nitrogen, oxygen, or sulfur. In some embodiments, Ring B is an unsubstituted 5-6 membered monocyclic heteroaryl ring having 1-3 heteroatoms independently selected from nitrogen, oxygen, or sulfur.

In some embodiments, Ring B is an optionally substituted 5 membered monocyclic heteroaryl ring having 1-3 heteroatoms independently selected from nitrogen, oxygen or sulfur. In some embodiments, Ring B is an optionally substituted 6 membered monocyclic heteroaryl ring having 1-3 heteroatoms independently selected from nitrogen, oxygen, or sulfur.

In some embodiments, Ring B is an optionally substituted 5-membered monocyclic heteroaryl ring having 1 heteroatom selected from nitrogen, oxygen, or sulfur. In some embodiments, Ring B is selected from pyrrolyl, furanyl, or thienyl.

In some embodiments, Ring B is an optionally substituted 5-membered heteroaryl ring having 2 heteroatoms independently selected from nitrogen, oxygen, or sulfur. In certain embodiments, Ring B is an optionally substituted 5-membered heteroaryl ring having 1 nitrogen atom, and an additional heteroatom selected from sulfur or oxygen. Exemplary Ring B groups include optionally substituted pyrazolyl, imidazolyl, thiazolyl, isothiazolyl, oxazolyl or isoxazolyl.

In some embodiments, Ring B is a 6-membered heteroaryl ring having 1-3 nitrogen atoms. In other embodiments, Ring B is an optionally substituted 6-membered heteroaryl ring having 1-2 nitrogen atoms. In some embodiments, Ring B is an optionally substituted 6-membered heteroaryl ring having 2 nitrogen atoms. In certain embodiments, Ring B is an optionally substituted 6-membered heteroaryl ring having 1 nitrogen. Exemplary Ring B groups include optionally substituted pyridinyl, pyrimidinyl, pyrazinyl, pyridazinyl, triazinyl, or tetrazinyl.

In some embodiments, Ring B is an optionally substituted 3-7 membered saturated or partially unsaturated heterocyclic ring having 1-2 heteroatoms independently selected from nitrogen, oxygen, or sulfur. In some embodiments, Ring B is a substituted 3-7 membered saturated or partially unsaturated heterocyclic ring having 1-2 heteroatoms independently selected from nitrogen, oxygen, or sulfur. In some embodiments, Ring B is an unsubstituted 3-7 membered saturated or partially unsaturated heterocyclic ring having 1-2 heteroatoms independently selected from nitrogen, oxygen, or sulfur.

In some embodiments, Ring B is an optionally substituted 6 membered saturated or partially unsaturated heterocyclic ring having 1-2 heteroatoms independently selected from nitrogen, oxygen, or sulfur. In some embodiments, Ring B is an optionally substituted 6 membered partially unsaturated heterocyclic ring having 2 heteroatoms independently selected from nitrogen, oxygen, or sulfur. In some embodiments, Ring B is an optionally substituted 6 membered partially unsaturated heterocyclic ring having 2 oxygen atom. In some embodiments, Ring B is an optionally substituted 6 membered partially unsaturated heterocyclic ring having 2 oxygen atom having the structure

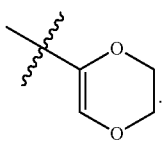 [SMILES: *C1=COCCO1]

In certain embodiments, Ring B is a 3-7 membered saturated or partially unsaturated heterocyclic ring having 1-2 heteroatoms independently selected from nitrogen, oxygen, or sulfur. In certain embodiments, Ring B is oxiranyl, oxetanyl, tetrahydrofuranyl, tetrahydropyranyl, oxepaneyl, aziridineyl, azetidineyl, pyrrolidinyl, piperidinyl, azepanyl, thiiranyl, thietanyl, tetrahydrothiophenyl, tetrahydrothiopyranyl, thiepanyl, dioxolanyl, oxathiolanyl, oxazolidinyl, imidazolidinyl, thiazolidinyl, dithiolanyl, dioxanyl, morpholinyl, oxathianyl, piperazinyl, thiomorpholinyl, dithianyl, dioxepanyl, oxazepanyl, oxathiepanyl, dithiepanyl, diazepanyl, dihydrofuranonyl, tetrahydropyranonyl, oxepanonyl, pyrrolidinonyl, piperidinonyl, azepanonyl, dihydrothiophenonyl, tetrahydrothiopyranonyl, thiepanonyl, oxazolidinonyl, oxazinanonyl, oxazepanonyl, dioxolanonyl, dioxanonyl, dioxepanonyl, oxathiolinonyl, oxathianonyl, oxathiepanonyl, thiazolidinonyl, thiazinanonyl, thiazepanonyl, imidazolidinonyl, tetrahydropyrimidinonyl, diazepanonyl, imidazolidinedionyl, oxazolidinedionyl, thiazolidinedionyl, dioxolanedionyl, oxathiolanedionyl, piperazinedionyl, morpholinedionyl, thiomorpholinedionyl, tetrahydropyranyl, tetrahydrofuranyl, morpholinyl, thiomorpholinyl, piperidinyl, piperazinyl, pyrrolidinyl, tetrahydrothiophenyl, or tetrahydrothiopyranyl. In some embodiments, Ring B is an optionally substituted 5 membered saturated or partially unsaturated heterocyclic ring having 1-2 heteroatoms independently selected from nitrogen, oxygen, or sulfur.

In certain embodiments, Ring B is an optionally substituted 5-6 membered partially unsaturated monocyclic ring having 1-2 heteroatoms independently selected from nitrogen, oxygen, or sulfur. In certain embodiments, Ring B is an optionally substituted tetrahydropyridinyl, dihydrothiazolyl, dihydrooxazolyl, or oxazolinyl group.

In some embodiments, Ring B is an optionally substituted 8-10 membered bicyclic saturated or partially unsaturated heterocyclic ring having 1-4 heteroatoms independently selected from nitrogen, oxygen, or sulfur. In some embodiments, Ring B is an optionally substituted indolinyl. In some embodiments, Ring B is an optionally substituted isoindolinyl. In some embodiments, Ring B is an optionally substituted 1,2,3,4-tetrahydroquinoline. In some embodiments, Ring B is an optionally substituted 1,2,3,4-tetrahydroisoquinoline. In some embodiments, Ring B is an optionally substituted group selected from

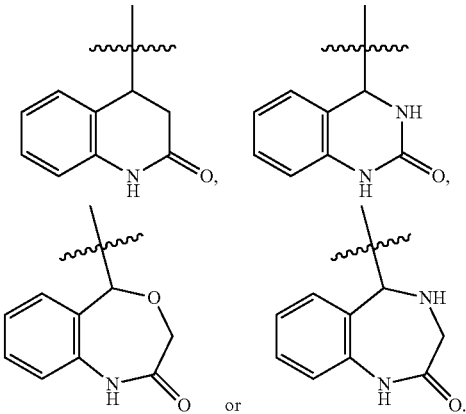

In certain embodiments, Ring B is an optionally substituted 8-10 membered bicyclic heteroaryl ring having 1-4 heteroatoms independently selected from nitrogen, oxygen, or sulfur. In some embodiments, Ring B is an optionally substituted 5,6-fused heteroaryl ring having 1-4 heteroatoms independently selected from nitrogen, oxygen, or sulfur. In other embodiments, Ring B is an optionally substituted 5,6-fused heteroaryl ring having 1-2 heteroatoms independently selected from nitrogen, oxygen, or sulfur. In certain embodiments, Ring B is an optionally substituted 5,6-fused heteroaryl ring having 1 heteroatom independently selected from nitrogen, oxygen, or sulfur. In some embodiments, Ring B is an optionally substituted indolyl. In some embodiments, Ring B is an optionally substituted azabicyclo[3.2.1]octanyl. In certain embodiments, Ring B is an optionally substituted 5,6-fused heteroaryl ring having 2 heteroatoms independently selected from nitrogen, oxygen, or sulfur. In some embodiments, Ring B is an optionally substituted azaindolyl. In some embodiments, Ring B is an optionally substituted benzimidazolyl. In some embodiments, Ring B is an optionally substituted benzothiazolyl. In some embodiments, Ring B is an optionally substituted benzoxazolyl. In some embodiments, Ring B is an optionally substituted indazolyl. In certain embodiments, Ring B is an optionally substituted 5,6-fused heteroaryl ring having 3 heteroatoms independently selected from nitrogen, oxygen, or sulfur.

In certain embodiments, Ring B is an optionally substituted 6,6-fused heteroaryl ring having 1-4 heteroatoms independently selected from nitrogen, oxygen, or sulfur. In some embodiments, Ring B is an optionally substituted 6,6-fused heteroaryl ring having 1-2 heteroatoms independently selected from nitrogen, oxygen, or sulfur. In other embodiments, Ring B is an optionally substituted 6,6-fused heteroaryl ring having 1 heteroatom independently selected from nitrogen, oxygen, or sulfur. In some embodiments, Ring B is an optionally substituted quinolinyl. In some embodiments, Ring B is an optionally substituted isoquinolinyl. According to one aspect, Ring B is an optionally substituted 6,6-fused heteroaryl ring having 2 heteroatoms independently selected from nitrogen, oxygen, or sulfur. In some embodiments, Ring B is a quinazoline or a quinoxaline.

In some embodiments, two substituents on Ring B are optionally taken together with their intervening atoms to form an optionally substituted, 3-7 membered saturated, partially unsaturated or aryl ring having 0-4 heteroatoms independently selected from nitrogen, oxygen or sulfur. In some embodiments, two substituents on Ring B are optionally taken together with their intervening atoms to form an optionally substituted phenyl. In some embodiments, two substituents on Ring B are optionally taken together with their intervening atoms to form an optionally substituted 3-7 membered saturated or partially unsaturated carbocyclic ring. In some embodiments, two substituents on Ring B are optionally taken together with their intervening atoms to form an optionally substituted 3-7 membered saturated or partially unsaturated heterocyclic ring having 1-4 heteroatoms independently selected from nitrogen, oxygen or sulfur. In some embodiments, two substituents on Ring B are optionally taken together with their intervening atoms to form an optionally substituted 5-6 membered heteroaryl ring having 1-4 heteroatoms independently selected from nitrogen, oxygen or sulfur.

As generally defined above, $L^1$ is independently a covalent bond or an optionally substituted bivalent $C_{1-6}$ hydrocarbon chain, wherein one or more methylene units of $L^1$ are optionally and independently replaced by —O—, —S—, —N(R')—, —C(O)—, —C(S)—, —C(NR')—, —C(O)N(R')—, —N(R')C(O)N(R')—, —N(R')C(O)—, —N(R')C(O)O—, —OC(O)N(R')—, —S(O)—, —S(O)$_2$—, —S(O)$_2$N(R')—, —N(R')S(O)$_2$—, —OC(O)—, or —C(O)O—, wherein each R' is independently as defined above and described herein.

In some embodiments, $L^1$ is a covalent bond.

In some embodiments, $L^1$ is an optionally substituted bivalent $C_{1-6}$ hydrocarbon chain, wherein one or more methylene units of $L^1$ are optionally and independently replaced by —O—, —S—, —N(R')—, —C(O)—, —C(S)—, —C(NR')—, —C(O)N(R')—, —N(R')C(O)N(R')—, —N(R')C(O)—, —N(R')C(O)O—, —OC(O)N(R')—, —S(O)—, —S(O)$_2$—, —S(O)$_2$N(R')—, —N(R')S(O)$_2$—, —OC(O)—, or —C(O)O—, wherein each R' is independently as defined above and described herein.

In some embodiments, $L^1$ is —C(O)NR'—, wherein R' is as defined above and described herein. In some embodiments, $L^1$ is —C(O)NR—, wherein R is as defined above and described herein. In some embodiments, $L^1$ is —CONH—. In some embodiments, $L^1$ is —NHCO—.

In some embodiments, Ring A is an optionally substituted group selected from

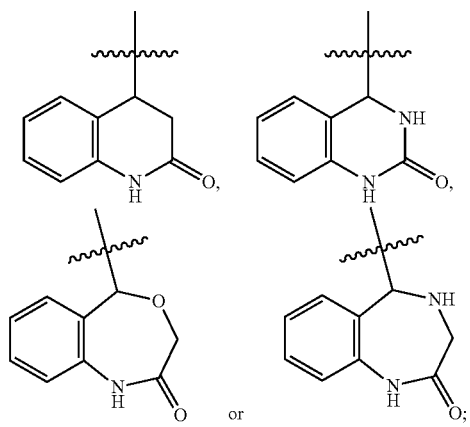

Ring B is optionally substituted phenyl; and $L^1$ is a covalent bond.

As generally defined above, each R' is independently —R, —C(O)R, —CO$_2$R, or —SO$_2$R, or:

two R' on the same nitrogen are taken together with their intervening atoms to form a 3-7 membered heterocyclic ring having 1-2 heteroatoms independently selected from nitrogen, oxygen, and sulfur.

In some embodiments, each R' is independently —R, —C(O)R, —CO$_2$R, or —SO$_2$R, wherein R is as defined above and described herein. In some embodiments, R' is R, wherein R is as defined above and described herein. In some embodiments, R' is hydrogen. In some embodiments, R' is —(CH$_2$)$_{1-6}$N(R)$_2$, wherein each R is independently as defined above and described herein. In some embodiments, R' is —(CH$_2$)$_2$N(CH$_3$)$_2$.

As generally defined above, each R is hydrogen, or an optionally substituted group selected from $C_{1-6}$ aliphatic, phenyl, a 3-7 membered saturated or partially unsaturated carbocyclic ring, an 8-10 membered bicyclic saturated, partially unsaturated or aryl carbocyclic ring, a 5-6 membered monocyclic heteroaryl ring having 1-3 heteroatoms independently selected from nitrogen, oxygen, or sulfur, a 3-7 membered saturated or partially unsaturated heterocyclic ring having 1-2 heteroatoms independently selected from nitrogen, oxygen, or sulfur, an 8-10 membered bicyclic saturated or partially unsaturated heterocyclic ring having 1-4 heteroatoms independently selected from nitrogen, oxygen, or sulfur, or an 8-10 membered bicyclic heteroaryl ring having 1-4 heteroatoms independently selected from nitrogen, oxygen, or sulfur.

In some embodiments, R is hydrogen.

In some embodiments, R is an optionally substituted group selected from $C_{1-6}$ aliphatic, phenyl, a 3-7 membered saturated or partially unsaturated carbocyclic ring, an 8-10 membered bicyclic saturated, partially unsaturated or aryl carbocyclic ring, a 5-6 membered monocyclic heteroaryl ring having 1-3 heteroatoms independently selected from nitrogen, oxygen, or sulfur, a 3-7 membered saturated or partially unsaturated heterocyclic ring having 1-2 heteroatoms independently selected from nitrogen, oxygen, or sulfur, an 8-10 membered bicyclic saturated or partially unsaturated heterocyclic ring having 1-4 heteroatoms independently selected from nitrogen, oxygen, or sulfur, or an 8-10 membered bicyclic heteroaryl ring having 1-4 heteroatoms independently selected from nitrogen, oxygen, or sulfur. In some embodiments, R is an optionally substituted $C_{1-6}$ aliphatic. In some embodiments, R is an optionally substituted phenyl. In some embodiments, R is an optionally substituted 3-7 membered saturated or partially unsaturated carbocyclic ring. In some embodiments, R is an optionally substituted 8-10 membered bicyclic saturated, partially unsaturated or aryl carbocyclic ring. In some embodiments, R is an optionally substituted a 5-6 membered monocyclic heteroaryl ring having 1-3 heteroatoms independently selected from nitrogen, oxygen, or sulfur. In some embodiments, R is an optionally substituted 3-7 membered saturated or partially unsaturated heterocyclic ring having 1-2 heteroatoms independently selected from nitrogen, oxygen, or sulfur. In some embodiments, R is an optionally substituted 8-10 membered bicyclic saturated or partially unsaturated heterocyclic ring having 1-4 heteroatoms independently selected from nitrogen, oxygen, or sulfur. In some embodiments, R is optionally substituted 8-10 membered bicyclic heteroaryl ring having 1-4 heteroatoms independently selected from nitrogen, oxygen, or sulfur.

In some embodiments, Ring A is an optionally substituted group selected from phenyl, or an 8-10 membered bicyclic heteroaryl ring having 1-4 heteroatoms independently selected from nitrogen, oxygen, or sulfur; Ring B is an optionally substituted 5-6 membered monocyclic heteroaryl ring having 1-3 heteroatoms independently selected from nitrogen, oxygen, or sulfur; and $L^1$ is —CONH— or —NHCO—.

In some embodiments, Ring A is an optionally substituted phenyl; Ring B is an optionally substituted 5 membered monocyclic heteroaryl ring having two heteroatoms independently selected from nitrogen, oxygen, or sulfur; and $L^1$ is —CONH— or —NHCO—.

In some embodiments, Ring A is an optionally substituted 8-10 membered bicyclic heteroaryl ring having 1-4 heteroatoms independently selected from nitrogen, oxygen, or sulfur; Ring B is an optionally substituted 5 membered monocyclic heteroaryl ring having two heteroatoms independently selected from nitrogen, oxygen, or sulfur; and $L^1$ is —CONH— or —NHCO—.

According to one embodiment, the present disclosure provides a compound of formula I having the structure of formula II:

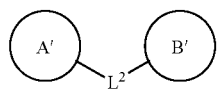

II or a pharmaceutically acceptable salt thereof, wherein:
each of Ring A' and Ring B' is independently an optionally substituted group selected from phenyl, an 8-10 membered bicyclic aryl ring, a 5-6 membered monocyclic heteroaryl ring having 1-3 heteroatoms independently selected from nitrogen, oxygen, or sulfur, or an 8-10 membered bicyclic heteroaryl ring having 1-4 heteroatoms independently selected from nitrogen, oxygen, or sulfur;
$L^2$ is —C(O)N(R')—; and
wherein each of R' and R is independently as defined above and described herein.

As generally defined above, Ring A' is independently an optionally substituted group selected from phenyl, an 8-10 membered bicyclic aryl ring, a 5-6 membered monocyclic heteroaryl ring having 1-3 heteroatoms independently selected from nitrogen, oxygen, or sulfur, or an 8-10 membered bicyclic heteroaryl ring having 1-4 heteroatoms independently selected from nitrogen, oxygen, or sulfur.

In some embodiments, Ring A' is an optionally substituted phenyl. In some embodiments, Ring A' is a substituted phenyl. In some embodiments, Ring A' is phenyl. In some embodiments, Ring A' is a phenyl substituted with one or more halogen atoms. In some embodiments, Ring A' is a phenyl substituted with two halogen atoms. In some embodiments, Ring A' is 2-fluoro-5-chlorophenyl. In some embodiments, Ring A' is 2-fluoro-5-bromophenyl. In some embodiments, Ring A' is 3-chloro-4-flluorophenyl.

In some embodiments, Ring A' is an optionally substituted 8-10 membered bicyclic aryl ring. In some embodiments, Ring A' is an optionally substituted 10 membered bicyclic aryl ring.

In some embodiments, Ring A' is an optionally substituted 5-6 membered monocyclic heteroaryl ring having 1-3 heteroatoms independently selected from nitrogen, oxygen, or sulfur. In some embodiments, Ring A' is a substituted 5-6 membered monocyclic heteroaryl ring having 1-3 heteroatoms independently selected from nitrogen, oxygen, or sulfur. In some embodiments, Ring A' is an unsubstituted 5-6 membered monocyclic heteroaryl ring having 1-3 heteroatoms independently selected from nitrogen, oxygen, or sulfur.

In some embodiments, Ring A' is an optionally substituted 5 membered monocyclic heteroaryl ring having 1-3 heteroatoms independently selected from nitrogen, oxygen or sulfur. In some embodiments, Ring A' is an optionally substituted 6 membered monocyclic heteroaryl ring having 1-3 heteroatoms independently selected from nitrogen, oxygen, or sulfur.

In some embodiments, Ring A' is an optionally substituted 5-membered monocyclic heteroaryl ring having 1 heteroatom selected from nitrogen, oxygen, or sulfur. In some embodiments, Ring A' is selected from pyrrolyl, furanyl, or thienyl.

In some embodiments, Ring A' is an optionally substituted 5-membered heteroaryl ring having 2 heteroatoms independently selected from nitrogen, oxygen, or sulfur. In certain embodiments, Ring A' is an optionally substituted 5-membered heteroaryl ring having 1 nitrogen atom, and an additional heteroatom selected from sulfur or oxygen. Exemplary Ring A groups include optionally substituted pyrazolyl, imidazolyl, thiazolyl, isothiazolyl, oxazolyl or isoxazolyl.

In some embodiments, Ring A' is a 6-membered heteroaryl ring having 1-3 nitrogen atoms. In other embodiments, Ring A' is an optionally substituted 6-membered heteroaryl ring having 1-2 nitrogen atoms. In some embodiments, Ring A' is an optionally substituted 6-membered heteroaryl ring having 2 nitrogen atoms. In certain embodiments, Ring A' is an optionally substituted 6-membered heteroaryl ring having 1 nitrogen. Exemplary Ring A' groups include optionally substituted pyridinyl, pyrimidinyl, pyrazinyl, pyridazinyl, triazinyl, or tetrazinyl.

In certain embodiments, Ring A' is an optionally substituted 8-10 membered bicyclic heteroaryl ring having 1-4 heteroatoms independently selected from nitrogen, oxygen, or sulfur. In some embodiments, Ring A' is an optionally substituted 5,6-fused heteroaryl ring having 1-4 heteroatoms independently selected from nitrogen, oxygen, or sulfur. In other embodiments, Ring A' is an optionally substituted 5,6-fused heteroaryl ring having 1-2 heteroatoms independently selected from nitrogen, oxygen, or sulfur. In certain embodiments, Ring A' is an optionally substituted 5,6-fused heteroaryl ring having 1 heteroatom independently selected from nitrogen, oxygen, or sulfur. In some embodiments, Ring A' is an optionally substituted indolyl. In some embodiments, Ring A' is an optionally substituted azabicyclo[3.2.1]octanyl. In certain embodiments, Ring A' is an optionally substituted 5,6-fused heteroaryl ring having 2 heteroatoms independently selected from nitrogen, oxygen, or sulfur. In some embodiments, Ring A' is an optionally substituted azaindolyl. In some embodiments, Ring A' is an optionally substituted benzimidazolyl. In some embodiments, Ring A' is an optionally substituted benzothiazolyl. In some embodiments, Ring A' is an optionally substituted benzoxazolyl. In some embodiments, Ring A' is an optionally substituted indazolyl. In certain embodiments, Ring A' is an optionally substituted 5,6-fused heteroaryl ring having 3 heteroatoms independently selected from nitrogen, oxygen, or sulfur.

In certain embodiments, Ring A' is an optionally substituted 6,6-fused heteroaryl ring having 1-4 heteroatoms independently selected from nitrogen, oxygen, or sulfur. In some embodiments, Ring A' is an optionally substituted 6,6-fused heteroaryl ring having 1-2 heteroatoms independently selected from nitrogen, oxygen, or sulfur. In other embodiments, Ring A' is an optionally substituted 6,6-fused heteroaryl ring having 1 heteroatom independently selected from nitrogen, oxygen, or sulfur. In some embodiments, Ring A' is an optionally substituted quinolinyl. In some embodiments, Ring A' is an optionally substituted isoquinolinyl. According to one aspect, Ring A' is an optionally substituted 6,6-fused heteroaryl ring having 2 heteroatoms independently selected from nitrogen, oxygen, or sulfur. In some embodiments, Ring A' is a quinazoline or a quinoxaline.

In some embodiments, two substituents on Ring A' are optionally taken together with their intervening atoms to form an optionally substituted, 3-7 membered saturated, partially unsaturated or aryl ring having 0-4 heteroatoms independently selected from nitrogen, oxygen or sulfur. In some embodiments, two substituents on Ring A' are optionally taken together with their intervening atoms to form an optionally substituted phenyl. In some embodiments, two substituents on Ring A' are optionally taken together with their intervening atoms to form an optionally substituted 3-7 membered saturated or partially unsaturated carbocyclic ring. In some embodiments, two substituents on Ring A' are optionally taken together with their intervening atoms to form an optionally substituted 3-7 membered saturated or partially unsaturated heterocyclic ring having 1-4 heteroatoms independently selected from nitrogen, oxygen or sulfur. In some embodiments, two substituents on Ring A' are optionally taken together with their intervening atoms to form an optionally substituted 5-6 membered heteroaryl ring having 1-4 heteroatoms independently selected from nitrogen, oxygen or sulfur.

As generally defined above, Ring B' is independently an optionally substituted group selected from phenyl, an 8-10 membered bicyclic aryl ring, a 5-6 membered monocyclic heteroaryl ring having 1-3 heteroatoms independently selected from nitrogen, oxygen, or sulfur, or an 8-10 membered bicyclic heteroaryl ring having 1-4 heteroatoms independently selected from nitrogen, oxygen, or sulfur.

In some embodiments, Ring B' is an optionally substituted phenyl. In some embodiments, Ring B' is a substituted phenyl. In some embodiments, Ring B' is phenyl. In some embodiments, Ring B' is a phenyl substituted with one or more halogen atoms. In some embodiments, Ring B' is a phenyl substituted with two halogen atoms. In some embodiments, Ring B' is 2-fluoro-5-chlorophenyl. In some embodiments, Ring B' is 2-fluoro-5-bromophenyl. In some embodiments, Ring B' is 3-chloro-4-flluorophenyl.

In some embodiments, Ring B' is an optionally substituted 8-10 membered bicyclic aryl ring. In some embodiments, Ring B' is an optionally substituted 10 membered bicyclic aryl ring.

In some embodiments, Ring B' is an optionally substituted 5-6 membered monocyclic heteroaryl ring having 1-3 heteroatoms independently selected from nitrogen, oxygen, or sulfur. In some embodiments, Ring B' is a substituted 5-6 membered monocyclic heteroaryl ring having 1-3 heteroatoms independently selected from nitrogen, oxygen, or sulfur. In some embodiments, Ring B' is an unsubstituted 5-6 membered monocyclic heteroaryl ring having 1-3 heteroatoms independently selected from nitrogen, oxygen, or sulfur.

In some embodiments, Ring B' is an optionally substituted 5 membered monocyclic heteroaryl ring having 1-3 heteroatoms independently selected from nitrogen, oxygen or sulfur. In some embodiments, Ring B' is an optionally substituted 6 membered monocyclic heteroaryl ring having 1-3 heteroatoms independently selected from nitrogen, oxygen, or sulfur.

In some embodiments, Ring B' is an optionally substituted 5-membered monocyclic heteroaryl ring having 1 heteroatom selected from nitrogen, oxygen, or sulfur. In some embodiments, Ring B' is selected from pyrrolyl, furanyl, or thienyl.

In some embodiments, Ring B' is an optionally substituted 5-membered heteroaryl ring having 2 heteroatoms independently selected from nitrogen, oxygen, or sulfur. In certain embodiments, Ring B' is an optionally substituted 5-membered heteroaryl ring having 1 nitrogen atom, and an additional heteroatom selected from sulfur or oxygen. Exemplary Ring B' groups include optionally substituted pyrazolyl, imidazolyl, thiazolyl, isothiazolyl, oxazolyl or isoxazolyl.

In some embodiments, Ring B' is a 6-membered heteroaryl ring having 1-3 nitrogen atoms. In other embodiments, Ring B' is an optionally substituted 6-membered heteroaryl ring having 1-2 nitrogen atoms. In some embodiments, Ring B' is an optionally substituted 6-membered heteroaryl ring having 2 nitrogen atoms. In certain embodiments, Ring B' is an optionally substituted 6-membered heteroaryl ring having 1 nitrogen. Exemplary Ring B' groups include optionally substituted pyridinyl, pyrimidinyl, pyrazinyl, pyridazinyl, triazinyl, or tetrazinyl.

In certain embodiments, Ring B' is an optionally substituted 8-10 membered bicyclic heteroaryl ring having 1-4 heteroatoms independently selected from nitrogen, oxygen, or sulfur. In some embodiments, Ring B' is an optionally substituted 5,6-fused heteroaryl ring having 1-4 heteroatoms independently selected from nitrogen, oxygen, or sulfur. In other embodiments, Ring B' is an optionally substituted 5,6-fused heteroaryl ring having 1-2 heteroatoms independently selected from nitrogen, oxygen, or sulfur. In certain embodiments, Ring B' is an optionally substituted 5,6-fused heteroaryl ring having 1 heteroatom independently selected from nitrogen, oxygen, or sulfur. In some embodiments, Ring B' is an optionally substituted indolyl. In some embodiments, Ring B' is an optionally substituted azabicyclo[3.2.1]octanyl. In certain embodiments, Ring B' is an optionally substituted 5,6-fused heteroaryl ring having 2 heteroatoms independently selected from nitrogen, oxygen, or sulfur. In some embodiments, Ring B' is an optionally substituted azaindolyl. In some embodiments, Ring B' is an optionally substituted benzimidazolyl. In some embodiments, Ring B' is an optionally substituted benzothiazolyl. In some embodiments, Ring B' is an optionally substituted benzoxazolyl. In some embodiments, Ring B' is an optionally substituted indazolyl. In certain embodiments, Ring B' is an optionally substituted 5,6-fused heteroaryl ring having 3 heteroatoms independently selected from nitrogen, oxygen, or sulfur.

In certain embodiments, Ring B' is an optionally substituted 6,6-fused heteroaryl ring having 1-4 heteroatoms independently selected from nitrogen, oxygen, or sulfur. In some embodiments, Ring B' is an optionally substituted 6,6-fused heteroaryl ring having 1-2 heteroatoms independently selected from nitrogen, oxygen, or sulfur. In other embodiments, Ring B' is an optionally substituted 6,6-fused heteroaryl ring having 1 heteroatom independently selected from nitrogen, oxygen, or sulfur. In some embodiments, Ring B' is an optionally substituted quinolinyl. In some embodiments, Ring B' is an optionally substituted isoquinolinyl. According to one aspect, Ring B' is an optionally substituted 6,6-fused heteroaryl ring having 2 heteroatoms independently selected from nitrogen, oxygen, or sulfur. In some embodiments, Ring B' is a quinazoline or a quinoxaline.

In some embodiments, two substituents on Ring B' are optionally taken together with their intervening atoms to form an optionally substituted, 3-7 membered saturated, partially unsaturated or aryl ring having 0-4 heteroatoms independently selected from nitrogen, oxygen or sulfur. In some embodiments, two substituents on Ring B' are optionally taken together with their intervening atoms to form an optionally substituted phenyl. In some embodiments, two substituents on Ring B' are optionally taken together with their intervening atoms to form an optionally substituted 3-7 membered saturated or partially unsaturated carbocyclic ring. In some embodiments, two substituents on Ring B' are optionally taken together with their intervening atoms to form an optionally substituted 3-7 membered saturated or partially unsaturated heterocyclic ring having 1-4 heteroatoms independently selected from nitrogen, oxygen or sulfur. In some embodiments, two substituents on Ring B' are optionally taken together with their intervening atoms to form an optionally substituted 5-6 membered heteroaryl ring having 1-4 heteroatoms independently selected from nitrogen, oxygen or sulfur.

As generally defined above, $L^2$ is —C(O)N(R')—, wherein R' is as defined above and described herein. In some embodiments, $L^2$ is —C(O)NH—. In some embodiments, $L^2$ is —C(O)N(R)—, wherein R is as defined above and described herein. In some embodiments, Ring A' is directly connected to the carbonyl group in $L^2$. In some embodiments, Ring B' is directly connected to the carbonyl group in $L^2$.

In some embodiments, the present disclosure provides a compound of formula II having the structure of formula II-a:

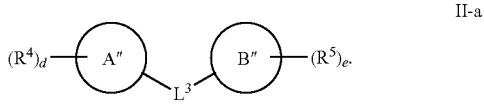

or a pharmaceutically acceptable salt thereof, wherein:
Ring A" is an optionally substituted phenyl or benzimidazolyl ring;
Ring B" is an optionally substituted 5-6 membered heteroaryl ring having 1-2 heteroatoms independently selected from nitrogen, oxygen, or sulfur;
$L^3$ is —C(O)NH—;
$R^4$ is halogen or R;
$R^5$ is an optionally substituted $C_{1-6}$ aliphatic;
each of d and e is independently 0-5; and
wherein R is as defined above and described herein.

As generally defined above, Ring A" is an optionally substituted phenyl or benzimidazolyl ring.

In some embodiments, Ring A" is optionally substituted phenyl. In some embodiments, Ring A" is unsubstituted phenyl. In some embodiments, Ring A" is substituted phenyl. In some embodiments, Ring A" is 3-chloro-4-fluorophenyl. In some embodiments, Ring A" is optionally substituted benzimidazolyl. In some embodiments, Ring A" is unsubstituted benzimidazolyl. In some embodiments, Ring A" is substituted benzimidazolyl.

As generally defined above, Ring B" is an optionally substituted 5-6 membered heteroaryl ring having 1-2 heteroatoms independently selected from nitrogen, oxygen, or sulfur.

In some embodiments, Ring B" is an optionally substituted 5 membered heteroaryl ring having 1-2 heteroatoms independently selected from nitrogen, oxygen or sulfur. In some embodiments, Ring B" is unsubstituted 5 membered heteroaryl ring having 1-2 heteroatoms independently selected from nitrogen, oxygen or sulfur. In some embodiments, Ring B" is substituted 5 membered heteroaryl ring having 1-2 heteroatoms independently selected from nitrogen, oxygen or sulfur. In certain embodiments, Ring B" is an optionally substituted 5-membered heteroaryl ring having 1 nitrogen atom, and an additional heteroatom selected from sulfur or oxygen. Exemplary Ring B" groups include optionally substituted pyrazolyl, imidazolyl, thiazolyl, isothiazolyl, oxazolyl or isoxazolyl.

In some embodiments, Ring B" is a 6-membered heteroaryl ring having 1-3 nitrogen atoms. In other embodiments, Ring B" is an optionally substituted 6-membered heteroaryl ring having 1-2 nitrogen atoms. In some embodiments, Ring B" is an optionally substituted 6-membered heteroaryl ring having 2 nitrogen atoms. In certain embodiments, Ring B" is an optionally substituted 6-membered heteroaryl ring having 1 nitrogen. Exemplary Ring B" groups include optionally substituted pyridinyl, pyrimidinyl, pyrazinyl, pyridazinyl, triazinyl, or tetrazinyl.

As generally defined above, each $R^4$ is independently halogen or R, wherein R is as defined above and described herein. In some embodiments, $R^4$ is halogen. In some embodiments, $R^4$ is —F. In some embodiments, $R^4$ is —Cl. In some embodiments, $R^4$ is —Br. In some embodiments, $R^4$ is —I. In some embodiments, $R^4$ is R, wherein R is as defined above and described herein.

As generally defined above, each $R^5$ is independently an optionally substituted $C_{1-6}$ aliphatic. In some embodiments, $R^5$ is optionally substituted straight or branched $C_{1-6}$ alkyl. In some embodiments, $R^5$ is optionally substituted hexyl, pentyl, butyl, propyl, ethyl or methyl. In some embodiments, $R^5$ is hexyl. In some embodiments, $R^5$ is pentyl. In some embodiments, $R^5$ is butyl. In some embodiments, $R^5$ is propyl. In some embodiments, $R^5$ is ethyl. In some embodiments, $R^5$ is methyl. In some embodiments, $R^5$ is isopropyl.

In some embodiments, $R^5$ is optionally substituted $C_{1-6}$ cycloalkyl. In some embodiments, $R^5$ is optionally substituted cyclohexyl. In some embodiments, $R^5$ is optionally substituted cyclopentyl. In some embodiments, $R^5$ is optionally substituted cyclobutyl. In some embodiments, $R^5$ is optionally substituted cyclopropyl. In some embodiments, $R^5$ is 1-hydroxycyclobutyl. In some embodiments, $R^5$ is cyclohexyl, cyclopentyl, cyclobutyl, or cyclopropyl.

As generally defined above, each of d and e is independently 0-5. In some embodiments, d is 0. In some embodiments, d is 1. In some embodiments, d is 2. In some embodiments, d is 3. In some embodiments, d is 4. In some embodiments, d is 5. In some embodiments, e is 0. In some embodiments, e is 1. In some embodiments, e is 2. In some embodiments, e is 3. In some embodiments, e is 4. In some embodiments, e is 5.

In some embodiments, a compound of formula II-a is selected from

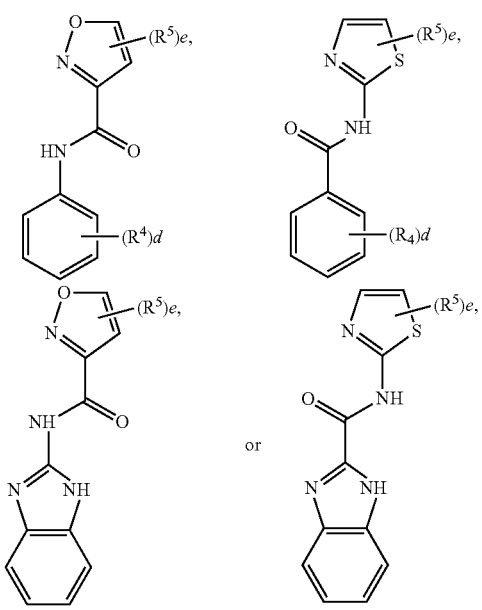

or a pharmaceutically acceptable salt thereof, wherein each variable is independently as defined above and described herein.

According to one embodiment, the present disclosure provides a compound of formula I having the structure of formula II:

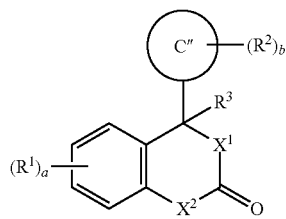

III or a pharmaceutically acceptable salt thereof, wherein:
Ring C" is independently an optionally substituted group selected from phenyl, an 8-10 membered bicyclic aryl ring, a 5-6 membered monocyclic heteroaryl ring having 1-3 heteroatoms independently selected from nitrogen, oxygen, or sulfur, or an 8-10 membered bicyclic heteroaryl ring having 1-4 heteroatoms independently selected from nitrogen, oxygen, or sulfur;
each of $R^1$, $R^2$ and $R^3$ is independently halogen, R, —C(O)R, —C(S)R, —CO$_2$R, —C(O)N(R')$_2$, —C(S)N(R')$_2$, —S(O)R', —SO$_2$R', —SO$_2$N(R')$_2$, —OR', —O—(C$_{1-6}$ aliphatic)-N(R')$_2$, —O—(C$_{1-6}$ aliphatic)-OR', —OC(O)R', —SR, —NO$_2$, —N(R')$_2$, —NR'C(O)R', —NR'C(O)OR', —NR'C(O)N(R')$_2$, —NR'SO$_2$R', —NR'SO$_2$N(R')$_2$, or —NR'OR';
a is 1-4;
b is 1-5;
$X^1$ is —C($R^x$)$_2$—, —NR$^x$—, —NR$^x$C($R^x$)$_2$— or —OC($R^x$)$_2$—;
$X^2$ is —C($R^x$)$_2$— or —NR$^x$—;
each $R^x$ is independently R, —(C$_{1-6}$ aliphatic)-N(R')$_2$, or —(C$_{1-6}$ aliphatic)-OR;
each R' is independently —R, —C(O)R, —CO$_2$R, or —SO$_2$R, or:
  two R' on the same nitrogen are taken together with their intervening atoms to form a 3-7 membered heterocyclic ring having 1-2 heteroatoms independently selected from nitrogen, oxygen, and sulfur; and
each R is hydrogen, or an optionally substituted group selected from C$_{1-6}$ aliphatic, phenyl, a 3-7 membered saturated or partially unsaturated carbocyclic ring, an 8-10 membered bicyclic saturated, partially unsaturated or aryl carbocyclic ring, a 5-6 membered monocyclic heteroaryl ring having 1-3 heteroatoms independently selected from nitrogen, oxygen, or sulfur, a 3-7 membered saturated or partially unsaturated heterocyclic ring having 1-2 heteroatoms independently selected from nitrogen, oxygen, or sulfur, an 8-10 membered bicyclic saturated or partially unsaturated heterocyclic ring having 1-4 heteroatoms independently selected from nitrogen, oxygen, or sulfur, or an 8-10 membered bicyclic heteroaryl ring having 1-4 heteroatoms independently selected from nitrogen, oxygen, or sulfur.

In some embodiments, Ring C" is optionally substituted phenyl. In some embodiments, Ring C" is substituted phenyl. In some embodiments, Ring C" is phenyl. In some embodiments, Ring C" is phenyl substituted with one or more halogen atoms. In some embodiments, Ring C" is phenyl substituted with two halogen atoms. In some embodiments, Ring C" is 2-fluoro-5-chlorophenyl. In some embodiments, Ring C" is 2-fluoro-5-bromophenyl. In some embodiments, Ring C" is 3-chloro-4-flluorophenyl.

In some embodiments, Ring C" is an optionally substituted 8-10 membered bicyclic aryl ring.
In some embodiments, Ring C" is an optionally substituted 5-6 membered monocyclic heteroaryl ring having 1-3 heteroatoms independently selected from nitrogen, oxygen, or sulfur. In some embodiments, Ring C" is an optionally substituted 5 membered heteroaryl ring having 1-2 heteroatoms independently selected from nitrogen, oxygen or sulfur. In some embodiments, Ring C" is unsubstituted 5 membered heteroaryl ring having 1-2 heteroatoms independently selected from nitrogen, oxygen or sulfur. In some embodiments, Ring C" is substituted 5 membered heteroaryl ring having 1-2 heteroatoms independently selected from nitrogen, oxygen or sulfur. In certain embodiments, Ring C" is an optionally substituted 5-membered heteroaryl ring having 1 nitrogen atom, and an additional heteroatom selected from sulfur or oxygen. Exemplary Ring C" groups include optionally substituted pyrazolyl, imidazolyl, thiazolyl, isothiazolyl, oxazolyl or isoxazolyl.

In some embodiments, Ring C" is a 6-membered heteroaryl ring having 1-3 nitrogen atoms. In other embodiments, Ring C" is an optionally substituted 6-membered heteroaryl ring having 1-2 nitrogen atoms. In some embodiments, Ring C" is an optionally substituted 6-membered heteroaryl ring having 2 nitrogen atoms. In certain embodiments, Ring C" is an optionally substituted 6-membered heteroaryl ring having 1 nitrogen. Exemplary Ring C" groups include optionally substituted pyridinyl, pyrimidinyl, pyrazinyl, pyridazinyl, triazinyl, or tetrazinyl. In some embodiments, Ring C" is optionally substituted pyridinyl.

In certain embodiments, Ring C" is an optionally substituted 8-10 membered bicyclic heteroaryl ring having 1-4 heteroatoms independently selected from nitrogen, oxygen, or sulfur. In some embodiments, Ring C" is an optionally substituted 5,6-fused heteroaryl ring having 1-4 heteroatoms independently selected from nitrogen, oxygen, or sulfur. In other embodiments, Ring C" is an optionally substituted 5,6-fused heteroaryl ring having 1-2 heteroatoms independently selected from nitrogen, oxygen, or sulfur. In certain embodiments, Ring C" is an optionally substituted 5,6-fused heteroaryl ring having 1 heteroatom independently selected from nitrogen, oxygen, or sulfur. In some embodiments, Ring C" is an optionally substituted indolyl. In some embodiments, Ring C" is an optionally substituted benzofuranyl. In some embodiments, Ring C" is an optionally substituted azabicyclo[3.2.1]octanyl. In certain embodiments, Ring C" is an optionally substituted 5,6-fused heteroaryl ring having 2 heteroatoms independently selected from nitrogen, oxygen, or sulfur. In some embodiments, Ring C" is an optionally substituted azaindolyl. In some embodiments, Ring C" is an optionally substituted benzimidazolyl. In some embodiments, Ring C" is an optionally substituted benzothiazolyl. In some embodiments, Ring C" is an optionally substituted benzoxazolyl. In some embodiments, Ring C" is an optionally substituted indazolyl. In certain embodiments, Ring C" is an optionally substituted 5,6-fused heteroaryl ring having 3 heteroatoms independently selected from nitrogen, oxygen, or sulfur.

In certain embodiments, Ring C" is an optionally substituted 6,6-fused heteroaryl ring having 1-4 heteroatoms independently selected from nitrogen, oxygen, or sulfur. In some embodiments, Ring C" is an optionally substituted 6,6-fused heteroaryl ring having 1-2 heteroatoms independently selected from nitrogen, oxygen, or sulfur. In other embodiments, Ring C" is an optionally substituted 6,6-fused heteroaryl ring having 1 heteroatom independently selected from nitrogen, oxygen, or sulfur. In some embodiments, Ring C" is an optionally substituted quinolinyl. In some embodiments, Ring C" is an optionally substituted isoquinolinyl. According to one aspect, Ring C" is an optionally substituted 6,6-fused heteroaryl ring having 2 heteroatoms independently selected from nitrogen, oxygen, or sulfur. In some embodiments, Ring C" is a quinazoline or a quinoxaline.

As generally defined above, each R' is independently halogen, R, —C(O)R, —C(S)R, —CO$_2$R, —C(O)N(R')$_2$, —C(S)N(R')$_2$, —S(O)R', —SO$_2$R', —SO$_2$N(R')$_2$, —OR', —O—($C_{1-6}$ aliphatic)-N(R')$_2$, —O—($C_{1-6}$ aliphatic)-OR', —OC(O)R', —SR', —NO$_2$, —N(R')$_2$, —NR'C(O)R', —NR'C(O)OR', —NR'C(O)N(R')$_2$, —NR'SO$_2$R', —NR'SO$_2$N(R')$_2$, or —NR'OR', wherein each R' is independently as defined above and described herein.

In some embodiments, $R^1$ is —OR', wherein R' is as defined above and described herein. In some embodiments, $R^1$ is OR, wherein R is as defined above and described herein. In some embodiments, $R^1$ is —OMe.

In some embodiments, $R^1$ is —O—($C_{1-6}$ aliphatic)-OR', wherein R' is as defined above and described herein. In some embodiments, $R^1$ is —O—($C_{1-6}$ aliphatic)-OR, wherein R is as defined above and described herein. In some embodiments, $R^1$ is —O—($C_{1-6}$ aliphatic)-OH. In some embodiments, $R^1$ is —O(CH$_2$)$_2$OH. In some embodiments, $R^1$ is —O—($C_{1-6}$ aliphatic)-OR, wherein R is $C_{1-6}$ alkyl. In some embodiments, $R^1$ is —O(CH$_2$)$_2$OMe.

In some embodiments, $R^1$ is —O—($C_{1-6}$ aliphatic)-N(R')$_2$, wherein each R' is independently as defined above and described herein. In some embodiments, $R^1$ is —O—($C_{1-6}$ aliphatic)-N(R')$_2$, wherein two R' on the same nitrogen are taken together with their intervening atoms to form a 3-7 membered heterocyclic ring having 1-2 heteroatoms independently selected from nitrogen, oxygen, and sulfur. In some embodiments, $R^1$ is —O—($C_{1-6}$ aliphatic)-N(R)$_2$, wherein each R is independently $C_{1-6}$ alkyl. In some embodiments, $R^1$ is —O(CH$_2$)$_2$N(R')$_2$, wherein each R' is independently $C_{1-6}$ alkyl. In some embodiments, $R^1$ is —O(CH$_2$)$_2$N(R')$_2$, wherein two R' on the same nitrogen are taken together with their intervening atoms to form a 3-7 membered heterocyclic ring having 1-2 heteroatoms independently selected from nitrogen, oxygen, and sulfur. In some embodiments, $R^1$ is

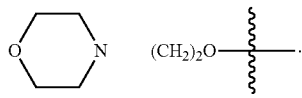

As generally defined above, each $R^2$ is independently halogen, R', —C(O)R', —C(S)R', —CO$_2$R', —C(O)N(R')$_2$, —C(S)N(R')$_2$, —S(O)R', —SO$_2$R', —SO$_2$N(R')$_2$, —OR', —O—($C_{1-6}$ aliphatic)-N(R')$_2$, —O—($C_{1-6}$ aliphatic)-OR', —OC(O)R', —SR', —NO$_2$, —N(R')$_2$, —NR'C(O)R', —NR'C(O)OR', —NR'C(O)N(R')$_2$, —NR'SO$_2$R', —NR'SO$_2$N(R')$_2$, or —NR'OR', wherein each R' is independently as defined above and described herein.

In some embodiments, $R^2$ is halogen. In some embodiments, $R^2$ is —F. In some embodiments, $R^2$ is —Cl. In some embodiments, $R^2$ is —Br. In some embodiments, $R^2$ is —I.

As generally defined above, each $R^3$ is independently halogen, R', —C(O)R', —C(S)R', —CO$_2$R', —C(O)N(R')$_2$, —C(S)N(R')$_2$, —S(O)R', —SO$_2$R', —SO$_2$N(R')$_2$, —OR', —O—($C_{1-6}$ aliphatic)-N(R')$_2$, —O—($C_{1-6}$ aliphatic)-OR', —OC(O)R', —SR', —NO$_2$, —N(R')$_2$, —NR'C(O)R', —NR'C(O)OR', —NR'C(O)N(R')$_2$, —NR'SO$_2$R', —NR'SO$_2$N(R')$_2$, or —NR'OR', wherein each R' is independently as defined above and described herein.

In some embodiments, $R^3$ is hydrogen.

As generally defined above, a is 1-4. In some embodiments, a is 1. In some embodiments, a is 2. In some embodiments, a is 4. In some embodiments, a is 4.

In some embodiments, a=3 and each R' is —OMe.

As generally defined above, b is 1-5. In some embodiments, b is 1. In some embodiments, b is 2. In some embodiments, b is 3. In some embodiments, b is 4. In some embodiments, b is 5.

As generally defined above, $X^1$ is —C($R^x$)$_2$—, —NR$^x$—, —NR$^x$C($R^x$)$_2$— or —OC($R^x$)$_2$—, wherein each $R^x$ is independently as defined above and described herein. In some embodiments, $X^1$ is —C($R^x$)$_2$—, wherein each $R^x$ is independently as defined above and described herein. In some embodiments, $X^1$ is —CH$_2$—. In some embodiments, $X^1$ is —NR$^x$—, wherein R' is as defined above and described herein. In some embodiments, $X^1$ is —NH—. In some embodiments, $X^1$ is —NR$^x$C($R^x$)$_2$—, wherein R' is independently as defined above and described herein. In some embodiments, $X^1$ is —NHCH$_2$—. In some embodiments, R' is —OC($R^x$)$_2$—, wherein R' is independently as defined above and described herein. In some embodiments, R' is —OCH$_2$—.

In some embodiments, $X^1$ is —NR'—, wherein R' is as defined above and described herein. In some embodiments, $X^1$ is —NR'—, wherein R' is optionally substituted $C_{1-6}$ alkyl. In some embodiments, $X^1$ is —NR'—, wherein R' is unsubstituted $C_{1-6}$ alkyl. In some embodiments, $X^1$ is —NR'— wherein R' is methyl. In some embodiments, $X^1$ is —NR'— wherein R' is propyl. In some embodiments, $X^1$ is —NR'— wherein R' is n-propyl. In some embodiments, $X^1$ is —NR'—, wherein R' is methyl. In some embodiments, $X^1$ is —NR'—, wherein R' is substituted $C_{1-6}$ alkyl.

In some embodiments, $X^1$ is —NR$^x$—, wherein $R^x$ is wherein $R^x$ is —($C_{1-6}$ aliphatic)-N(R')$_2$, wherein each R' is independently as defined above and described herein. In some embodiments, —NR$^x$— is —(CH$_2$)$_{1-6}$N(R')$_2$, wherein each R' is independently as defined above and described herein. In some embodiments, —NR$^x$— is —(CH$_2$)$_{1-6}$N(R')$_2$, wherein each R' is optionally substituted $C_{1-6}$ alkyl. In some embodiments, —NR$^x$— is —(CH$_2$)$_2$N(R')$_2$, wherein each R' is optionally substituted $C_{1-6}$ alkyl. In some embodiments, $X^1$ is —N[(CH$_2$)$_2$N(CH$_3$)$_2$]—.

As generally defined above, $X^2$ is —C($R^x$)$_2$— or —NR$^x$—, wherein each $R^x$ is independently as defined above and described herein. In some embodiments, $X^2$ is —C(R')$_2$—, wherein each R' is independently as defined above and described herein. In some embodiments, $X^2$ is —CH$_2$—. In some embodiments, $X^2$ is —NR'—, wherein R' is as defined above and described herein. In some embodiments, $X^2$ is —NH—.

In some embodiments, the present disclosure provides a compound of formula III having the structure of formula III-a:

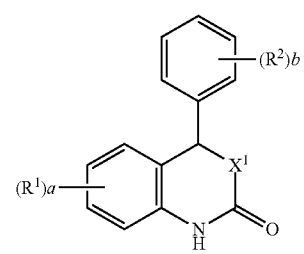

or a pharmaceutically acceptable salt thereof, wherein each variable is independently as defined above and described herein.

In some embodiments, the present disclosure provides a compound of formula III having the structure of formula III-b:

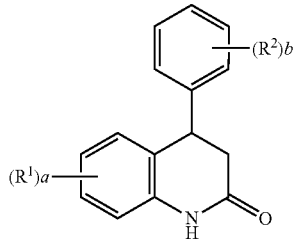

III-b or a pharmaceutically acceptable salt thereof, wherein each variable is independently as defined above and described herein.

In some embodiments, the present disclosure provides a compound of formula III having the structure of formula III-c:

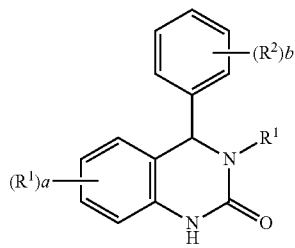

III-c or a pharmaceutically acceptable salt thereof, wherein each variable is independently as defined above and described herein.

In some embodiments, the present disclosure provides a compound of formula III having the structure of formula III-d:

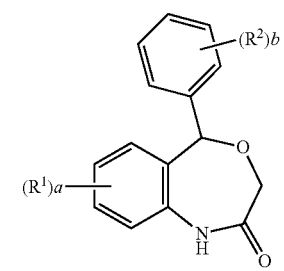

III-d or a pharmaceutically acceptable salt thereof, wherein each variable is independently as defined above and described herein.

In some embodiments, the present disclosure provides a compound of formula III having the structure of formula III-e:

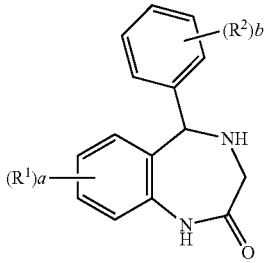

III-e or a pharmaceutically acceptable salt thereof, wherein each variable is independently as defined above and described herein.

In some embodiments, the present disclosure provides a compound of formula III having the structure of formula III-f:

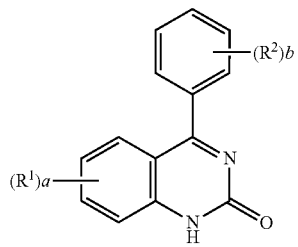

III-f or a pharmaceutically acceptable salt thereof, wherein each variable is independently as defined above and described herein.

In some embodiments, the present disclosure provides a compound of formula III having the structure of formula III-g:

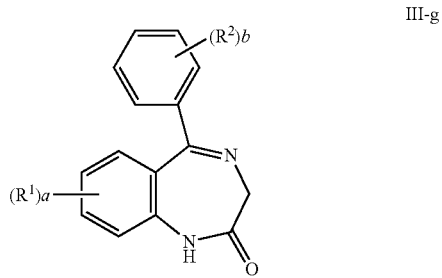

III-g or a pharmaceutically acceptable salt thereof, wherein each variable is independently as defined above and described herein.

Exemplary compounds are set forth in Table 1, below.

TABLE 1
Exemplary Compounds
1
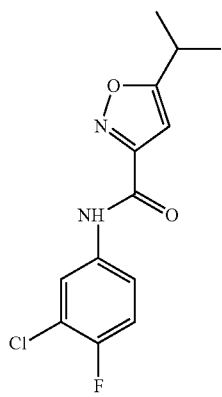
LSN-75654
2
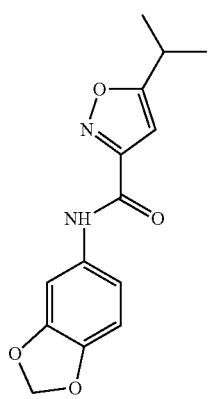
LDN-75676
3
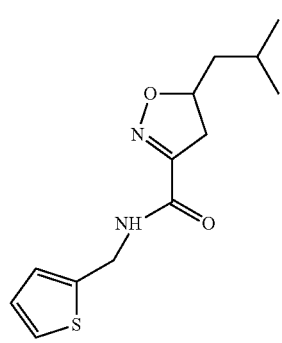
LDN-75847
4
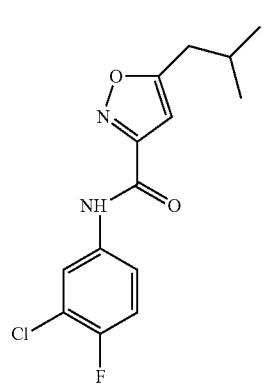
LDN-75879
TABLE 1-continued
Exemplary Compounds
5
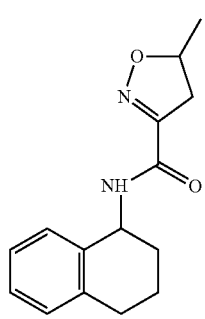 [SMILES: CC1CC(C(=O)NC2CCCc3ccccc32)=NO1]
6
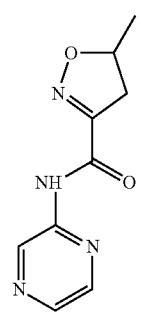
7
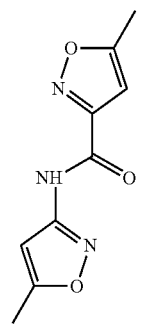
8
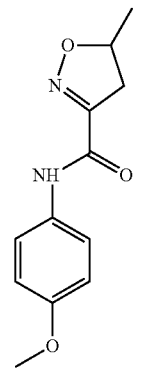 [SMILES: COc1ccc(NC(=O)C2=NOC(C)C2)cc1]

TABLE 1-continued
Exemplary Compounds
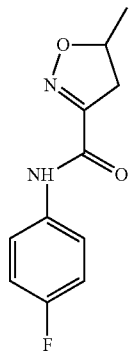 [SMILES: CC1CC(C(=O)Nc2ccc(F)cc2)=NO1]
9
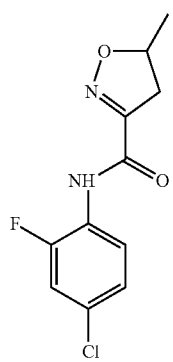
10
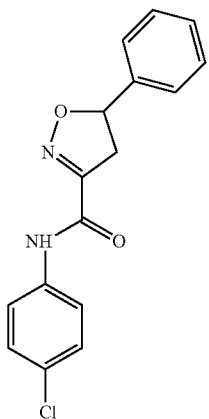 [SMILES: O=C(Nc1ccc(Cl)cc1)C1=NOC(c2ccccc2)C1]
11
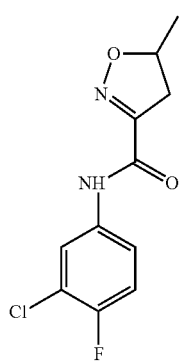 [SMILES: CC1CC(C(=O)Nc2ccc(F)c(Cl)c2)=NO1]
12
TABLE 1-continued
Exemplary Compounds
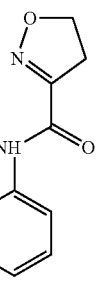
13
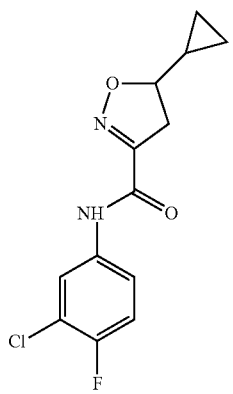 [SMILES: O=C(Nc1ccc(F)c(Cl)c1)C1=NOC(C2CC2)C1]
14
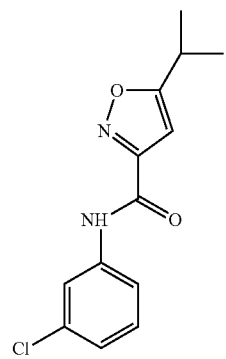 [SMILES: CC(C)c1cc(C(=O)Nc2cccc(Cl)c2)no1]
15
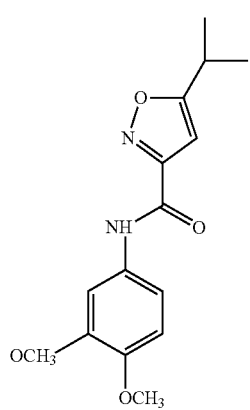 [SMILES: COc1ccc(NC(=O)c2cc(C(C)C)on2)cc1OC]
16

TABLE 1-continued
Exemplary Compounds
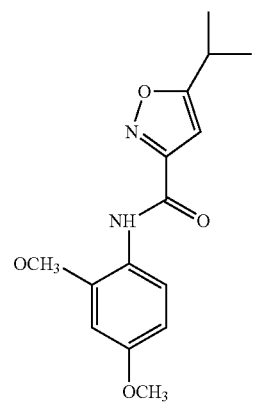 [SMILES: COc1ccc(NC(=O)c2cc(C(C)C)on2)c(OC)c1]
17
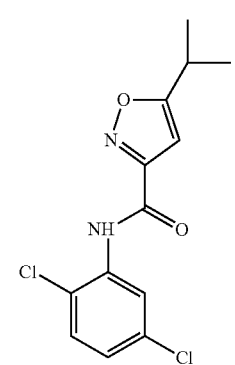 [SMILES: CC(C)c1cc(C(=O)Nc2cc(Cl)ccc2Cl)no1]
18
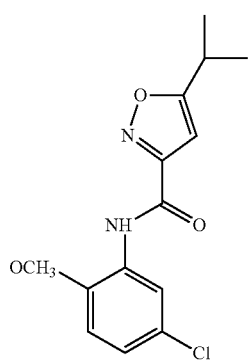 [SMILES: COc1ccc(Cl)cc1NC(=O)c1cc(C(C)C)on1]
19
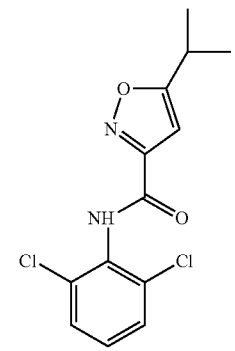 [SMILES: CC(C)c1cc(C(=O)Nc2c(Cl)cccc2Cl)no1]
20
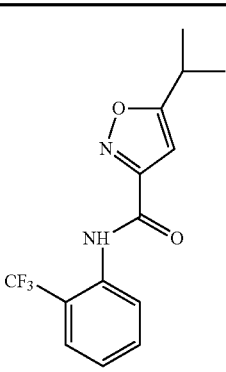
21
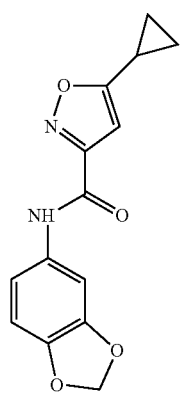 [SMILES: O=C(Nc1ccc2c(c1)OCO2)c1cc(C2CC2)on1]
22
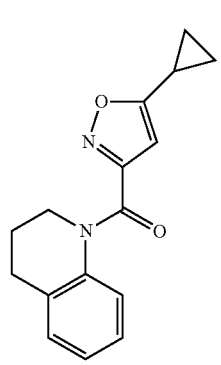 [SMILES: O=C(c1cc(C2CC2)on1)N1CCCc2ccccc21]
23
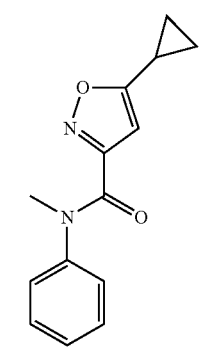 [SMILES: CN(C(=O)c1cc(C2CC2)on1)c1ccccc1]
24

TABLE 1-continued
Exemplary Compounds
25
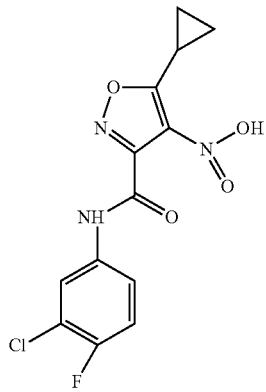
26
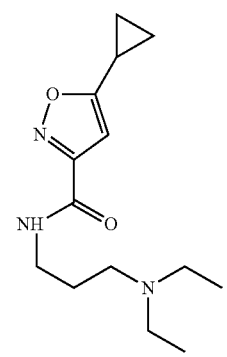 [SMILES: CCN(CC)CCCNC(=O)c1cc(C2CC2)on1]
27
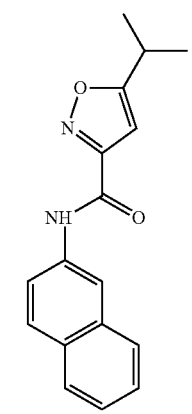 [SMILES: CC(C)c1cc(C(=O)Nc2ccc3ccccc3c2)no1]
28
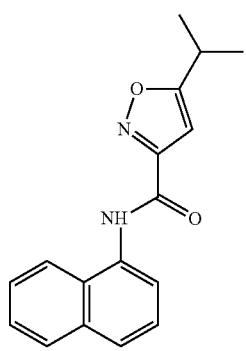 [SMILES: CC(C)c1cc(C(=O)Nc2cccc3ccccc23)no1]
TABLE 1-continued
Exemplary Compounds
29
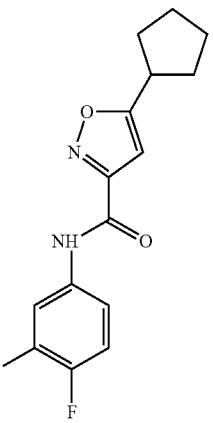
30
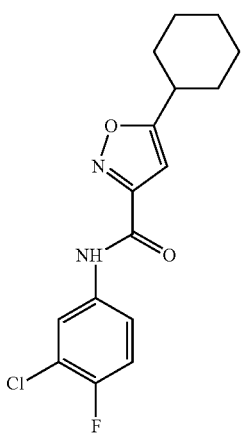 [SMILES: O=C(Nc1ccc(F)c(Cl)c1)c1cc(C2CCCCC2)on1]
31
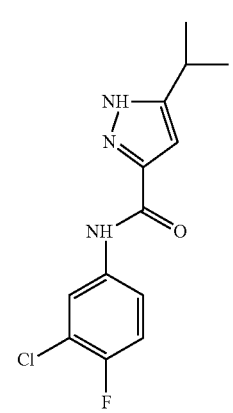 [SMILES: CC(C)c1cc(C(=O)Nc2ccc(F)c(Cl)c2)n[nH]1]

TABLE 1-continued
Exemplary Compounds
32 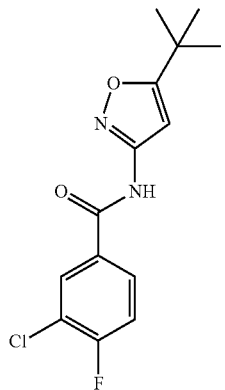 [SMILES: CC(C)(C)c1cc(NC(=O)c2ccc(F)c(Cl)c2)no1]
33 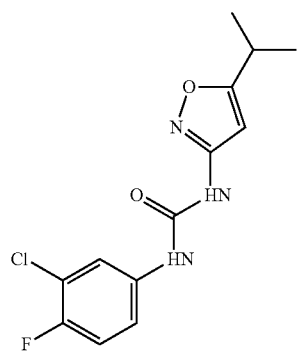 [SMILES: CC(C)c1cc(NC(=O)Nc2ccc(F)c(Cl)c2)no1]
34 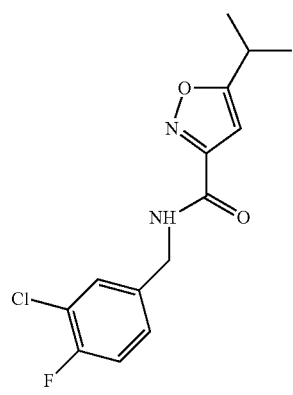 [SMILES: CC(C)c1cc(C(=O)NCc2ccc(F)c(Cl)c2)no1]
35 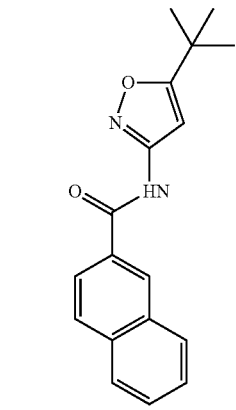 [SMILES: CC(C)(C)c1cc(NC(=O)c2ccc3ccccc3c2)no1]
TABLE 1-continued
Exemplary Compounds
36 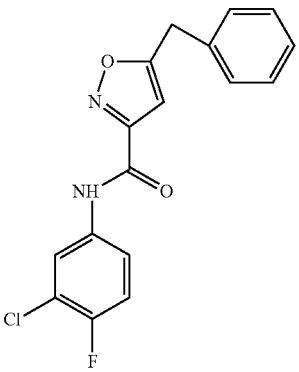 [SMILES: O=C(Nc1ccc(F)c(Cl)c1)c1cc(Cc2ccccc2)on1]
37 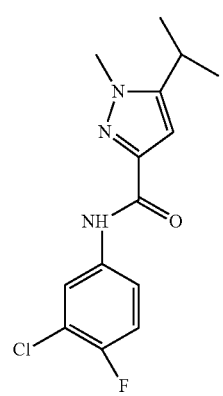 [SMILES: CC(C)c1cc(C(=O)Nc2ccc(F)c(Cl)c2)nn1C]
38 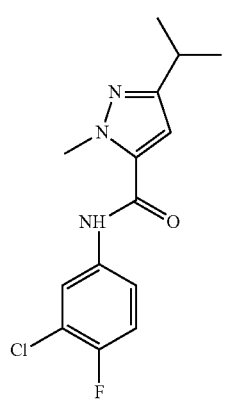 [SMILES: CC(C)c1cc(C(=O)Nc2ccc(F)c(Cl)c2)n(C)n1]
39 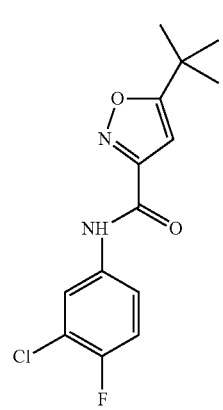 [SMILES: CC(C)(C)c1cc(C(=O)Nc2ccc(F)c(Cl)c2)no1]

TABLE 1-continued
Exemplary Compounds
40
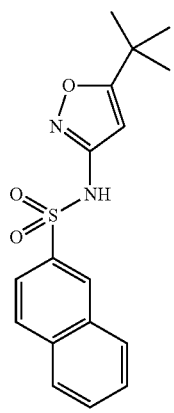 [SMILES: CC(C)(C)c1cc(NS(=O)(=O)c2ccc3ccccc3c2)no1]
41
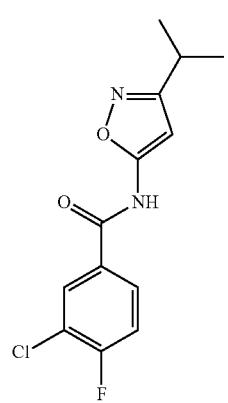 [SMILES: CC(C)c1cc(NC(=O)c2ccc(F)c(Cl)c2)on1]
42
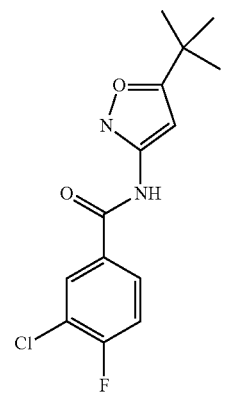
43
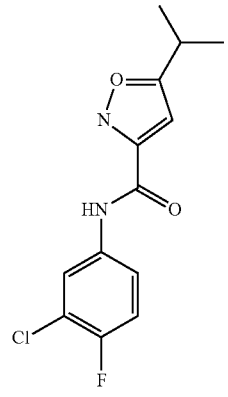
TABLE 1-continued
Exemplary Compounds
44
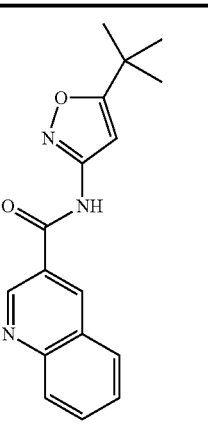
45
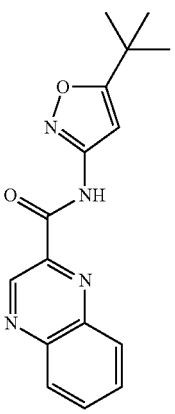
46
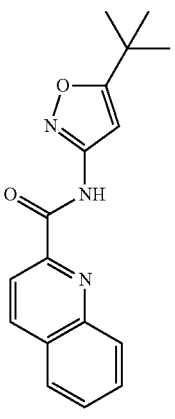 [SMILES: CC(C)(C)c1cc(NC(=O)c2ccc3ccccc3n2)no1]

TABLE 1-continued
Exemplary Compounds
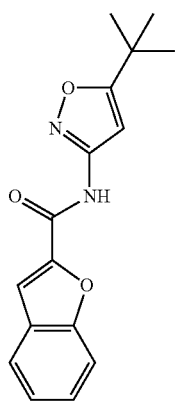
47
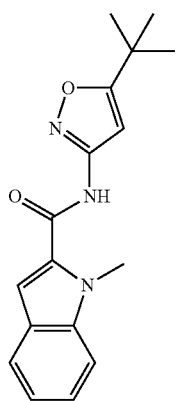 [SMILES: Cn1c(C(=O)Nc2cc(C(C)(C)C)on2)cc2ccccc21]
48
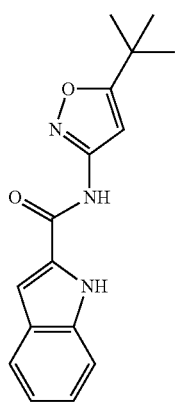 [SMILES: CC(C)(C)c1cc(NC(=O)c2cc3ccccc3[nH]2)no1]
49
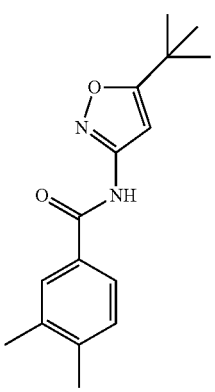 [SMILES: Cc1ccc(C(=O)Nc2cc(C(C)(C)C)on2)cc1C]
50
TABLE 1-continued
Exemplary Compounds
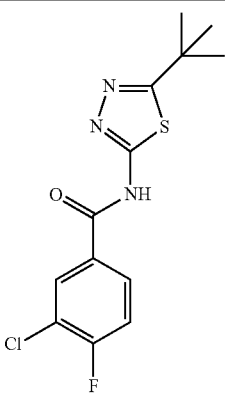
51
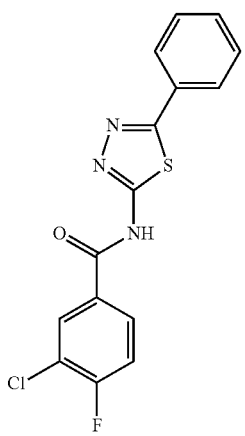 [SMILES: O=C(Nc1nnc(-c2ccccc2)s1)c1ccc(F)c(Cl)c1]
52
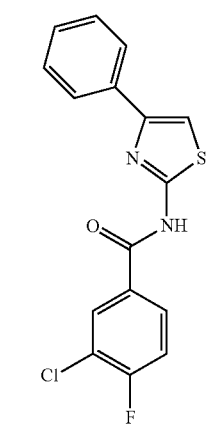 [SMILES: O=C(Nc1nc(-c2ccccc2)cs1)c1ccc(F)c(Cl)c1]
53
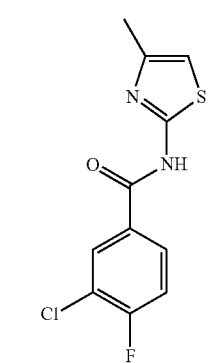
54

TABLE 1-continued
Exemplary Compounds
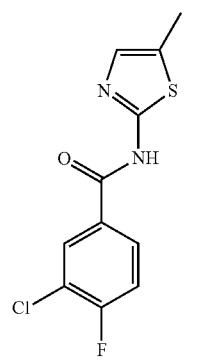 [SMILES: Cc1cnc(NC(=O)c2ccc(F)c(Cl)c2)s1]
55
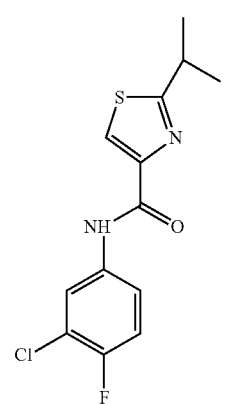 [SMILES: CC(C)c1nc(C(=O)Nc2ccc(F)c(Cl)c2)cs1]
56
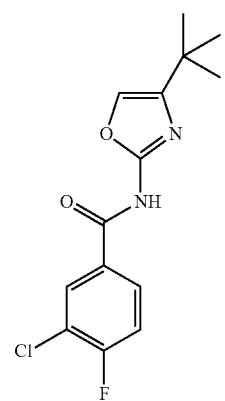 [SMILES: CC(C)(C)c1coc(NC(=O)c2ccc(F)c(Cl)c2)n1]
57
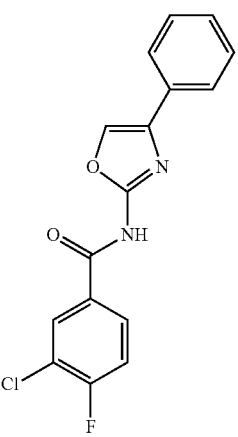 [SMILES: O=C(Nc1nc(-c2ccccc2)co1)c1ccc(F)c(Cl)c1]
58
TABLE 1-continued
Exemplary Compounds
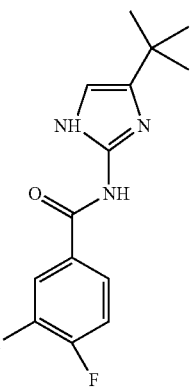
59
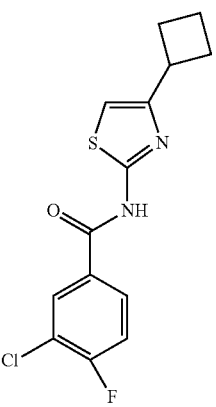 [SMILES: O=C(Nc1nc(C2CCC2)cs1)c1ccc(F)c(Cl)c1]
60
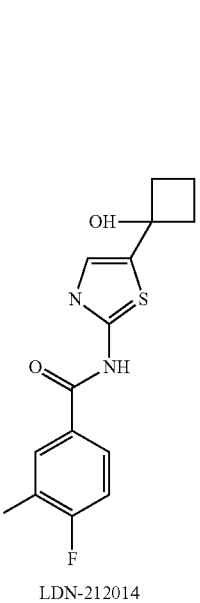
61
LDN-212014

TABLE 1-continued
Exemplary Compounds
62 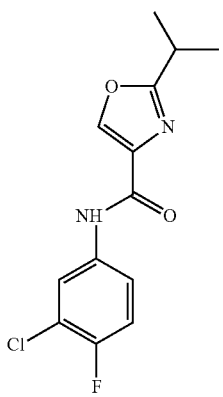 [SMILES: CC(C)c1nc(C(=O)Nc2ccc(F)c(Cl)c2)co1]
63 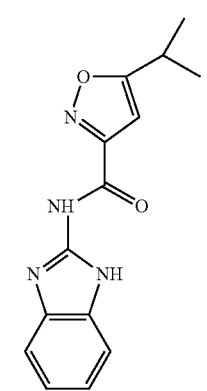 [SMILES: CC(C)c1cc(C(=O)Nc2nc3ccccc3[nH]2)no1]
64 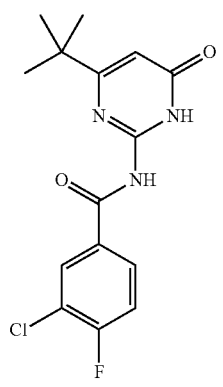
65 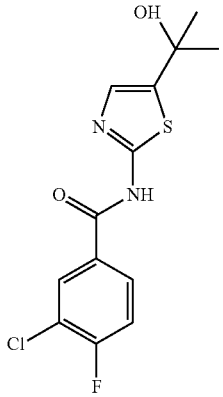 [SMILES: CC(C)(O)c1cnc(NC(=O)c2ccc(F)c(Cl)c2)s1]
TABLE 1-continued
Exemplary Compounds
66 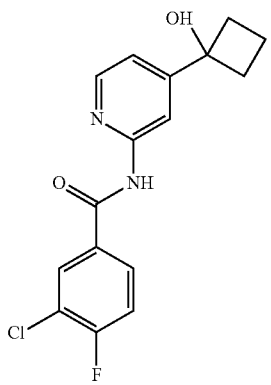 [SMILES: O=C(Nc1cc(C2(O)CCC2)ccn1)c1ccc(F)c(Cl)c1]
67 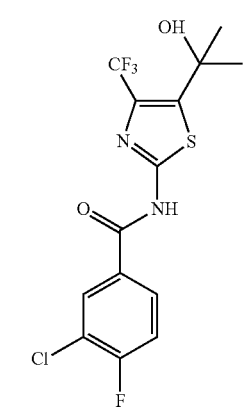 [SMILES: CC(C)(O)c1sc(NC(=O)c2ccc(F)c(Cl)c2)nc1C(F)(F)F]
68 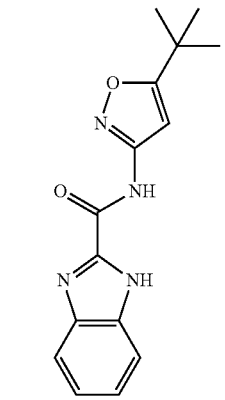 [SMILES: CC(C)(C)c1cc(NC(=O)c2nc3ccccc3[nH]2)no1]
69 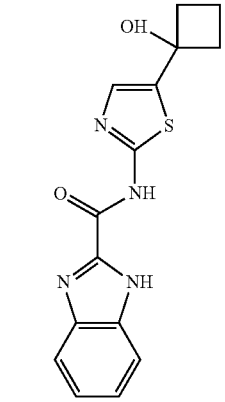 [SMILES: O=C(Nc1ncc(C2(O)CCC2)s1)c1nc2ccccc2[nH]1]

TABLE 1-continued
Exemplary Compounds
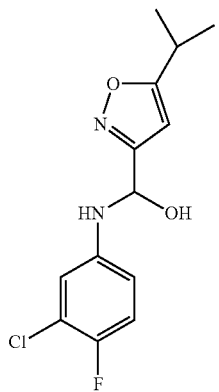 [SMILES: CC(C)c1cc(C(O)Nc2ccc(F)c(Cl)c2)no1]
70
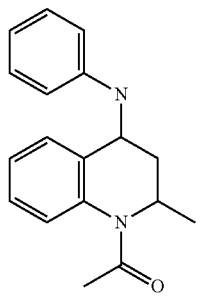 [SMILES: CC(=O)N1c2ccccc2C(Nc2ccccc2)CC1C]
71
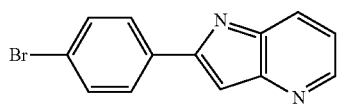
72
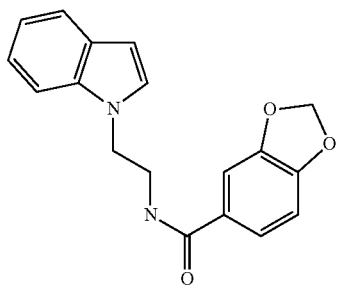 [SMILES: O=C(NCCn1ccc2ccccc21)c1ccc2c(c1)OCO2]
73
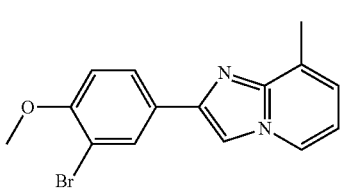
74
TABLE 1-continued
Exemplary Compounds
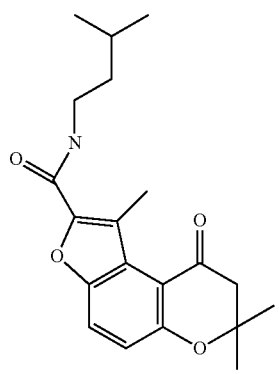
75
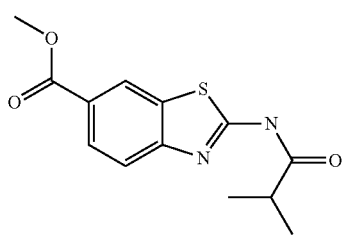 [SMILES: COC(=O)c1ccc2nc(NC(=O)C(C)C)sc2c1]
LDN-79199
76
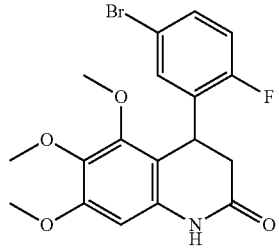
77
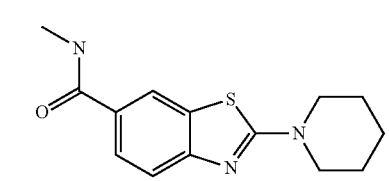 [SMILES: CNC(=O)c1ccc2nc(N3CCCCC3)sc2c1]
LDN-76070
78
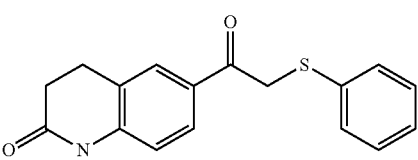 [SMILES: O=C1CCc2cc(C(=O)CSc3ccccc3)ccc2N1]
79
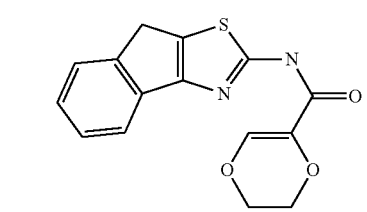 [SMILES: O=C(Nc1nc2c(s1)Cc1ccccc1-2)C1=COCCO1]
80

TABLE 1-continued
Exemplary Compounds
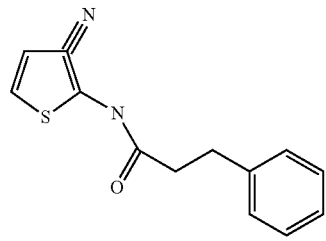
81
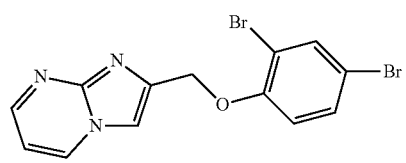 [SMILES: Brc1ccc(OCc2cn3cccnc3n2)c(Br)c1]
82
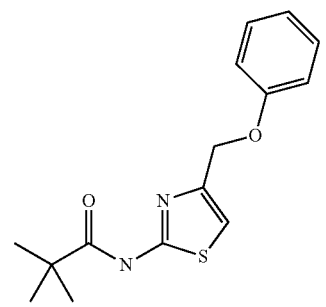 [SMILES: CC(C)(C)C(=O)Nc1nc(COc2ccccc2)cs1]
83
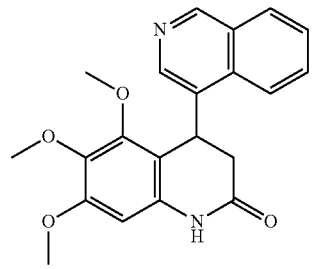
LDN-212356
84
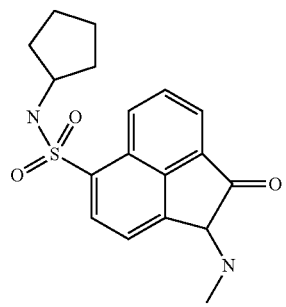
LDN-109657
85
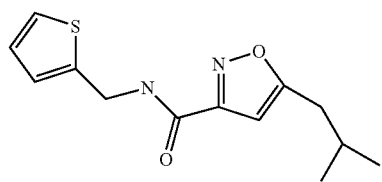 [SMILES: CC(C)Cc1cc(C(=O)NCc2cccs2)no1]
86
TABLE 1-continued
Exemplary Compounds
LDN-72939
87
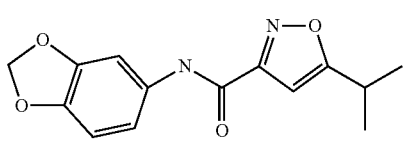 [SMILES: CC(C)c1cc(C(=O)Nc2ccc3c(c2)OCO3)no1]
88
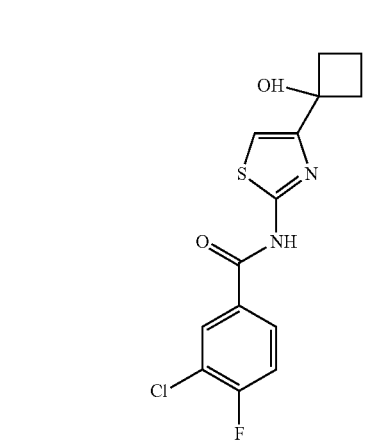 [SMILES: O=C(Nc1nc(C2(O)CCC2)cs1)c1ccc(F)c(Cl)c1]
89
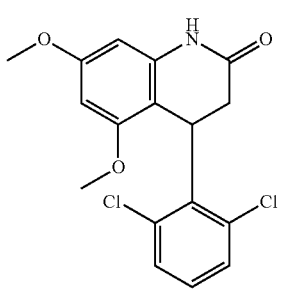
LDN-76515
90
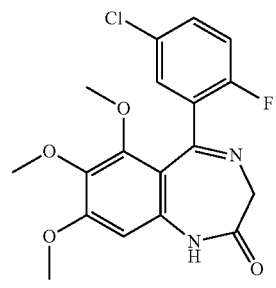
LDN-213767
91

TABLE 1-continued
Exemplary Compounds
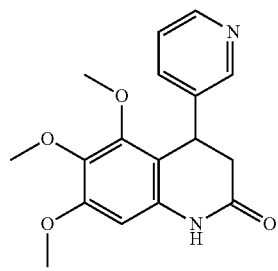
LDN-76158
92
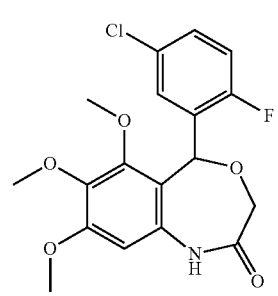
LDN-213768
93
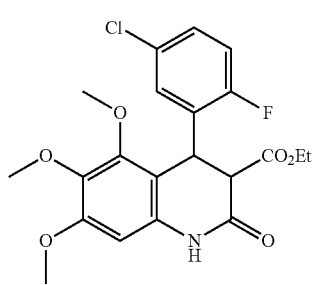
LDN-212388
94
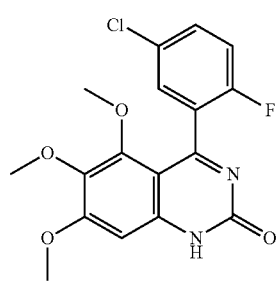
LDN-213769
95
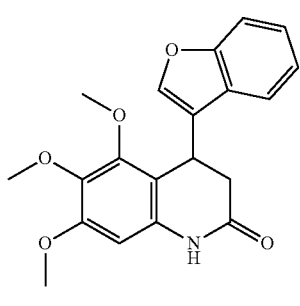
LDN-212389
96
TABLE 1-continued
Exemplary Compounds
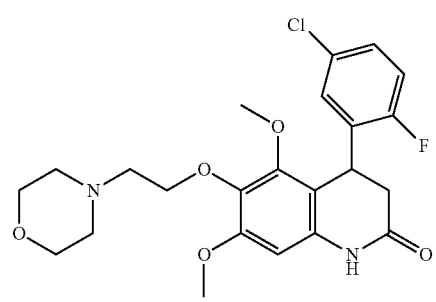 [SMILES: COc1cc2c(c(OC)c1OCCN1CCOCC1)C(c1cc(Cl)ccc1F)CC(=O)N2]
97
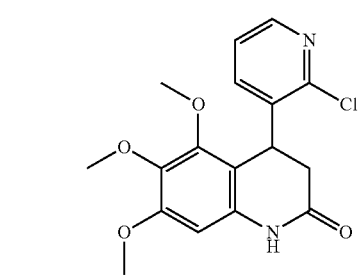
LDN-212390
98
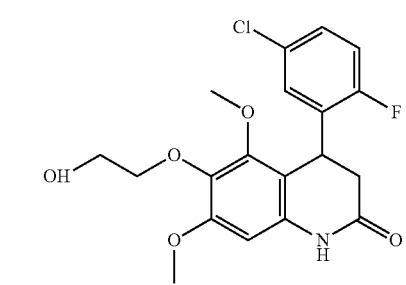
LDN-213771
99
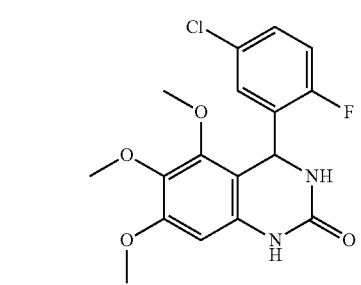
LDN-212391
100
LDN-213772
101

TABLE 1-continued
Exemplary Compounds
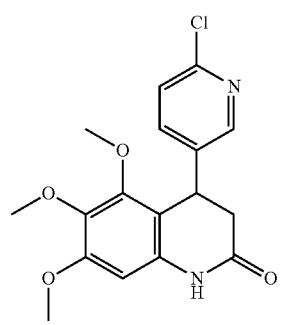 [SMILES: COc1cc2c(c(OC)c1OC)C(c1ccc(Cl)nc1)CC(=O)N2]
102
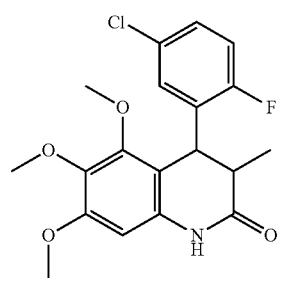
LDN-213773
103
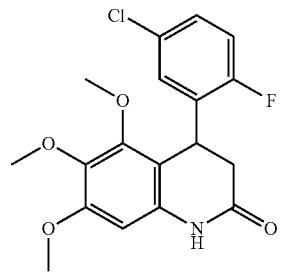
LDN-212351
104
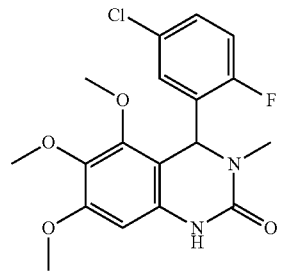
LDN-214085
105
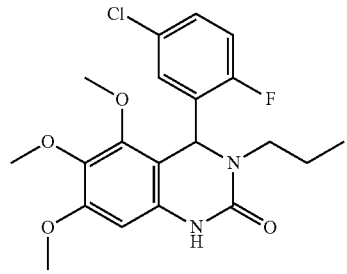
LDN-214096
106
TABLE 1-continued
Exemplary Compounds
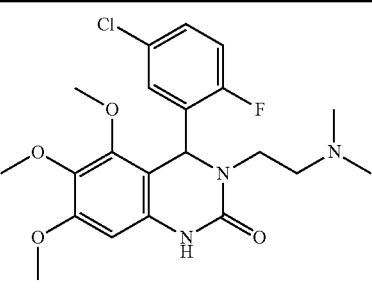
LDN-214097
107
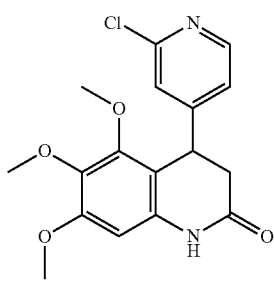
LDN-212393
108
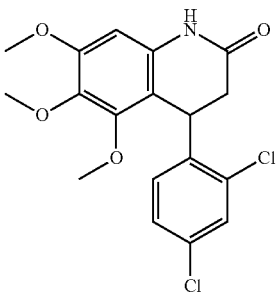
LDN-76074
109
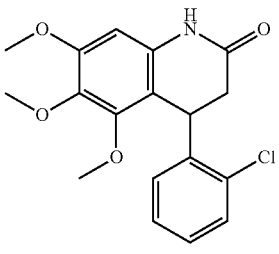 [SMILES: COc1cc2c(c(OC)c1OC)C(c1ccccc1Cl)CC(=O)N2]
110
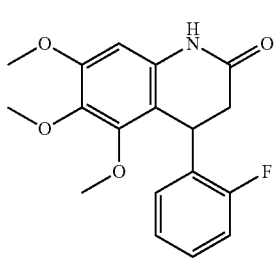 [SMILES: COc1cc2c(c(OC)c1OC)C(c1ccccc1F)CC(=O)N2]
111

TABLE 1-continued
Exemplary Compounds
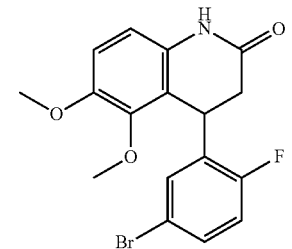 [SMILES: COc1ccc2c(c1OC)C(c1cc(Br)ccc1F)CC(=O)N2] 112
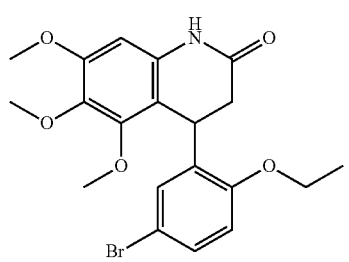 [SMILES: CCOc1ccc(Br)cc1C1CC(=O)Nc2cc(OC)c(OC)c(OC)c21] 113
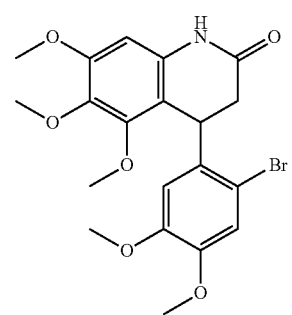 [SMILES: COc1cc(Br)c(C2CC(=O)Nc3cc(OC)c(OC)c(OC)c32)cc1OC] 114
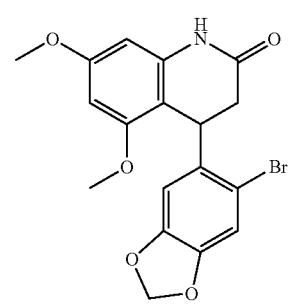 [SMILES: COc1cc2c(c(OC)c1)C(c1cc3c(cc1Br)OCO3)CC(=O)N2] 115
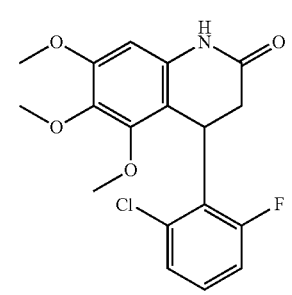 116
TABLE 1-continued
Exemplary Compounds
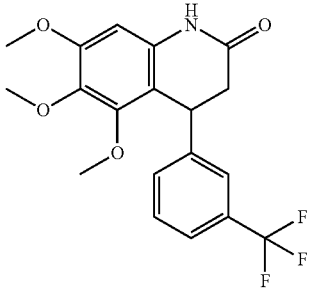 [SMILES: COc1cc2c(c(OC)c1OC)C(c1cccc(C(F)(F)F)c1)CC(=O)N2] 117
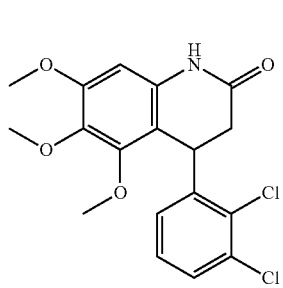 [SMILES: COc1cc2c(c(OC)c1OC)C(c1cccc(Cl)c1Cl)CC(=O)N2] 118
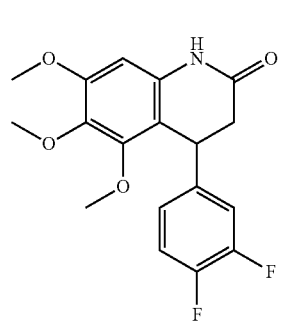 [SMILES: COc1cc2c(c(OC)c1OC)C(c1ccc(F)c(F)c1)CC(=O)N2] 119
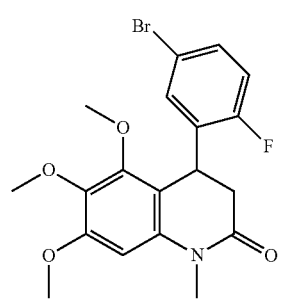 [SMILES: COc1cc2c(c(OC)c1OC)C(c1cc(Br)ccc1F)CC(=O)N2C] 120
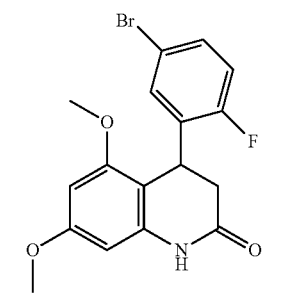 [SMILES: COc1cc2c(c(OC)c1)C(c1cc(Br)ccc1F)CC(=O)N2] 121

TABLE 1-continued

Exemplary Compounds

TABLE 1-continued

Exemplary Compounds

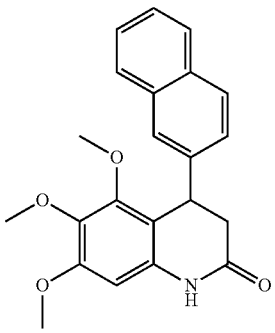

LDN-212357

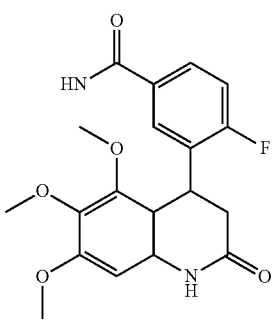

LDN-212358

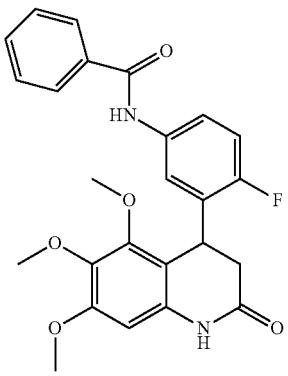

LDN-212359

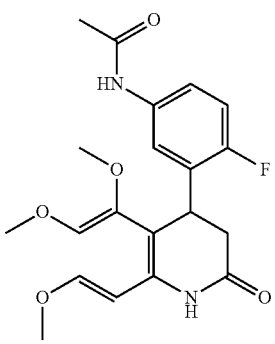

LDN-212360

TABLE 1-continued

Exemplary Compounds

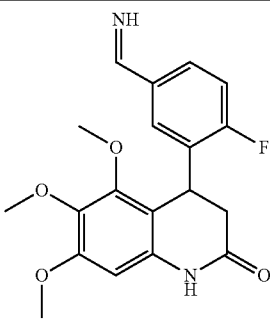

LDN-212361

In some embodiments, the present disclosure provides a compound depicted in Table 1, above, or a pharmaceutically acceptable salt thereof.

4. General Methods of Providing the Present Compounds

The compounds of this disclosure may be prepared or isolated in general by synthetic and/or semi-synthetic methods known to those skilled in the art for analogous compounds.

Pharmaceutically Acceptable Compositions

It will be appreciated that certain of the compounds of present disclosure can exist in free form for treatment, or where appropriate, as a pharmaceutically acceptable salt thereof.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. A "pharmaceutically acceptable salt" means any non-toxic salt or salt of an ester of a compound of this disclosure that, upon administration to a recipient, is capable of providing, either directly or indirectly, a compound of this disclosure or a pharmaceutically active metabolite or residue thereof. As used herein, the term "pharmaceutically active metabolite or residue thereof" means that a metabolite or residue thereof is also a pharmaceutically active compound in accordance with the present disclosure.

Pharmaceutically acceptable salts are well known in the art. For example, S. M. Berge et al., describes pharmaceutically acceptable salts in detail in *J. Pharmaceutical Sciences*, 1977, 66, 1-19, incorporated herein by reference to the extent it is consistent herewith. Pharmaceutically acceptable salts of the compounds of this disclosure include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxyethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}\text{ alkyl})_4$ salts. This disclosure also envisions the quaternization of any basic nitrogen-containing groups of the compounds disclosed herein. Water or oil-soluble or dispersable products may be obtained by such quaternization. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower-alkyl sulfonate and aryl sulfonate.

In some cases, compounds of the present disclosure may contain one or more acidic functional groups and, thus, may be capable of forming pharmaceutically-acceptable salts with pharmaceutically-acceptable bases. The term "pharmaceutically-acceptable salts" in these instances refers to the relatively non-toxic, inorganic and organic base addition salts of compounds of the present disclosure. These salts can likewise be prepared in situ in the administration vehicle or the dosage form manufacturing process, or by separately reacting the purified compound in its free acid form with a suitable base, such as the hydroxide, carbonate or bicarbonate of a pharmaceutically-acceptable metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethyldiamine, ethanolamine, diethanolamine, piperazine and the like.

According to another aspect of the present disclosure, pharmaceutically acceptable compositions are provided, wherein these compositions comprise any of the compounds as described herein, and optionally comprise a pharmaceutically acceptable carrier, adjuvant or vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired.

Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof. Except insofar as any conventional carrier medium is incompatible with the compounds of the disclosure, such as by producing any undesirable biological effect or otherwise interacting in a deleterious manner with any other component(s) of the pharmaceutically acceptable composition, its use is contemplated to be within the scope of this disclosure. Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethyl-polyoxypropyl-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propyl glycol or polyethyl glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. In some embodiments, the compositions of the present disclosure additionally comprise one or more of DMSO, PEG400, Tween-80, and hydropropyl beta cyclodextrin. In some embodiments, the compositions of the present disclosure additionally comprise 2% DMSO, 2% PEG400, 0.2% Tween80, and 20% hydropropyl beta cyclodextrin.

The compositions provided by the present disclosure can be employed in combination therapies, meaning that the present compositions can be administered concurrently with, prior to, or subsequent to, one or more other desired therapeutic agents or medical procedures. The particular combination of therapies (therapeutic agents or procedures) to employ in a combination regimen will take into account compatibility of the desired therapeutic agents and/or procedures and the desired therapeutic effect to be achieved. It will also be appreciated that the therapies employed may achieve a desired effect for the same disorder (for example, a compound described herein may be administered concurrently with another therapeutic agent used to treat the same disorder), or they may achieve different effects (e.g., control of any adverse effects).

The amount of additional therapeutic agent present in the compositions of this disclosure will be no more than the amount that would normally be administered in a composition comprising that therapeutic agent as the only active agent. In certain embodiments, the amount of additional therapeutic agent in the present compositions will range from about 50% to 100% of the amount normally present in a composition comprising that agent as the only therapeutically active agent.

In an alternate embodiment, the methods of this disclosure that utilize compositions that do not contain an additional therapeutic agent, comprise the additional step of separately administering to said patient an additional therapeutic agent. When these additional therapeutic agents are administered separately they may be administered to the patient prior to, sequentially with or following administration of the compositions of this disclosure.

The pharmaceutically acceptable compositions of this disclosure can be administered to humans and other animals orally, rectally, parenterally, intravenously, intracisternally, intravaginally, intraperitoneally, topically (as by powders, ointments, or drops), bucally, as an oral or nasal spray, or the like, depending on the severity of the disorder being treated.

Liquid dosage forms for oral administration include, but are not limited to, pharmaceutically acceptable emulsions, microemulsions, solutions, suspensions, syrups and elixirs.

In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propyl glycol, 1,3-butyl glycol, dimethylformamide, oils (in particular, cottonseed, groundnut, corn, germ, olive, castor, and sesame oils), glycerol, tetrahydrofurfuryl alcohol, polyethyl glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present disclosure, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly (orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this disclosure with suitable non-irritating excipients or carriers such as cocoa butter, polyethyl glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with one or more inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethyl glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethyl glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polyethyl glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms, the active compound may be admixed with one or more inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this disclosure include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this disclosure. Additionally, the present disclosure contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

Uses of Compounds and Pharmaceutically Acceptable Compositions

The compounds of the disclosure are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present disclosure (also referred to herein as "therapeutically effective amount") will be decided by the attending physician within the scope of sound medical judgment. More particularly, as used herein, the phrase "therapeutically effective amount" of the compound used in the methods of the present disclosure refers to a sufficient amount of a compound to treat SMA as defined herein, at a reasonable benefit/risk ratio applicable to any medical treatment. It can be understood, however, that the total daily usage of the compound and pharmaceutically acceptable compositions including the compound for use in the methods of the present disclosure can be decided by the attending physician within the scope of sound medical judgment. The specific therapeutically effective dose level for any particular patient can depend upon a variety of factors including the loss of motor neuron function episode being treated and the severity of the episode; activity of the specific compound employed; the specific pharmaceutically acceptable composition employed; the age, body weight, general health, sex and diet of the patient; the time of administration, route of administration, and rate of excretion of the compound employed; the duration of the treatment; drugs used in combination or coincidental with the specific compound employed; and like factors well-known in the medical arts. For example, it is well within the skill of the art to start doses of the compound at levels lower than required to achieve the desired therapeutic effect and to gradually increase the dosage until the desired effect is achieved.

In certain embodiments, the compounds of the disclosure may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

The term "patient," as used herein, means an animal, preferably a mammal, and most preferably a human. Particularly, the patient refers to a subject that is susceptible to or has SMA. As used herein, "susceptible to" refers to having little resistance to a certain disease, disorder or condition, and in particular, to SMA, including being genetically predisposed, having a family history of, and/or having symptoms of the disease, disorder or condition. Accordingly, in some embodiments, the compounds and/or pharmaceutically acceptable compositions can be administered to a subset of subjects in need of preventing/minimizing/controlling loss of motor neuron function, progressive motor weakness, muscle wasting, and paralysis. Some subjects that are in specific need of restored/maintained motor neuron function may include patients who are susceptible to, or at elevated risk of, experiencing loss of motor neuron function, including subjects susceptible to, or at elevated risk of, areflexia, muscle weakness, poor muscle tone, muscle wasting, paralysis, fasciculations of the tongue, difficulty sucking or swallowing, arthrogryposis, low weight, and the like. In one particular embodiment, the methods can be administered to a patient who has, or is susceptible to, or at elevated risk of, SMA. Subjects may be susceptible to, or at elevated risk of, experiencing SMA, and generally, loss of motor neuron function, areflexia, muscle weakness, poor muscle tone, muscle wasting, paralysis, fasciculations of the tongue, difficulty sucking or swallowing, arthrogryposis, low weight due to family history, age, environment, and/or lifestyle. Based on the foregoing, because some of the method embodiments of the present disclosure are directed to specific subsets or subclasses of identified subjects (that is, the subset or subclass of patients susceptible to one or more specific conditions noted herein), not all subjects will fall within the subset or subclass of subjects as described herein for certain diseases, disorders or conditions.

Various functions and advantages of these and other embodiments of the present disclosure will be more fully understood from the examples described below. The following examples are intended to illustrate the benefits of the present disclosure, but do not exemplify the full scope of the disclosure.

EXAMPLES

Example 1

In this Example, the assay method of the present disclosure was utilized to identify compounds that increase SMN2 expression.

Materials and Methods

Cloning

The luciferase minigene from previous reporter vectors SMN1-luc (T-luc) or SMN2-luc (C-luc) was shortened by digestion with Sma I and Swa I to remove 2 kB from intron 6. The SMN exon 1-5 fragment was generated by PCR from human cDNA (exon 1 forward: ccacaaatgtgggagggcgataacc (SEQ ID NO: 1) and exon 6 reverse: tatctcgagtggtccagaaggaaatggaggcagcc (SEQ ID NO: 2)). The SMN promoter elements were from p3.4$^T$ and p3.4$^C$ SMN (Monani et al., Promoter analysis of the human centromeric and telomeric survival motor neuron genes (SMNC and SMNT), Biochim Biophys Acta 1999, 1445 (3), 330-336). These were combined into pIRES cloning vector (BD Clontech) at the multiple cloning site. The entire reporter fragment was excised from pIRES and ligated into a pCEP4 (Invitrogen) plasmid that also expressed renilla luciferase from nucleotides 299-1259 of phRL-null (Promega) from the CMV promoter.

Cell Culture

Cells were incubated at 37° C. with 5% $CO_2$. HEK-293 cells were cultured in D-MEM (GIBCO 11995) with 10% fetal bovine serum (FBS, ATLAS) and 1× pen-strep (GIBCO 15140). Reporter cell lines containing SMN1, SMN2, or control luciferase reporter were selected and maintained in D-MEM with 10% FBS and 1× pen-strep with 200 µg/mL hygromycin B (Invitrogen 10687-010). 3813 and 3814 fibroblasts were cultured in D-MEM (GIBCO 11995) with 15% fetal bovine serum (FBS, ATLAS) and 1× pen-strep (GIBCO 15140).

Luciferase Reporter Assay

The reporter cell lines were plated at 50,000 cells per well in 96-well plates and incubated overnight. Compounds were added to each well and incubated at 37° C. overnight. The final DMSO concentration was 0.1%. Luciferase activity was assayed using either STEADYGLO (PROMEGA E2510) or DUALGLO (PROMEGA E2920) luciferase using the WALLAC ENVISION multilabel reader. For detailed assay conditions see Table 2A. All data points were transformed from CPS to percent increase over basal expression in the treated control wells (DMSO or $H_2O$ as appropriate).

Protein Detection

For analysis of SMN-luciferase fusion, cells were treated with compound or DMSO for 25 hours. Cells were lysed with protein lysis buffer (100 mM Tris pH 8.0, 100 mM NaCl, 0.1% NP-40, 8.0 M urea, and protease inhibitor). Each sample was separated on a 10% SDS-page gel, transferred to Immobilon-P membrane (MILLIPORE IVPH00010) and blotted for the SMN-luciferase fusion with anti-luciferase antibody (PROMEGA, #G7541), SMN with the 4f11 mouse monoclonal antibody (described in Mattis et al., "Detection of human survival motor neuron (SMN) protein in mice containing the SMN2 transgene: Applicability to preclinical therapy development for spinal muscular atrophy" J. Neurosci Methods, 2008), HA-tag with 12CA5 monoclonal, actin (Sigma A2066) or a-tubulin (DM1a; Sigma T6199).

For detection of SMN protein in patient fibroblasts, 8,000 cells per cm were plated 24 hours prior to drug addition. Fresh media and compound were added every 24 hours. After 72 hours, cells were harvested, washed with cold PBS, and lysed as above. It has been determined that 10 μg total protein per lane is within the linear range for immunoblot detection of SMN and a-tubulin. Western blots were probed for SMN with the 4f11 mouse monoclonal antibody and a-tubulin.

Quantification of protein was performed with FUJIFILM LAS-4000 Multifunctional Imaging System. The signal intensity was measured for each band on an immunoblot, normalized to the loading control, and the fold increase was determined in relation to the appropriate DMSO treated control.

Overexpression Assays

Cells were plated at a density of $2\times10^6$ per 60 cm dish and incubated overnight. Cells were transfected with up to 6 μg of HA-tagged expression vector using FUGENE 6 at a 3:1 fugene:DNA ratio and incubated overnight. After 24 hours cells were re-plated at $1\times10^5$ cells per well in a 96-well plate or $1\times10^6$ cells per well in 6-well dishes. Cells were tested 24 to 48 hours later. Luciferase was assayed using DUALGLO luciferase as described above. Protein lysates and RNA samples were collected using protein lysis buffer or Trizol respectively. Protein was analyzed by western blot and RNA was analyzed by qRT-PCR.

PCR and RT-PCR

Compounds were tested at three concentrations that display maximal activity in the luciferase assay. Cells were treated as described above for the luciferase assay. Cells were harvested by trypsinization, neutralized with trypsin inhibitor, and washed. RNA was isolated from the cells using TRIZOL Reagent (Invitrogen 15596-026). cDNA was generated using the IMPROM-II Reverse Transcription System (Promega A3801).

The forward primer pair recognizes the exon 5-6 junction, which includes a restriction site that was engineered into the reporter and will exclude amplification of endogenous SMN mRNA. The reverse primers recognize either exon 7 or luciferase for detection of full-length or total SMN-luciferase transcripts respectively. For a reference control, cDNA from the housekeeping gene glyceraldehyde-3-phosphate dehydrogenase (GAPDH) was amplified. The primers used include SMN exon5-forward (catttccttctggaccactcgag) (SEQ ID NO: 3), luciferase-reverse (atagcttctgccaaccgaacgg) (SEQ ID NO: 4), exon7-reverse (taaggaatgtgagcaccttccttc) (SEQ ID NO: 5), GAPDH-reverse (G3A) (tccaccaccctgttgctgta) (SEQ ID NO: 6) and GAPDH-forward (G3S) (accacagtccatgccatcac) (SEQ ID NO: 7). qPCR was performed as described in the protocol for iQ SYBRGREEN SUPERMIX (Biorad 170-8882) using an EPPENDORF Mastercycler ep realplex$^4$ Thermo Cycler. Reactions were incubated for a 10 minute, 94° C. hot start followed by 45 cycles of the following: 94° C. for 45 second, 60° C. for 15 seconds, 72° C. for 45 seconds. Melting curves for each reaction were obtained. Each sample was assayed in triplicate and every plate contained a 5-point cDNA dilution course to calculate amplification efficiency for each primer pair. The Pfaffl method was used to determine the change in transcript levels relative to the DMSO and normalized to GAPDH (Pfaffl, M. W., "A new mathematical model for relative quantification in real-time RT-PCR," Nucleic Acids Res 2001, 29(9), 3e45).

Screening Protocol

Cells were plated in phenol red-free D-MEM (Gibco 21063) with sodium pyruvate (Gibco 11360) and 10% FBS in the absence of hygromycin B and pen-strep and allowed to adhere 1 hour prior to addition of compound. Each compound was added to a single well with a BECKMAN COULTER BIOMEK FX 384 to a final concentration of approximately 2 μM from compound stocks, based on an average molecular weight of 500. The final DMSO concentration in test and control wells was 0.13%. Plates were sealed with porous paper tape and incubated for 24 hours. Luciferase expression was measured using the STEADYLITE luciferase (Perkin Elmer 6016981) substrate and the LJL Analyst HT, and read for counts per second (CPS) at an integration time of 100,000 μS. For comparison, data points were transformed from CPS to percent activation over basal expression in the DMSO treated control wells. This is summarized in Table 2B.

Library Composition

A compound library of approximately 115,000 small molecules, including compounds approved by the Food and Drug Administration (FDA), a purified natural products library, compounds purchased from PEAKDALE (High Peak, UK), MAYBRIDGE Plc. (Cornwall, UK), Cerep (Paris, France), BIONET RESEARCH Ltd. (Cornwall, UK), PRESTWICK (Ilkirch, France), SPECS and BIOSPECS (CP Rijswijk, the Netherlands), ENAMINE (Kiev, Ukraine), I.F. Lab LTD (Burlington, Canada), and Chemical Diversity Labs (San Diego, Calif.), and small molecules from academic institutions was tested. Compounds were selected from vendors by applying a series of filters including clogP and predicted solubility. All of the small molecules generally adhere to Lipinski's rules (Lipinski et al. "Experimental and computational approaches to estimate solubility and permeability in drug discover and development settings," Adv Drug Deliv Rev 2001, 46(1-3), 3-26) and contain a low proportion of known toxicophores (i.e. Michael acceptors and alkylating agents) and unwanted functionalities (i.e. imines, thiols, and quartemary amines) and have been optimized for molecular diversity. Compound source plates for the assay were prepared by spotting 0.4 μl of 1.67 mM compound in DMSO in each well of a Greiner 384-well plate, with columns 23 and 24 spotted with neat DMSO for positive and negative controls. These were then sealed with aluminum plate seals and stored at −20° C.

Results

Development of a New Reporter

Over time, the original C33a reporter cell lines displayed a decrease in the difference in luciferase signal from SMN1 and SMN2 (FIG. 7) and showed inconsistent responses to treatment with drugs known to increase SMN expression (data not shown). These original reporters were also driven by the CMV promoter and displayed much higher basal levels of SMN1- and SMN2-luciferase activity in the absence of treatment (FIG. 7), which could diminish the reporters' ability to detect compounds that are less potent and more selective. To address this, a new reporter assay was designed that would be more responsive to molecular cues that regulate the levels of SMN expression through multiple pathways. The SMN promoter and exon 7 splicing cassette were combined into a single construct to simultaneously identify compounds that increase SMN transcription or exon 7 inclusion (FIGS. 1A-1D). The presence of the native SMN promoter may also influence recruitment of splicing factors to the transcript and better reproduce the context in which the endogenous gene is processed and expressed. Since a subset of compounds might stabilize the SMN RNA or protein, for example, by interfering with its metabolism or ubiquitination, exons 1-5 were included in the new reporter. This reporter produces a full-length SMN-luciferase fusion protein that should be regulated and metabolized in a manner that is more consistent with the endogenous SMN protein. The entire reporter was cloned into an Epstein Barr Virus (EBV) vector that is maintained autonomously as stable episomes in some human cell lines.

To summarize, the new assay design: i) replaced the CMV promoter with 3.4 kb of the SMN1 or SMN2 promoters with an intact transcription start site; ii) included the cDNA for exons 1-5 following the authentic promoter and translational ATG; iii) deleted a portion of intron 6 since the size of the entire 6 kb intron complicated cloning; iv) included the exon 7 splicing cassette with the firefly luciferase reporter; v) cloned renilla luciferase expressed from the CMV promoter into the construct for monitoring copy number, cell viability and specificity of the transcriptional effects; and vi) transferred the 9 kb reporter SMN1 and SMN2 cassettes into EBV ori based pCEP4. The result is reporters with sequences from SMN1 and SMN2 in the context of their respective promoters. These constructs, each ~19 kb, will produce increased SMN-luciferase fusion protein if there is an induction of 1) transcription from the SMN promoter; 2) inclusion of exon 7; or 3) stabilization of the SMN-luciferase mRNA or fusion protein. Not only will this reporter be able to identify potential positive modifiers of SMN expression, but the design of the screen and the renilla control also reduces the likelihood of selecting compounds that are toxic or cause non-specific increases in transcription. These reporters were transfected into HEK 293 cells. These human cells are easy to culture and expand, highly transfectable, and maintain EBV based plasmids extrachromosomally. Stable clonal cell lines were isolated that express the full-length SMN-luciferase protein as appropriate in both the SMN1-luc or SMN2-luc reporters.

Analysis of SMN1-Luc and SMN2-Luc Clonal Cell Lines Population

Figure 7:
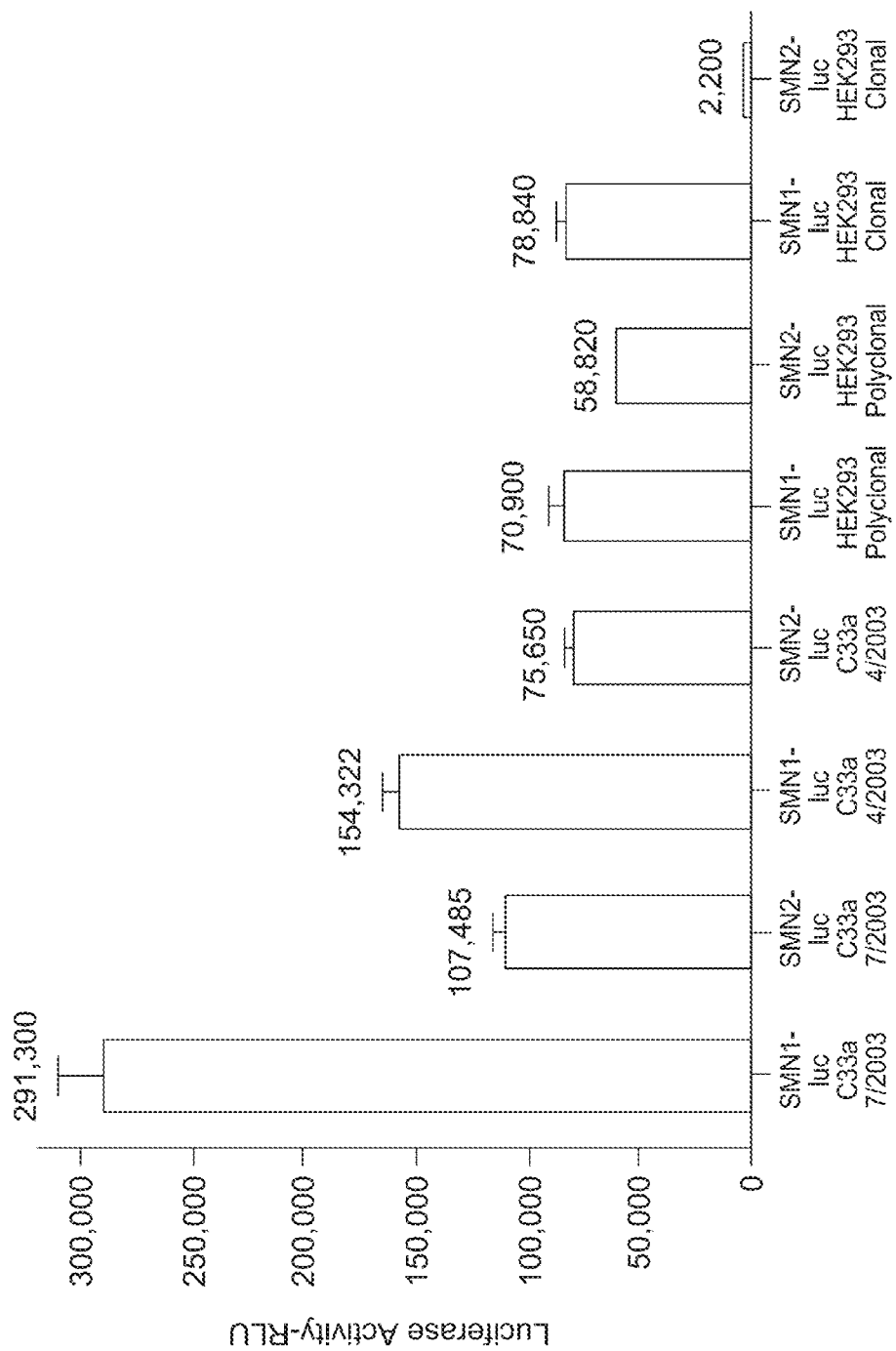
FIG. 7 shows original and new reporter assay comparison. Comparison of luciferase activity for equivalent numbers of previous generation reporter cells, mixed population SMN1-luc, mixed population SMN2-luc, clonal SMN1-luc and clonal SMN2-luc cells. Luciferase activity was scored as relative light units (RLU).
Figure 8:
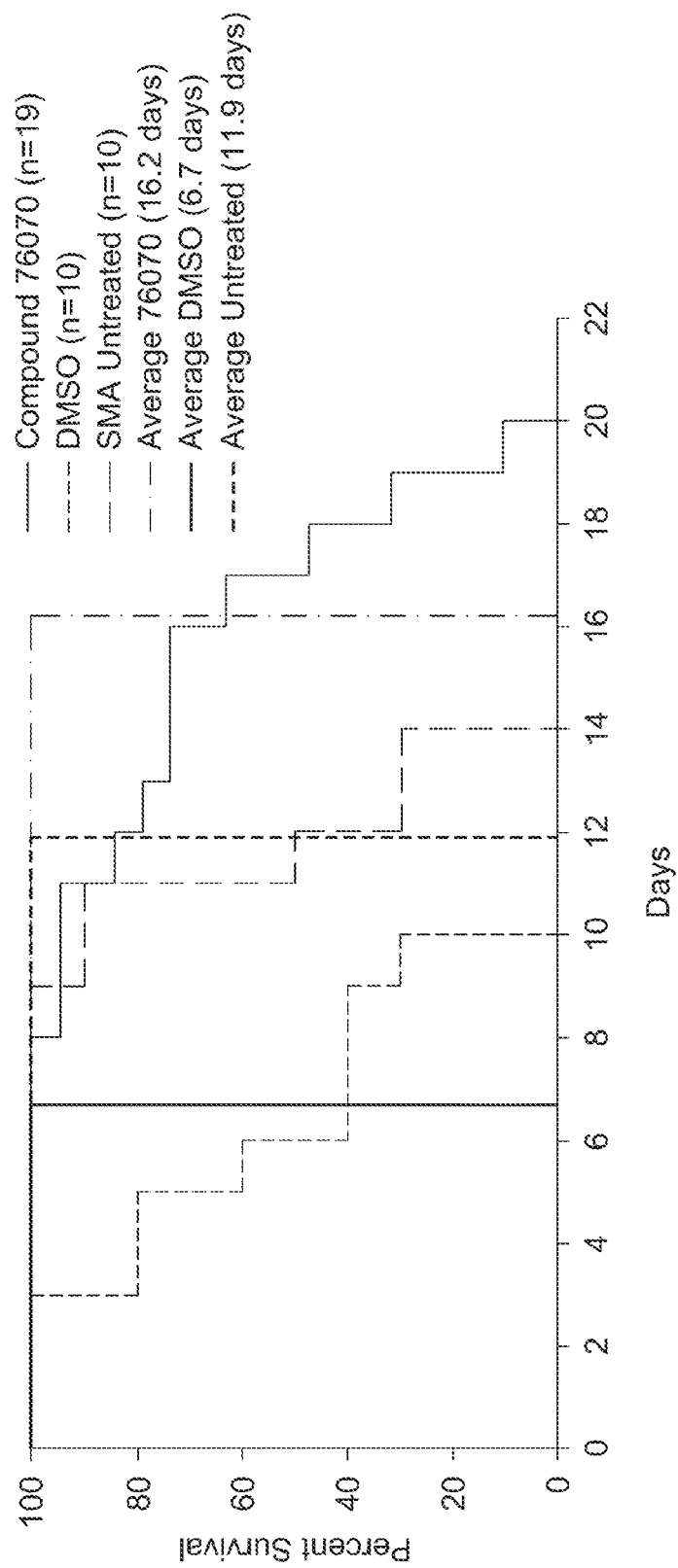
FIG. 8 shows survival proportions of animals in a mouse model of spinal muscular atrophy treated with compound 76070, DMSO, or untreated.
Figure 9:
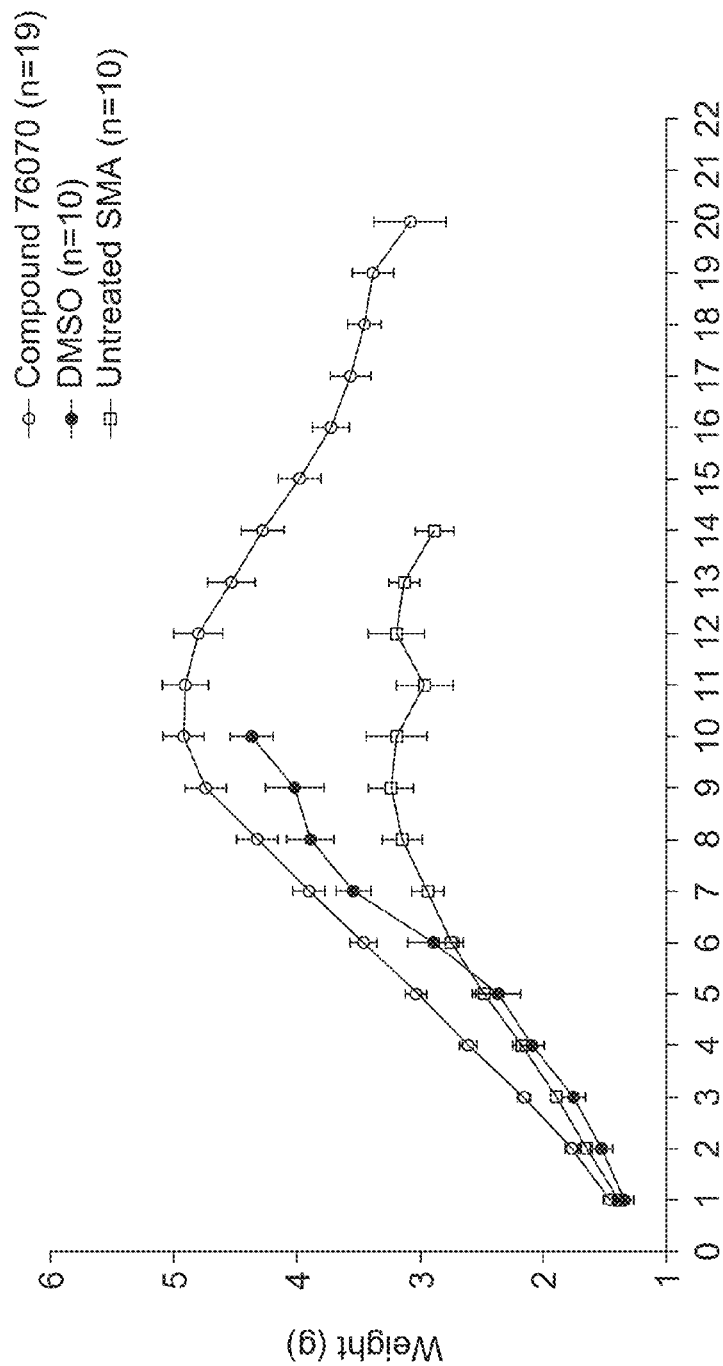
FIG. 9 shows average weights of animals in a mouse model of spinal muscular atrophy treated with compound 76070, DMSO, or untreated.
Figure 10:
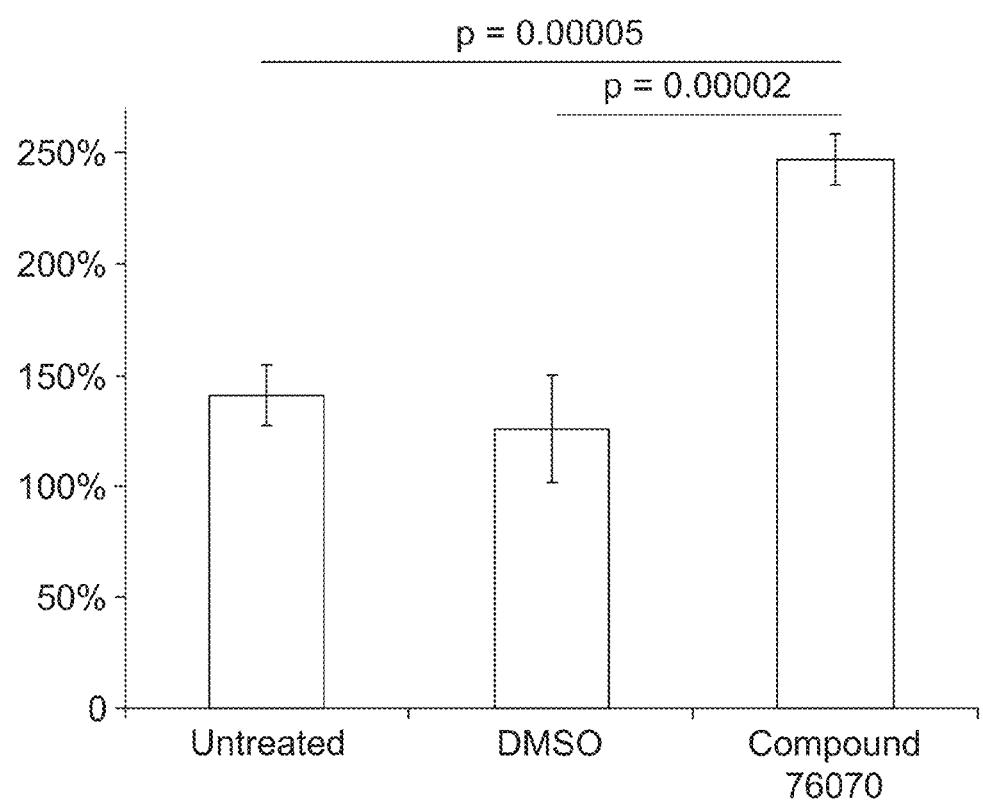
FIG. 10 shows percent weight gained from birth to peak of animals in a mouse model of spinal muscular atrophy treated with compound 76070, DMSO, or untreated.
Figure 11:
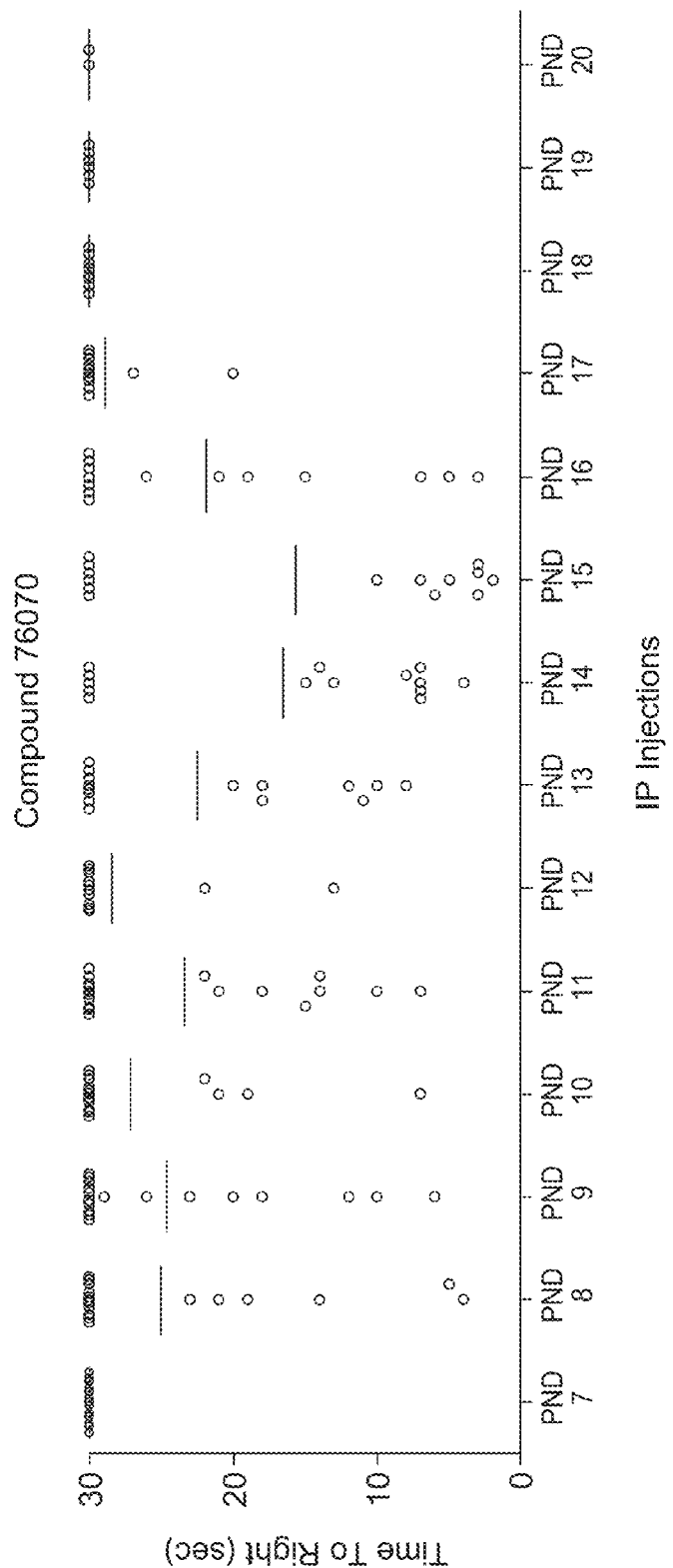
FIG. 11 shows actual time to right of the compound 76070-treated group. Animals are placed on their backs and assayed for the time it requires for them to right themselves. Thirty (30) seconds or greater is considered a failure to right and scored as 30 sec.
Figure 12:
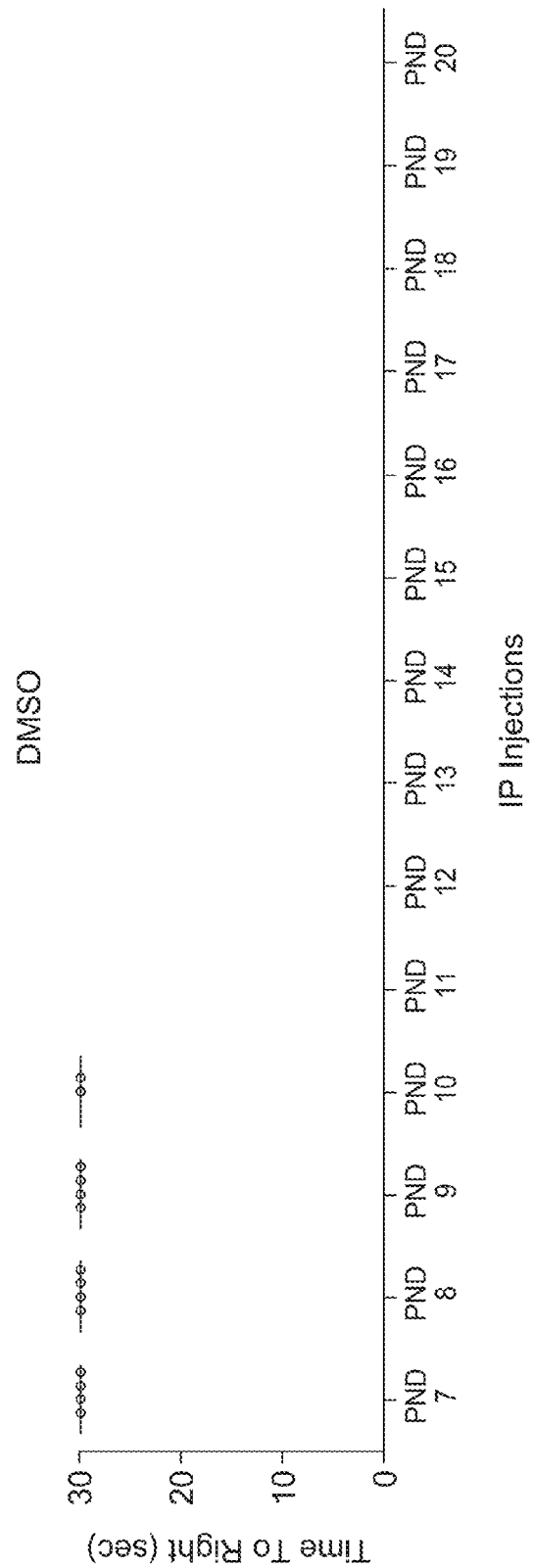
FIG. 12 shows actual time to right of the DMSO-treated group. Animals are placed on their backs and assayed for the time it requires for them to right themselves. Thirty (30) seconds or greater is considered a failure to right and scored as 30 sec.
Figure 13:
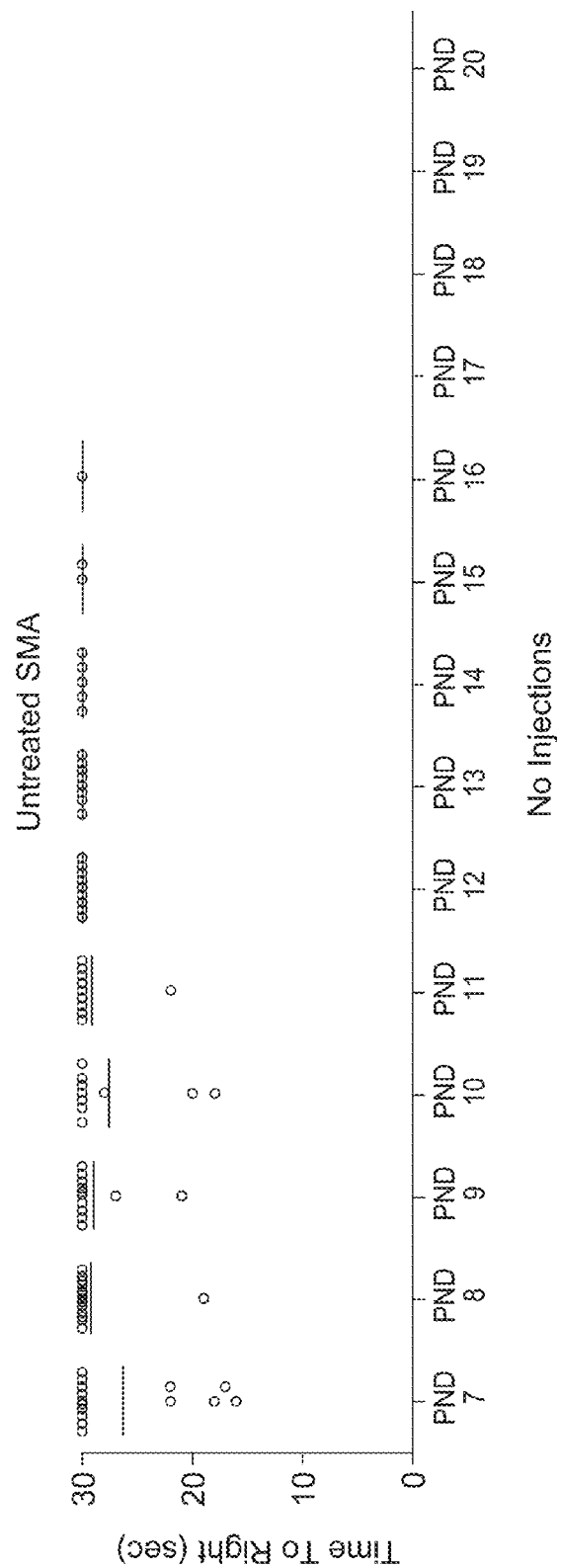
FIG. 13 shows actual time to right of the untreated group. Animals are placed on their backs and assayed for the time it requires for them to right themselves. Thirty (30) seconds or greater is considered a failure to right and scored as 30 sec.
Figure 14:
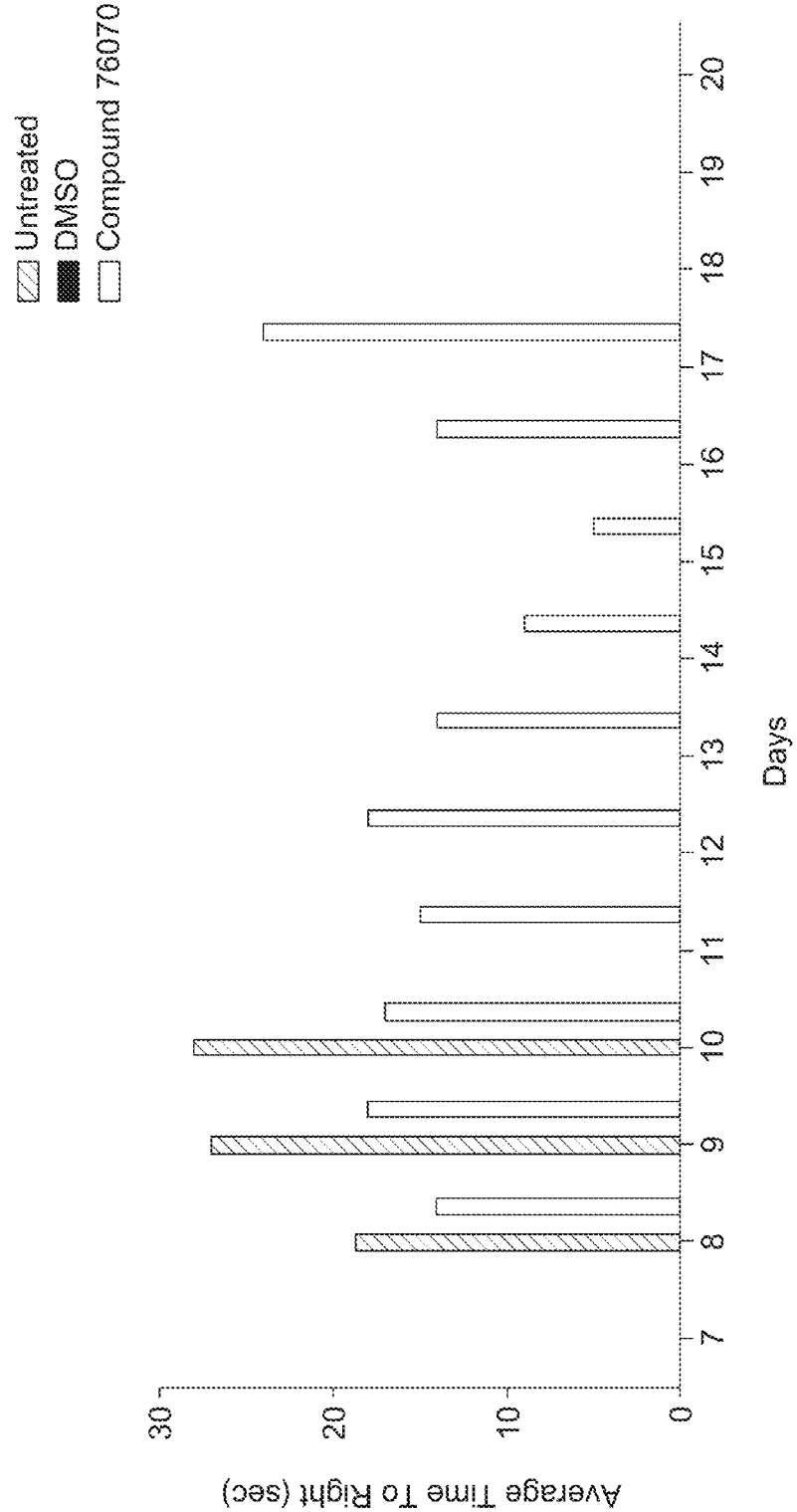
FIG. 14 shows the average time to right between postnatal day 7 and postnatal day 20 of the untreated, DMSO, and compound 76070-treated groups. Animals are placed on their backs and assayed for the time it requires for them to right themselves. Thirty (30) seconds or greater is considered a failure to right and scored as 30 sec.
Figure 15:
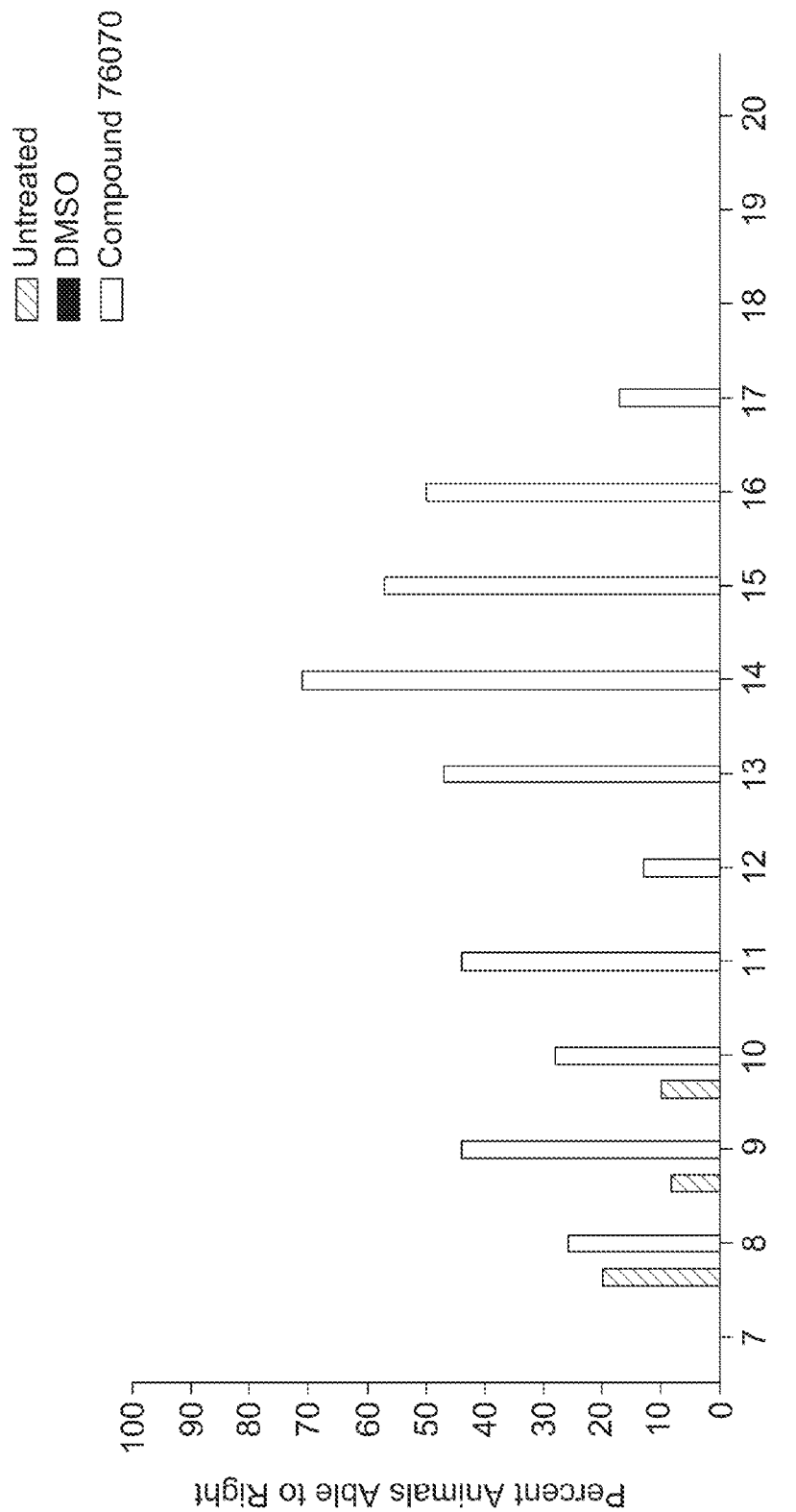
FIG. 15 shows the percentage of animals able to right between postnatal day 7 and postnatal day 20 of the untreated, DMSO, and compound 76070-treated groups.
Figure 16:
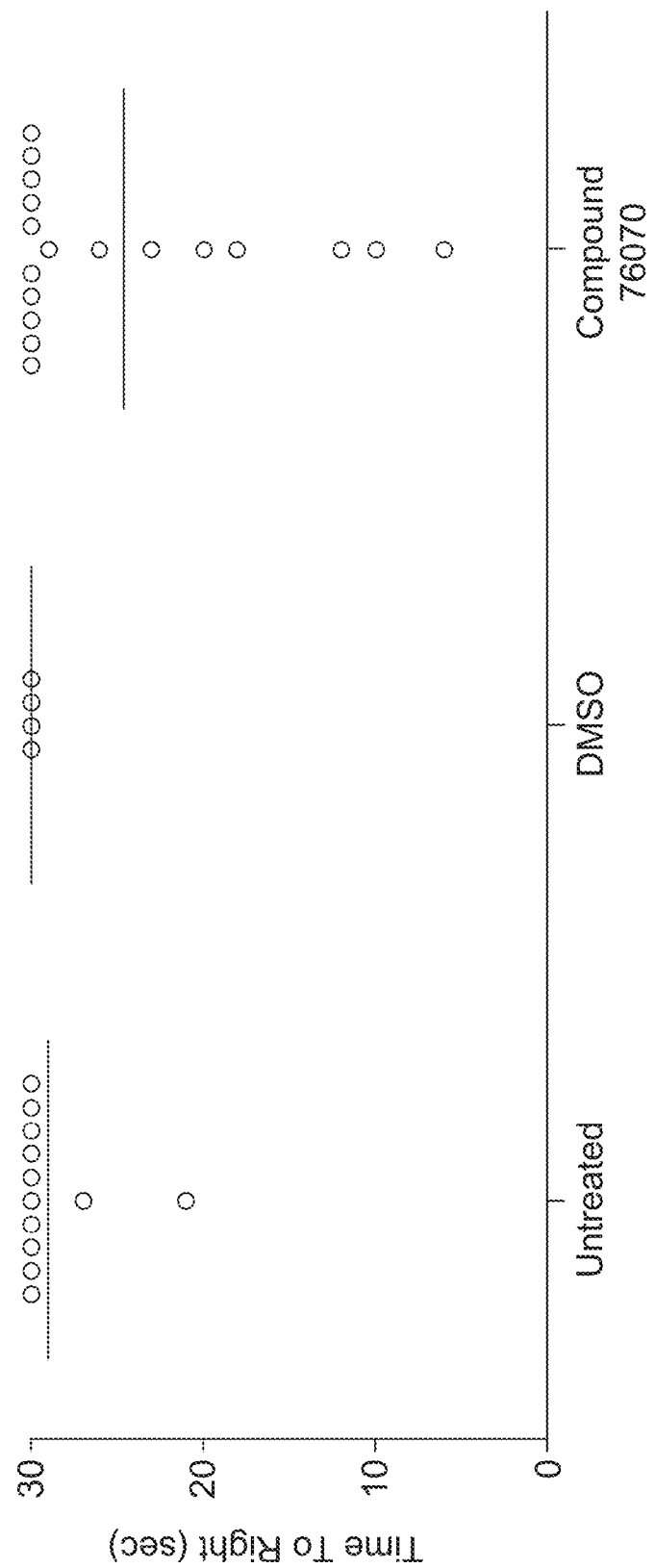
FIG. 16 shows the actual time to right on postnatal day 9 of untreated, DMSO, and compound 76070-treated groups.
Figure 17:
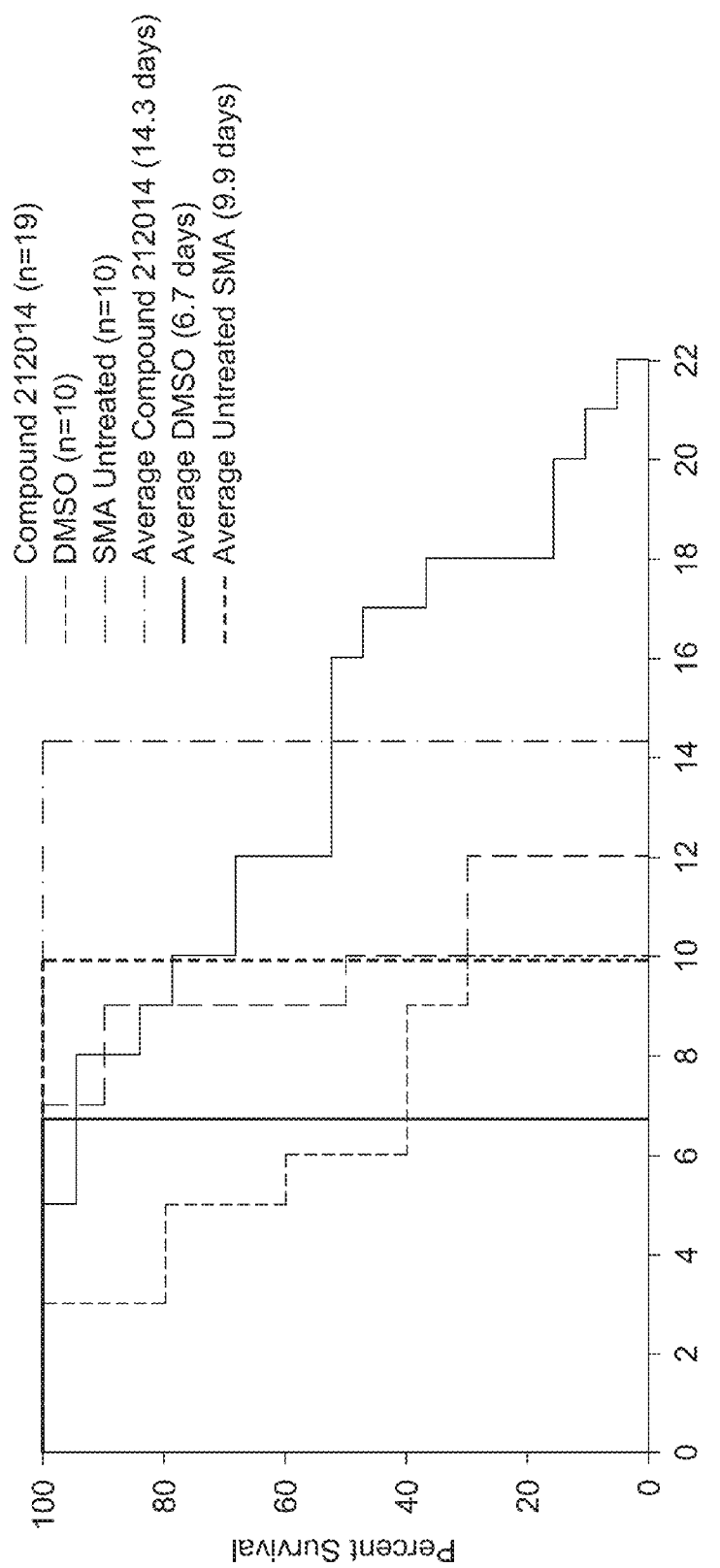
FIG. 17 shows survival proportions of animals in a mouse model of spinal muscular atrophy treated with compound 212014, DMSO, or untreated.
Figure 18:
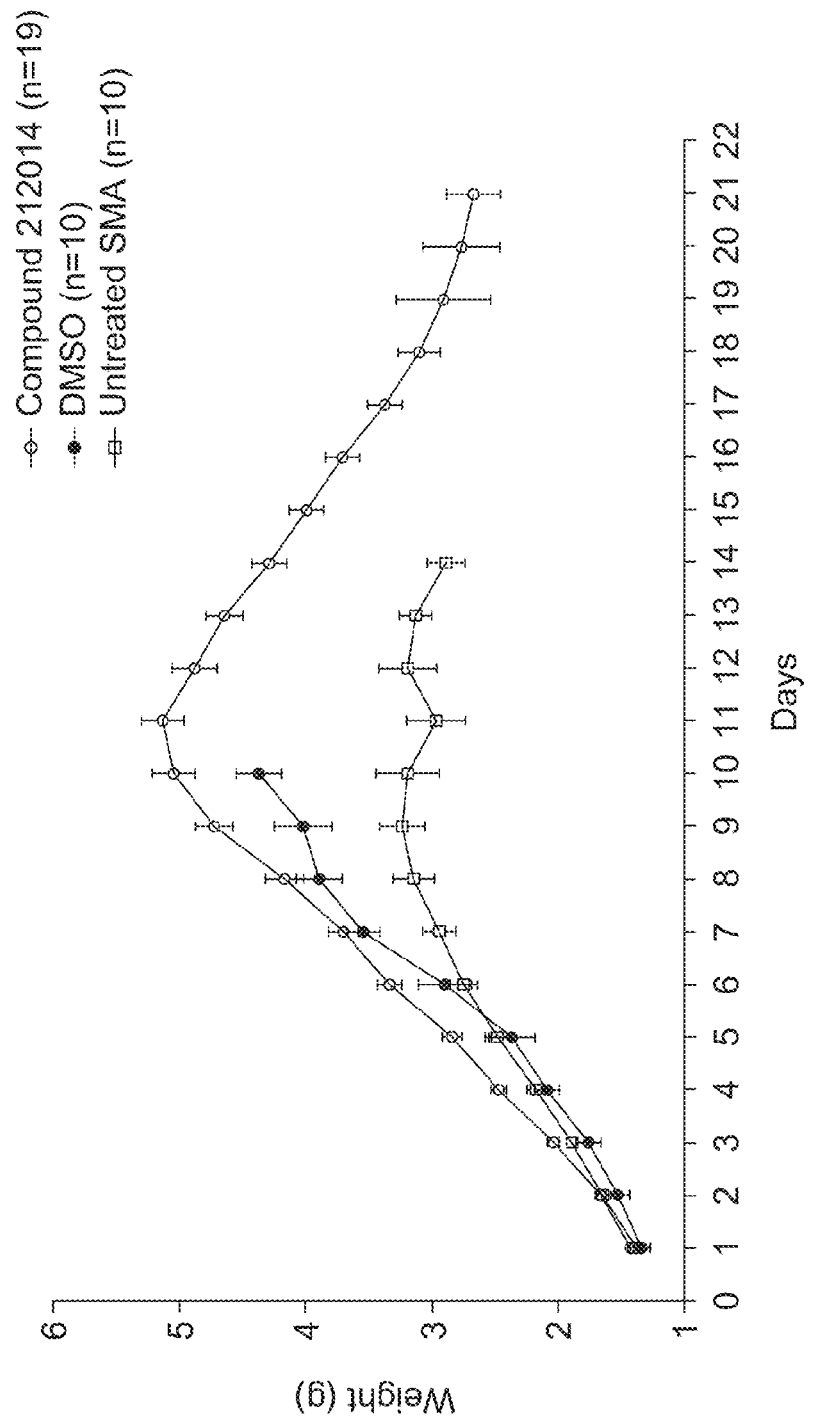
FIG. 18 shows average weights of animals in a mouse model of spinal muscular atrophy treated with compound 212014, DMSO, or untreated.
Figure 19:
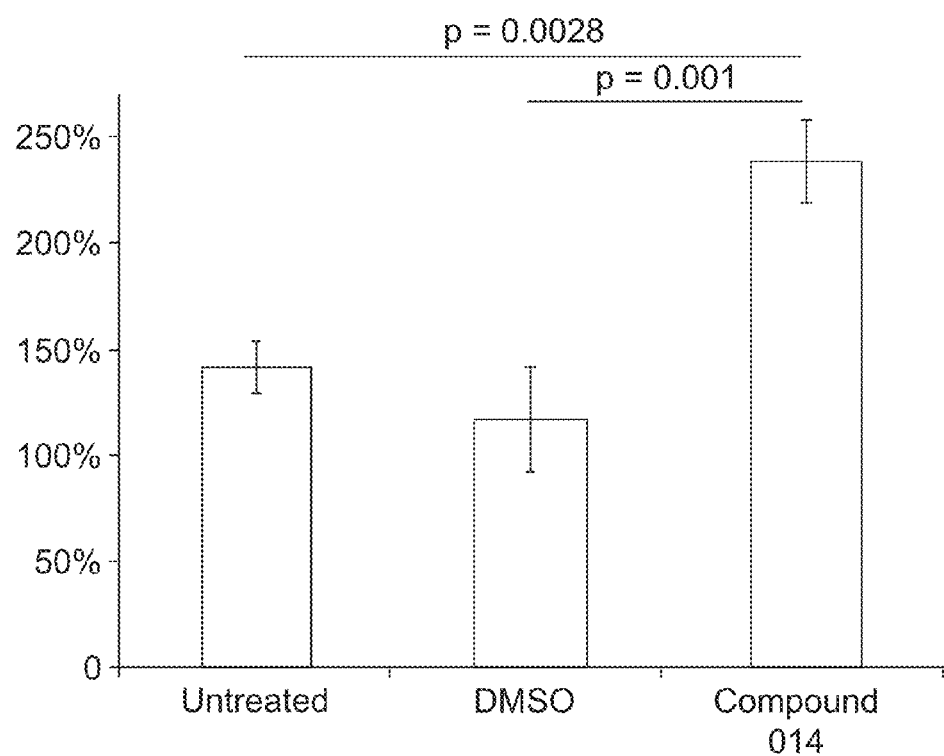
FIG. 19 shows percent weight gained from birth to peak of animals in a mouse model of spinal muscular atrophy treated with compound 212014, DMSO, or untreated.
Figure 20:
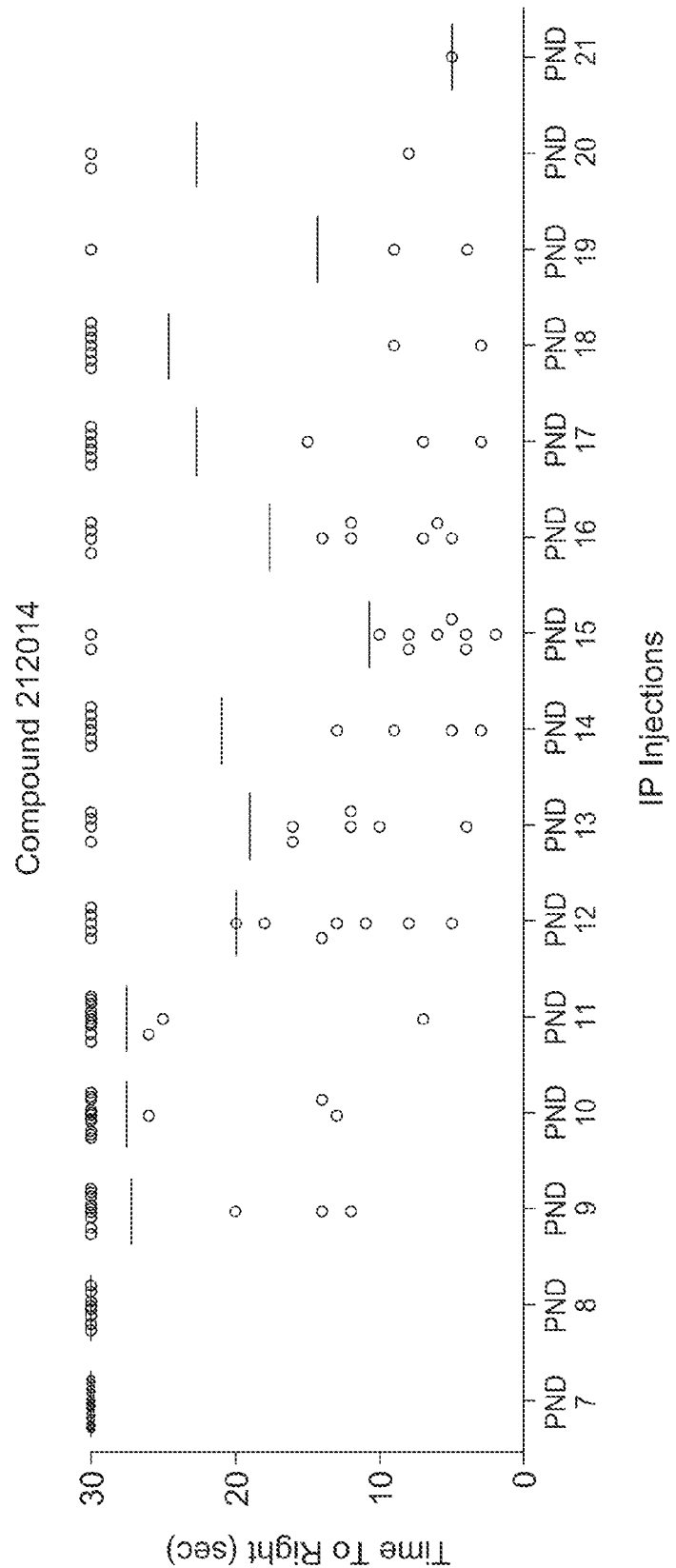
FIG. 20 shows actual time to right of the compound 212014-treated group.
Figure 21:
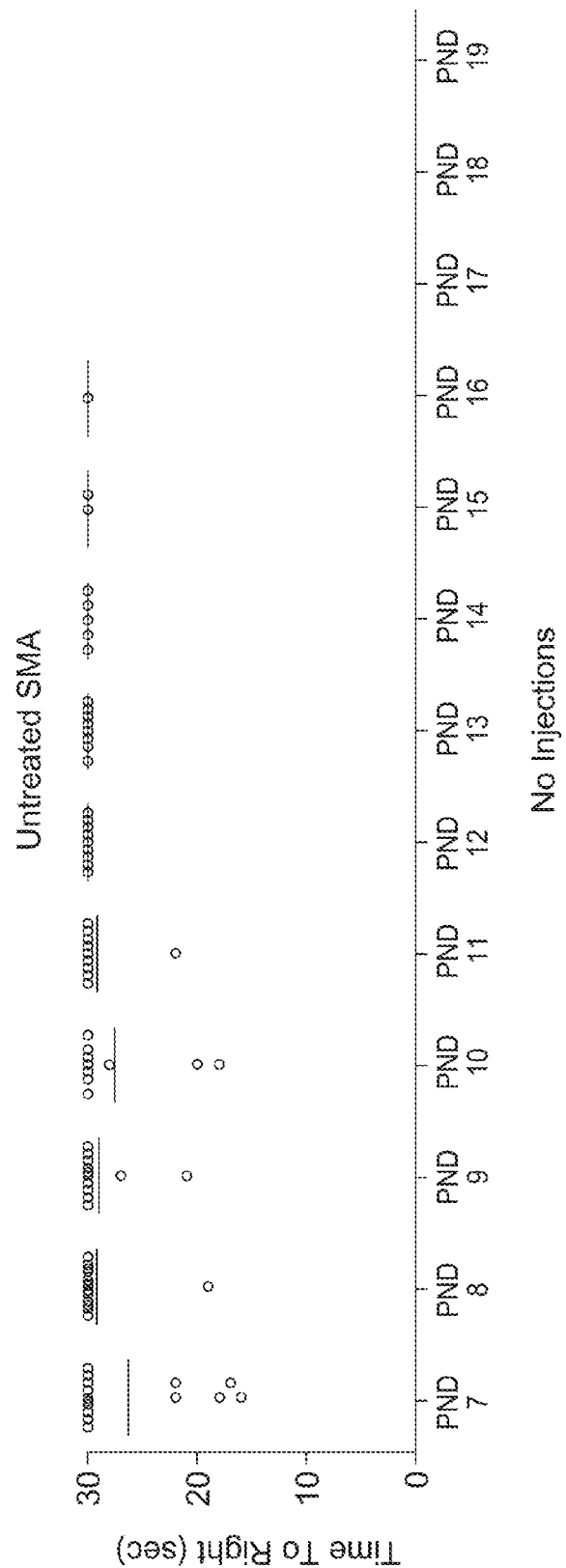
FIG. 21 shows actual time to right of the untreated group.
Figure 22:
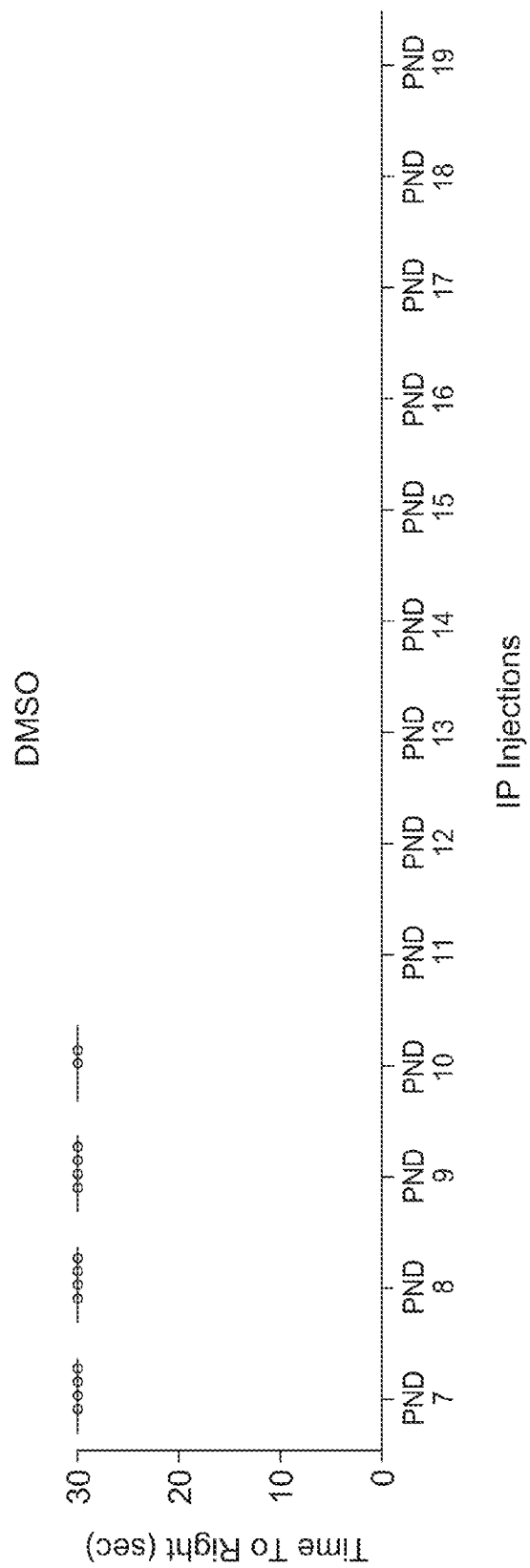
FIG. 22 shows actual time to right of the DMSO-treated group.
Figure 23:
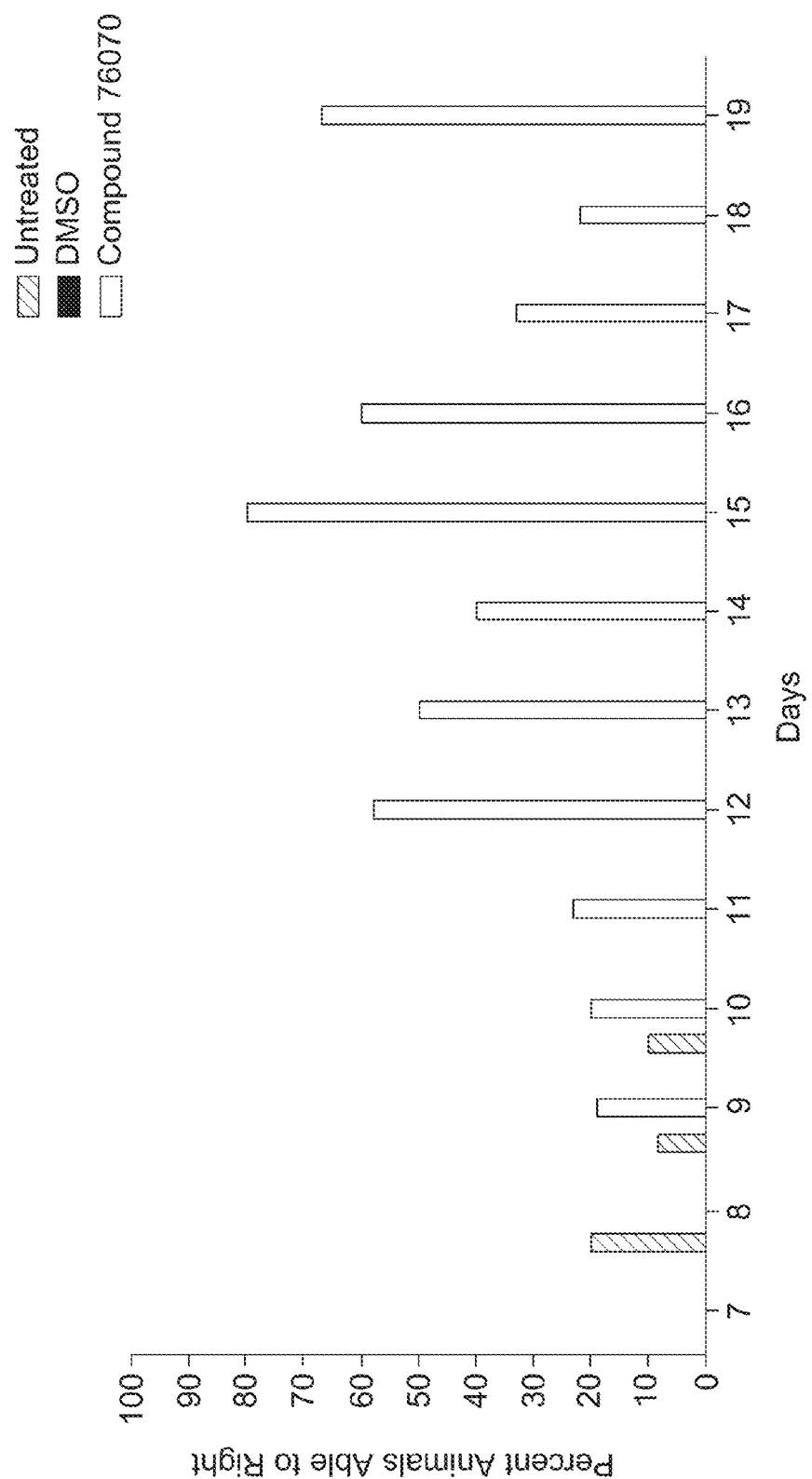
FIG. 23 shows percentage of animals able to right between postnatal day 7 and postnatal day 19 of the untreated, DMSO, and compound 212014-treated groups.
Figure 24:
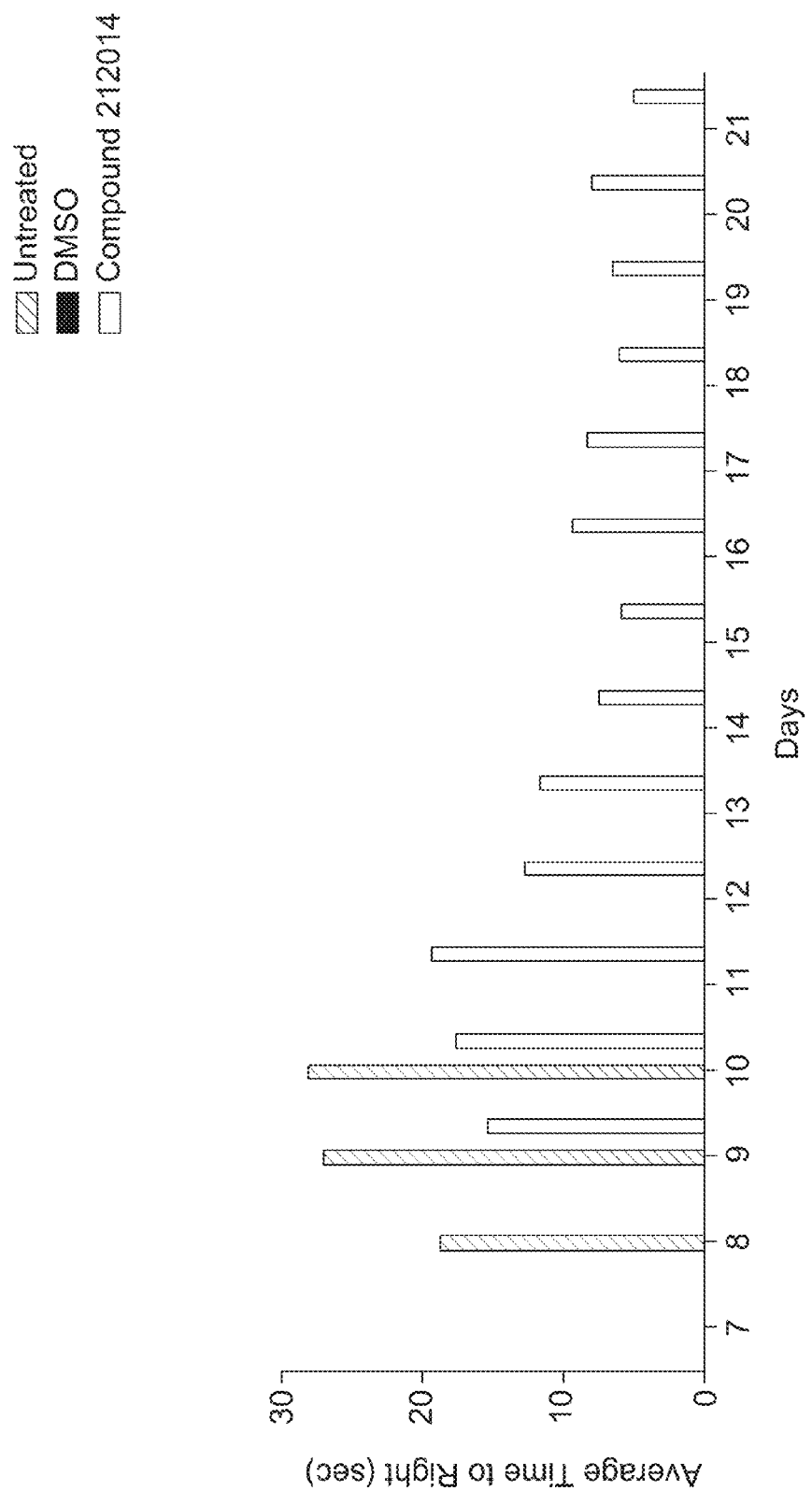
FIG. 24 shows the average time to right between postnatal day 7 and postnatal day 21 of the untreated, DMSO, and compound 212014-treated groups.

Luciferase expression was analyzed in the stable HEK293 cell lines containing the SMN1- and SMN2-luciferase reporters. In the initial stable mixed cell populations, mixed SMN1-luc cells displayed 30% more luciferase activity than the mixed SMN2-luc cells. A pair of clonal cell lines was isolated, clonal SMN1-luc and clonal-SMN2-luc, in which the clonal-SMN1-luc cell line has 50-fold higher luciferase activity when compared to clonal-SMN2-luc cell line (FIG. 2A). This range of expression provides a large window for potential activation of SMN2 expression with drug treatment. Since these reporters were designed for use in either high or low throughput screens, the dynamic range of activation is very important. The selection of SMN2-luc clones that maintain low levels of basal SMN-luciferase expression was instrumental in establishing this range of activation and was a dramatic improvement over not only the original C33a based reporter cell lines but also the mix population HEK293 SMN1-luc and SMN2-luc cell lines (FIG. 7).

Figure 2D:
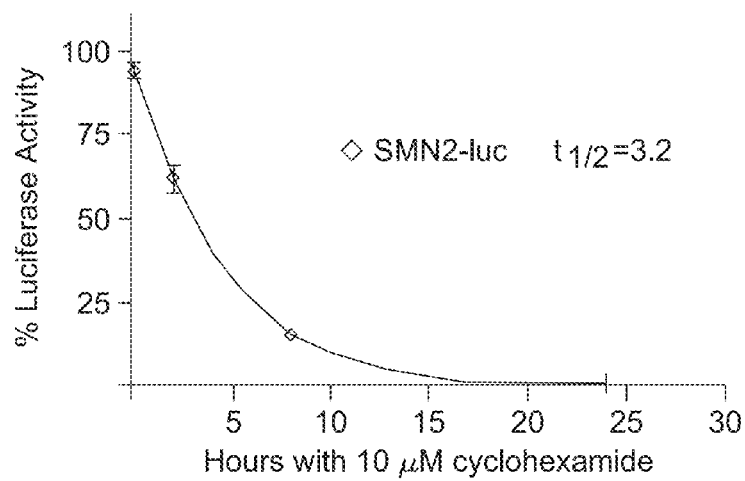
Figure 2B:
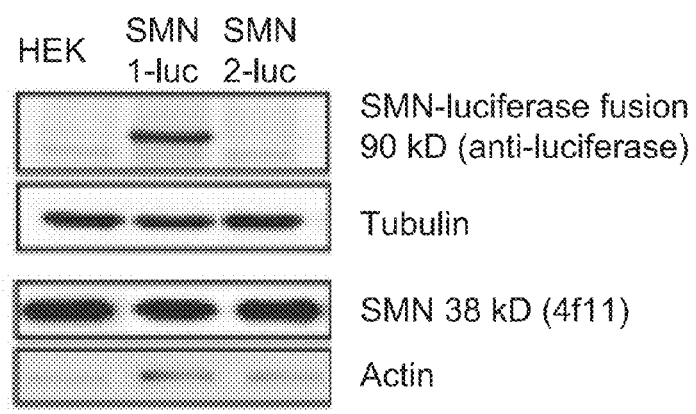

Expression of the SMN-luciferase protein fusion was confirmed by western blot (FIG. 2B). All cells express endogenous SMN (38 kD) but only the SMN1-luc cell line expresses detectable levels of the SMN-luciferase fusion protein. The SMN-luciferase fusion protein could only be detected in the SMN2-luc cell line upon induction with compounds that increase SMN expression (SAHA and sodium butyrate in FIG. 3B).

Figure 2C:
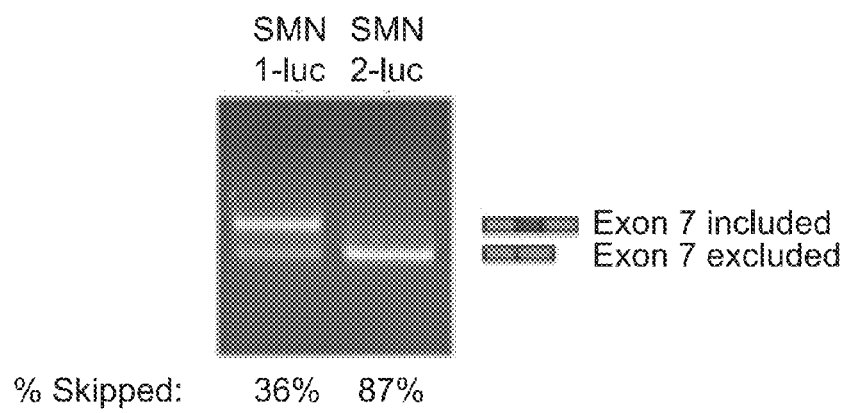

These clonal cell lines display the expected patterns of exon 7 inclusion in the reporter transcripts for both the SMN1-luc and SMN2-luc cell lines. Published studies have determined that 90% of transcripts from SMN1 include exon 7, while only 10-20% of transcripts from SMN2 include exon 7. In FIG. 2C, end-point RT-PCR for each cell line is shown and inclusion of exon 7 was calculated as 64% for SMN1-luc and 13% for SMN2-luc. By quantitative reverse transcription-PCR (qRT-PCR) using the primers illustrated in FIG. 4A, the percent inclusion for transcripts in each reporter was calculated more precisely; 95.1%±6.7 for SMN1-luc and 10.2%±0.9 for SMN2-luc. Using these primers, the number of copies of each reporter in these clonal cell lines was estimated. SMN1-luc has 1 copy of the episomal reporter per cell and the SMN2-luc cell line has about 10 copies of the reporter per cell.

To determine the half-life of the SMN-fusion protein in these cell lines, cells were treated with cycloheximide and assayed for residual luciferase activity for 24 hours. The luciferase activity in the SMN2-luc cell line had a $t_{1/2}$ of 3.2 hours (FIG. 2D). This matches well with published data for endogenous SMN protein. This data suggests that any changes in protein stability for the SMN-luciferase fusion protein would be easily detected within 24 to 48 hours.

When the cell-lines were tested for tolerance to DMSO, it was found the luciferase expression was virtually unchanged when the final DMSO concentration in the reaction ranged from 0-1%. Concentrations above 1% decreased luciferase activity and were very likely detrimental to cell viability. Compounds are routinely screened at a final DMSO concentration equal to or less than 0.1%. Basal activity and response to compounds did not vary with serial cell passage and was very reproducible after the clones were thawed from liquid nitrogen storage.

SMN-Luciferase Reporter Cell Response to Compound Treatment.

In this assay, cells were treated with compounds previously shown to increase SMN2 protein levels and luciferase expression read for counts per second (CPS) at an integration time of 100,000 µS (see Table 2A for detailed assay conditions). For comparison, all data points are expressed as percent increase over basal luciferase expression in the control cells.

Figure 3A:
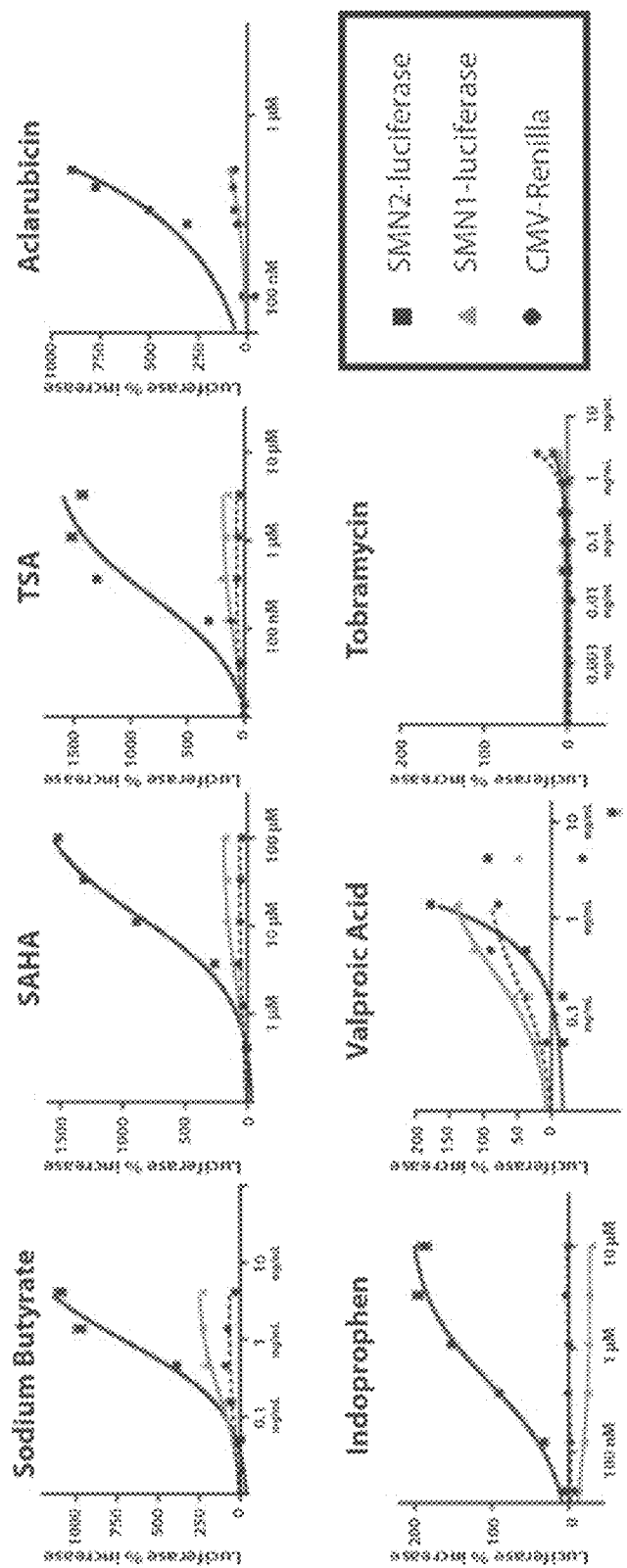
FIGS. 3A-3E show activity of known compounds in the reporter cells.

Compounds that were previously shown to increase SMN expression including SAHA, sodium butyrate, aclarubicin, TSA, indoprofen, and tobramycin were tested in the cell lines (FIG. 3A). These compounds were screened in both the SMN1-luc and SMN2-luc cell lines and % increase of luciferase activity was plotted for SMN1-luciferase, SMN2-luciferase, and the CMV driven internal renilla luciferase control. The activity for each compound, except tobramycin, matched or exceeded the published activities for these compounds (FIG. 3A and Table 4). Tobramycin displayed no response in these cell lines. Tobramycin is an aminoglycoside that increases stable SMN protein levels from the SMN2 gene through transcriptional read-through of the termination codon in exon 8. By design, the reporter requires the inclusion of exon 7 and the frameshift mutation therein to restore the reading frame for luciferase. In the absence of exon 7, luciferase is out of frame. Read-through will not correct the frame shift, so tobramycin cannot and did not increase SMN-luciferase protein levels in the SMN-luciferase reporter cell lines.

Figure 3B:
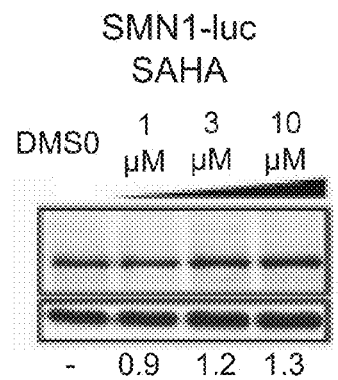
Figure 3D:
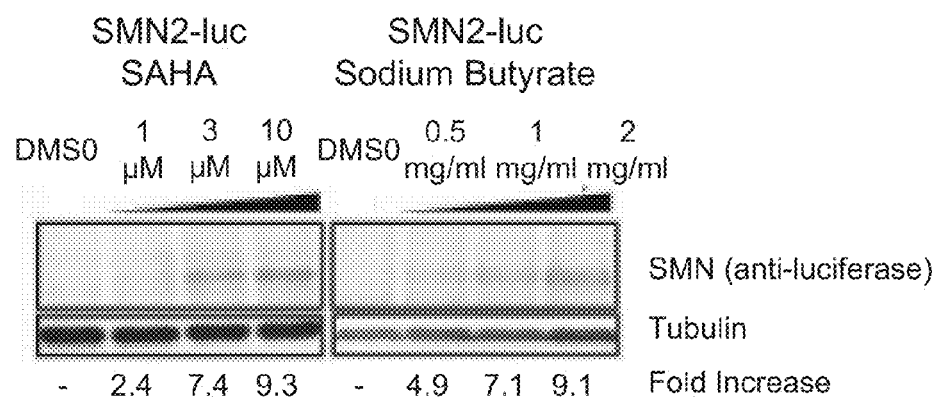
Figure 3C:
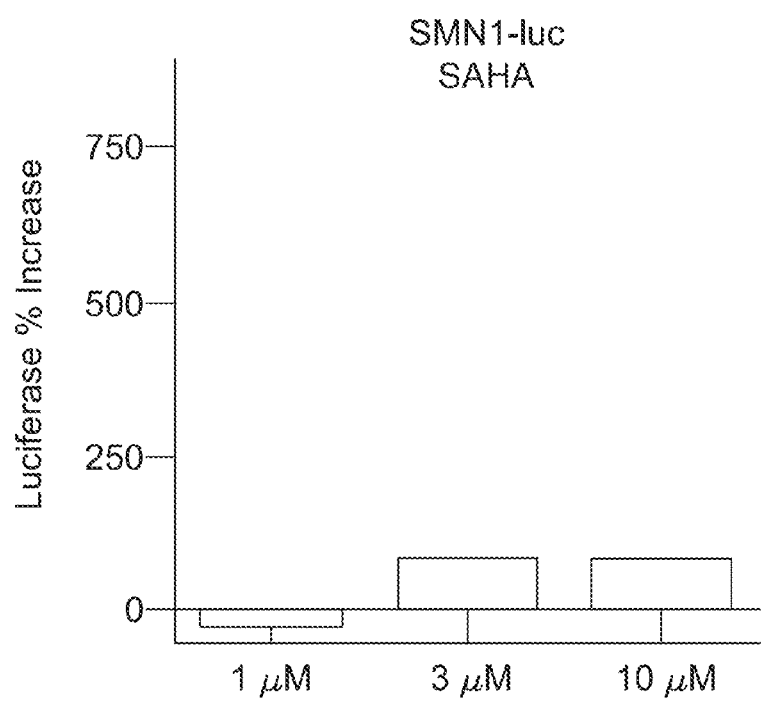
Figure 3E:
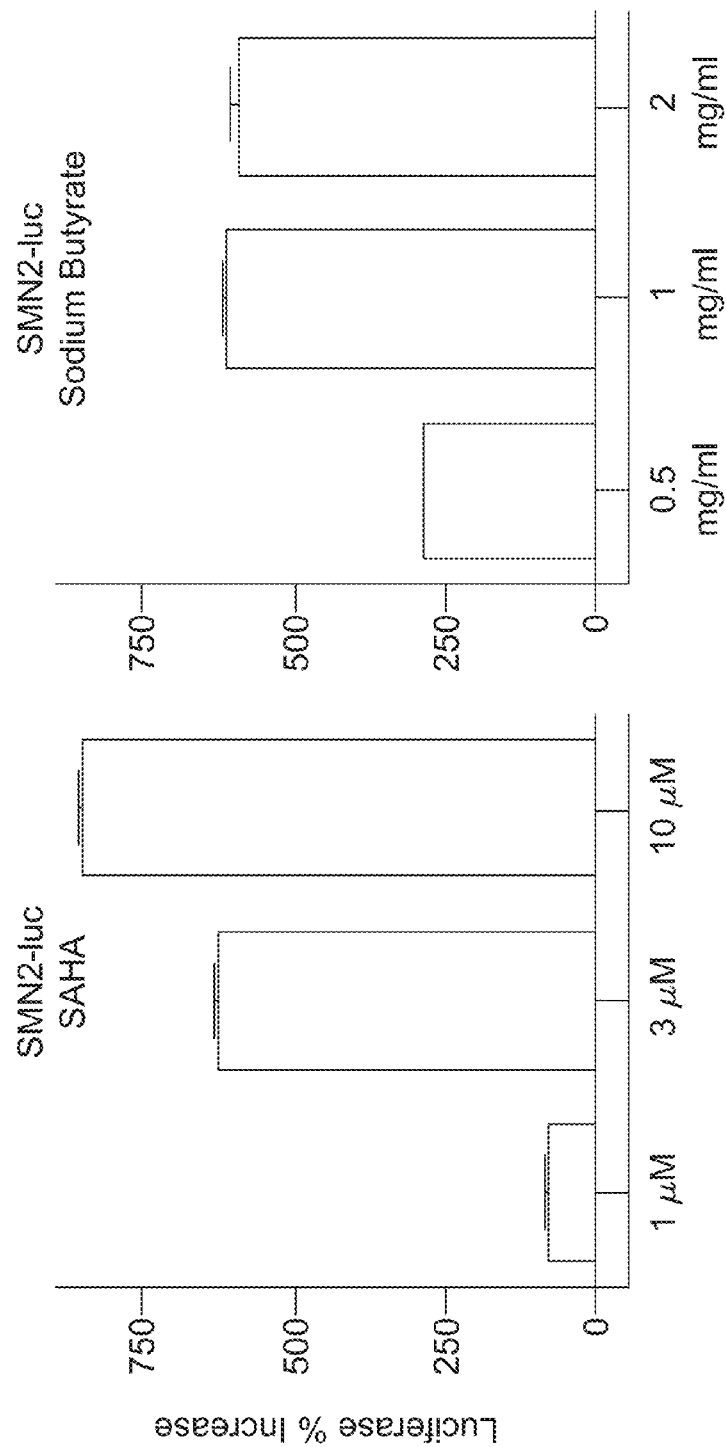

Changes in the SMN-luciferase fusion protein levels were confirmed with SAHA in both the SMN1-luc and SMN2-luc cell lines and with sodium butyrate in the SMN2-luc cell line. There was a moderate increase in SMN-luciferase protein in the SMN1-luc cell line with increasing SAHA (FIG. 3B), which corresponds to the increase in luciferase activity (FIG. 3C). A greater than 9-fold increase in SMN-luciferase protein was observed when the SMN2-luc cell line was treated with either SAHA or sodium butyrate (FIG. 3B). This protein increase corresponds to an increase in luciferase activity (FIG. 3C). These data confirm the correlation between luciferase activity and levels of full-length SMN-luciferase protein.

Analysis of mRNA in SMN2-Luciferase Reporter by qRT-PCR

Based on the new reporter design, it was predicted that this screen could detect increased SMN-luciferase protein levels caused by compounds that stimulate SMN2 transcription, exon 7 inclusion, or by increasing the half-life of the SMN mRNA or protein. Quantitative reverse transcriptase PCR (qRT-PCR) was used to analyze SMN-luciferase mRNAs. All assays used RNA from control and compound-treated SMN2-luc cells and primers pairs were chosen to amplify only the SMN-luciferase derived transcripts (FIG. 4A). A pair of primers were used that specifically detects both full-length (exon 7 included) and Δ7 (exon 7 excluded) SMN-luciferase transcripts (primers 1 and 3). To measure changes in exon 7 splicing efficiency, a primer pair was used that detects only the full-length (exon 7 included) SMN-luciferase transcript (primers 1 and 2).

For each sample, the percent increase in the amount of total SMN-luciferase transcripts (gray bar) and exon 7 included full-length SMN-luciferase transcripts (white bar) was plotted (FIG. 4). Compounds that increase transcription should show increased total SMN-luciferase transcripts (gray bar) with a proportional increase for exon 7 included transcripts (white bar), assuming that proper splicing of exon 7 is not rate limiting. Compounds that stimulate exon 7 inclusion should increase the amount of exon 7 included full-length transcript (white bar) detected with little to no change in the expression of total SMN-luciferase transcripts (gray bar). In these experiments, cells were treated with compound, harvested, and each cell pellet was divided for isolation of RNA and to assay luciferase activity. Each qRT-PCR sample was normalized to the housekeeping gene glyceraldehyde-3-phosphate dehydrogenase (GAPDH). The Pfaffl method was used to calculate the change in the amount of total SMN mRNA and determine whether compound treatments increased SMN transcripts.

With the pan HDAC inhibitor compounds SAHA, TSA, valproic acid, and sodium butyrate, increases in both the total and exon 7 included full-length SMN-luciferase transcripts were observed. The increase in total SMN-luciferase mRNA suggests that these compounds are increasing transcription, as would be expected for HDAC inhibitors. These compounds also display a dramatic increase in exon 7 included full-length transcripts that was greater in magnitude than the increase of total SMN-luciferase transcripts. This suggests that the HDAC inhibitors stimulate both SMN transcription and exon 7 recognition and inclusion. With aclarubicin at 300 nM, there was a potent increase in total SMN-luciferase transcript. This increase was accompanied by a lesser increase in exon 7 included transcript, indicating that aclarubicin increases transcription of SMN2. In a cell in which transcription is increased and splicing efficiency is unchanged, the percent increase in exon 7 included transcripts (gray bar) would be equal to the increase in total transcripts (white bar). In this case, the amount of exon 7 included transcripts has decreased even as the number of total transcripts increased. While aclarubicin does increase transcription, it appears to antagonize exon 7 recognition and inclusion. No consistent change in transcript levels was observed with indoprofen.

Genetic Modulation of SMN-Luciferase Protein Expression.

Figure 5B:
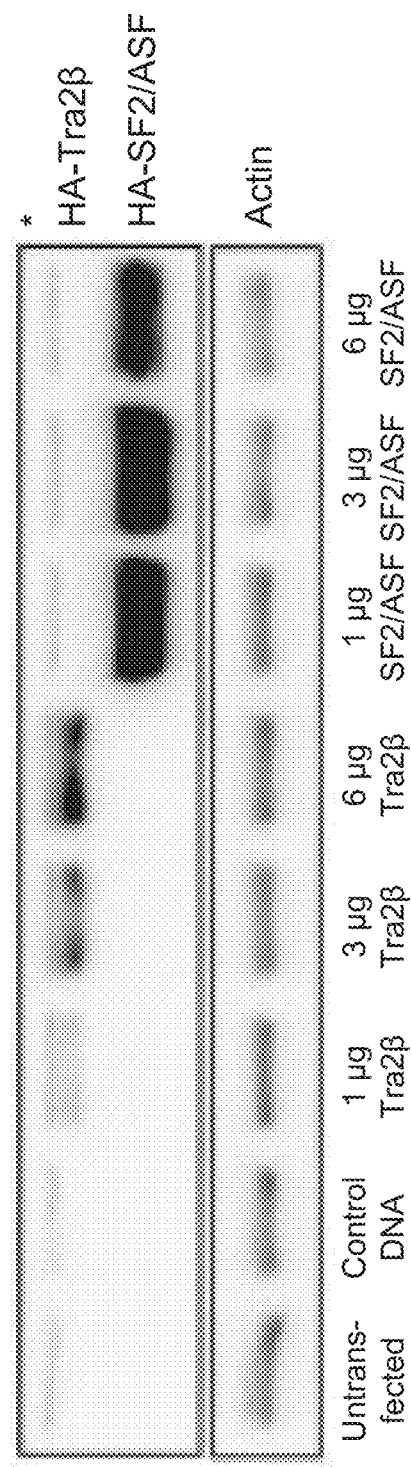

To confirm that the reporter could also respond to protein-induced changes in SMN expression, the splicing factors SF2/ASF and Tra2β were overexpressed. SF2/ASF recognizes a splicing enhancer that includes C in the +6 position at the 5' end of exon 7 in SMN1 to promote exon 7 inclusion. This interaction is antagonized by hnRNPA1, which binds at an overlapping splicing silencer that is created by the C to T transition at the +6 position in exon 7 in the SMN2 transcripts. Little to no increase in luciferase activity or change in RNA was observed in the SMN2-luciferase reporter cell-line (FIGS. 5A and C). This was expected, since hnRNPA1 has a high affinity for the silencing element in exon 7 of SMN2. Even at its highest levels of overexpression, SF2/ASF was unable to effectively stimulate the weakened enhancer element (FIG. 5B).

Tra2β is known to increase exon 7 inclusion in SMN2. Despite low levels of Tra2β expression (FIG. 5B), transfected Tra2β stimulated luciferase activity 2-3 fold greater than the negative control (FIG. 5A). With increasing amounts of Tra2β expressed there was up to a 6-fold increase in exon 7 included transcripts (white bar) with only a 1.4-fold increase in total transcripts (gray bar) (FIG. 5C). Analysis of the reporter mRNA confirmed that this SMN2-luciferase reporter detects increased inclusion of exon 7. From these data, the efficiency of exon 7 splicing of the reporter construct was calculated. Inclusion of exon 7 was 6.5% in the negative control sample, and no increase was observed with heterologous SF2/ASF expression. Exon 7 inclusion increased to 20% with the highest amount of transfected Tra2β. This validates the use of the SMN2-luciferase reporter cells to detect and quantify changes in exon 7 inclusion as well as changes in SMN expression in response to drug treatment and protein overexpression.

Assay Validation for High-Throughput

To evaluate the suitability of the SMN2-luc cells for HTS, test plates in both 96-well and 384-well format were prepared to determine signal strength, well-to-well percent coefficient of variation (% CV), amplitude of drug response, optimal cell density, and time of treatment. It was observed that these HEK derived cell lines displayed signal variability at low cell densities. As can be seen in Table 3, the correlation between luciferase signal and cell number was not linear. This is most clear in the 384-well format. At low cell densities, these cells grow slowly and are less responsive to treatment. A cell density of 50,000 or 10,000 per well was found to be optimal in the 96- and 384-well plates, respectively. To assess responsiveness, 500 g/mL sodium butyrate was selected as a stimulus. While sodium butyrate is an HDAC inhibitor that can cause non-specific transcriptional activation, it has been reported to stimulate SMN2 transcription and SMN2 exon 7 inclusion. Cells were treated for 24 or 48 hours and while increases in overall signal intensity were observed at the 48 hour time point, there was no difference in the % activation with sodium butyrate over control. However, there was an increase in the well-to-well % CV. Therefore 24 hours was chosen as the optimal time point for treatment. In the 96-well format, luciferase activity in the SMN2-luc cell increased by more than 3 fold with sodium butyrate and well-to-well % CV was 5% for both treated and control cells. In 384-well format, the % CV for control cells was 11% and 3% for treated. The "z" scores were calculated as 0.74 in 96-well and 0.78 in the 384-well formats, confirming that these assay conditions are suitable for HTS. These data are summarized in Table 3.

High-Throughput Screening and Hit Selection

An 115,000 compound library was screened using the screening protocol outlined in Table 2B. Each compound was added to a single well to a final concentration of ~2.2 µM. The final DMSO concentration in test and control wells was 0.13%. Each plate included negative controls of 0.13% DMSO (n=16) and positive controls of 500 mg/mL sodium butyrate with 0.13% DMSO (n=16). For the entire screen, the average % CV was 9.1% for DMSO alone and 9.8% for sodium butyrate treated wells. The average increase with 500 mg/mL was 3.1 fold or 210%. A hit was defined by activation of greater than 6 times the % CV; 60%. 462 hits were identified for an overall 0.4% hit rate.

Hit Confirmation

The 462 hits were re-plated from the screening library into master plates and then re-screened at 0.1, 1, and 5 µM in quadruplicate under conditions identical to the original HTS. Each compound was counter-screened against an unrelated luciferase control cell line that expresses luciferase from the minimal SV40 promoter and lacks an intron. This reporter should not respond to compounds that specifically affect the SMN promoter or compounds that change regulation of splicing. This allowed exclusion of compounds that may cause non-specific increases in luciferase expression. Of the 462 initial hits, 168 failed to reproduce at least 60% activation with the SMN2-luciferase reporter clone and were categorized as false positives (34% false positive rate). The remaining 294 compounds were limited to a high priority group of 19 scaffolds based on potency, strength of activation, dose dependency, specificity against luciferase control, and favorable chemical properties. All 19 compounds showed greater than 100% increase in reporter expression in the re-screen and stimulated the control reporter less than 40%. All 19 lacked overtly toxic functional groups and had chemical scaffolds that were tractable to chemical modification.

Compounds then re-screened in quadruplicate using a twelve-point dose response under the same conditions as the first two rounds of screening with both the SMN2-luc and SMN1-luc cell lines and using the SV40 luciferase control cell line. Since the SMN1 and SMN2 promoters are nearly identical, compounds that increased transcription of the SMN2-luc reporter would also increase transcription of the SMN1-luc reporter. The SMN1-luc cells should therefore be responsive to compounds that increase transcription from the SMN promoter. However, since the SMN gene in the SMN1 cells includes exon 7 efficiently (>90%) only a small increase in % activation is possible with compounds that stimulate exon 7 inclusion.

Figure 6B:
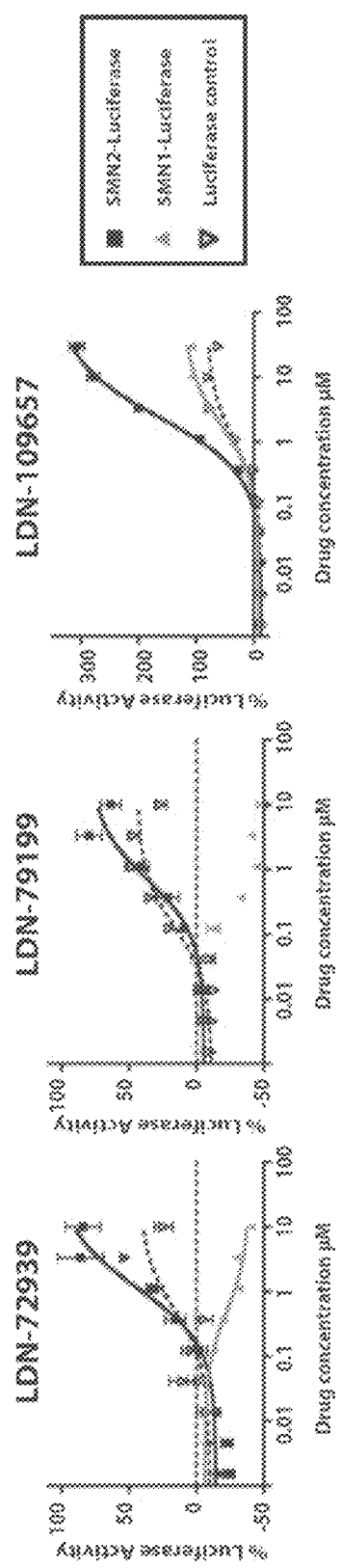

Overall, this panel of reporter cell lines offers the ability to discriminate between compounds that increase SMN expression through promoter and splicing specific mechanisms and rule out non-specific activators. For example LDN-109657 (FIG. 6B) increased SMN2-luciferase levels up to 300% (4 fold), but also increased luciferase expression in the SMN-luc1 reporter and, to a lesser extent, the luciferase control cells. These data suggest that this compound acts by either increasing SMN transcription or protein stabilization. Several compounds decreased SMN1-luciferase expressed in the SMN1-luc reporter cell line, but still increased SMN2-luciferase expression in the SMN2-luc cell line (LDN-72939 and LDN-79199 FIG. 6B). Of 17 compounds tested in the twelve-point dose response, 13 increased luciferase expression by >60%, four did not. Initial confirmation and characterization of three of these compounds, LDN-72939, LDN-79199, and LDN-109657 is reported here. Overall, the amplitude of SMN-luciferase increase varied, but all three compounds displayed an $EC_{50}$ in the low micromolar range; 1.1 µM, 750 nM, and 2.4 µM respectively.

To further evaluate the compounds, their effects on endogenous SMN protein levels were examined. Any cell containing even one copy of the SMN1 gene will produce enough SMN protein from SMN1 to mask the effects of the compounds on protein expression from the SMN2 gene. SMN null cells are not viable. The current standard is to test primary human fibroblast cells derived from a severe type 1 SMA patient. Most commonly used are the 3813 cells ($SMN1^{-/-}$; $SMN2^{+/+}$). These cells express very low basal levels of full-length SMN protein. For comparison, 3814 primary fibroblasts from the carrier parent ($SMN1^{+/-}$; $SMN2^{+/+}$) of this SMA infant are available. By quantitative immunoblot for full-length SMN protein, the heterozygous 3814 cells express 3-5 times more full-length SMN protein than in the 3813 cells[28] (FIG. 6C).

Figure 6C:
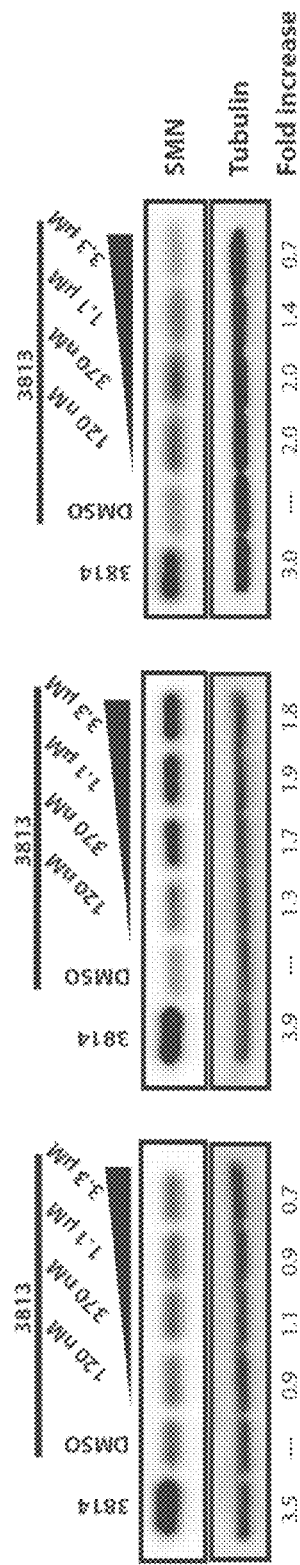

The selected compounds were tested for their effect on total endogenous SMN protein levels. 3813 fibroblasts were treated with varying concentrations of each compound for 72 hours (FIG. 6C). It was observed that these primary fibroblasts were sensitive to lower concentrations of compound than those used in the immortal reporter cell lines. Not all compounds increase endogenous SMN levels in the fibroblasts as well as others, regardless of their activity in the reporter cell lines. LDN-72939 was more active in the reporter cell line but showed little activity in the fibroblasts. LDN-79199 was less active in the reporter cells, but increased endogenous SMN level 2-fold at 370 nM. LDN-109657 displayed high activity in both the reporter assay and in fibroblasts. It increased endogenous SMN levels 2-fold at 120 nM. The decrease in SMN at higher concentrations (1.1 µM and 3.3 µM) is likely due to either poor solubility or a decrease in cell proliferation in the fibroblasts.

DISCUSSION

Spinal muscular atrophy is caused by an insufficient amount of functional, full-length SMN protein, usually resulting from deletion or disruption of both SMN1 alleles. All SMA patients retain at least one SMN2 gene and disease severity inversely correlates with SMN2 copy number. Since the SMN2 gene has the potential to express functional full-length SMN protein, it is an attractive therapeutic target for the treatment for SMA.

Figure 4B:
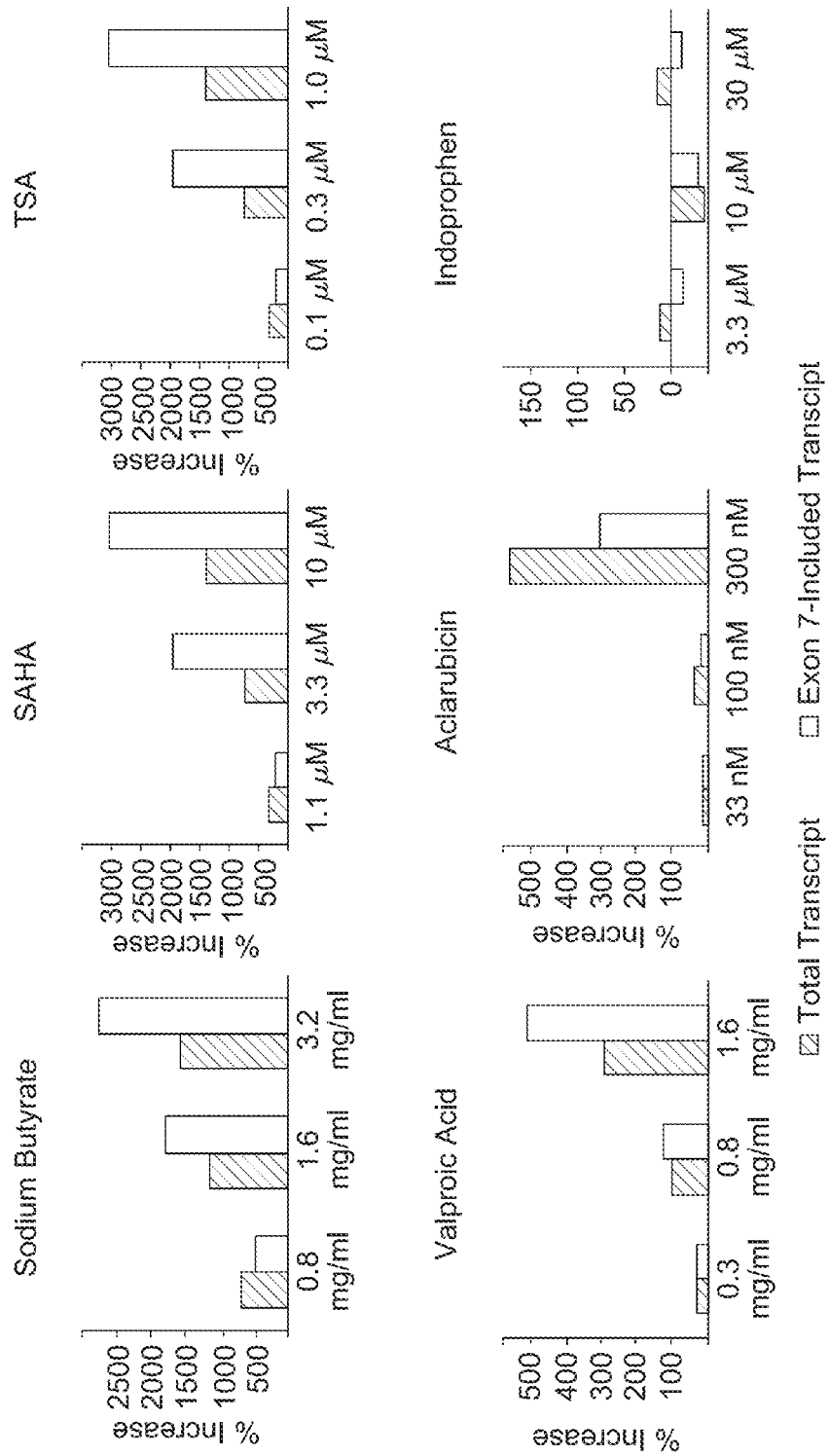

SMN2 expression can be increased through upregulation of transcription, promotion of exon 7 inclusion, stabilization of SMN2 mRNA and protein, or elevation of translation efficiency. HDAC inhibitors are known to influence transcription through histone deacetylation, which causes chromatin remodeling. HDAC inhibitors sodium butyrate, TSA, VPA, and SAHA all increased the amount of total and exon 7 included SMN2-luc reporter transcripts (FIG. 4B). Not only do these pan-HDAC inhibitors increase the quantity of SMN-luciferase transcripts, but a higher percentage of those transcripts are correctly spliced (FIG. 4B). This bimodal mechanism for pan-HDAC inhibitor regulation of SMN2 expression may explain the high potency and efficacy observed with these compounds, but may also predict other potential and possibly detrimental off-target effects.

Splicing of exon 7 is tightly regulated in both the SMN1 and SMN2 mRNAs. Conserved splicing enhancer and splicing silencing elements within exon 7 recruit splicing factors to the mRNA in order to regulate exon 7 recognition. Two of these splicing factors, hTra2β and SF2/ASF, were tested in the SMN2-luc reporter cell line. SF2/ASF had no impact on SMN2-luciferase expression (FIGS. 5A-5C). hTra2β binds to a splicing enhancer downstream of the hnRNP A1 site and can stabilize U1 snRNP binding at the 5' splice site of exon 7. This should increase exon 7 recognition and increase its splicing efficiency. An increase in SMN-luciferase activity was observed, and an increase in exon 7 included full-length SMN2-luciferase transcripts with hTra2(3 overexpression (FIGS. 5A-5C). The small increase in total reporter mRNA that accompanies this effect may be due to changes in the stability of the full-length, exon 7 included mRNA and not an actual increase in transcription of the reporter.

Disruption or regulation of the mRNA or protein turnover machinery could also increase steady-state SMN levels. This could be the mechanism for the activity of indoprofen, the aminoglycosides, and the quinazoline compounds. Indoprofen, a non-steroidal anti-inflammatory drug, was identified using a first generation reporter assay. Its mechanism of action has not been determined but recent evidence suggests that it has anti-terminator activity that may stabilize the SMN Δ7 protein. It is possible that the quinazoline compounds could increase the translation efficiency of SMN mRNA, as suggested by the recent report of interaction with the RNA decapping factor DcpS.

The SMN2 reporter cell line described herein combines the benefits of previous reporters and expands their potential to identify new regulatory circuitry for SMN2 expression. This assay has proven to be stable and reliable in 96, 384, and 1536-well formats and has been used in at three independent screening centers to identify novel modulators of SMN2 protein expression. Interestingly, the HTS at the NIH Chemical Genomics Center identified chemically distinct activators. In addition to novel compounds, these screens also identified compounds known to modify SMN2 protein expression, including indoprofen, resveratrol, hydroxyurea, and aclarubicin.

Characterization of LDN-72939, LDN-79199, and LDN-109657 are shown herein. Each of these compounds increases SMN-luciferase expression by at least 60%. LDN-79199 and LDN-109657 increased the levels of endogenous SMN protein in SMA-derived primary fibroblasts.

One of the drawbacks of the previous C33a reporter cell line was its high basal level of SMN-luciferase expression. This made detection of small increases in SMN-luciferase difficult. High basal level expression was initially encountered with the new HEK293 mixed-population reporter cells as well. By isolating and expanding clonal cell lines, cells could be selected for lower levels of basal SMN2-luciferase expression. Another issue with the previous C33a reporter was a progressive loss of luciferase signal intensity and decreased responsiveness to drug treatment. This variability in signal strength and drug response made the previous generation reporter unsuitable for high-throughput screening. The new HEK293 cell lines have maintained constant luciferase expression and reproducible induction with drug treatment over hundreds of population doublings. The improvement in this reporter assay is likely due to a combination of factors, including the new reporter design, the episomal nature of the vector, isolation of clonal cell lines, and use of HEK293 cells.

Spinal muscular atrophy is fatal for approximately 5,000 children each year in the United States, while tens of thousands of others live with limited mobility and progressive muscle weakness. There is presently no FDA approved drug for the treatment of spinal muscular atrophy. It has been established that the amount of SMN protein expressed has an inverse relationship to the severity to the disease. Compounds that safely increase SMN protein levels would dramatically improve the quality of life for individuals with SMA. The assay described herein is a valuable tool for identifying new compounds, characterizing existing compounds, and driving medicinal chemistry programs on active chemical scaffolds.

TABLE 2a

SMN-luciferase standard conditions - 96 well format

| Sequence | Parameter | Value | Description |
|---|---|---|---|
| 1 | Cells | 100 µL | 50,000 cells/well 96 TC treated white plate (See below for media [a]) |
| 2 | Time | 24 hours | 37° C. 5% $CO_2$ |
| 3 | Compound | 100 µL | With compound 2x concentration |
| 4 | Time | 24 hours | 37° C. 5% $CO_2$ |
| 5 | | | Remove media from wells |
| 6 | Reagent | 30 µL | SteadyGlo or DualGlo reagent (Promega) |
| 7 | Time | 30 sec | Room Temp |
| 8 | Detector | See below [b] | Wallac Envision |

TABLE 2b

SMN2-luciferase conditions for HTS - 384 well format

| Sequence | Parameter | Value | Description |
|---|---|---|---|
| 1 | Cells | 40 µL | 10,000 cells/well 384 TC treated white plate (See below for media [c]) |
| 2 | Time | 1 hour | 37° C. 5% $CO_2$ |
| 3 | Compound | 2.2 mM | Final of 0.13% DMSO |
| 4 | Time | 25 hours | 37° C. 5% $CO_2$ |
| 5 | Reagent | 25 µL | Perkin Elmer SteadyLite |
| 6 | Time | 30 minutes | Room Temp |
| 7 | Detector | See Below [d] | LJL Analyst HT |

[a]Media: phenol red free DMEM + 10% FBS and 1x Pen/Strep
[b]Wallac settings; luminescent read, 1.0 sec integration
[c]Media: Phenol-free DMEM + 10% FBSand 1x Pen/Strep
[d]LJL Analyst HT settings; luminescent read, 10 sec integration

TABLE 3

SMN2-luciferase Reporter validation with 0.5 mg/mL sodium butyrate

| | Format | | | | | | | |
|---|---|---|---|---|---|---|---|---|
| | 96-well validation | | | | 384-well validation | | | 384-well LDDN screen |
| Cells per well | 25,000 | 50,000 | 25,000 | 50,000 | 5,000 | 7,500 | 10,000 | 10,000 |
| Time point | 24 hrs | 24 hrs | 48 hrs | 48 hrs | 24 hrs | 24 hrs | 24 hrs | 24 hrs |
| Na-But RLU* ave | 2046 | 4798 | 3696 | 7505 | 1332 | 2832 | 39287 | 13894 |
| Na-But stdev | 138 | 234 | 536 | 756 | 131 | 329 | 1337 | 1272.55 |
| CV Na-But | 0.07 | 0.05 | 0.15 | 0.10 | 0.10 | 0.12 | 0.03 | 0.09 |
| DMSO RLU* ave | 684 | 1357 | 1425 | 2626 | 521 | 1008 | 8054 | 4677 |
| DMSO stdev | 44 | 64 | 61.7 | 248 | 98 | 123 | 910 | 387 |
| CV DMSO | 0.06 | 0.05 | 0.04 | 0.09 | 0.19 | 0.12 | 0.11 | 0.08 |

TABLE 3-continued

SMN2-luciferase Reporter validation with 0.5 mg/mL sodium butyrate

| | Format | | | | | | | |
|---|---|---|---|---|---|---|---|---|
| | 96-well validation | | | | 384-well validation | | | 384-well LDDN screen |
| S/B | 3.0 | 3.5 | 2.6 | 2.9 | 2.6 | 2.8 | 4.9 | 3.0 |
| Z' | 0.60 | 0.74 | 0.21 | 0.38 | 0.15 | 0.26 | 0.78 | 0.46 |

*Relative Light Units (RLU) vary based on luciferase substrate, plate reader, and protocol

TABLE 4

Cell-based reporter response to known SMN2 modulating compounds

| | Max. fold increase | $EC_{50}$ |
|---|---|---|
| Aclarubicin | 10 | 298 nM |
| Indoprofen | 3 | 460 nM |
| Sodium Butyrate | 10 | 1 mg/mL |
| Trichostatin A | 15 | 230 nM |
| SAHA | 15 | 12 μM |
| Valproic Acid | 2.5 | 10 mM |
| Tobramycin | inactive[a] | inactive[a] |

[a] Transcriptional read-through compounds do not score in this assay

TABLE 5

Activity of compounds tested in reporter assay

| Structure | LND # | % activation |
|---|---|---|
| | 66854 | 210% |
| | 66278 | 114% |
| | 107992 | 121% |
| 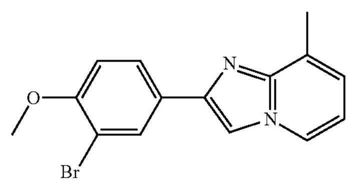 | 32531 | 108% |
| 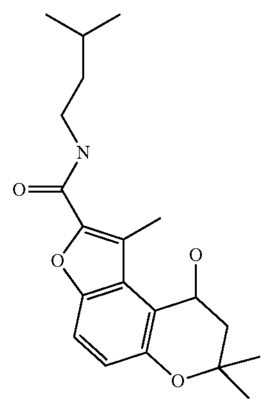 [SMILES: Cc1c(C(=O)NCCC(C)C)oc2ccc3c(c12)C(O)CC(C)(C)O3] | 79199 | 102% |
| 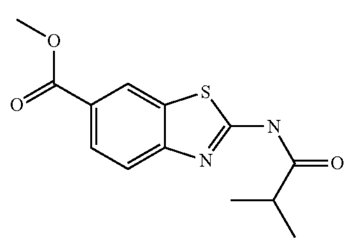 [SMILES: COC(=O)c1ccc2nc(NC(=O)C(C)C)sc2c1] | 110116 | 97% |
| 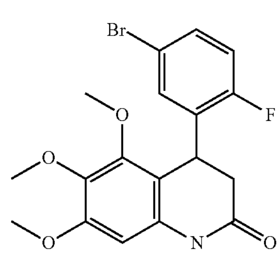 [SMILES: COc1cc2c(c(OC)c1OC)C(c1cc(Br)ccc1F)CC(=O)N2] | 76070 | 122% |

TABLE 5-continued

Activity of compounds tested in reporter assay

| Structure | LND # | % activation |
|---|---|---|
| (structure) | 79213 | 90% |
| (structure) | 98541 | 124% |
| (structure) | 110181 | 120% |
| (structure) | 110425 | 93% |
| (structure) | 67615 | 105% |
| (structure) | 109981 | 98% |
| (structure) | 75654 | 106% |
| (structure) | 109657 | 152% |
| (structure) | 75847 | 85% |
| (structure) | 72939 | 102% |
| (structure) | 75676 | 136% |

TABLE 6
| Compound | Structure | Active | Ec50 (μM) | Max % Activity |
|---|---|---|---|---|
| LDN-75654 | 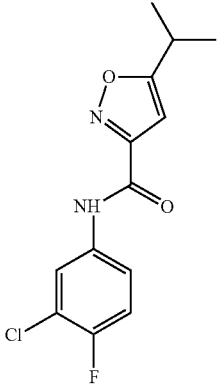 [SMILES: CC(C)c1cc(C(=O)Nc2ccc(F)c(Cl)c2)no1] | Yes | 1.8 | 274 |
| LDN-75676 | 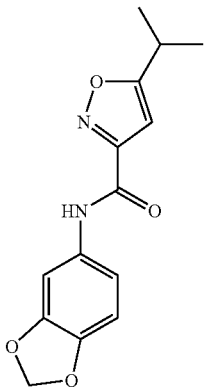 [SMILES: CC(C)c1cc(C(=O)Nc2ccc3c(c2)OCO3)no1] | Yes | 2.6 | 337 |
| LDN-75847 | 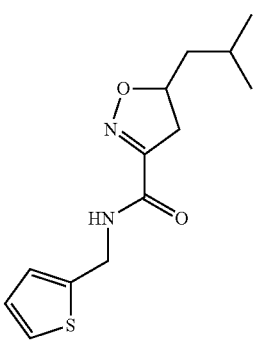 [SMILES: CC(C)CC1CC(C(=O)NCc2cccs2)=NO1] | Yes | 9.9 | 333 |
| LDN-75879 | 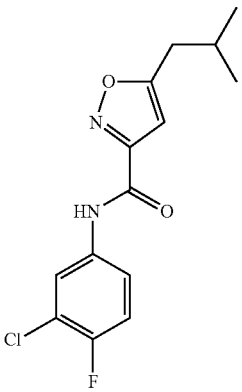 [SMILES: CC(C)Cc1cc(C(=O)Nc2ccc(F)c(Cl)c2)no1] | Yes | 1.5 | 180 |

TABLE 6-continued

Additional compounds tested in the reporter assay

| Compound | Structure | Active | Ec50 (μM) | Max % Activity |
|---|---|---|---|---|
| CAL-1 | (5-methyl-4,5-dihydroisoxazol-3-yl)-C(O)NH-(1,2,3,4-tetrahydronaphthalen-1-yl) | No | — | — |
| CAL-2 | (5-methyl-4,5-dihydroisoxazol-3-yl)-C(O)NH-(pyrazin-2-yl) | No | — | — |
| CAL-3 | (5-methyl-4,5-dihydroisoxazol-3-yl)-C(O)NH-(5-methylisoxazol-3-yl) | No | — | — |
| CAL-4 | (5-methyl-4,5-dihydroisoxazol-3-yl)-C(O)NH-(4-methoxyphenyl) | Yes | 8 | 211 |

TABLE 6-continued
Additional compounds tested in the reporter assay
| Compound | Structure | Active | Ec50 (μM) | Max % Activity |
|---|---|---|---|---|
| CAL-5 | 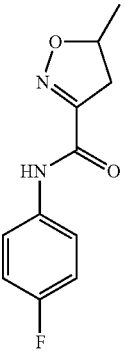 [SMILES: CC1CC(C(=O)Nc2ccc(F)cc2)=NO1] | Yes | 10 | 108 |
| CAL-6 | 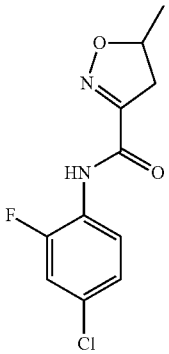 [SMILES: CC1CC(C(=O)Nc2ccc(Cl)cc2F)=NO1] | Yes | 6.5 | 180 |
| CAL-7 | 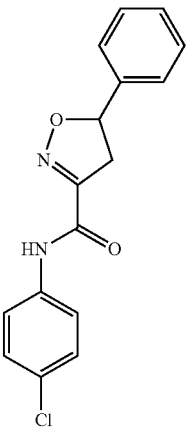 [SMILES: O=C(Nc1ccc(Cl)cc1)C1=NOC(c2ccccc2)C1] | Yes | 10 | 134 |
| CAL-8 | 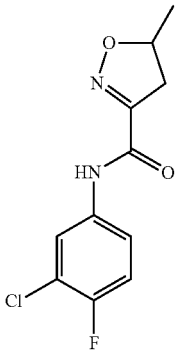 [SMILES: CC1CC(C(=O)Nc2ccc(F)c(Cl)c2)=NO1] | Weak | 10 | 120 |

TABLE 6-continued

Additional compounds tested in the reporter assay

| Compound | Structure | Active | Ec50 (μM) | Max % Activity |
|---|---|---|---|---|
| CAL-9 | 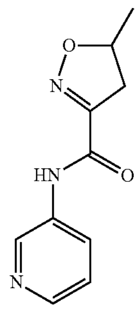 | No | — | — |
| CAL-10 | 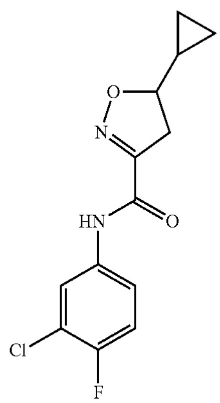 [SMILES: O=C(Nc1ccc(F)c(Cl)c1)C1=NOC(C2CC2)C1] | Yes | 2 | 250 |
| CAL-25 | 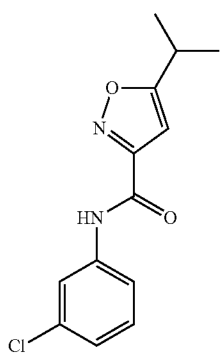 [SMILES: CC(C)c1cc(C(=O)Nc2cccc(Cl)c2)no1] | Yes | 0.35 | 237 |
| CAL-26 | 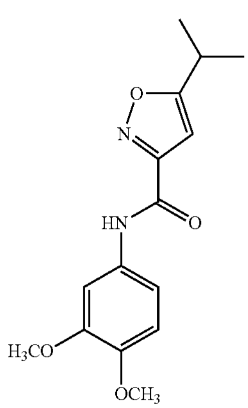 [SMILES: COc1ccc(NC(=O)c2cc(C(C)C)on2)cc1OC] | Yes | 94 | 160 |

TABLE 6-continued

Additional compounds tested in the reporter assay

| Compound | Structure | Active | Ec50 (μM) | Max % Activity |
|---|---|---|---|---|
| CAL-27 | 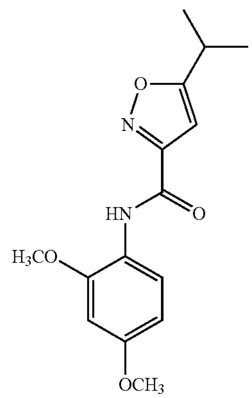 [SMILES: COc1ccc(NC(=O)c2cc(C(C)C)on2)c(OC)c1] | Yes | 1 | 125 |
| CAL-28 | 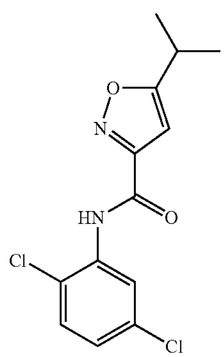 [SMILES: CC(C)c1cc(C(=O)Nc2cc(Cl)ccc2Cl)no1] | Yes | 0.9 | 59 |
| CAL-29 | 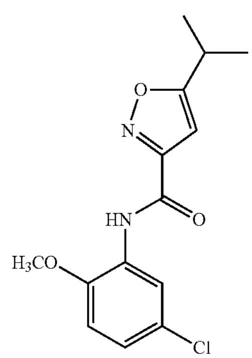 [SMILES: COc1ccc(Cl)cc1NC(=O)c1cc(C(C)C)on1] | No | — | — |
| CAL-30 | 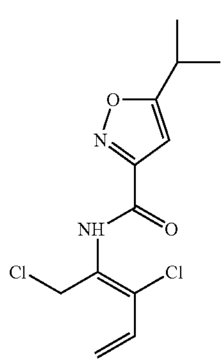 [SMILES: C=C/C(Cl)=C(\CCl)NC(=O)c1cc(C(C)C)on1] | No | — | — |

TABLE 6-continued

Additional compounds tested in the reporter assay

| Compound | Structure | Active | Ec50 (μM) | Max % Activity |
|---|---|---|---|---|
| CAL-31 | (5-isopropyl-isoxazole-3-carboxamide with 2-trifluoromethylphenyl) | Yes | 16 | 154 |
| CAL-33 | (5-cyclopropyl-isoxazole-3-carboxamide with benzo[d][1,3]dioxol-5-yl) | Yes | 1.7 | 217 |
| CAL-36 | (5-cyclopropyl-isoxazole-3-carbonyl-1,2,3,4-tetrahydroquinoline) | No | — | — |
| CAL-37 | (5-cyclopropyl-isoxazole-3-carboxamide, N-methyl-N-phenyl) | Yes | 30 | 143 |

TABLE 6-continued

Additional compounds tested in the reporter assay

| Compound | Structure | Active | Ec50 (μM) | Max % Activity |
|---|---|---|---|---|
| CAL-38 | 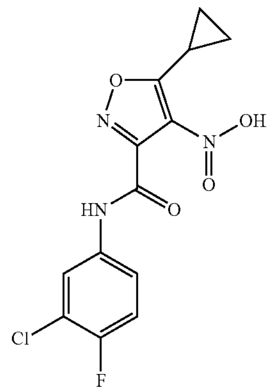 | No | — | — |
| CAL-42 | 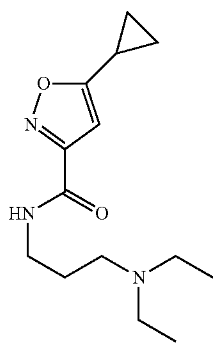 [SMILES: CCN(CC)CCCNC(=O)c1cc(C2CC2)on1] | No | — | — |
| LDN-211826 | 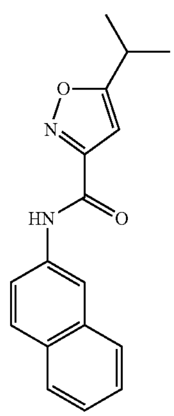 [SMILES: CC(C)c1cc(C(=O)Nc2ccc3ccccc3c2)no1] | Yes | 1.1 | 150 |
| LDN-211827 | 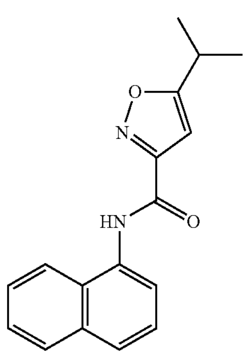 [SMILES: CC(C)c1cc(C(=O)Nc2cccc3ccccc23)no1] | No/Weak | — | — |

TABLE 6-continued

Additional compounds tested in the reporter assay

| Compound | Structure | Active | Ec50 (μM) | Max % Activity |
|---|---|---|---|---|
| LDN-211828 | 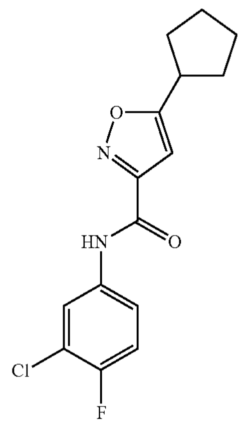 [SMILES: O=C(Nc1ccc(F)c(Cl)c1)c1cc(C2CCCC2)on1] | Yes | 20 | 100 |
| LDN-211829 | 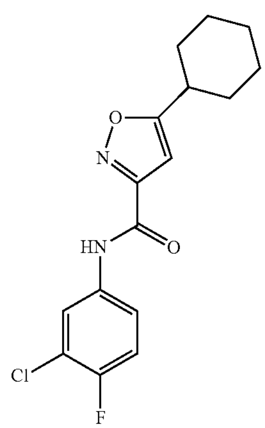 [SMILES: O=C(Nc1ccc(F)c(Cl)c1)c1cc(C2CCCCC2)on1] | No/Weak | — | — |
| LDN-211830 | 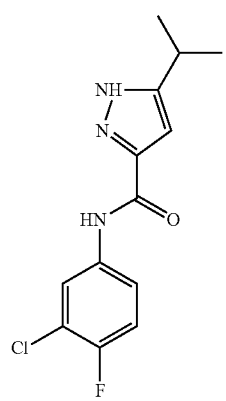 [SMILES: CC(C)c1cc(C(=O)Nc2ccc(F)c(Cl)c2)n[nH]1] | No | — | — |

TABLE 6-continued
Additional compounds tested in the reporter assay
| Compound | Structure | Active | Ec50 (μM) | Max % Activity |
|---|---|---|---|---|
| LDN-211831 | 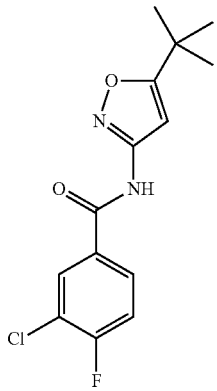 [SMILES: CC(C)(C)c1cc(NC(=O)c2ccc(F)c(Cl)c2)no1] | Yes | 3 | 150 |
| LDN-211832 | 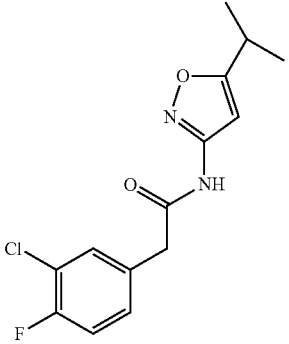 [SMILES: CC(C)c1cc(NC(=O)Cc2ccc(F)c(Cl)c2)no1] | No | — | — |
| LDN-211834 | 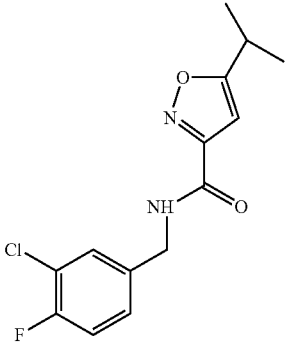 [SMILES: CC(C)c1cc(C(=O)NCc2ccc(F)c(Cl)c2)no1] | No | — | — |
| LDN-211854 | 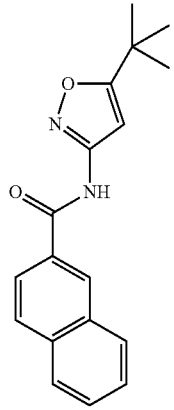 [SMILES: CC(C)(C)c1cc(NC(=O)c2ccc3ccccc3c2)no1] | Yes | 0.5 | 200 |

TABLE 6-continued
Additional compounds tested in the reporter assay
| Compound | Structure | Active | Ec50 (μM) | Max % Activity |
|---|---|---|---|---|
| LDN-211855 | 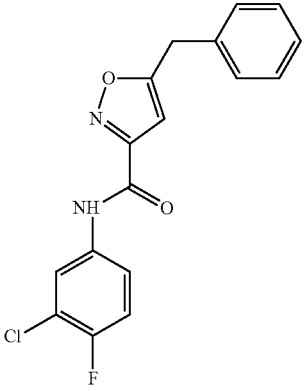 [SMILES: O=C(Nc1ccc(F)c(Cl)c1)c1cc(Cc2ccccc2)on1] | Yes | 1.5 | 125 |
| LDN-211856 | 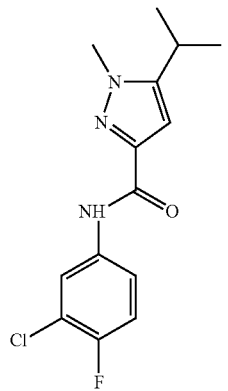 [SMILES: CC(C)c1cc(C(=O)Nc2ccc(F)c(Cl)c2)nn1C] | No | — | — |
| LDN-211857 | 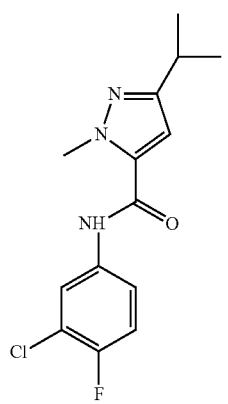 [SMILES: CC(C)c1cc(C(=O)Nc2ccc(F)c(Cl)c2)n(C)n1] | No | — | — |

TABLE 6-continued
Additional compounds tested in the reporter assay
| Compound | Structure | Active | Ec50 (μM) | Max % Activity |
|---|---|---|---|---|
| LDN-211858 | 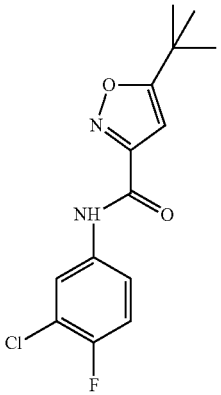 [SMILES: CC(C)(C)c1cc(C(=O)Nc2ccc(F)c(Cl)c2)no1] | No | — | — |
| LDN-211859 | 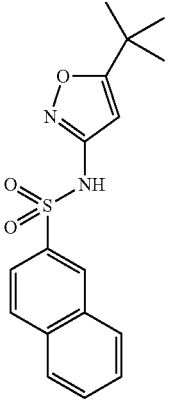 | No | — | — |
| LDN-211860 | 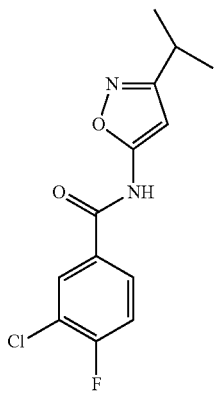 [SMILES: CC(C)c1cc(NC(=O)c2ccc(F)c(Cl)c2)on1] | Yes | 2.5 | 125 |

TABLE 6-continued
Additional compounds tested in the reporter assay
| Compound | Structure | Active | Ec50 (µM) | Max % Activity |
|---|---|---|---|---|
| LDN-211861 | 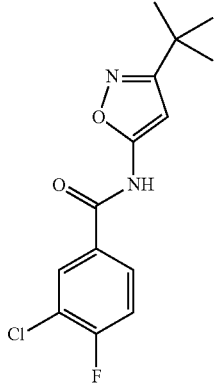 [SMILES: CC(C)(C)c1cc(NC(=O)c2ccc(F)c(Cl)c2)on1] | Yes | 3.7 | 100 |
| LDN-211862 | 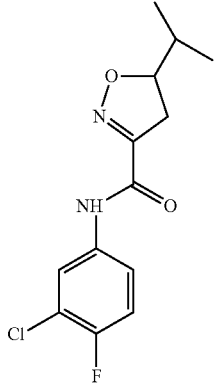 [SMILES: CC(C)C1CC(C(=O)Nc2ccc(F)c(Cl)c2)=NO1] | Nonspecific | — | — |
| LDN-211906 | 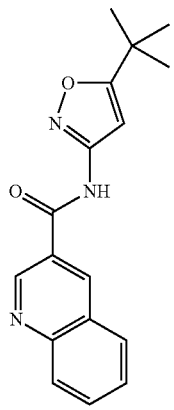 [SMILES: CC(C)(C)c1cc(NC(=O)c2cnc3ccccc3c2)no1] | Yes | 0.8 | 250 |

TABLE 6-continued

Additional compounds tested in the reporter assay

| Compound | Structure | Active | Ec50 (μM) | Max % Activity |
|---|---|---|---|---|
| LDN-211907 | 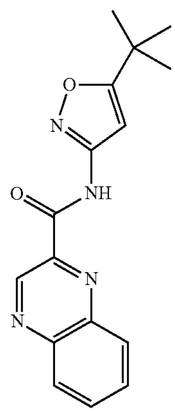 | No/Weak | — | — |
| LDN-211908 | 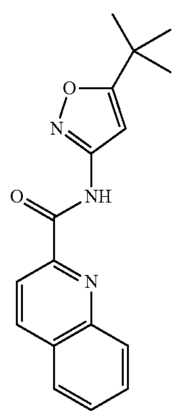 [SMILES: CC(C)(C)c1cc(NC(=O)c2ccc3ccccc3n2)no1] | No/Weak | — | — |
| LDN-211909 | 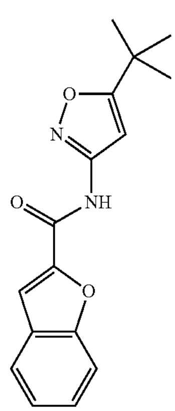 [SMILES: CC(C)(C)c1cc(NC(=O)c2cc3ccccc3o2)no1] | No/Weak | — | — |

TABLE 6-continued
Additional compounds tested in the reporter assay
| Compound | Structure | Active | Ec50 (μM) | Max % Activity |
|---|---|---|---|---|
| LDN-211910 | 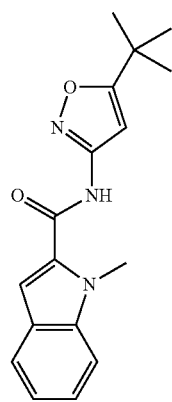 [SMILES: Cn1c(C(=O)Nc2cc(C(C)(C)C)on2)cc2ccccc21] | Yes | 0.7 | 100 |
| LDN-211911 | 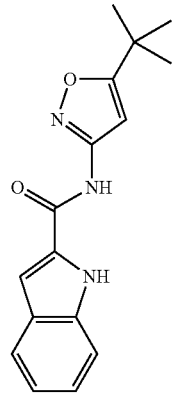 [SMILES: CC(C)(C)c1cc(NC(=O)c2cc3ccccc3[nH]2)no1] | Yes | 0.4 | 175 |
| LDN-211912 | 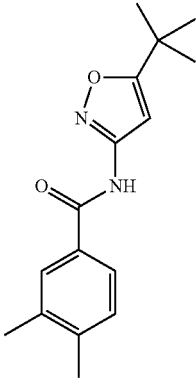 [SMILES: Cc1ccc(C(=O)Nc2cc(C(C)(C)C)on2)cc1C] | Yes | 1.1 | 150 |

TABLE 6-continued
Additional compounds tested in the reporter assay
| Compound | Structure | Active | Ec50 (μM) | Max % Activity |
|---|---|---|---|---|
| LDN-211981 | 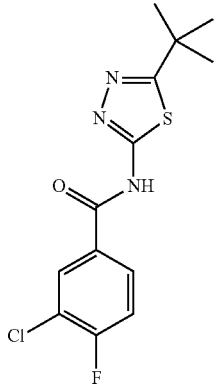 [SMILES: CC(C)(C)c1nnc(NC(=O)c2ccc(F)c(Cl)c2)s1] | Yes | 5.9 | 100 |
| LDN-211982 | 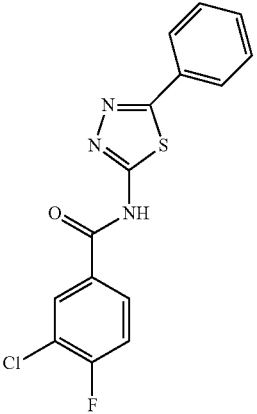 [SMILES: O=C(Nc1nnc(-c2ccccc2)s1)c1ccc(F)c(Cl)c1] | No | — | — |
| LDN-211983 | 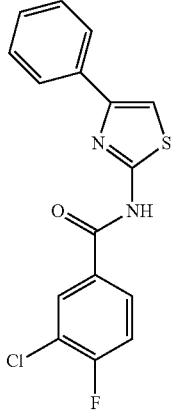 [SMILES: O=C(Nc1nc(-c2ccccc2)cs1)c1ccc(F)c(Cl)c1] | No | — | — |

TABLE 6-continued

Additional compounds tested in the reporter assay

| Compound | Structure | Active | Ec50 (μM) | Max % Activity |
|---|---|---|---|---|
| LDN-211984 | 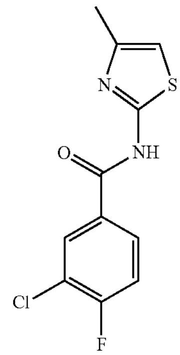 [SMILES: Cc1csc(NC(=O)c2ccc(F)c(Cl)c2)n1] | Yes | 2.1 | 200 |
| LDN-211985 | 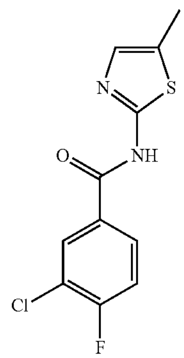 [SMILES: Cc1cnc(NC(=O)c2ccc(F)c(Cl)c2)s1] | Yes | 0.8 | 150 |
| LDN-211986 | 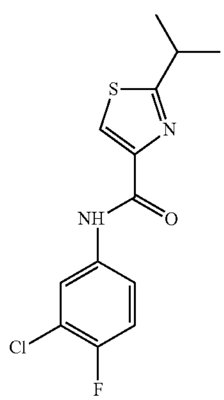 | Yes | 1.5 | 100 |
| LDN-211992 | 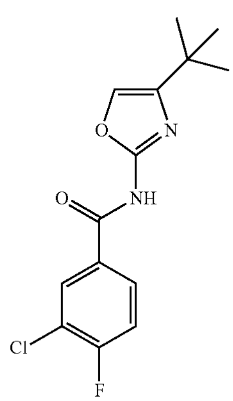 [SMILES: CC(C)(C)c1coc(NC(=O)c2ccc(F)c(Cl)c2)n1] | Yes | 0.15 | 100 |

TABLE 6-continued

Additional compounds tested in the reporter assay

| Compound | Structure | Active | Ec50 (μM) | Max % Activity |
|---|---|---|---|---|
| LDN-212011 | 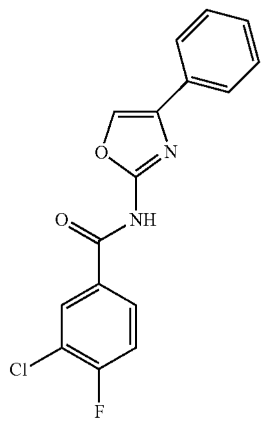 [SMILES: O=C(Nc1nc(-c2ccccc2)co1)c1ccc(F)c(Cl)c1] | No | — | — |
| LDN-212012 | 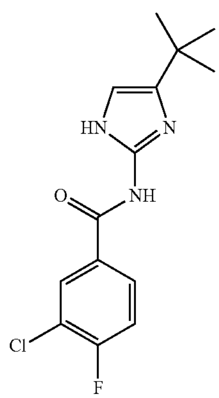 [SMILES: CC(C)(C)c1c[nH]c(NC(=O)c2ccc(F)c(Cl)c2)n1] | No | — | — |
| LDN-212013 | 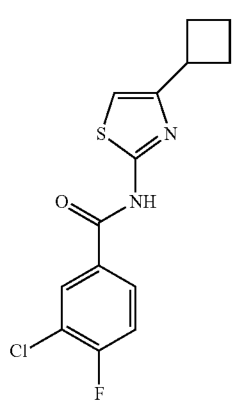 [SMILES: O=C(Nc1nc(C2CCC2)cs1)c1ccc(F)c(Cl)c1] | Yes | 0.5 | 100 |

TABLE 6-continued

Additional compounds tested in the reporter assay

| Compound | Structure | Active | Ec50 (μM) | Max % Activity |
|---|---|---|---|---|
| LDN-212014 | 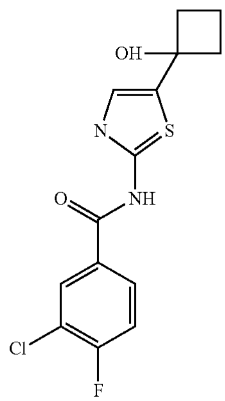 | Yes | 0.5 | 180 |
| LDN-212015 | 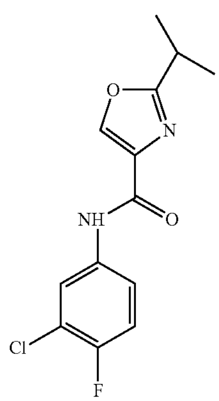 [SMILES: CC(C)c1nc(C(=O)Nc2ccc(F)c(Cl)c2)co1] | Yes | 1.7 | 100 |
| LDN-212016 | 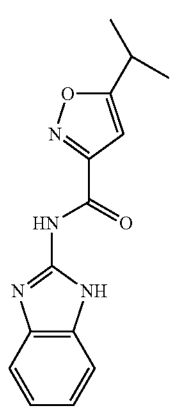 [SMILES: CC(C)c1cc(C(=O)Nc2nc3ccccc3[nH]2)no1] | Yes | 0.3 | 250 |

TABLE 6-continued

Additional compounds tested in the reporter assay

| Compound | Structure | Active | Ec50 (μM) | Max % Activity |
|---|---|---|---|---|
| LDN-212026 | 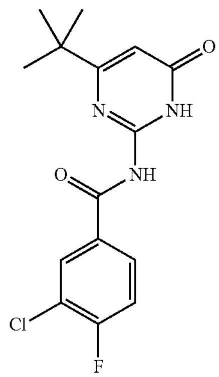 [SMILES: CC(C)(C)c1cc(=O)[nH]c(NC(=O)c2ccc(F)c(Cl)c2)n1] | No | — | — |
| LDN-212255 | 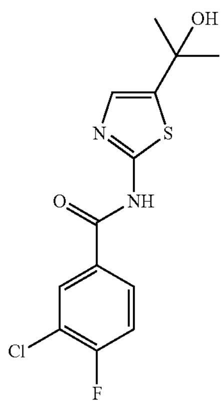 [SMILES: CC(C)(O)c1cnc(NC(=O)c2ccc(F)c(Cl)c2)s1] | Yes | 0.4 | 117 |
| LDN-212256 | 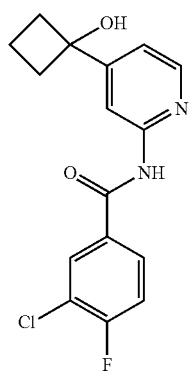 [SMILES: O=C(Nc1cc(C2(O)CCC2)ccn1)c1ccc(F)c(Cl)c1] | Yes | 0.4 | 114 |
| LDN-213766 | 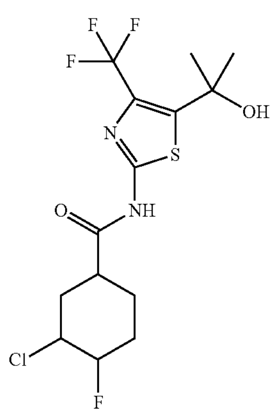 [SMILES: CC(C)(O)c1sc(NC(=O)C2CCC(F)C(Cl)C2)nc1C(F)(F)F] | No | — | — |

TABLE 6-continued

Additional compounds tested in the reporter assay

| Compound | Structure | Active | Ec50 (μM) | Max % Activity |
|---|---|---|---|---|
| LDN-214095 | 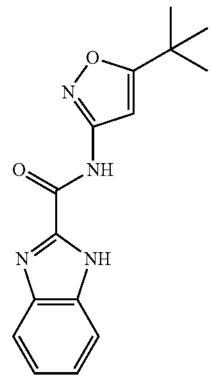 [SMILES: CC(C)(C)c1cc(NC(=O)c2nc3ccccc3[nH]2)no1] | No | — | — |
| LDN-214098 | 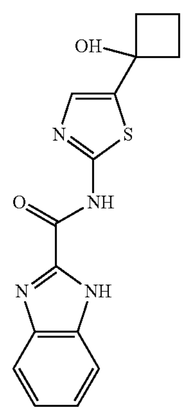 [SMILES: O=C(Nc1ncc(C2(O)CCC2)s1)c1nc2ccccc2[nH]1] | Yes | 0.15 | 200 |
| LDN-76070 | 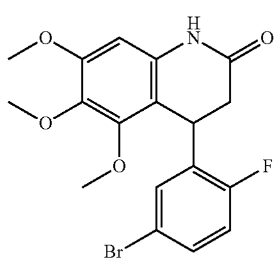 | Yes | 6.6 | 198 |
| LDN-76158 | 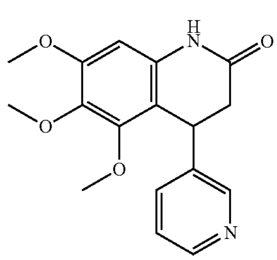 [SMILES: COc1cc2c(c(OC)c1OC)C(c1cccnc1)CC(=O)N2] | No | — | — |

TABLE 6-continued
Additional compounds tested in the reporter assay
| Compound | Structure | Active | Ec50 (μM) | Max % Activity |
|---|---|---|---|---|
| LDN-76515 | 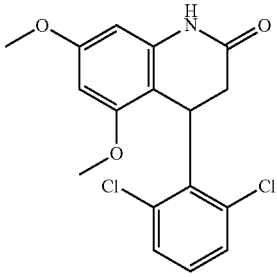 [SMILES: COc1cc2c(c(OC)c1)C(c1c(Cl)cccc1Cl)CC(=O)N2] | No | — | — |
| LDN-76074 | 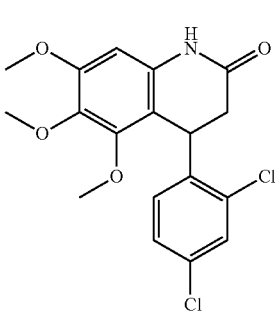 [SMILES: COc1cc2c(c(OC)c1OC)C(c1ccc(Cl)cc1Cl)CC(=O)N2] | No/Weak | — | — |
| CAL-21 | 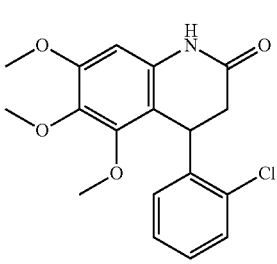 [SMILES: COc1cc2c(c(OC)c1OC)C(c1ccccc1Cl)CC(=O)N2] | Yes | 251 | 14 |
| CAL-22 | 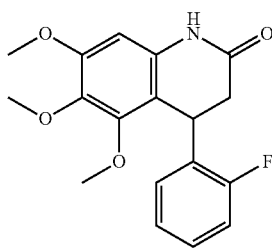 [SMILES: COc1cc2c(c(OC)c1OC)C(c1ccccc1F)CC(=O)N2] | No | — | — |
| CAL-23 | 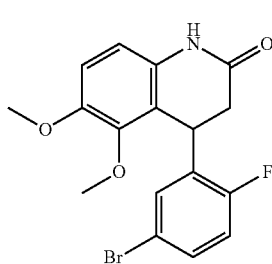 [SMILES: COc1ccc2c(c1OC)C(c1cc(Br)ccc1F)CC(=O)N2] | No | — | — |

TABLE 6-continued

Additional compounds tested in the reporter assay

| Compound | Structure | Active | Ec50 (μM) | Max % Activity |
|---|---|---|---|---|
| CAL-50 | 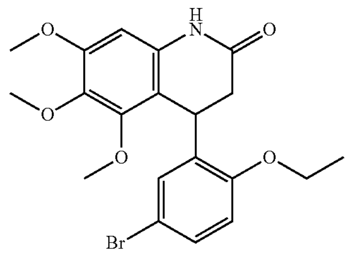 [SMILES: CCOc1ccc(Br)cc1C1CC(=O)Nc2cc(OC)c(OC)c(OC)c21] | No | — | — |
| CAL-51 | 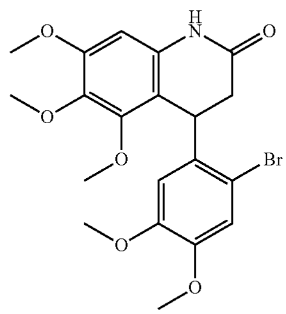 [SMILES: COc1cc(Br)c(C2CC(=O)Nc3cc(OC)c(OC)c(OC)c32)cc1OC] | No | — | — |
| CAL-52 | 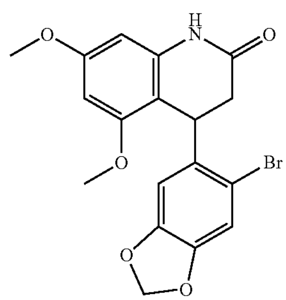 [SMILES: COc1cc2c(c(OC)c1)C(c1cc3c(cc1Br)OCO3)CC(=O)N2] | No | — | — |
| CAL-53 | 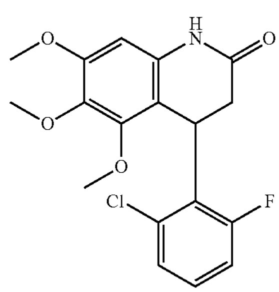 [SMILES: COc1cc2c(c(OC)c1OC)C(c1c(F)cccc1Cl)CC(=O)N2] | Yes | 91 | 27 |
| CAL-55 | 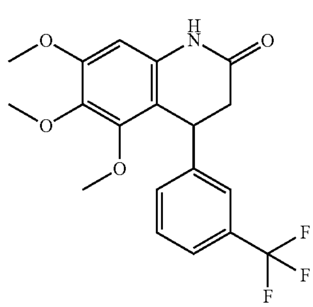 [SMILES: COc1cc2c(c(OC)c1OC)C(c1cccc(C(F)(F)F)c1)CC(=O)N2] | No | — | — |

TABLE 6-continued
Additional compounds tested in the reporter assay
| Compound | Structure | Active | Ec50 (μM) | Max % Activity |
|---|---|---|---|---|
| CAL-56 | 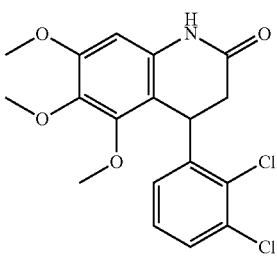 [SMILES: COc1cc2c(c(OC)c1OC)C(c1cccc(Cl)c1Cl)CC(=O)N2] | No | — | — |
| CAL-57 | 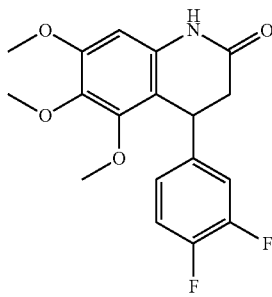 [SMILES: COc1cc2c(c(OC)c1OC)C(c1ccc(F)c(F)c1)CC(=O)N2] | No | — | — |
| LDN-212263 | 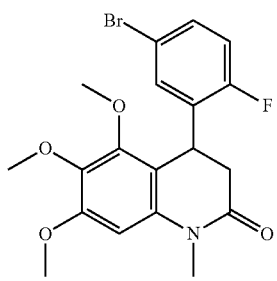 [SMILES: COc1cc2c(c(OC)c1OC)C(c1cc(Br)ccc1F)CC(=O)N2C] | No | — | — |
| LDN-212264 | 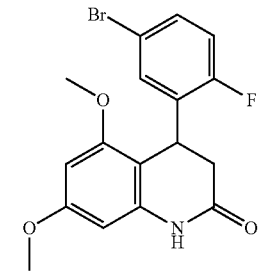 [SMILES: COc1cc2c(c(OC)c1)C(c1cc(Br)ccc1F)CC(=O)N2] | No | — | — |
| LDN-212265 | 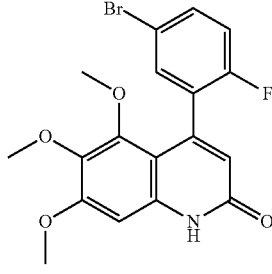 [SMILES: COc1cc2[nH]c(=O)cc(-c3cc(Br)ccc3F)c2c(OC)c1OC] | No | — | — |

TABLE 6-continued

*Additional compounds tested in the reporter assay*

| Compound | Structure | Active | Ec50 (μM) | Max % Activity |
|---|---|---|---|---|
| LDN-212266 | 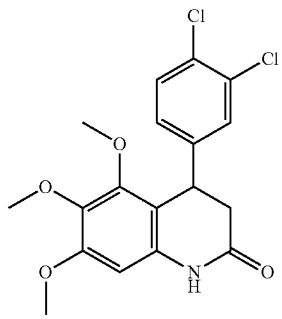 [SMILES: COc1cc2c(c(OC)c1OC)C(c1ccc(Cl)c(Cl)c1)CC(=O)N2] | No/Weak | — | — |
| LDN-212267 | 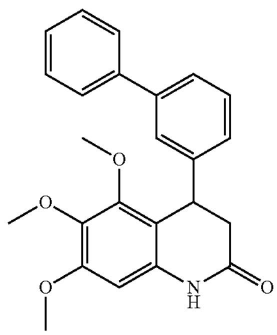 [SMILES: COc1cc2c(c(OC)c1OC)C(c1cccc(-c3ccccc3)c1)CC(=O)N2] | No | — | — |
| LDN-212350 | 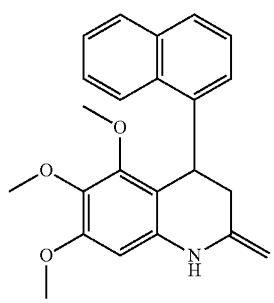 | No/Weak | — | — |
| LDN-212351 | 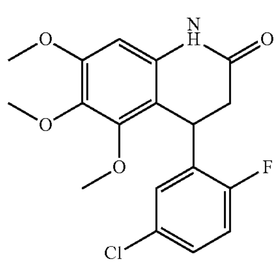 [SMILES: COc1cc2c(c(OC)c1OC)C(c1cc(Cl)ccc1F)CC(=O)N2] | Yes | 12 | 150 |
| LDN-212352 | 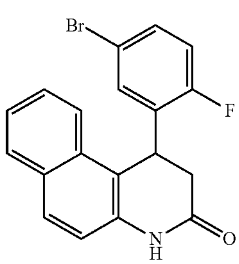 [SMILES: O=C1CC(c2cc(Br)ccc2F)c2c(ccc3ccccc23)N1] | No | — | — |

TABLE 6-continued
Additional compounds tested in the reporter assay
| Compound | Structure | Active | Ec50 (μM) | Max % Activity |
|---|---|---|---|---|
| LDN-212353 | 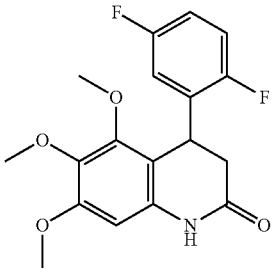 [SMILES: COc1cc2c(c(OC)c1OC)C(c1cc(F)ccc1F)CC(=O)N2] | No/Weak | — | — |
| LDN-212354 | 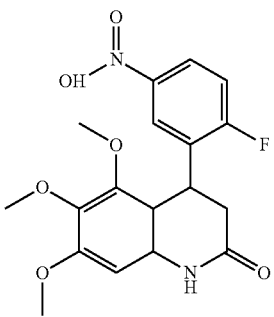 | No/Weak | — | — |
| LDN-212355 | 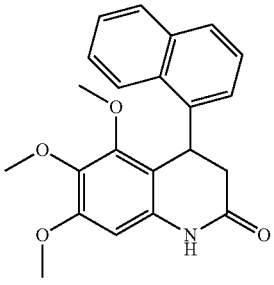 [SMILES: COc1cc2c(c(OC)c1OC)C(c1cccc3ccccc13)CC(=O)N2] | No/Weak | — | — |
| LDN-212356 | 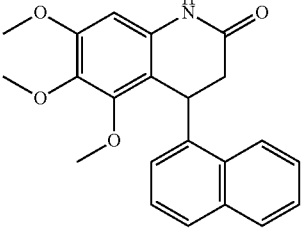 | Yes | 43 | 150 |
| LDN-212357 | 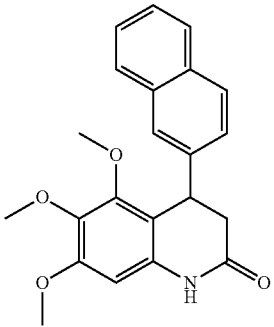 [SMILES: COc1cc2c(c(OC)c1OC)C(c1ccc3ccccc3c1)CC(=O)N2] | No | — | — |

TABLE 6-continued

Additional compounds tested in the reporter assay

| Compound | Structure | Active | Ec50 (μM) | Max % Activity |
|---|---|---|---|---|
| LDN-212358 | 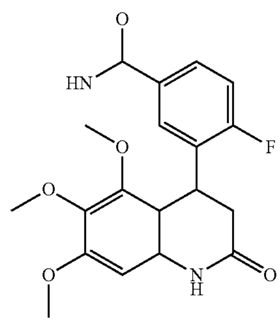 [SMILES: COC1=CC2NC(=O)CC(c3cc(C(N)O)ccc3F)C2C(OC)=C1OC] | No | — | — |
| LDN-212359 | 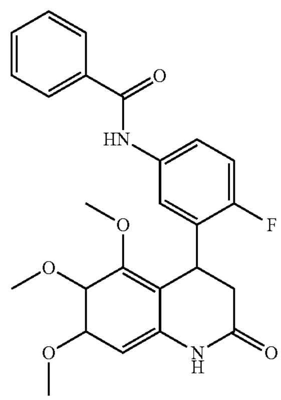 [SMILES: COC1=C2C(=CC(OC)C1OC)NC(=O)CC2c1cc(NC(=O)c2ccccc2)ccc1F] | No | — | — |
| LDN-212360 | 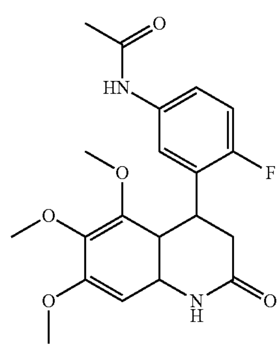 [SMILES: COC1=CC2NC(=O)CC(c3cc(NC(C)=O)ccc3F)C2C(OC)=C1OC] | No | — | — |
| LDN-212361 | 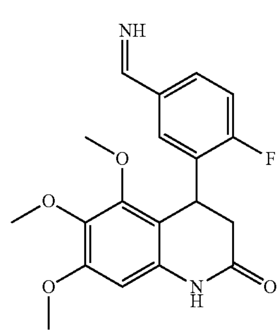 [SMILES: COc1cc2c(c(OC)c1OC)C(c1cc(C=N)ccc1F)CC(=O)N2] | No | — | — |

TABLE 6-continued

Additional compounds tested in the reporter assay

| Compound | Structure | Active | Ec50 (μM) | Max % Activity |
|---|---|---|---|---|
| LDN-212388 | 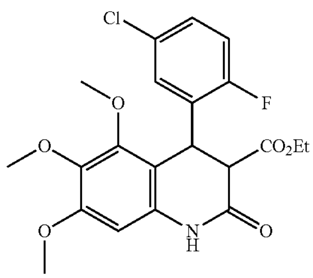 [SMILES: CCOC(=O)C1C(=O)Nc2cc(OC)c(OC)c(OC)c2C1c1cc(Cl)ccc1F] | No | — | — |
| LDN-212389 | 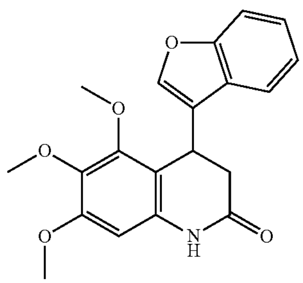 [SMILES: COc1cc2c(c(OC)c1OC)C(c1coc3ccccc13)CC(=O)N2] | No/Weak | — | — |
| LDN-212390 | 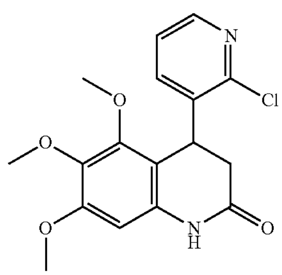 [SMILES: COc1cc2c(c(OC)c1OC)C(c1cccnc1Cl)CC(=O)N2] | No | — | — |
| LDN-212391 | 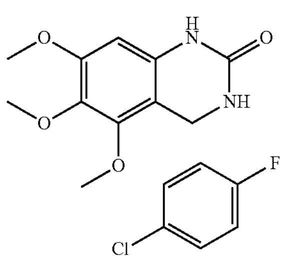 | Yes | 4.4 | 267 |
| LDN-212392 | 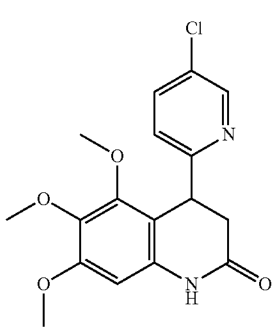 [SMILES: COc1cc2c(c(OC)c1OC)C(c1ccc(Cl)cn1)CC(=O)N2] | No | — | — |

TABLE 6-continued

Additional compounds tested in the reporter assay

| Compound | Structure | Active | Ec50 (µM) | Max % Activity |
|---|---|---|---|---|
| LDN-212393 | 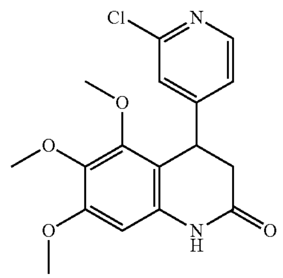 [SMILES: COc1cc2c(c(OC)c1OC)C(c1ccnc(Cl)c1)CC(=O)N2] | No/Weak | — | — |
| LDN-213767 | 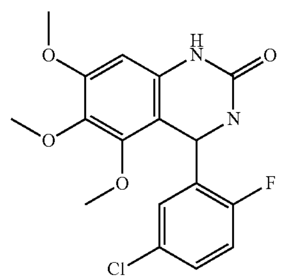 [SMILES: COc1cc2c(c(OC)c1OC)C(c1cc(Cl)ccc1F)NC(=O)N2] | Yes | 8.4 | 125 |
| LDN-213768 | 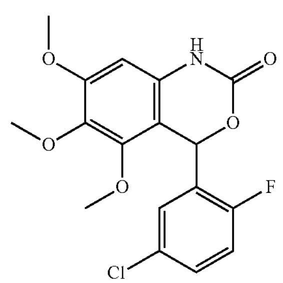 [SMILES: COc1cc2c(c(OC)c1OC)C(c1cc(Cl)ccc1F)OC(=O)N2] | Yes | 5.9 | 150 |
| LDN-213769 | 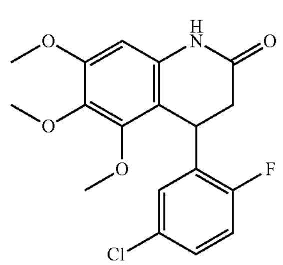 [SMILES: COc1cc2c(c(OC)c1OC)C(c1cc(Cl)ccc1F)CC(=O)N2] | No | — | — |
| LDN-213770 | 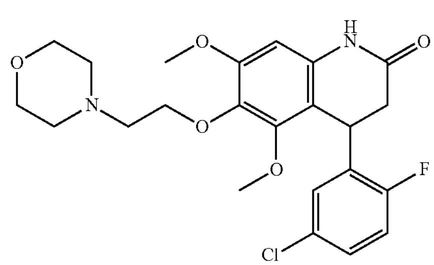 [SMILES: COc1cc2c(c(OC)c1OCCN1CCOCC1)C(c1cc(Cl)ccc1F)CC(=O)N2] | No | — | — |

TABLE 6-continued

Additional compounds tested in the reporter assay

| Compound | Structure | Active | Ec50 (μM) | Max % Activity |
|---|---|---|---|---|
| LDN-213771 | 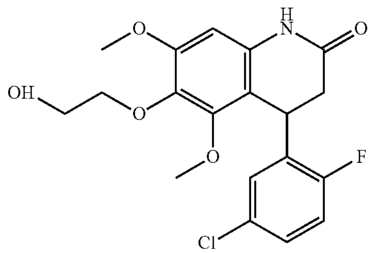 [SMILES: COc1cc2c(c(OC)c1OCCO)C(c1cc(Cl)ccc1F)CC(=O)N2] | No | — | — |
| LDN-213772 | 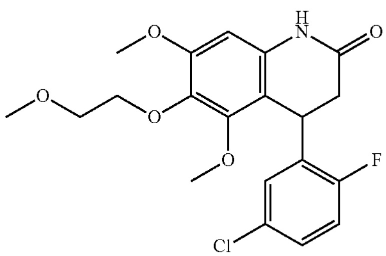 [SMILES: COCCOc1c(OC)cc2c(c1OC)C(c1cc(Cl)ccc1F)CC(=O)N2] | No | — | — |
| LDN-213773 | 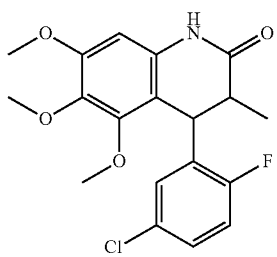 | No | — | — |
| LDN-214085 | 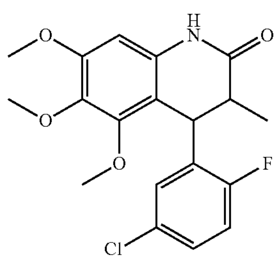 | Yes | 6 | 180 |
| LDN-214096 | 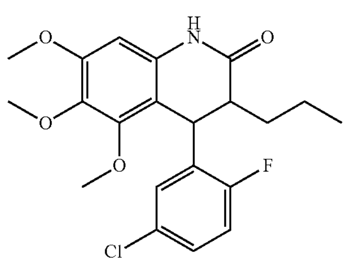 [SMILES: CCCC1C(=O)Nc2cc(OC)c(OC)c(OC)c2C1c1cc(Cl)ccc1F] | No | — | — |
| LDN-214097 | 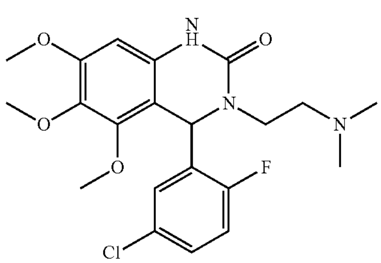 | No | — | — |

TABLE 7

Structure activity data

| | Maximum % activation | EC$_{50}$ | T$_{1/2}$ in liver microsomes | Maximal solubility in PBS |
|---|---|---|---|---|
| 75654 | 242.4 ± 35.1 | 2.0 μM ± 0.9 | 15 min | >2 mM |
| 212016 | 162.4 ± 62.4 | 0.3 μM ± 0.1 | Not tested | 500 μM |
| 212014 | 156.6 ± 30.7 | 0.3 μM ± 0.3 | 39 min | >2 mM |
| 76070 | 185.7 ± 48.0 | 8.3 μM ± 4.5 | Not tested | 500 μM |
| 212351 | 168.5 ± 10.6 | 9.8 μM ± 4.1 | 45 min | 500 μM |
| 212391 | 238.3 ± 28.5 | 5.0 μM ± 0.8 | 13 min | 1 mM |

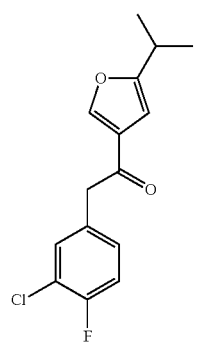

LDN-75654
IC$_{50}$ 1 μM
210% activation

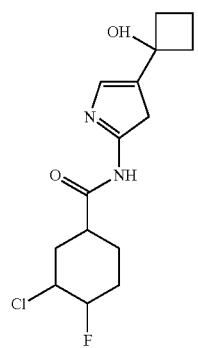

LDN-212014
IC$_{50}$ 500 μM
180% activation

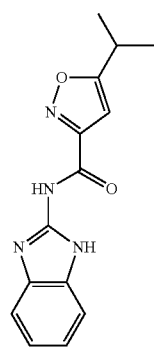

LDN-212016
IC$_{50}$ 260 nM
250% activation

TABLE 7-continued

Structure activity data

| | Maximum % activation | EC$_{50}$ | T$_{1/2}$ in liver microsomes | Maximal solubility in PBS |
|---|---|---|---|---|

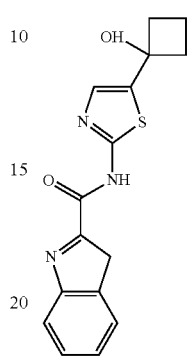

LDN-214098
IC$_{50}$ 480 nM
200% activation

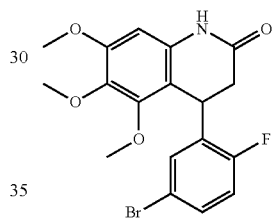

LDN-76070
IC$_{50}$ 5.5 μM
150% activation

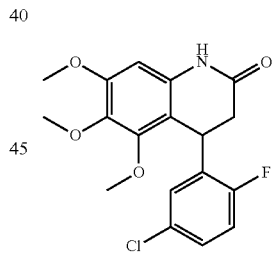

LDN-212351
IC$_{50}$ 7.7 μM
100% activation

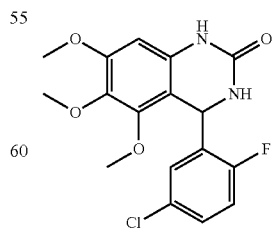

LDN-212391
IC$_{50}$ 3.25 μM
180% activation

TABLE 7-continued

Structure activity data

| Maximum % activation | EC$_{50}$ | T$_{1/2}$ in liver microsomes | Maximal solubility in PBS |
|---|---|---|---|

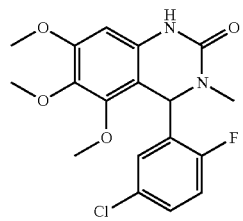

LDN-214085
IC$_{50}$ 6 μM
180% activation

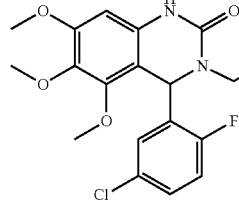

~~LDN-214096~~
inactive

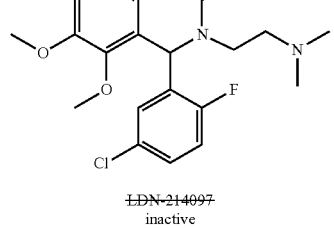

~~LDN-214097~~
inactive

Example 2

In this Example, compounds were tested using SMN2 reporter cells. Particularly, over >150,000 compounds were tested using SMN2 reporter cells. Secondary assays were performed to measure SMN protein levels using SMA type 1 patient-derived fibroblasts (3813 cells) by Western blot, gem counts, and quantitative RT-PCR of SMN transcripts.

Figure 25A:
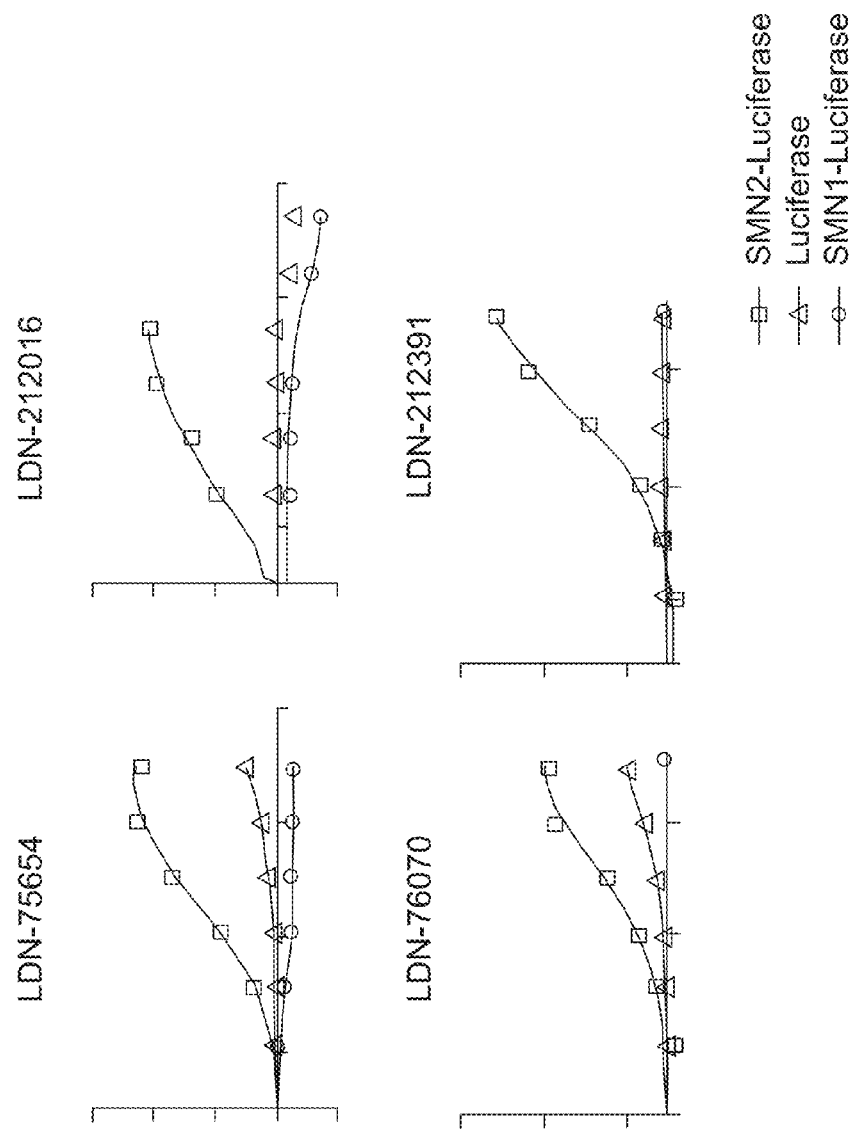
FIG. 25A shows luciferase activities (-□-) in SMN2 reporter cells treated with LDDN-75654, LDN-212016, LDN-76070, and LDN-212391. The curve represented by -Δ is the internal control renilla luciferase and the curve represented by -o- is the luciferase activity in SMN1 reporter cells.
Figure 25B:
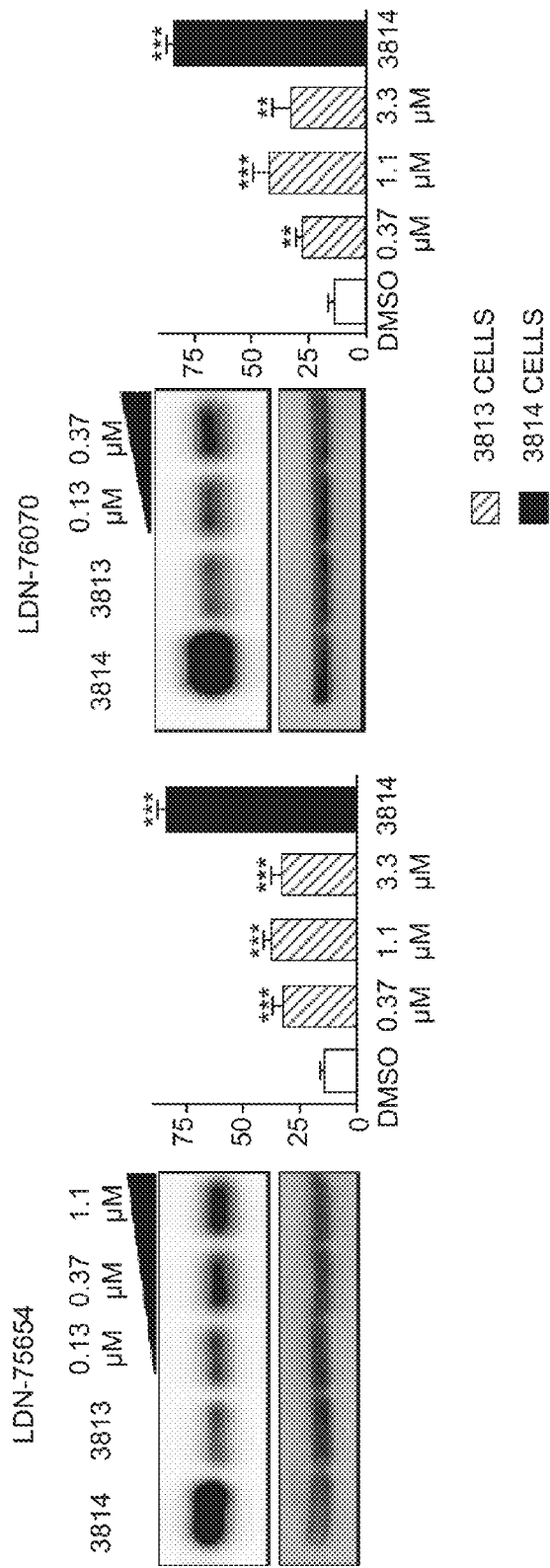
FIG. 25B shows SMN protein levels in 3813 cells by immunoblot and gem counts. Cells were treated with LDN-75654 (left two panels) or LDN-76070 (right two panels) for 48 hours. Graphs plot the number of gems per 100 nuclei where 3813 cells are designated by lined bars and 3814 by solid bars. Data are presented as mean±SEM for three experiments and were analyzed using Prism4 (GraphPad Software Inc.). Each data point was compared to DMSO control using t-test. *(P<0.05) (P<0.01) *(P<0.001).

Two of the compounds, LDN-75654 and LDN-76070, were further tested. Analogs of both were synthesized and characterized first in the SMN2-luc reporter assays and later by Western blot or gem count using 3813 SMA fibroblasts (FIGS. 25A and 25B). Those compounds that were validated and had tractable chemistry progressed to a synthetic phase in which scaffolds are modified and their properties evaluated. The compounds identified by this iterative process are included in this application.

Seventy-six (76) LDN 75654 analogs were tested to explore three different regions of the molecule, including introducing a hydroxyl group to various aliphatic substituents on the central heterocycle, replacing the isoxazole with other heterocycles (i.e. thiazole and pyridine) and creating variations to the anilide group. Exemplary compounds are shown below:

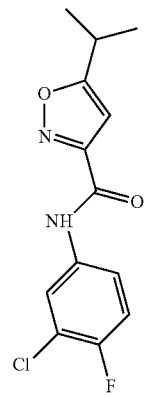

LDN-75654

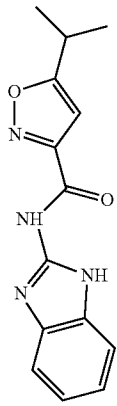

LDN-212016

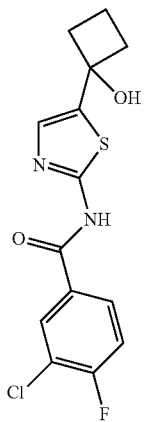

LDN-212014

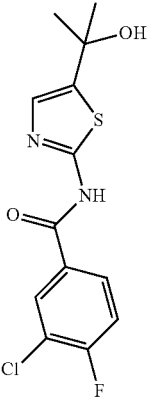

LDN-212255

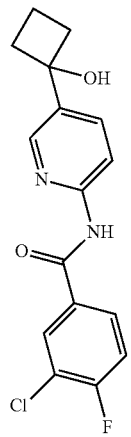

LDN-212256

Exemplary analogs that emerged with activity are LDN-212016 (see FIG. 25A), LDN-212014, LDN-212255, and LDN-212256. Some of the compounds have different metabolic stability. For example, LDN-212014 had a $t_{1/2}$ of 39 minutes in mouse liver microsomes compared to 14 min for LDN-75654.

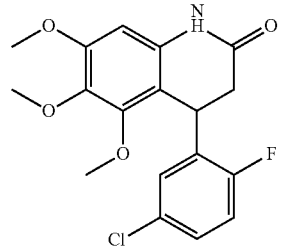

LDN-212351

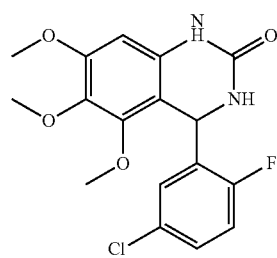

LDN-212391

Modifications of the pendent phenyl were examined. In some embodiments, the 2,5-dihalo substituted compounds showed activity. The 2,5-dihalo substituted compounds had improved activity, such as LDN-212351. The change of bromine to chlorine increased stability, which may be advantageous. Not wishing to be limited by theory, the increased stability could be due to C—Cl bonds being stronger than C—Br bonds. LDN-212351 demonstrated a $t_{1/2}$ of 45 min in mouse liver microsomes. Incorporation of an additional nitrogen atom into the central ring to generate urea LDN-212391 was tolerated (see FIG. 25A).

Exemplary results are listed in Table 8, below.

TABLE 8

Exemplary compound test results.

| 75654 | 212014 | 212016 | 214098 | 76070 | 212351 | 212391 | 214085 | |
|---|---|---|---|---|---|---|---|---|
| +++ | ++++ | ++++ | ++++ | ++ | ++ | +++ | ++ | Potency Luc Reporter |
| ++++ | +++ | +++ | +++ | ++ | ++ | +++ | ++ | Activity Luc Reporter |
| ++ | ? | ? | ? | ++++ (n = 16) | +++ (n = 4) | +++ (n = 4) | ? | Fibroblasts |
| − | ++++ (n = 16) | +++ (n = 4) | ? | ++++ (n = 16) | +++ (n = 4) | +++ (n = 4) | ? | IP injections/ Activity in Mice |
| + | + | − | + | − | − | +/− | ? | Solubility in aqueous solution |
| 15 min | 39 min | 3 min | 59 min | ? | 45 min | 13-20 min | ? | Stability in liver microsomes |

Example 3

Forty eight (48) LDN-76070 analogs were evaluated. Exemplary compounds are shown below:

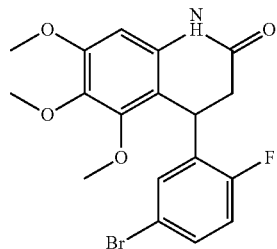

LDN-76070

Pilot experiments with the LDN compounds were initiated in SMA mice. Compounds LDN-75654 and LDN-76070 were tested in SMA mice to evaluate SMN-inducing activity in vivo. The compounds were injected intracerebroventricular (ICV) into SMA mice. Injections were performed daily for 3 days, and animals were harvested on day 3. LDN-76070 increased SMN protein in muscle and liver. Importantly, SMN was also significantly elevated in spinal cord and brain (Table 9). LDN-75654 did not increase SMN protein levels in these animals. Without the intention to be limited by theory, it is proposed that this may be due to the instability observed in the liver microsomal stability assay.

TABLE 9

Exemplary test results in SMA mice*.

| 75654 | 212014 | 212016 | 214058 | 76070 | 212351 | 212391 | 214085 | |
|---|---|---|---|---|---|---|---|---|
| +++ | ++++ | ++++ | ++++ | ++ | ++ | +++ | ++ | Potency Luc Reporter |
| ++++ | +++ | +++ | +++ | ++ | ++ | +++ | ++ | Activity Luc Reporter |
| ++ | ? | ? | ? | ++ | ? | ? | ? | Fibroblasts |
| − | ++++ (n = 16) | +++ (n = 4) | ? | ++++ (n = 16) | +++ (n = 4) | +++ (n = 4) | ? | IP Injections |
| + | + | − | + | − | − | +/− | ? | Solubility |
| 15 min | 39 min | 3 min | 59 min | ? | 45 min | 13-20 min | ? | Stability |

*Neonatal SMN D 7 mice (Smn−/− SMN2+/+ SMNΔ7+/+) were injected intraperitoneally twice daily for 3 days with compound or DMSO starting at post-natal day 2. Tissues were harvested and immunoblotted for SMN and actin. Representative data from brain.

Figure 26B:
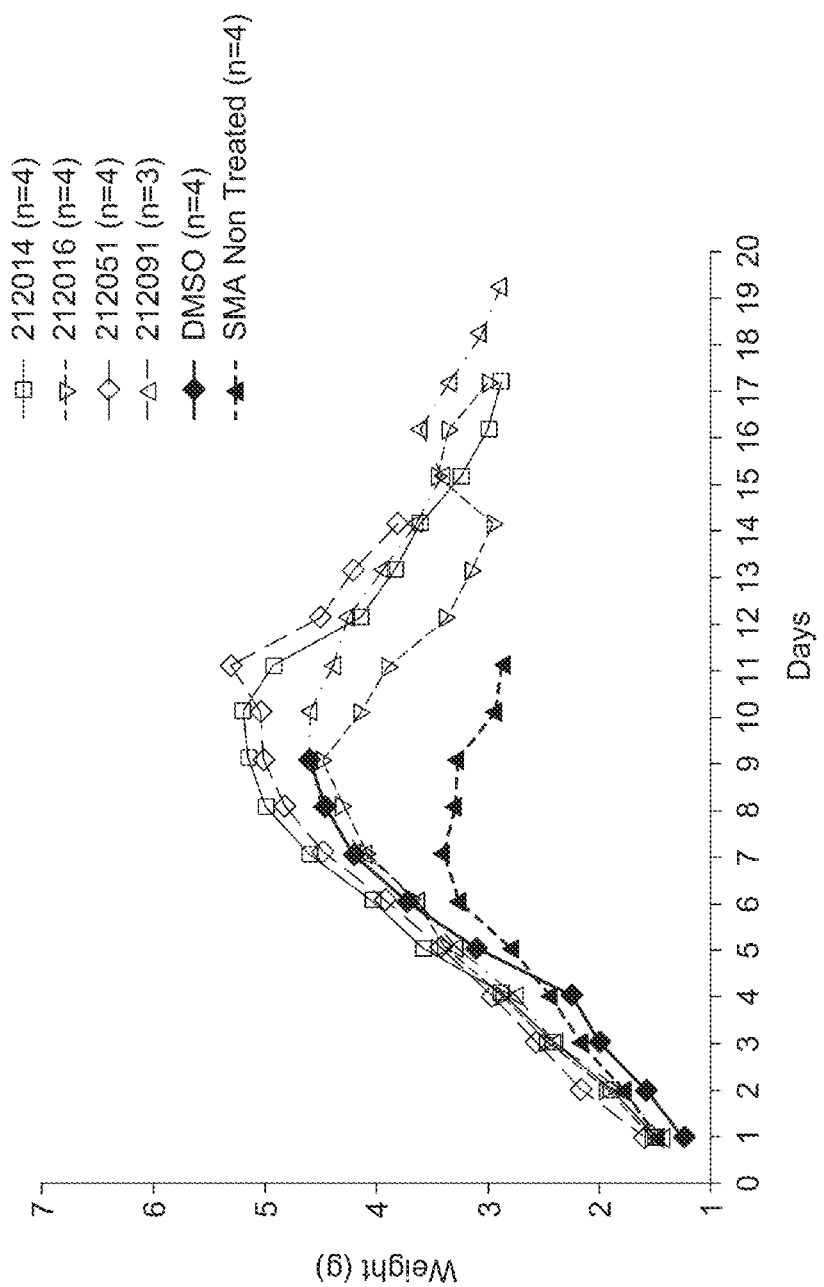
FIG. 26B shows average weights of animals in a mouse model of spinal muscular atrophy treated with compounds.
Figure 27:
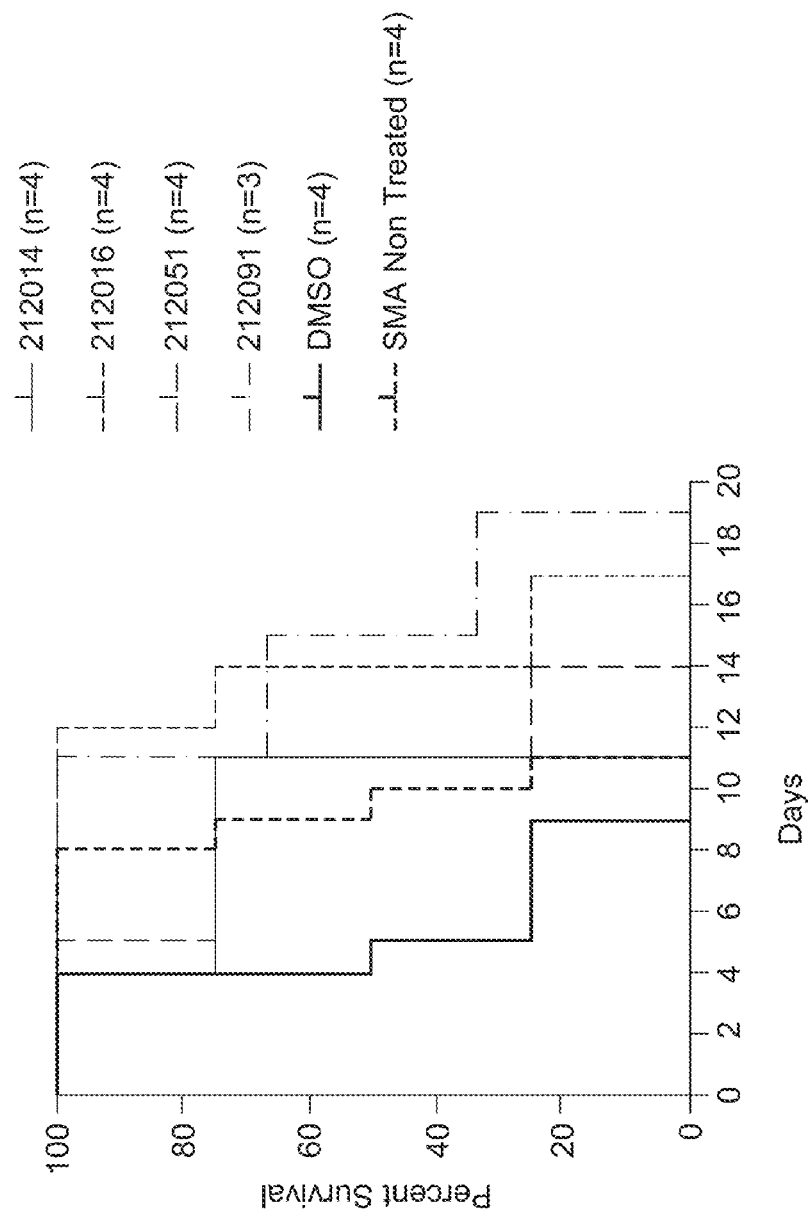
FIG. 27 shows survival proportions of animals in a mouse model of spinal muscular atrophy treated with compounds. Animals were treated once a day with 20 mg/kg by IP injection starting on post natal day (PND) 1.
Figure 28:
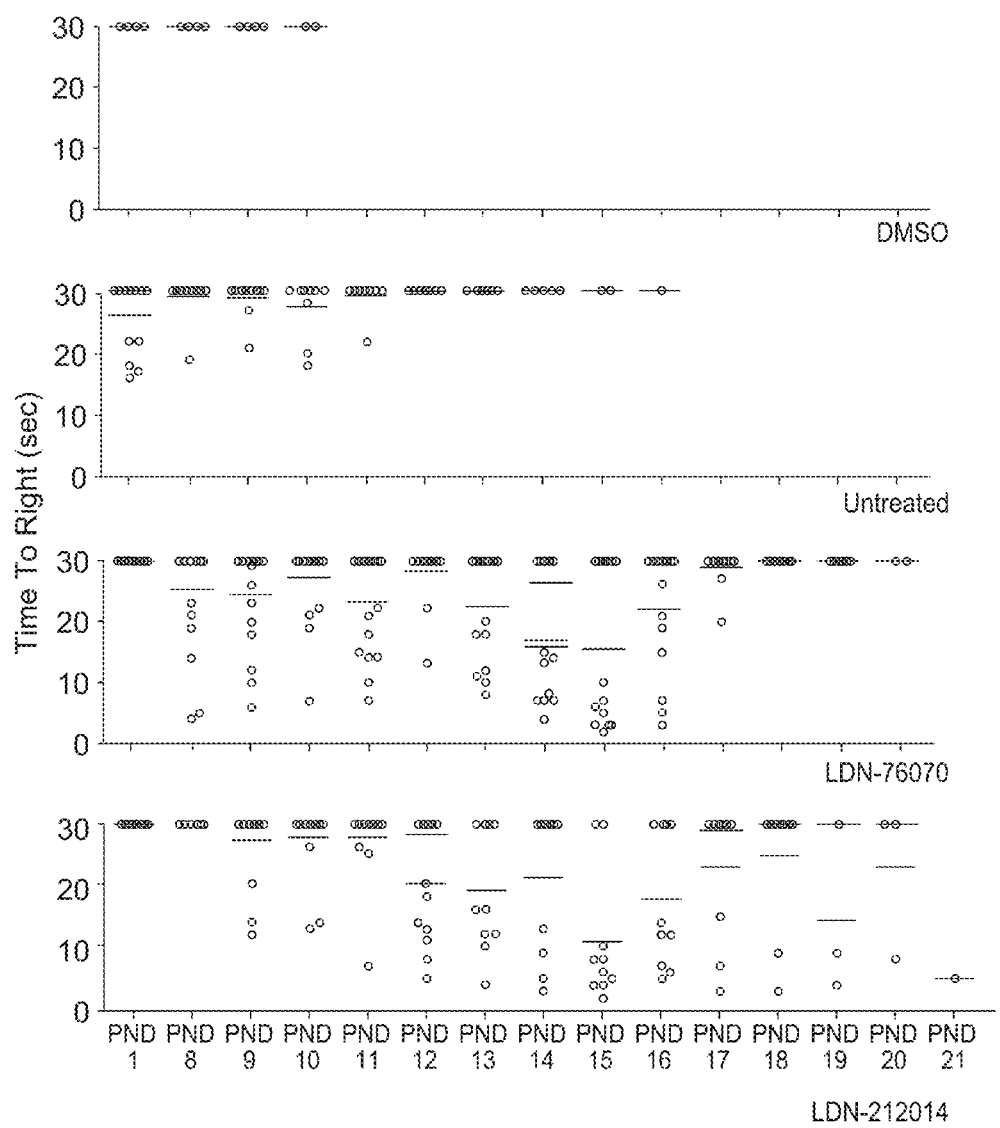
FIG. 28 shows time to right of mice treated with compounds. Animals are placed on their backs and assayed for the time it requires for them to right themselves. Thirty (30) seconds or greater is considered a failure to right and scored as 30 sec.

The animal studies included new derivatives of LDN-76070 and LDN-75654. Mice were injected intraperitoneally once daily from post-natal day 1-10. Weight increase, time to right onto four legs, and extension of lifespan were chosen as parameters for efficacy. Compounds LDN-212014, LDN-212016, LDN-212351, and LDN-212391 were injected into a cohort of animals (3-4 each). Mice showed an extension of lifespan. In the Kaplan-Meier curve that DMSO control decreased survival by 50%—the compounds were in 20% DMSO (FIG. 26A). The weight of the treated animals also increased and some of the animals were able to right themselves starting at day 6 (FIG. 26B and Table 10).

These experiments also demonstrated there was a concomitant increase in motor function in the treated animals. In 'time to right' experiments, animals are placed on their backs and the duration for animals to right themselves is recorded. Animals that are unable to right in less than 30 seconds are scored as a failure. DMSO treated animals were unable to right themselves, while a small percentage of untreated animals display the ability to right themselves for up to postnatal day (PND) 11. A larger percentage of treated animals can right themselves past PND 17, and in the case of one animal as late as PND 21.

To assess SMN protein level, tissues were harvested from three treated animals from each experiment at PND 7 and

TABLE 10

Time to right in seconds. Fail = >30 sec (raw data).

| Pup | Inj. | DOB | PND 6 | PND 7 | PND 8 | PND 9 | PND 10 | PND 11 | PND 12 | PND 13 | PND 14 | PND 15 | PND 16 | PND 17 | PND 18 | PND 19 | PND 20 |
|---|---|---|---|---|---|---|---|---|---|---|---|---|---|---|---|---|---|
| 4527.5 | 212014 | Apr. 5, 2011 | Fail | Fail | Fail | Fail | Fail | 5 | 16 | Fail | 5 | 14 | Fail | Fail | dead | dead | dead |
| 4389.4 | 212014 | Apr. 5, 2011 | dead | dead | dead | dead | dead | dead | dead | dead | dead | dead | dead | dead | dead | dead | dead |
| 4378.4 | 212014 | Apr. 5, 2011 | Fail | Fail | Fail | 26 | Fail | Fail | dead | dead | dead | dead | dead | dead | dead | dead | dead |
| 4514.3 | 212014 | Apr. 5, 2011 | Fail | Fail | Fail | Fail | Fail | Fail | dead | dead | dead | dead | dead | dead | dead | dead | dead |
| 4527.7 | 212016 | Apr. 5, 2011 | Fail | Fail | Fail | Fail | Fail | Fail | Fail | dead | dead | dead | dead | dead | dead | dead | dead |
| 4389.1 | 212016 | Apr. 5, 2011 | Fail | Fail | Fail | Fail | Fail | Fail | Fail | Fail | dead | dead | dead | dead | dead | dead | dead |
| 4378.5 | 212016 | Apr. 5, 2011 | Fail | 25 | Fail | Fail | Fail | Fail | Fail | Fail | Fail | dead | dead | dead | dead | dead | dead |
| 4515.5 | 212016 | Apr. 5, 2011 | Fail | Fail | Fail | Fail | 12 | 9 | Fail | 11 | Fail | Fail | Fail | Fail | dead | dead | dead |
| 4516.3 | 212351 | Apr. 5, 2011 | dead | dead | dead | dead | dead | dead | dead | dead | dead | dead | dead | dead | dead | dead | dead |
| 4533.5 | 212351 | Apr. 5, 2011 | Fail | Fail | Fail | 13 | Fail | dead | dead | dead | dead | dead | dead | dead | dead | dead | dead |
| 4358.4 | 212351 | Apr. 5, 2011 | Fail | Fail | Fail | Fail | Fail | dead | dead | dead | dead | dead | dead | dead | dead | dead | dead |
| 4354.1 | 212351 | Apr. 5, 2011 | 3 | 5 | Fail | Fail | Fail | Fail | Fail | Fail | Fail | dead | dead | dead | dead | dead | dead |
| 4518.4 | 212391 | Apr. 5, 2011 | Fail | Fail | Fail | Fail | Fail | Fail | dead | dead | dead | dead | dead | dead | dead | dead | dead |
| 4514.2 | 212391 | Apr. 5, 2011 | Fail | Fail | Fail | Fail | Fail | Fail | Fail | Fail | Fail | Fail | Fail | Fail | Fail | Fail | dead |
| 4354.4 | 212391 | Apr. 5, 2011 | Fail | Fail | Fail | 18 | 20 | Fail | Fail | Fail | Fail | Fail | dead | dead | dead | dead | dead |
| 4378.2 | DMSO | Apr. 5, 2011 | Fail | Fail | Fail | Fail | dead | dead | dead | dead | dead | dead | dead | dead | dead | dead | dead |
| 4258.6 | DMSO | Apr. 5, 2011 | dead | dead | dead | dead | dead | dead | dead | dead | dead | dead | dead | dead | dead | dead | dead |
| 4514.1 | DMSO | Apr. 5, 2011 | dead | dead | dead | dead | dead | dead | dead | dead | dead | dead | dead | dead | dead | dead | dead |
| 4515.6 | DMSO | Apr. 5, 2011 | dead | dead | dead | dead | dead | dead | dead | dead | dead | dead | dead | dead | dead | dead | dead |

Figure 29:
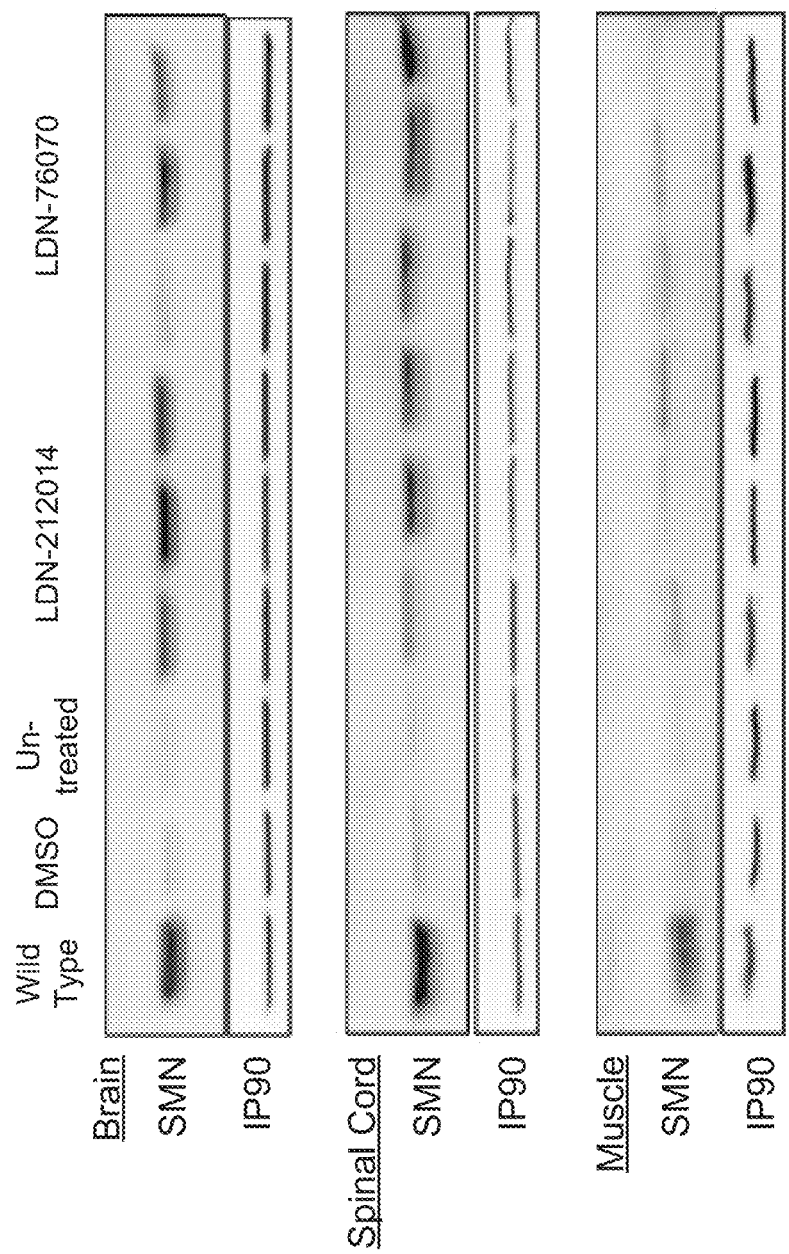
FIG. 29 shows SMN protein levels in treated animals. Animals were harvested on postnatal day 7 and blotted for SMN and IP90.
Figure 30:
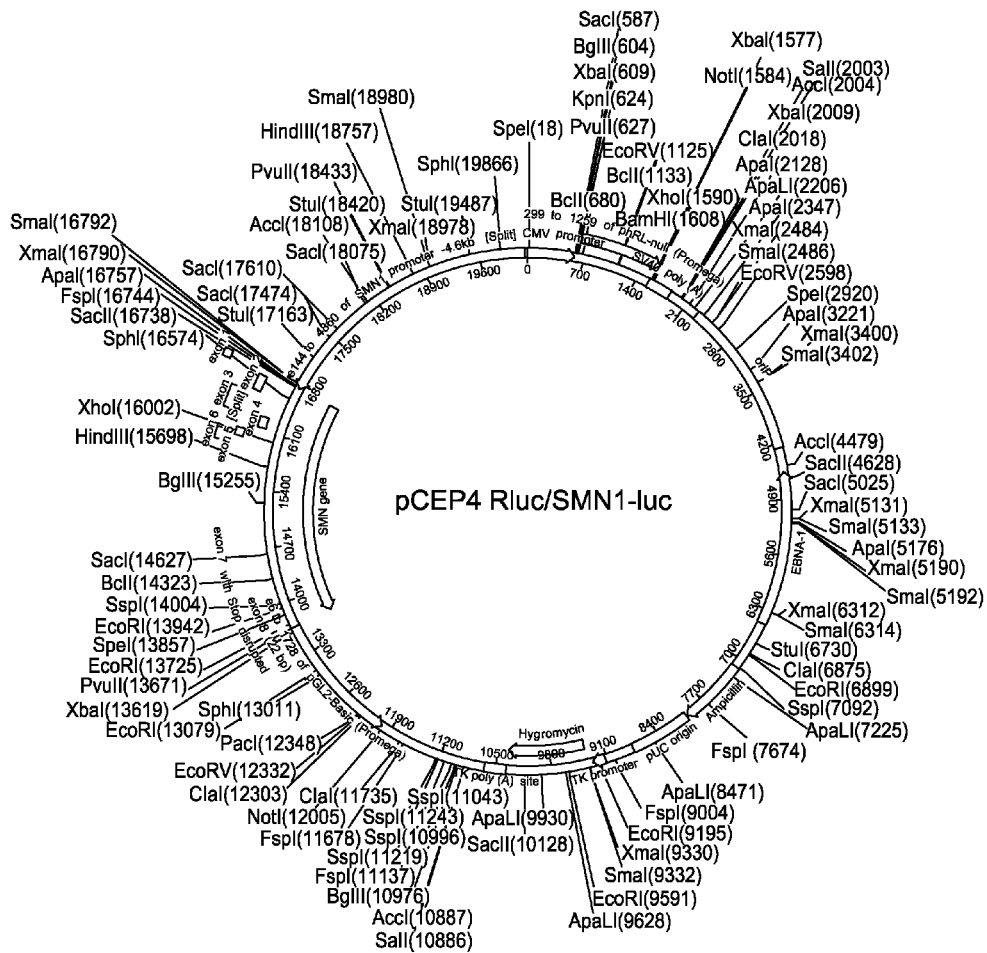
FIG. 30 shows a vector map of the SMN1 luciferase vector (SEQ ID NO:8).
Figure 31:
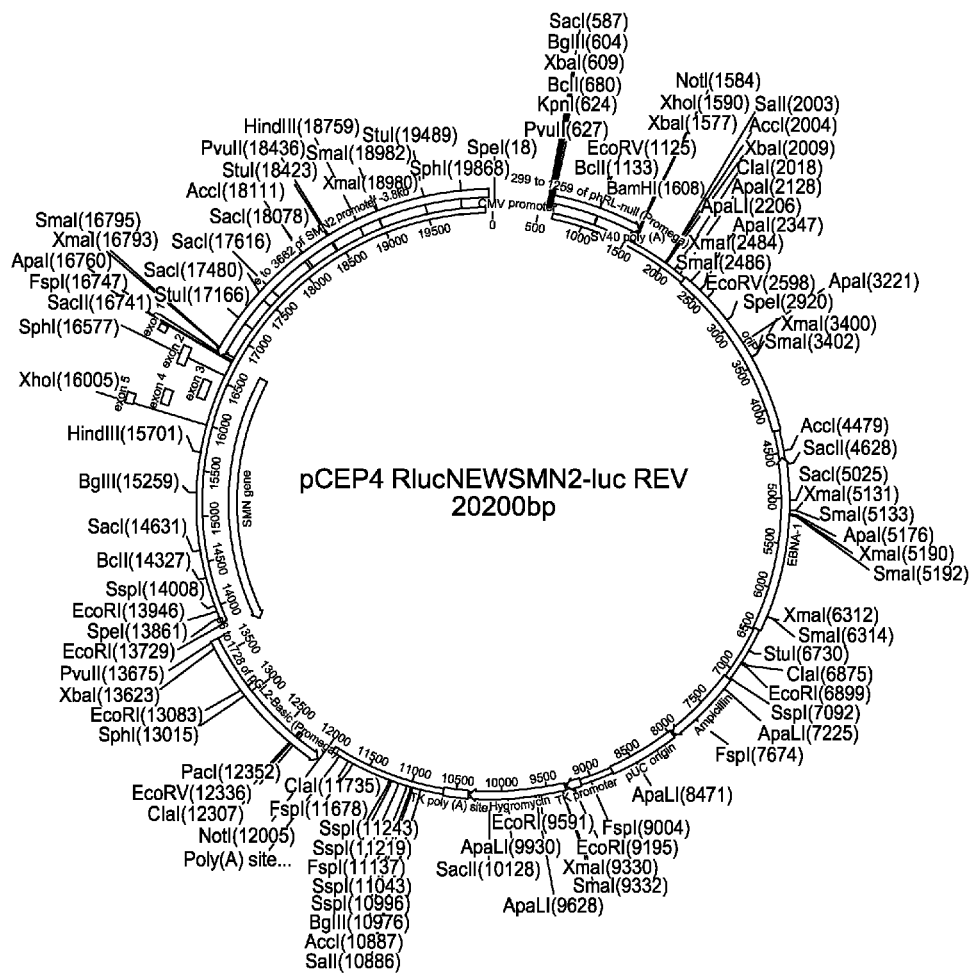
FIG. 31 shows a vector map of the SMN2 luniferase vector (SEQ ID NO:9).

LDN-212014 and LDN-76070 were further tested in A7 SMA model mice. Mice were dosed using compounds dissolved in 100% DMSO injected at 20 mg/kg with each dose administered once daily by intraperitoneal injection. As shown in the black curves in the Kaplan-Meier plot, control animals lived 4-5 days longer than the DMSO vehicle treated animals, indicating toxicity. Nonetheless, both 76070 and 212014 compounds significantly increased lifespan despite this DMSO associated toxicity (p<0.0001). In fact, the compounds display a statistically significant increase in survival compared with the untreated animals. These compounds extend the lifespan of SMA mice despite the DMSO toxicity. Test results of LDN-212014 and LDN-76070 were shown in FIGS. 8-24, 27-28 and others.

compared to wild type, untreated, and DMSO treated animals. Tissues from brain, spinal cord, and muscle were assayed. As shown in the western blots (FIG. 29), both compounds increase SMN protein levels in brain and spinal cord to greater than 75% that of wild type animals. They also promoted an increase of about 25% that of wild type in muscle. High levels of increase in these tissues are very desirable, especially in tissues of the CNS, suggesting that these compounds can pass through the blood brain barrier.

Exemplary Synthesis of Compounds

In some embodiments, certain compounds described in the application are prepared using the general procedure outlined in Scheme 1 (*Synthesis* 2006, (22), 3805; *Jiegou Huaxue* 2007, 26(5), 533; *Tetrahedron Lett.* 2005, 46, 7169):

Scheme 1

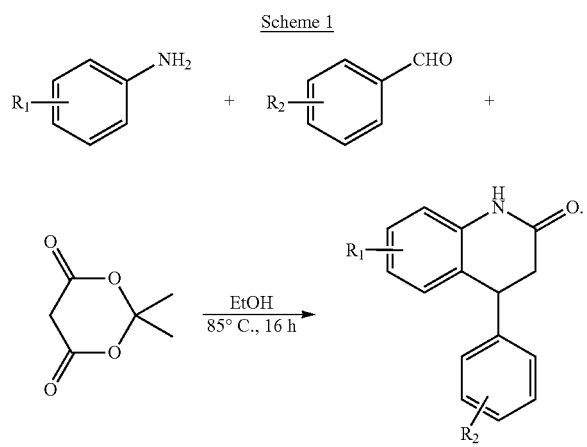

In some embodiments, several of the urea analogs are prepared using the procedures outlined in Scheme 2 (*Perkins Trans 2* 2001, 2226 and *J. Heterocycl Chem* 1982, 19, 1453):

Scheme 2

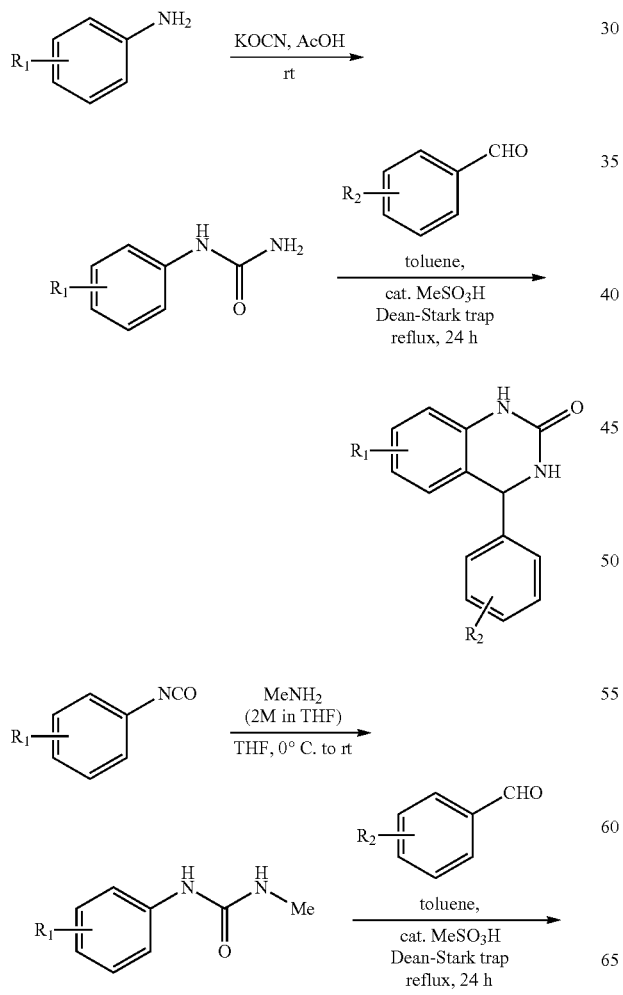

-continued

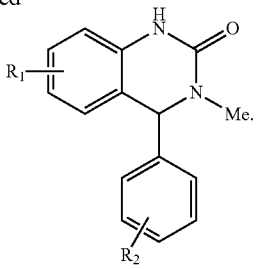

In other embodiments, several seven-member ring analogs are prepared using the procedures outlined in Scheme 3 (*J. Am. Chem. Soc.* 1954, 76, 4550; *J. Med Chem.* 1974, 17, 668; *J. Med Chem.* 2006, 49, 3520-3535; *J. Org. Chem.* 1986, 51, 5001-5002):

Scheme 3

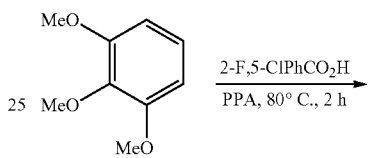

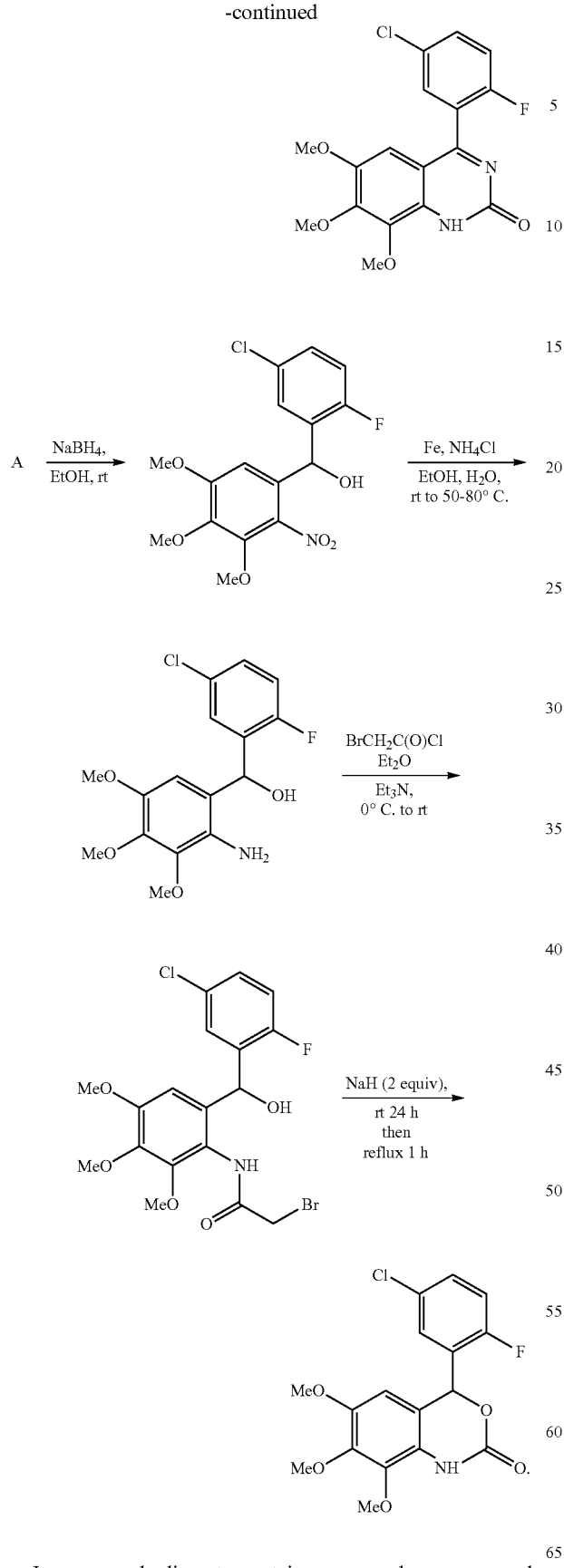

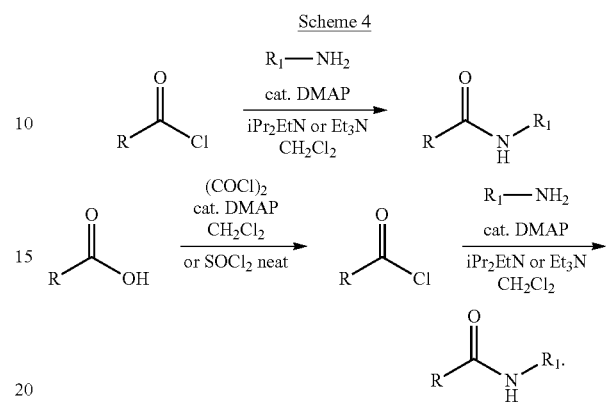

eroaryl acyl chlorides and aryl or heteroaryl amines. In other embodiments, a two-step process is used starting with aryl or heteroaryl carboxylic acids.

In some embodiments, certain heteroaryl carboxylic acids are prepared using the procedure outlined in Scheme 5 (*Eur. J. Org. Chem.* 2007, 4352-4359) and in Scheme 6 (*J. Am. Chem. Soc.* 1992, 114, 9450 and *J. Org. Chem.* 1993, 58, 4495).

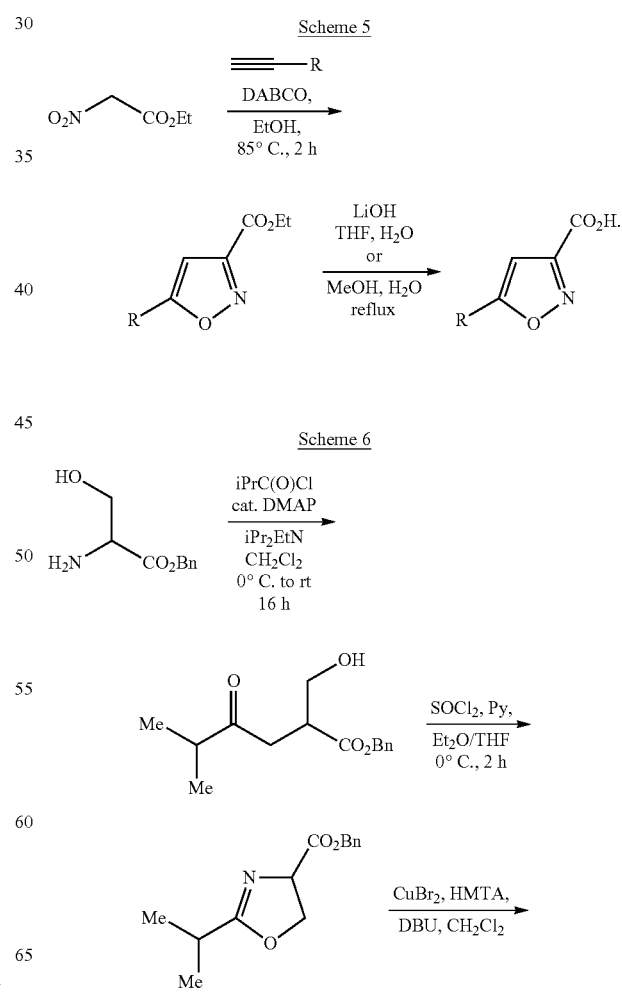

In some embodiments, certain compounds are prepared using the procedure outline in Scheme 4 with aryl or het-

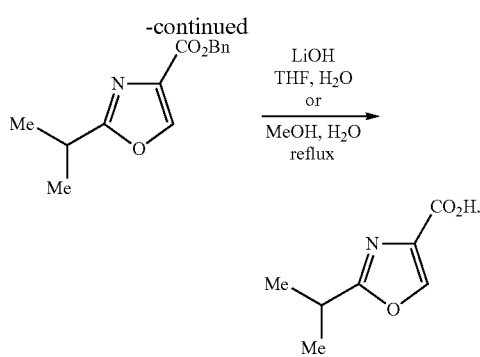

In some embodiments, the cyclohexyl analog is prepared using the procedure outlined in Scheme 7 (*Synthesis* 1992, 769).

Scheme 7

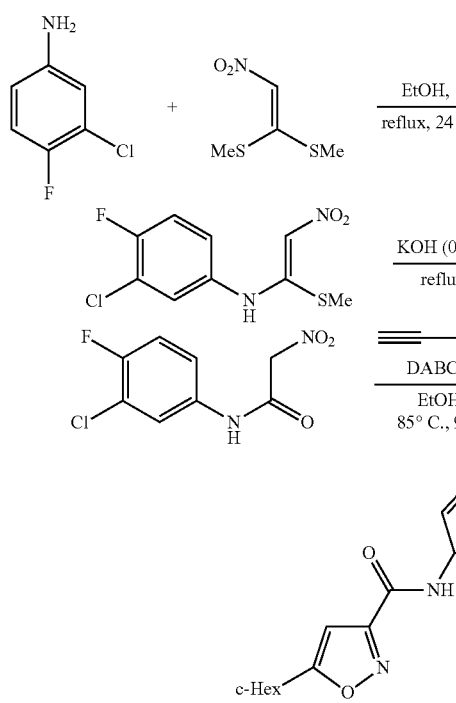

In some embodiments, certain heteroaryl amines are prepared using the procedure outlined in Scheme 8.

Scheme 8

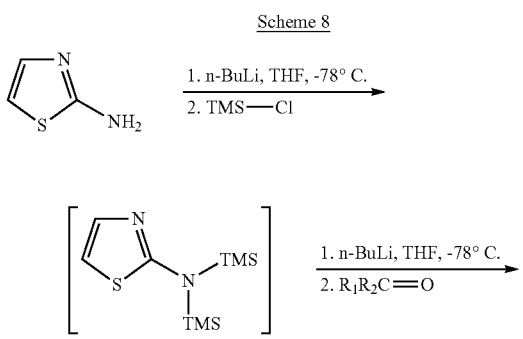

What is claimed is:

1. A vector comprising: a survival motor neuron (SMN) promoter selected from the group consisting of a survival motor neuron 1 (SMN1) promoter and a survival motor neuron 2 (SMN2) promoter; a transcription start site; exons 1-8 of the SMN gene; a truncated intron 6 of the SMN gene; and a reporter gene.

2. The vector of claim 1, wherein the reporter gene encodes a reporter protein selected from the group consisting of luciferase, green fluorescent protein, and red fluorescent protein.

3. The vector of claim 1, wherein the truncated intron 6 comprises a 2 kilobase deletion.

4. A host cell comprising the vector of claim 1.

5. The host cell of claim 4 selected from the group consisting of a C33 cell; a HEK-293 cell; a spinal muscular atrophy type 1 (GM3813) fibroblast; and a 3814 (GM3814) fibroblast.

6. A vector comprising: a survival motor neuron 1 (SMN1) promoter; a transcription start site; exons 1-8 of the SMN1 gene; a truncated intron 6 of the SMN1 gene; and a reporter gene.

7. The vector of claim 6, wherein the reporter gene encodes a reporter protein selected from the group consisting of luciferase, green fluorescent protein, and red fluorescent protein.

8. The vector of claim 6, wherein the truncated intron 6 comprises a 2 kilobase deletion.

9. A host cell comprising the vector of claim 6.

10. The host cell of claim 9 selected from the group consisting of a C33 cell; a HEK-293 cell; a spinal muscular atrophy type 1 (GM3813) fibroblast; and a 3814 (GM3814) fibroblast.

11. A vector comprising: a survival motor neuron 2 (SMN2) promoter; a transcription start site; exons 1-8 of the SMN2 gene; a truncated intron 6 of the SMN2 gene; and a reporter gene.

12. The vector of claim 11, wherein the reporter gene encodes a reporter protein selected from the group consisting of luciferase, green fluorescent protein, and red fluorescent protein.

13. The vector of claim 11, wherein the truncated intron 6 comprises a 2 kilobase deletion.

14. A host cell comprising the vector of claim 11.

15. The host cell of claim 14 selected from the group consisting of a C33 cell; a HEK-293 cell; a spinal muscular atrophy type 1 (GM3813) fibroblast; and a 3814 (GM3814) fibroblast.

* * * * *

SEQUENCE LISTING

```
<160> NUMBER OF SEQ ID NOS: 9

<210> SEQ ID NO 1
<211> LENGTH: 25
<212> TYPE: DNA
<213> ORGANISM: Artificial Sequence
<220> FEATURE:
<223> OTHER INFORMATION: Synthetic

<400> SEQUENCE: 1
ccacaaatgt gggagggcga taacc                                              25

<210> SEQ ID NO 2
<211> LENGTH: 35
<212> TYPE: DNA
<213> ORGANISM: Artificial Sequence
```

```
<220> FEATURE:
<223> OTHER INFORMATION: Synthetic

<400> SEQUENCE: 2
tatctcgagt ggtccagaag gaaatggagg cagcc                                    35

<210> SEQ ID NO 3
<211> LENGTH: 23
<212> TYPE: DNA
<213> ORGANISM: Artificial Sequence
<220> FEATURE:
<223> OTHER INFORMATION: Synthetic

<400> SEQUENCE: 3
catttccttc tggaccactc gag                                                 23

<210> SEQ ID NO 4
<211> LENGTH: 22
<212> TYPE: DNA
<213> ORGANISM: Artificial Sequence
<220> FEATURE:
<223> OTHER INFORMATION: Synthetic

<400> SEQUENCE: 4
atagcttctg ccaaccgaac gg                                                  22

<210> SEQ ID NO 5
<211> LENGTH: 24
<212> TYPE: DNA
<213> ORGANISM: Artificial Sequence
<220> FEATURE:
<223> OTHER INFORMATION: Synthetic

<400> SEQUENCE: 5
taaggaatgt gagcaccttc cttc                                                24

<210> SEQ ID NO 6
<211> LENGTH: 20
<212> TYPE: DNA
<213> ORGANISM: Artificial Sequence
<220> FEATURE:
<223> OTHER INFORMATION: Synthetic

<400> SEQUENCE: 6
tccaccaccc tgttgctgta                                                     20

<210> SEQ ID NO 7
<211> LENGTH: 20
<212> TYPE: DNA
<213> ORGANISM: Artificial Sequence
<220> FEATURE:
<223> OTHER INFORMATION: Synthetic

<400> SEQUENCE: 7
accacagtcc atgccatcac                                                     20

<210> SEQ ID NO 8
<211> LENGTH: 20198
<212> TYPE: DNA
<213> ORGANISM: Artificial Sequence
<220> FEATURE:
<223> OTHER INFORMATION: Synthetic
```

<400> SEQUENCE: 8

```
gttgacattg attattgact agttattaat agtaatcaat tacggggtca ttagttcata      60
gcccatatat ggagttccgc gttacataac ttacggtaaa tggcccgcct ggctgaccgc     120
ccaacgaccc ccgcccattg acgtcaataa tgacgtatgt tcccatagta acgccaatag     180
ggactttcca ttgacgtcaa tgggtggagt atttacggta aactgcccac ttggcagtac     240
atcaagtgta tcatatgcca agtccgcccc ctattgacgt caatgacggt aaatggcccg     300
cctggcatta tgcccagtac atgaccttac gggactttcc tacttggcag tacatctacg     360
tattagtcat cgctattacc atggtgatgc ggttttggca gtacaccaat gggcgtggat     420
agcggtttga ctcacgggga tttccaagtc tccaccccat tgacgtcaat gggagtttgt     480
tttggcacca aaatcaacgg gactttccaa aatgtcgtaa taaccccgcc ccgttgacgc     540
aaatgggcgg taggcgtgta cggtgggagg tctatataag cagagctcgt ttagtgaacc     600
gtcagatctc tagaagctgg gtaccagctg ctagccacca tggcttccaa ggtgtacgac     660
cccgagcaac gcaaacgcat gatcactggg cctcagtggt gggctcgctg caagcaaatg     720
aacgtgctgg actccttcat caactactat gattccgaga agcacgccga gaacgccgtg     780
atttttctgc atggtaacgc tgcctccagc tacctgtgga ggcacgtcgt gcctcacatc     840
gagcccgtgg ctagatgcat catccctgat ctgatcggaa tgggtaagtc cggcaagagc     900
gggaatggct catatcgcct cctggatcac tacaagtacc tcaccgcttg gttcgagctg     960
ctgaaccttc caaagaaaat catctttgtg ggccacgact gggggcttg tctggccttt    1020
cactactcct acgagcacca agacaagatc aaggccatcg tccatgctga gagtgtcgtg    1080
gacgtgatcg agtcctggga cgagtggcct gacatcgagg aggatatcgc cctgatcaag    1140
agcgaagagg gcgagaaaat ggtgcttgag aataacttct tcgtcgagac catgctccca    1200
agcaagatca tgcggaaact ggagcctgag gagttcgctg cctacctgga gccattcaag    1260
gagaagggcg aggttagacg gcctaccctc tcctggcctc gcgagatccc tctcgttaag    1320
ggaggcaagc ccgacgtcgt ccagattgtc cgcaactaca acgcctacct tcgggccagc    1380
gacgatctgc ctaagatgtt catcgagtcc gaccctgggt tcttttccaa cgctattgtc    1440
gagggagcta agaagttccc taacaccgag ttcgtgaagg tgaagggcct ccacttcagc    1500
caggaggacg ctccagatga aatgggtaag tacatcaaga gcttcgtgga gcgcgtgctg    1560
aagaacgagc agtaattcta gagcggccgc tcgaggccgg caaggccgga tccagacatg    1620
ataagataca ttgatgagtt tggacaaacc acaactagaa tgcagtgaaa aaaatgcttt    1680
atttgtgaaa tttgtgatgc tattgcttta tttgtaacca ttataagctg caataaacaa    1740
gttaacaaca acaattgcat tcattttatg tttcaggttc agggggaggt gtgggaggtt    1800
ttttaaagca agtaaaacct ctacaaatgt ggtatggctg attatgatcc ggctgcctcg    1860
cgcgtttcgg tgatgacggt gaaaacctct gacacatgca gctcccggag acggtcacag    1920
cttgtctgta agcggatgcc gggagcagac aagcccgtca gcgtcagcg ggtgttggcg    1980
ggtgtcgggg cgcagccatg aggtcgactc tagaggatcg atgccccgcc ccggacgaac    2040
taaacctgac tacgacatct ctgccccttc ttcgcgggc agtgcatgta atcccttcag    2100
ttggttggta caacttgcca actgggccct gttccacatg tgacacgggg ggggaccaaa    2160
cacaaagggg ttctctgact gtagttgaca tccttataaa tggatgtgca catttgccaa    2220
cactgagtgg ctttcatcct ggagcagact ttgcagtctg tggactgcaa cacaacattg    2280
cctttatgtg taactcttgg ctgaagctct tacaccaatg ctgggggaca tgtacctccc    2340
```

```
agggggcccag gaagactacg ggaggctaca ccaacgtcaa tcagaggggc ctgtgtagct    2400
accgataagc ggaccctcaa gagggcatta gcaatagtgt ttataaggcc cccttgttaa    2460
ccctaaacgg gtagcatatg cttcccgggt agtagtatat actatccaga ctaaccctaa    2520
ttcaatagca tatgttaccc aacgggaagc atatgctatc gaattagggt tagtaaaagg    2580
gtcctaagga acagcgatat ctcccacccc atgagctgtc acggttttat ttacatgggg    2640
tcaggattcc acgagggtag tgaaccattt tagtcacaag ggcagtggct gaagatcaag    2700
gagcgggcag tgaactctcc tgaatcttcg cctgcttctt cattctcctt cgtttagcta    2760
atagaataac tgctgagttg tgaacagtaa ggtgtatgtg aggtgctcga aaacaaggtt    2820
tcaggtgacg cccccagaat aaaatttgga cgggggttc agtggtggca ttgtgctatg     2880
acaccaatat aaccctcaca aaccccttgg gcaataaata ctagtgtagg aatgaaacat    2940
tctgaatatc tttaacaata gaaatccatg gggtggggac aagccgtaaa gactggatgt    3000
ccatctcaca cgaatttatg gctatgggca acacataatc ctagtgcaat atgatactgg    3060
ggttattaag atgtgtccca gcagggacc aagacaggtg aaccatgttg ttacactcta     3120
tttgtaacaa ggggaaagag agtggacgcc gacagcagcg gactccactg gttgtctcta    3180 acaccccga aaattaaacg gggctccacg ccaatggggc ccataaacaa agacaagtgg     3240
ccactctttt ttttgaaatt gtggagtggg ggcacgcgtc agcccccaca cgccgccctg    3300
cggttttgga ctgtaaaata agggtgtaat aacttggctg attgtaaccc cgctaaccac    3360
tgcggtcaaa ccacttgccc acaaaaccac taatggcacc ccggggaata cctgcataag    3420
taggtgggcg ggccaagata ggggcgcgat tgctgcgatc tggaggacaa attacacaca    3480
cttgcgcctg agcgccaagc acagggttgt tggtcctcat attcacgagg tcgctgagag    3540
cacggtgggc taatgttgcc atgggtagca tatactaccc aaatatctgg atagcatatg    3600
ctatcctaat ctatatctgg gtagcatagg ctatcctaat ctatatctgg gtagcatatg    3660
ctatcctaat ctatatctgg gtagtatatg ctatcctaat ttatatctgg gtagcatagg    3720
ctatcctaat ctatatctgg gtagcatatg ctatcctaat ctatatctgg gtagtatatg    3780
ctatcctaat ctgtatccgg gtagcatatg ctatcctaat agagattagg gtagtatatg    3840
ctatcctaat ttatatctgg gtagcatata ctacccaaat atctggatag catatgctat    3900
cctaatctat atctgggtag catatgctat cctaatctat atctgggtag cataggctat    3960
cctaatctat atctgggtag catatgctat cctaatctat atctgggtag tatatgctat    4020
cctaatttat atctgggtag cataggctat cctaatctat atctgggtag catatgctat    4080
cctaatctat atctgggtag tatatgctat cctaatctgt atccgggtag catatgctat    4140
cctcatgcat atacagtcag catatgatac ccagtagtag agtgggagtg ctatcctttg    4200
catatgccgc cacctcccaa ggggcgtga attttcgctg cttgtccttt tcctgctggt     4260
tgctcccatt cttaggtgaa tttaaggagg ccaggctaaa gccgtcgcat gtctgattgc    4320
tcaccaggta aatgtcgcta atgttttcca acgcgagaag gtgttgagcg cggagctgag    4380
tgacgtgaca acatgggtat gcccaattgc cccatgttgg gaggacgaaa atggtgacaa    4440
gacagatggc cagaaataca ccaacagcac gcatgatgtc tactgggggat ttattcttta    4500 gtgcggggga atacacggct tttaatacga ttgagggcgt ctcctaacaa gttacatcac    4560
tcctgccctt cctcaccctc atctccatca cctccttcat ctccgtcatc tccgtcatca    4620
ccctccgcgg cagccccttc caccataggt ggaaaccagg gaggcaaatc tactccatcg    4680
tcaaagctgc acacagtcac cctgatattg caggtaggag cgggctttgt cataacaagg    4740
```

```
tccttaatcg catccttcaa aacctcagca aatatatgag tttgtaaaaa gaccatgaaa    4800
taacagacaa tggactccct tagcgggcca ggttgtgggc cgggtccagg ggccattcca    4860
aaggggagac gactcaatgg tgtaagacga cattgtggaa tagcaagggc agttcctcgc    4920
cttaggttgt aaagggaggt cttactacct ccatatacga acacaccggc gacccaagtt    4980
ccttcgtcgg tagtcctttc tacgtgactc ctagccagga gagctcttaa accttctgca    5040
atgttctcaa atttcgggtt ggaacctcct tgaccacgat gcttttccaa accaccctcc    5100
tttttttgcgc cctgcctcca tcaccctgac cccggggtcc agtgcttggg ccttctcctg    5160
ggtcatctgc ggggccctgc tctatcgctc cggggggcac gtcaggctca ccatctgggc    5220
caccttcttg gtggtattca aaataatcgg cttcccctac agggtggaaa aatggccttc    5280
tacctggagg gggcctgcgc ggtggagacc cggatgatga tgactgacta ctgggactcc    5340
tgggcctctt ttctccacgt ccacgacctc tcccctggc tctttcacga cttcccccc    5400
tggctctttc acgtcctcta ccccggcggc ctccactacc tcctcgaccc cggcctccac    5460
tacctcctcg accccggcct ccactgcctc ctcgaccccg gcctcacct cctgctcctg    5520
cccctcctgc tcctgcccct cctcctgctc ctgcccctcc tgcccctcct gtcctgccc    5580
ctcctgcccc tcctgctcct gccccctctg cccctcctgc tcctgcccct cctgcccctc    5640
ctcctgctcc tgcccctcct gcccctcctc ctgctcctgc ccctcctgcc ctcctgctc    5700
ctgcccctcc tgcccctcct gtcctgccc ctcctgcccc tcctgcccct gccccctctg    5760
ctcctgcccc tcctgctcct gcccctcctg ctcctgcccc tcctgcccct cctgcccctc    5820
ctcctgctcc tgcccctcct gtcctgccc ctcctgcccc tcctgcccct gccccctctg    5880
cccctcctcc tgctcctgcc ctcctgcccc ctcctgcccc tcctcctgct cctgcccctc    5940
ctgcccctcc tcctgctcct gccccctcctc ctgctcctgc ccctcctgcc cctcctgccc    6000
ctcctcctgc tcctgcccct cctgcccctc ctcctgctcc tgcccctcct cctgctcctg    6060
cccctcctgc cctcctgcc cctcctcctg tcctgcccc tcctcctgct cctgcccctc    6120
ctgcccctcc tgcccctcct gccccctcctc ctgctcctgc ccctcctcct gctcctgccc    6180
ctcctgctcc tgcccctccc gctcctgctc ctgctcctgt tccaccgtgg gtcccttgc    6240
agccaatgca acttggacgt ttttgggtc tccggacacc atctctatgt cttggccctg    6300
atcctgagcc gccggggct cctggtcttc cgcctcctcg tcctcgtcct cttccccgtc    6360
ctcgtccatg gttatcaccc cctcttcttt gaggtccact gccgccggag ccttctggtc    6420
cagatgtgtc tcccttctct cctaggccat ttccaggtcc tgtacctggc ccctcgtcag    6480
acatgattca cactaaaaga gatcaataga catctttatt agacgacgct cagtgaatac    6540
agggagtgca gactcctgcc ccctccaaca gcccccccac cctcatcccc ttcatggtcg    6600
ctgtcagaca gatccaggtc tgaaaattcc ccatcctccg aaccatcctc gtcctcatca    6660
ccaattactc gcagcccgga aaactcccgc tgaacatcct caagatttgc gtcctgagcc    6720
tcaagccagg cctcaaattc ctcgtccccc tttttgctgg acggtaggga tgggattct    6780
cgggaccct cctcttcctc ttcaaggtca ccagacagag atgctactgg ggcaacggaa    6840
gaaaagctgg gtgcggcctg tgaggatcag cttatcgatg ataagctgtc aaacatgaga    6900
attcttgaag acgaaagggc ctcgtgatac gcctattttt ataggttaat gtcatgataa    6960
taatggtttc ttagacgtca ggtggcactt tcggggaaa tgtgcgcgga acccctattt    7020
gtttattttt ctaaatacat tcaaatatgt atccgctcat gagacaataa ccctgataaa    7080
tgcttcaata atattgaaaa aggaagagta tgagtattca acatttccgt gtcgccctta    7140
```

```
ttcccttttt tgcggcattt tgccttcctg tttttgctca cccagaaacg ctggtgaaag    7200
taaaagatgc tgaagatcag ttgggtgcac gagtgggtta catcgaactg gatctcaaca    7260
gcggtaagat ccttgagagt tttcgccccg aagaacgttt tccaatgatg agcactttta    7320
aagttctgct atgtggcgcg gtattatccc gtgttgacgc cgggcaagag caactcggtc    7380
gccgcataca ctattctcag aatgacttgg ttgagtactc accagtcaca gaaaagcatc    7440
ttacggatgg catgacagta agagaattat gcagtgctgc cataaccatg agtgataaca    7500
ctgcggccaa cttacttctg acaacgatcg gaggaccgaa ggagctaacc gcttttttgc    7560
acaacatggg ggatcatgta actcgccttg atcgttggga accggagctg aatgaagcca    7620
taccaaacga cgagcgtgac accacgatgc ctgcagcaat ggcaacaacg ttgcgcaaac    7680
tattaactgg cgaactactt actctagctt cccggcaaca attaatagac tggatggagg    7740
cggataaagt tgcaggacca cttctgcgct cggcccttcc ggctggctgg tttattgctg    7800
ataaatctgg agccggtgag cgtgggtctc gcggtatcat tgcagcactg gggccagatg    7860
gtaagccctc ccgtatcgta gttatctaca cgacggggag tcaggcaact atggatgaac    7920
gaaatagaca gatcgctgag ataggtgcct cactgattaa gcattggtaa ctgtcagacc    7980
aagtttactc atatatactt tagattgatt taaaacttca ttttaatttt aaaaggatct    8040
aggtgaagat cctttttgat aatctcatga ccaaaatccc ttaacgtgag ttttcgttcc    8100
actgagcgtc agaccccgta gaaaagatca aaggatcttc ttgagatcct ttttttctgc    8160
gcgtaatctg ctgcttgcaa acaaaaaaac caccgctacc agcggtggtt tgtttgccgg    8220
atcaagagct accaactctt tttccgaagg taactggctt cagcagagcg cagataccaa    8280
atactgtcct tctagtgtag ccgtagttag gccaccactt caagaactct gtagcaccgc    8340
ctacatacct cgctctgcta atcctgttac cagtggctgc tgccagtggc gataagtcgt    8400
gtcttaccgg gttggactca agacgatagt taccggataa ggcgcagcgg tcgggctgaa    8460
cggggggttc gtgcacacag cccagcttgg agcgaacgac ctacaccgaa ctgagatacc    8520
tacagcgtga gctatgagaa agcgccacgc ttcccgaagg gagaaaggcg gacaggtatc    8580
cggtaagcgg cagggtcgga acaggagagc gcacgaggga gcttccaggg ggaaacgcct    8640
ggtatcttta tagtcctgtc gggtttcgcc acctctgact tgagcgtcga ttttttgtgat    8700 gctcgtcagg gggcggagc ctatggaaaa acgccagcaa cgcggccttt ttacggttcc    8760
tggccttttg ctggccttga agctgtccct gatggtcgtc atctacctgc ctggacagca    8820
tggcctgcaa cgcgggcatc ccgatgccgc cggaagcgag aagaatcata atggggaagg    8880
ccatccagcc tcgcgtcgcg aacgccagca agacgtagcc cagcgcgtcg gccccgagat    8940
gcgccgcgtg cggctgctgg agatggcgga cgcgatggat atgttctgcc aagggttggt    9000
ttgcgcattc acagttctcc gcaagaattg attggctcca attcttggag tggtgaatcc    9060
gttagcgagg tgccgccctg cttcatcccc gtggcccgtt gctcgcgttt gctggcggtg    9120
tccccggaag aaatatattt gcatgtcttt agttctatga tgacacaaac cccgcccagc    9180
gtcttgtcat tggcgaattc gaacacgcag atgcagtcgg ggcggcgcgg tccgaggtcc    9240
acttcgcata ttaaggtgac gcgtgtggcc tcgaacaccg agcgaccctg cagcgacccg    9300
cttaacagcg tcaacagcgt gccgcagatc ccgggggggca atgagatatg aaaaagcctg    9360
aactcaccgc gacgtctgtc gagaagtttc tgatcgaaaa gttcgacagc gtctccgacc    9420
tgatgcagct ctcggagggc gaagaatctc gtgctttcag cttcgatgta ggagggcgtg    9480
gatatgtcct gcgggtaaat agctgcgccg atggtttcta caaagatcgt tatgtttatc    9540
```

```
ggcactttgc atcggccgcg ctcccgattc cggaagtgct tgacattggg gaattcagcg    9600
agagcctgac ctattgcatc tcccgccgtg cacagggtgt cacgttgcaa gacctgcctg    9660
aaaccgaact gcccgctgtt ctgcagccgg tcgcggaggc catggatgcg atcgctgcgg    9720
ccgatcttag ccagacgagc gggttcggcc cattcggacc gcaaggaatc ggtcaataca    9780
ctacatggcg tgatttcata tgcgcgattg ctgatcccca tgtgtatcac tggcaaactg    9840
tgatggacga caccgtcagt gcgtccgtcg cgcaggctct cgatgagctg atgctttggg    9900
ccgaggactg ccccgaagtc cggcacctcg tgcacgcgga tttcggctcc aacaatgtcc    9960
tgacggacaa tggccgcata acagcggtca ttgactggag cgaggcgatg ttcggggatt   10020
cccaatacga ggtcgccaac atcttcttct ggaggccgtg gttggcttgt atggagcagc   10080
agacgcgcta cttcgagcgg aggcatccgg agcttgcagg atcgccgcgg ctccgggcgt   10140
atatgctccg cattggtctt gaccaactct atcagagctt ggttgacggc aatttcgatg   10200
atgcagcttg ggcgcagggt cgatgcgacg caatcgtccg atccgagcc gggactgtcg    10260
ggcgtacaca aatcgcccgc agaagcgcgg ccgtctggac cgatggctgt gtagaagtac   10320
tcgccgatag tggaaaccga cgccccagca ctcgtccgga tcgggagatg ggggaggcta   10380
actgaaacac ggaaggagac aataccgaa ggaacccgcg ctatgacggc aataaaaaga    10440
cagaataaaa cgcacgggtg ttgggtcgtt tgttcataaa cgcggggttc ggtcccaggg   10500
ctggcactct gtcgataccc caccgagacc ccattggggc caatacgccc cgtttcttc    10560
cttttccccca ccccaccccc caagttcggg tgaaggccca gggctcgcag ccaacgtcgg   10620
ggcggcaggc cctgccatag ccactggccc cgtgggttag ggacggggtc ccccatgggg   10680
aatggtttat ggttcgtggg ggttattatt ttgggcgttg cgtggggtca ggtccacgac   10740
tggactgagc agacagaccc atggttttg gatggcctgg gcatggaccg catgtactgg    10800
cgcgacacga acaccgggcg tctgtggctg ccaaacaccc ccgacccca aaaccaccg    10860
cgcggatttc tggcgtgcca agctagtcga ccaattctca tgtttgacag cttatcatcg   10920
cagatccggg caacgttgtt gccattgctg caggcgcaga actggtaggt atggaagatc   10980
tatacattga atcaatattg gcaattagcc atattagtca ttggttatat agcataaatc   11040
aatattggct attggccatt gcatacgttg tatctatatc ataatatgta cctaaccaag   11100
ttcctctttc agaggttatt tcaggccatg gtgctgcgca gatccgcgta tgcggtgtga   11160
aataccgcac agatgcgtaa ggagaaaata ccgcatcagg cgaaattgta aacgttaata   11220
ttttgttaaa attcgcgtta aatatttgtt aaatcagctc attttttaac caataggccg   11280
aaatcggcaa aatcccttat aaatcaaaag aatagaccga gatagggttg agtgttgttc   11340
cagtttggaa caagagtcca ctattaaaga acgtggactc caacgtcaaa gggcgaaaaa   11400
ccgtctatca gggcgatggc ccactacgtg aaccatcacc caaatcaagt ttttgcggt    11460
cgaggtgccg taaagctcta atcggaacc ctaaagggag cccccgattt agagcttgac    11520
ggggaaagcc ggcgaacgtg gcgagaaagg aagggaagaa agcgaaagga gcgggcgcta   11580
gggcgctggc aagtgtagcg gtcacgctgc gcgtaaccac cacacccgcc gcgcttaatg   11640
cgccgctaca gggcgcgtcc attcgccatt caggctgcgc aactgttggg aagggcgatc   11700
ggtgcgggcc tcttcgctat tacgccagcc cggatcgatc cttatcggat tttaccacat   11760
ttgtagaggt tttacttgct ttaaaaaacc tcccacatct cccctgaac ctgaaacata    11820
aaatgaatgc aattgttgtt gttaacttgt ttattgcagc ttataatggt tacaaataaa   11880
gcaatagcat cacaaatttc acaaataaag catttttttc actgcattct agttgtggtt   11940
```

```
tgtccaaact catcaatgta tcttatcatg tctgctcgaa gcattaaccc tcactaaagg    12000
gaagcggccg cttacatttt acaatttgga ctttccgccc ttcttggcct ttatgaggat    12060
ctctctgatt tttcttgcgt cgagttttcc ggtaagacct ttcggtactt cgtccacaaa    12120
cacaactcct ccgcgcaact ttttcgcggt tgttacttga ctggcgacgt aatccacgat    12180 ctcttttttcc gtcatcgtct ttccgtgctc caaaacaaca acggcggcgg gaagttcacc   12240
ggcgtcatcg tcgggaagac ctgccacgcc cgcgtcgaag atgttggggt gttgtaacaa    12300
tatcgattcc aattcagcgg gggccacctg atatcctttg tatttaatta aagacttcaa    12360
gcggtcaact atgaagaagt gttcgtcttc gtcccagtaa gctatgtctc cagaatgtag    12420
ccatccatcc ttgtcaatca aggcgttggt cgcttccgga ttgtttacat aaccggacat    12480
aatcataggt cctctgacac ataattcgcc tctctgatta cgcccagcg ttttcccggt     12540 atccagatcc acaaccttcg cttcaaaaaa tggaacaact ttaccgaccg cgcccggttt    12600
atcatccccc tcgggtgtaa tcagaatagc tgatgtagtc tcagtgagcc catatccttg    12660
tcgtatccct ggaagatgga agcgttttgc aaccgcttcc ccgacttctt tcgaaagagg    12720
tgcgccccca gaagcaattt cgtgtaaatt agataaatcg tatttgtcaa tcagagtgct    12780
tttggcgaag aatgaaaata gggttggtac tagcaacgca ctttgaattt tgtaatcctg    12840
aagggatcgt aaaaacagct cttcttcaaa tctatacatt aagacgactc gaaatccaca    12900
tatcaaatat ccgagtgtag taaacattcc aaaaccgtga tggaatggaa caacacttaa    12960
aatcgcagta tccggaatga tttgattgcc aaaaatagga tctctggcat gcgagaatct    13020
gacgcaggca gttctatgcg gaagggccac acccttaggt aacccagtag atccagagga    13080
attcattatc agtgcaattg ttttgtcacg atcaaaggac tctggtacaa aatcgtattc    13140
attaaaaccg ggaggtagat gagatgtgac gaacgtgtac atcgactgaa atccctggta    13200
atccgtttta gaatccatga taataatttt ctggattatt ggtaattttt tttgcacgtt    13260
caaaattttt tgcaaccccct ttttggaaac aaacactacg gtaggctgcg aaatgttcat   13320
actgttgagc aattcacgtt cattataaat gtcgttcgcg ggcgcaactg caactccgat    13380
aaataacgcg cccaacaccg gcataaagaa ttgaagagag ttttcactgc atacgacgat    13440
tctgtgattt gtattcagcc catatcgttt catagcttct gccaaccgaa cggacatttc    13500
gaagtattcc gcgtacgtga tgttcacctc gatatgtgca tctgtaaaag caattgttcc    13560
aggaaccagg gcgtatctct tcatagcctt atgcagttgc tctccagcgg ttccatcctc    13620
tagaggatag aatggcgccg ggcctttctt tatgtttttg gcgtcttcca gctgctctat    13680
gccagcattt cctgcaaatg agaaattaga accagaggct tgacgaattc cagttaaacc    13740
atgtcctctg tggacaccag ttaaacttga ctagagcact tcatatgtca gagtgtacag    13800
tgcagtatgc ctaggttatc ccatatcaca ataaaaaaaa gtctgctggt ctgcctacta    13860
gtgatataaa atggcatcat atcctaaagc tctttattgt gaaagtatgt tcttccaca    13920 taaccaacca gttaagtatg agaattctag tagggatgta gattaacctt ttatctaata    13980
gttttggcat caaaattctt taatattgat tgttttacat taaccttca acttttaac     14040 atctgaactt tttaaatgtt caaaacatt tgttttccac aaaccataaa gttttacaaa     14100
agtaagattc actttcataa tgctggcaga cttactcctt agatttaagg aatgtgagca    14160
ccttccttct ttttgatttt gtctgaaacc ctgtaaggaa aataaggaa gttaaaaaaa    14220 atagctatat agacatagat agctatatat agatagcttt atatggatgt taaaaagcat    14280
tttgtttcac aagacatttt acttatttta ttcaacaaaa tatgatcaga aattaagttg    14340
```

```
atagtctttt aatgtacttt aaaagttatc ccaaagaaaa caattattag gctgcagtta   14400
aggttttctt gcagtggctc atgcctacaa tcccacaact tgggaggcg gaggtagggg    14460
gatcacttga gacctggagc ttgacaccac cctgggcaac ataatgagac cctgtctcta   14520
caaaaaattt aaaaattagg ccggcgtggt ggctcaggct aggcacagtg gctcacgcct   14580
gtaatcccag cactttggga ggccgagaca gttggatcac ctgagctcag gagttcgaga   14640
acagcctggc caacatggca aaccccatt tctactgaaa gtacaaaaaa ttagccaggc    14700
atggtggtgg ggacctctaa tcccagctac ttgggaggct gaggcaggag aatcacttga   14760
acccaggagg cggaggctgc agtgagctga gatttacacc actgcactcc agcctgggtg   14820
acagagcaag actctgtctc aaaaaaaaat aaataaataa aaataaaaat tagccaggtg   14880
cagtggcatt atcactgtag tcccagctac tcgggaaact gaggtgagag gactgcttga   14940
gccctggagg tcaaggctgc agtgagctgt gaatgtgccc ttgcactcca gcctgagcaa   15000
tagagtgaga cctggtctct aaaaaataaa atttggagg cggagcttgc agtgagccga    15060
gactgcgcca ctgtactcca gcctgggtga cagagcgaga ctccgtctca aaaaaaaaa    15120
aaaaataaaa taaataaaa taattttaaa tgttctgact aaaatacaat agaacatgtc    15180
cgtaggagac taacgtataa agtgacaagt ttgaagccat actccccaag gttcaatgtg   15240
gtacacatta ccccagatct ttgtgcatta aaaaatttc atttctcttg gaaggccgag    15300
gcgggtggat cacggggtca ggagattgag accatcctgg ctaacacagt gaaaccctgt   15360
ctttacaaaa aaatacaaaa aattagacag gcgtggtggc aggcacctgt agtcccagct   15420
acctctgagg ctgaggcagg agaatggcgt gaatccagaa ggcagagctt gctgtgagcc   15480
aagatcacgc cattgcactc cagcctgggc aacagagcaa gactccgtct caaaaaaaaa   15540
aaaaaaaaa aaagaatttc attttttcatt tatgaaaaat tatcccatct tttccattcc   15600
ctacaatcaa tttcaaatca gagattaaaa cattatttag aaaagtata atttcaattc    15660
aaaagtgtat aatcaaaata atctaacaat agcatgaaag cttttttaaaa ttaactaaaa   15720
ttatacttag ggacaatgca agagtaattt aagcctcaga cagttgtatt ttttttatttt   15780
tatttttag taatataaag agagaagcaa gtagtattt ataaatttac aaaacaaagt    15840
cacataacta caaaaaaatt gtcaggaaaa gatgctgagt gattacttac catataatag   15900
ccagtatgat agccactcat gtaccatgaa attaacatac ttcccaaagc atcagcatca   15960
tcaagagaat ctggacatat gggaggtggt ggggaatta tctcgagtgg tccagaagga    16020
aatggaggca gccagcatga tagtaagtgg ggtggtggtg gtggcggtgg cggtggtggg   16080
ccattgaatt ttagacctgg cttcctggt cccagtcttg gccctggcat gggggtggt     16140
ggagggagaa aagagttcca tggagcagat ttgggcttga tgttatctga tttatttcca   16200
ggagacctgg agttctcact ttcatctgtt gaaacttggc tttcattttc attctcttga   16260
gcattctgtt ctatattatt agctacttca cagattgggg aaagtagatc ggacagattt   16320
tgctcctctc tatttccata tccagtgtaa accacaacac aggtttctct cttaaaatca   16380
attgaagcaa tggtagctgg gtaaatgcaa ccgtcttctg accaaatggc agaacatttg   16440
tccccaactt tccactgttg taaggaagct gcagtattct tcttttggct tttattcttc   16500
ttagcaggtt ttcttttagg tgtggttttt ggtttacccg aagtttcaca aatgtcacca   16560
ttctttagag catgcttaaa tgaagccaca gctttatcat atgcttttat cagtgctgta   16620
tcatcccaaa tgtcagaatc atcgctctgg cctgtgccgc gccggaacag cacggaatcc   16680
tcctgctccg ggacgccgcc accactgccg ccgctgctca tcgccatagc aaacccgcgg   16740
```

```
gtgcgcagcg tggggccccg tcccttctta agagtgacga cttccgccgc ccggggcttc   16800
tgggagcgga acagtacggt ggccgggagg accgcttgta gtaacttctc acgctttcta   16860
cgagtggtta tcgccctccc acatttgtgg cgtgtatatt tttcatttct ctcaatcctt   16920
tcatttcact gtgttatatt tcctttcctt ttttttttgt ttgtttgttt tgagacagag   16980
cctcgccctg tcgctcaggc tggagtgcag cggcgcgatc tcggctcact gcagcctcga   17040
cttcttgggc tcaagcgatc ctcccacctc agcctcccca gtagctagga ctataggcgt   17100
gcgccaccac gctcagctat tttttgtatt tagtagagac ggggtttcgg catgttgctt   17160
aggcctcgtc tcgaactcca gtgtgtgtgt gtgtgtgtgt gtgtgtgtgt gtgtgtgtgt   17220
agatatttat tcccctcccc ccttggaaaa gtaaatgtaa gctcctacta ggaatttaaa   17280
acctgcttga tctatataaa gacaaacaag gaaagacaaa catggggggca ggaaggaagg   17340 cggcagatcc ttaaacacta aagatatttt gatcccccaa ccttatttgt tgtttgtttt   17400
gagacggagt ctcgctctgt cgtcagagtg cagtggcacc atctcggctc attgcagcct   17460
cgacctcccg agctcaagcg atcctcccgc ctcaacctcc caagtagcta ggaccacagg   17520
ggcacgccac cacacccggc tagtttctgt atgttttgta gaggcggcgt ttggagcata   17580
ttgtgtaggc tggtctcgaa ctcctgagct caagatattc cgcccgcctc tggcatccca   17640
aaatgctggg attacaggtg tgagccacct cgcccagcct ccagtattct ttttttttt   17700 tgcgacagag tattgctctg tcacccaggc tggaatgcag tggcgtgatc tcagctcact   17760
gcaacctctg cctcccaggt tcaagcaatt ctcctgcctc agcccccga gtagctggga   17820 ttacaggcgc ccaccaccac acccggctaa ttttttgtatt tttagtaaag atgggggtttc   17880 accatgttgg ccaggctggt cttgaactcc tgaccttgta atccgaccgc ctcggcctcc   17940
caaagtgctg ggattacagg tgtgagccac cacaccgggc ctccagtatt ctttattaag   18000
catctagggt tgctaaatgg cttatatgta catagtatat atatattttt aactccacga   18060
aaggaacttt gagctcttcc cccaaaatac ccttggcttc tatatagtat acaagaaata   18120
tctgtggagg aaggggagaa tgggatgatg ttgaccaagt gtacaaaaat ggtaactccg   18180
tagaggtaat atgtggaatg taatcatttc acaatgtata tctaaacatc aaatggtaca   18240
ccttaaatat atacaatttt taggggtctg gtacggtggc tcatgcctat aatcccagca   18300
ctttgggagg ccaaggtggg tggatcactt gaggtcagga gttcaagacc agcctggcca   18360
acatggtgaa accctgtttc tcctaaaaat acaaaaatca gccgggtgtg gtggtgcagg   18420
cctgtaatga cagctgcttg ggaggctgag gcaggagaat ctcttgaact cgggaggcgg   18480
aggttgcagt gagccaagat cacgccactg cactccagcc tgagtgacag agtgcgactc   18540
catctcaaac aaataaatat gtacaatttt tatgtgtcaa aaaagttaaa ttgtcacaag   18600
ataaaaaaaa aaattttaaa tctcatgtca ggaaagtaat gtgccaaagg tacatctcac   18660
agataaacat gaaaacctgc actccagcct gggcgacaga gtgaggctgt gtctcagaaa   18720
aaaaaaaaaa agtaaaaaaa aaagtatgtt tttataaagc ttgcttagat ttttctgaat   18780
cataaaaatt ctcacaattg catttgatgt caaaatttaa acaaattacg tggacatatt   18840
acatgatggt taaaaaaata aatttaaaca aaatatagaa ccaggtttct ttttgttttt   18900
taattttttt cttttttgaga cggagtctcg ctctgccacc cagactggag tgcagtggct   18960
cactgcaacc tctgcctccc gggttcaagt gattctcctg tctcagcttc ccgagtacct   19020
gggattacag gcgtgtgcca ccacgcccag ctaattttg tatttttagt agagacgggg   19080
ttttgccatg ttggtcaggt tggtctcaaa ctcctgacct tgtgatccgc ccgcctcagc   19140
```

| | | | | |
|---|---|---|---|---|
| ctcccaaagt | gctgcgatta | caggcatgag | ccaccgcacc | cagccatttc ttttgttttt 19200 |
| tattatttag | agatataatt | gatatactat | agaattaatc | gttttagaga gtacaattga 19260 |
| atggtagata | gagcggaaac | cttaatatat | tcacaaggtt | gtgcaaccat cactactatc 19320 |
| taactccaga | acattttaat | cacccaccaa | agaaactctg | tttcctttag cagtgcgctg 19380 |
| ccatgctcag | ctatttttg | ggagagaagg | ggtctcccca | tgttgtccac gctggtctca 19440 |
| aactcggttg | cttaagcagt | cctcccactt | gagccgctgt | gcccaggcct gagttactat 19500 |
| atttataaaa | gttatttcat | atgatagaca | aatcattcaa | acataatga ggtaaactgc 19560 |
| caaaagaaac | cattttacca | tatttgaagg | catttaatgt | aaatgttgaa tttaatttca 19620 |
| tgtactggaa | tcagtctttt | tgcatatgta | atttcatac | caaaaatctg tcttcagttg 19680 |
| actcctggaa | ctctctcatg | ataaaataaa | agtttcaaat | aatgtcgggg tggtggctaa 19740 |
| cacctgtaat | cccagcactg | tgggagtccg | aggcaggtgg | atcacatgag gtcaggagtt 19800 |
| tgagaccagc | ctagccaaca | tggcaacact | aaagatatga | aagtcagcca ggcatggtgg 19860 |
| tgcatgcctg | taatctcagc | tactagggag | gctgaggcac | aaaaatcact tgaaactggg 19920 |
| aggtggaggt | tgcaatgagc | tgagatcgtg | ccactgcaca | ccagcctgtg agacagagca 19980 |
| agactctgtc | tcaaaaaaaa | aaaaaaaaaa | aaaaaaaaa | gggccaagta tggtggctca 20040 |
| tgcctgtaat | cctagcactt | tgggaggctg | agtgggagag | gatcatttga gcccaagtaa 20100 |
| catggtcagg | ccccatctct | acaaaaataa | attagctggg | catggtggta tgggcttgtg 20160 |
| gtacatttat | attggctcat | gtccaatatg | accgccat | 20198 |

<210> SEQ ID NO 9
<211> LENGTH: 20200
<212> TYPE: DNA
<213> ORGANISM: Artificial Sequence
<220> FEATURE:
<223> OTHER INFORMATION: Synthetic

<400> SEQUENCE: 9

| | | | | |
|---|---|---|---|---|
| gttgacattg | attattgact | agttattaat | agtaatcaat | tacgggtca ttagttcata 60 |
| gcccatatat | ggagttccgc | gttacataac | ttacggtaaa | tggcccgcct ggctgaccgc 120 |
| ccaacgaccc | ccgcccattg | acgtcaataa | tgacgtatgt | tcccatagta acgccaatag 180 |
| ggactttcca | ttgacgtcaa | tgggtggagt | atttacggta | aactgcccac ttggcagtac 240 |
| atcaagtgta | tcatatgcca | agtccgcccc | ctattgacgt | caatgacggt aaatggcccg 300 |
| cctggcatta | tgcccagtac | atgaccttac | gggactttcc | tacttggcag tacatctacg 360 |
| tattagtcat | cgctattacc | atggtgatgc | ggttttggca | gtacaccaat gggcgtggat 420 |
| agcggtttga | ctcacgggga | tttccaagtc | tccaccccat | tgacgtcaat gggagtttgt 480 |
| tttggcacca | aaatcaacgg | gactttccaa | aatgtcgtaa | taaccccgcc ccgttgacgc 540 |
| aaatgggcgg | taggcgtgta | cggtgggagg | tctatataag | cagagctcgt ttagtgaacc 600 |
| gtcagatctc | tagaagctgg | gtaccagctg | ctagccacca | tggcttccaa ggtgtacgac 660 |
| cccgagcaac | gcaaacgcat | gatcactggg | cctcagtggt | gggctcgctg caagcaaatg 720 |
| aacgtgctgg | actccttcat | caactactat | gattccgaga | agcacgccga gaacgccgtg 780 |
| attttctgc | atggtaacgc | tgcctccagc | tacctgtgga | ggcacgtcgt gcctcacatc 840 |
| gagcccgtgg | ctagatgcat | catccctgat | ctgatcggaa | tgggtaagtc cggcaagagc 900 |
| gggaatggct | catatcgcct | cctggatcac | tacaagtacc | tcaccgcttg gttcgagctg 960 |
| ctgaaccttc | caaagaaaat | catctttgtg | ggccacgact | gggggggcttg tctggccttt 1020 |

```
cactactcct acgagcacca agacaagatc aaggccatcg tccatgctga gagtgtcgtg    1080
gacgtgatcg agtcctggga cgagtggcct gacatcgagg aggatatcgc cctgatcaag    1140
agcgaagagg gcgagaaaat ggtgcttgag aataacttct tcgtcgagac catgctccca    1200
agcaagatca tgcggaaact ggagcctgag gagttcgctg cctacctgga gccattcaag    1260
gagaagggcg aggttagacg gcctaccctc tcctggcctc gcgagatccc tctcgttaag    1320
ggaggcaagc ccgacgtcgt ccagattgtc cgcaactaca acgcctacct tcgggccagc    1380
gacgatctgc ctaagatgtt catcgagtcc gaccctgggt tcttttccaa cgctattgtc    1440
gagggagcta agaagttccc taacaccgag ttcgtgaagg tgaagggcct ccacttcagc    1500
caggaggacg ctccagatga aatgggtaag tacatcaaga gcttcgtgga gcgcgtgctg    1560
aagaacgagc agtaattcta gagcggccgc tcgaggccgg caaggccgga tccagacatg    1620
ataagataca ttgatgagtt tggacaaacc acaactagaa tgcagtgaaa aaaatgcttt    1680
atttgtgaaa tttgtgatgc tattgcttta tttgtaacca ttataagctg caataaacaa    1740
gttaacaaca acaattgcat tcattttatg tttcaggttc agggggaggt gtgggaggtt    1800
ttttaaagca agtaaaacct ctacaaatgt ggtatggctg attatgatcc ggctgcctcg    1860
cgcgtttcgg tgatgacggt gaaaacctct gacacatgca gctcccggag acggtcacag    1920
cttgtctgta agcggatgcc gggagcagac aagcccgtca ggcgtcagcg ggtgttggcg    1980
ggtgtcgggg cgcagccatg aggtcgactc tagaggatcg atgccccgcc ccggacgaac    2040
taaacctgac tacgacatct ctgccccttc ttcgcggggc agtgcatgta atcccttcag    2100
ttggttggta caacttgcca actgggccct gttccacatg tgacacgggg ggggaccaaa    2160
cacaaagggg ttctctgact gtagttgaca tccttataaa tggatgtgca catttgccaa    2220
cactgagtgg ctttcatcct ggagcagact ttgcagtctg tggactgcaa cacaacattg    2280
cctttatgtg taactcttgg ctgaagctct tacaccaatg ctgggggaca tgtacctccc    2340
aggggcccag gaagactacg ggaggctaca ccaacgtcaa tcagagggc ctgtgtagct    2400 accgataagc ggaccctcaa gagggcatta gcaatagtgt ttataaggcc cccttgttaa    2460
ccctaaacgg gtagcatatg cttcccgggt agtagtatat actatccaga ctaaccctaa    2520
ttcaatagca tatgttaccc aacgggaagc atatgctatc gaattagggt tagtaaaagg    2580
gtcctaagga acagcgatat ctcccacccc atgagctgtc acggttttat ttacatgggg    2640
tcaggattcc acgagggtag tgaaccattt tagtcacaag ggcagtggct gaagatcaag    2700
gagcgggcag tgaactctcc tgaatcttcg cctgcttctt cattctcctt cgtttagcta    2760
atagaataac tgctgagttg tgaacagtaa ggtgtatgtg aggtgctcga aacaaggtt    2820 tcaggtgacg cccccagaat aaaatttgga cgggggttc agtggtggca ttgtgctatg    2880
acaccaatat aaccctcaca aacccttgg gcaataaata ctagtgtagg aatgaaacat    2940
tctgaatatc tttaacaata gaaatccatg gggtggggac aagccgtaaa gactggatgt    3000
ccatctcaca cgaatttatg gctatgggca acacataatc ctagtgcaat atgatactgg    3060
ggttattaag atgtgtccca ggcagggacc aagacaggtg aaccatgttg ttacactcta    3120
tttgtaacaa ggggaaagag agtggacgcc gacagcagcg gactccactg gttgtctcta    3180
acaccccgga aaattaaacg gggctccacg ccaatggggc ccataaacaa agacaagtgg    3240
ccactctttt ttttgaaatt gtggagtggg ggcacgcgtc agcccccaca cgccgccctg    3300
cggttttgga ctgtaaaata agggtgtaat aacttggctg attgtaaccc cgctaaccac    3360
tgcggtcaaa ccacttgccc acaaaaccac taatggcacc ccggggaata cctgcataag    3420
```

```
taggtgggcg ggccaagata gggcgcgat tgctgcgatc tggaggacaa attacacaca    3480
cttgcgcctg agcgccaagc acaggttgt tggtcctcat attcacgagg tcgctgagag    3540
cacggtgggc taatgttgcc atgggtagca tatactaccc aaatatctgg atagcatatg   3600
ctatcctaat ctatatctgg gtagcatagg ctatcctaat ctatatctgg gtagcatatg   3660
ctatcctaat ctatatctgg gtagtatatg ctatcctaat ttatatctgg gtagcatagg   3720
ctatcctaat ctatatctgg gtagcatatg ctatcctaat ctatatctgg gtagtatatg   3780
ctatcctaat ctgtatccgg gtagcatatg ctatcctaat agagattagg gtagtatatg   3840
ctatcctaat ttatatctgg gtagcatata ctacccaaat atctggatag catatgctat   3900
cctaatctat atctgggtag catatgctat cctaatctat atctgggtag cataggctat   3960
cctaatctat atctgggtag catatgctat cctaatctat atctgggtag tatatgctat   4020
cctaatttat atctgggtag cataggctat cctaatctat atctgggtag catatgctat   4080
cctaatctat atctgggtag tatatgctat cctaatctgt atccgggtag catatgctat   4140
cctcatgcat atacagtcag catatgatac ccagtagtag agtgggagtg ctatcctttg   4200
catatgccgc cacctcccaa gggggcgtga atttttcgctg cttgtccttt tcctgctggt   4260
tgctcccatt cttaggtgaa tttaaggagg ccaggctaaa gccgtcgcat gtctgattgc   4320
tcaccaggta aatgtcgcta atgttttcca acgcgagaag gtgttgagcg cggagctgag   4380
tgacgtgaca acatgggtat gcccaattgc cccatgttgg gaggacgaaa atggtgacaa   4440
gacagatggc cagaaataca ccaacagcac gcatgatgtc tactggggat ttattcttta   4500
gtgcggggga atacacggct tttaatacga ttgagggcgt ctcctaacaa gttacatcac   4560
tcctgccctt cctcaccctc atctccatca cctccttcat ctccgtcatc tccgtcatca   4620
ccctccgcgg cagccccttc caccataggt ggaaaccagg gaggcaaatc tactccatcg   4680
tcaaagctgc acacagtcac cctgatattg caggtaggag cgggctttgt cataacaagg   4740
tccttaatcg catccttcaa aacctcagca aatatatgag tttgtaaaaa gaccatgaaa   4800
taacagacaa tggactccct tagcgggcca ggttgtgggc cgggtccagg ggccattcca   4860
aaggggagac gactcaatgg tgtaagacga cattgtggaa tagcaagggc agttcctcgc   4920
cttaggttgt aaagggaggt cttactacct ccatatacga acacaccggc gacccaagtt   4980
ccttcgtcgg tagtcctttc tacgtgactc ctagccagga gagctcttaa accttctgca   5040
atgttctcaa atttcgggtt ggaacctcct tgaccacgat gcttttccaa accaccctcc   5100
tttttttgcgc cctgcctcca tcaccctgac cccggggtcc agtgcttggg ccttctcctg   5160
ggtcatctgc ggggccctgc tctatcgctc ccgggggcac gtcaggctca ccatctgggc   5220
caccttcttg gtggtattca aaataatcgg cttcccctac agggtggaaa atggccttc    5280
tacctggagg gggcctgcgc ggtggagacc cggatgatga tgactgacta ctgggactcc   5340
tgggcctctt ttctccacgt ccacgacctc tccccctggc tctttcacga cttccccccc   5400
tggctctttc acgtcctcta ccccggcggc ctccactacc tcctcgaccc cggcctccac   5460
tacctcctcg accccggcct ccactgcctc ctcgacccg gcctccacct cctgctcctg   5520
cccctcctgc tctgcccct cctcctgctc ctgcccctcc tgccctcct gctcctgccc   5580
ctcctgctcc tgcccctcctg cccctcctg cctgcccct cctgcccctc   5640
ctcctgctcc tgcccctcct gcccctcctc ctgctcctgc cctcctgcc ctcctgctc    5700
ctgcccctcc tgcccctcct gctcctgccc ctcctgcccc tcctgctcct gcccctcctg   5760
ctcctgcccc tcctgctcct gcccctcctg ctcctgcccc tcctgccct cctgcccctc    5820
```

```
ctcctgctcc tgccctcct gctcctgccc ctcctgcccc cctgctcctg      5880 ccctcctcc tgctcctgcc cctcctgccc ctcctgcccc cctcctgct cctgcccctc      5940 ctgcccctcc tcctgctcct gccctcctc ctgctcctgc cctcctgcc cctcctgccc      6000 ctcctcctgc tcctgcccct cctgcccctc ctcctgctcc tgcccctcct cctgctcctg      6060 ccctcctgc cctcctgcc cctcctcctg ctcctgcccc tcctcctgct cctgcccctc      6120
ctgcccctcc tgcccctcct gccctcctc ctgctcctgc cctcctcct gctcctgccc      6180 ctcctgctcc tgcccctccc gctcctgctc ctgctcctgt ccaccgtgg gtcccttgc      6240 agccaatgca acttggacgt ttttggggtc tccggacacc atctctatgt cttggccctg      6300
atcctgagcc gcccggggct cctggtcttc cgcctcctcg tcctcgtcct cttccccgtc      6360
ctcgtccatg ttatcaccc cctcttcttt gaggtccact gccgccggag ccttctggtc      6420
cagatgtgtc tcccttctct cctaggccat ttccaggtcc tgtacctggc ccctcgtcag      6480
acatgattca cactaaaaga gatcaataga catctttatt agacgacgct cagtgaatac      6540
agggagtgca gactcctgcc ccctccaaca gcccccccac cctcatcccc ttcatggtcg      6600
ctgtcagaca gatccaggtc tgaaaattcc ccatcctccg aaccatcctc gtcctcatca      6660
ccaattactc gcagcccgga aaactcccgc tgaacatcct caagatttgc gtcctgagcc      6720
tcaagccagg cctcaaattc ctcgtccccc tttttgctgg acggtaggga tggggattct      6780
cgggacccct cctcttcctc ttcaaggtca ccagacagag atgctactgg ggcaacggaa      6840
gaaaagctgg gtgcggcctg tgaggatcag cttatcgatg ataagctgtc aaacatgaga      6900
attcttgaag acgaaagggc ctcgtgatac gcctattttt ataggttaat gtcatgataa      6960
taatggtttc ttagacgtca ggtggcactt tcggggaaa tgtgcgcgga acccctattt      7020
gtttattttt ctaaatacat tcaaatatgt atccgctcat gagacaataa ccctgataaa      7080
tgcttcaata atattgaaaa aggaagagta tgagtattca acatttccgt gtcgccctta      7140 ttccctttt tgcggcattt tgccttcctg tttttgctca cccagaaacg ctggtgaaag      7200
taaaagatgc tgaagatcag ttgggtgcac gagtgggtta tcgaactg gatctcaaca      7260 gcggtaagat ccttgagagt tttcgccccg aagaacgttt tccaatgatg agcacttta      7320 aagttctgct atgtggcgcg gtattatccc gtgttgacgc cgggcaagag caactcggtc      7380
gccgcataca ctattctcag aatgacttgg ttgagtactc accagtcaca gaaaagcatc      7440
ttacggatgg catgacagta agagaattat gcagtgctgc cataaccatg agtgataaca      7500
ctgcggccaa cttacttctg acaacgatcg gaggaccgaa ggagctaacc gcttttttgc      7560
acaacatggg ggatcatgta actcgccttg atcgttggga accggagctg aatgaagcca      7620
taccaaacga cgagcgtgac accacgatgc ctgcagcaat ggcaacaacg ttgcgcaaac      7680
tattaactgg cgaactactt actctagctt cccggcaaca attaatagac tggatggagg      7740
cggataaagt tgcaggacca cttctgcgct cggcccttcc ggctggctgg tttattgctg      7800
ataaatctgg agccggtgag cgtgggtctc gcggtatcat tgcagcactg gggccagatg      7860
gtaagccctc ccgtatcgta gttatctaca cgacgggag tcaggcaact atggatgaac      7920
gaaatagaca gatcgctgag ataggtgcct cactgattaa gcattggtaa ctgtcagacc      7980
aagtttactc atatatactt tagattgatt taaaacttca ttttaatttt aaaaggatct      8040
aggtgaagat cctttttgat aatctcatga ccaaaatccc ttaacgtgag ttttcgttcc      8100
actgagcgta gaccccgta gaaaagatca aaggatcttc ttgagatcct ttttttctgc      8160
gcgtaatctg ctgcttgcaa acaaaaaaac caccgctacc agcggtggtt tgtttgccgg      8220
```

```
atcaagagct accaactctt tttccgaagg taactggctt cagcagagcg cagataccaa    8280
atactgtcct tctagtgtag ccgtagttag gccaccactt caagaactct gtagcaccgc    8340
ctacatacct cgctctgcta atcctgttac cagtggctgc tgccagtggc gataagtcgt    8400
gtcttaccgg gttggactca agacgatagt taccggataa ggcgcagcgg tcgggctgaa    8460
cggggggttc gtgcacacag cccagcttgg agcgaacgac ctacaccgaa ctgagatacc    8520
tacagcgtga gctatgagaa agcgccacgc ttcccgaagg gagaaaggcg gacaggtatc    8580
cggtaagcgg cagggtcgga acaggagagc gcacgaggga gcttccaggg ggaaacgcct    8640
ggtatcttta tagtcctgtc gggtttcgcc acctctgact tgagcgtcga ttttgtgat    8700
gctcgtcagg ggggcggagc ctatggaaaa acgccagcaa cgcggccttt ttacggttcc    8760
tggccttttg ctggccttga agctgtccct gatggtcgtc atctacctgc ctggacagca    8820
tggcctgcaa cgcgggcatc ccgatgccgc cggaagcgag aagaatcata atggggaagg    8880
ccatccagcc tcgcgtcgcg aacgccagca agacgtagcc cagcgcgtcg gccccgagat    8940
gcgccgcgtg cggctgctgg agatggcgga cgcgatggat atgttctgcc aagggttggt    9000
ttgcgcattc acagttctcc gcaagaattg attggctcca attcttggag tggtgaatcc    9060
gttagcgagg tgccgccctg cttcatcccc gtggcccgtt gctcgcgttt gctggcggtg    9120
tccccggaag aaatatattt gcatgtcttt agttctatga tgacacaaac cccgcccagc    9180
gtcttgtcat tggcgaattc gaacacgcag atgcagtcgg ggcggcgcgg tccgaggtcc    9240
acttcgcata ttaaggtgac gcgtgtggcc tcgaacaccg agcgaccctg cagcgacccg    9300
cttaacagcg tcaacagcgt gccgcagatc cgggggggca atgagatatg aaaaagcctg    9360
aactcaccgc gacgtctgtc gagaagtttc tgatcgaaaa gttcgacagc gtctccgacc    9420
tgatgcagct ctcggagggc gaagaatctc gtgctttcag cttcgatgta ggagggcgtg    9480
gatatgtcct gcgggtaaat agctgcgccg atggtttcta caaagatcgt tatgtttatc    9540
ggcactttgc atcggccgcg ctcccgattc cggaagtgct tgacattggg gaattcagcg    9600
agagcctgac ctattgcatc tcccgccgtg cacagggtgt cacgttgcaa gacctgcctg    9660
aaaccgaact gcccgctgtt ctgcagccgg tcgcggaggc catggatgcg atcgctgcgg    9720
ccgatcttag ccagacgagc gggttcggcc cattcggacc gcaaggaatc ggtcaataca    9780
ctacatggcg tgatttcata tgcgcgattg ctgatcccca tgtgtatcac tggcaaactg    9840
tgatggacga caccgtcagt gcgtccgtcg cgcaggctct cgatgagctg atgctttggg    9900
ccgaggactg ccccgaagtc cggcacctcg tgcacgcgga tttcggctcc aacaatgtcc    9960
tgacggacaa tggccgcata acagcggtca ttgactggag cgaggcgatg ttcggggatt   10020
cccaatacga ggtcgccaac atcttcttct ggaggccgtg gttggcttgt atggagcagc   10080
agacgcgcta cttcgagcgg aggcatccgg agcttgcagg atcgccgcgg ctccgggcgt   10140
atatgctccg cattggtctt gaccaactct atcagagctt ggttgacggc aatttcgatg   10200
atgcagcttg ggcgcagggt cgatgcgacg caatcgtccg atccggagcc gggactgtcg   10260
ggcgtacaca aatcgcccgc agaagcgcgg ccgtctggac cgatggctgt gtagaagtac   10320
tcgccgatag tggaaaccga cgccccagca ctcgtccgga tcgggagatg ggggaggcta   10380
actgaaacac ggaaggagac aataccggaa ggaacccgcg ctatgacggc aataaaaaga   10440
cagaataaaa cgcacgggtg ttgggtcgtt tgttcataaa cgcggggttc ggtcccaggg   10500
ctggcactct gtcgataccc caccgagacc ccattgggc caatacgccc gcgtttcttc   10560
cttttcccca ccccacccc caagttcggg tgaaggccca gggctcgcag ccaacgtcgg   10620
```

```
ggcggcaggc cctgccatag ccactggccc cgtgggttag ggacggggtc ccccatgggg    10680
aatggtttat ggttcgtggg ggttattatt ttgggcgttg cgtggggtca ggtccacgac    10740
tggactgagc agacagaccc atggtttttg gatggcctgg gcatggaccg catgtactgg    10800
cgcgacacga acaccgggcg tctgtggctg ccaaacaccc ccgaccccca aaaaccaccg    10860
cgcggatttc tggcgtgcca agctagtcga ccaattctca tgtttgacag cttatcatcg    10920
cagatccggg caacgttgtt gccattgctg caggcgcaga actggtaggt atggaagatc    10980
tatacattga atcaatattg gcaattagcc atattagtca ttggttatat agcataaatc    11040
aatattggct attggccatt gcatacgttg tatctatatc ataatatgta cctaaccaag    11100
ttcctctttc agaggttatt tcaggccatg gtgctgcgca gatccgcgta tgcggtgtga    11160
aataccgcac agatgcgtaa ggagaaaata ccgcatcagg cgaaattgta acgttaata    11220 ttttgttaaa attcgcgtta aatatttgtt aaatcagctc attttttaac caataggccg    11280
aaatcggcaa aatcccttat aaatcaaaag aatagaccga tagggttg agtgttgttc    11340 cagtttggaa caagagtcca ctattaaaga acgtggactc caacgtcaaa gggcgaaaaa    11400
ccgtctatca gggcgatggc ccactacgtg aaccatcacc caaatcaagt ttttgcggt    11460 cgaggtgccg taaagctcta aatcggaacc ctaaagggag cccccgattt agagcttgac    11520
ggggaaagcc ggcgaacgtg gcgagaaagg aagggaagaa agcgaaagga gcgggcgcta    11580
gggcgctggc aagtgtagcg gtcacgctgc gcgtaaccac cacacccgcc gcgcttaatg    11640
cgccgctaca gggcgcgtcc attcgccatt caggctgcgc aactgttggg aagggcgatc    11700
ggtgcgggcc tcttcgctat tacgccagcc cggatcgatc cttatcggat tttaccacat    11760
ttgtagaggt tttacttgct ttaaaaaacc tcccacatct cccctgaac ctgaaacata    11820 aaatgaatgc aattgttgtt gttaacttgt ttattgcagc ttataatggt tacaaataaa    11880
gcaatagcat cacaaatttc acaaataaag cattttttc actgcattct agttgtggtt    11940
tgtccaaact catcaatgta tcttatcatg tctgctcgaa gcattaaccc tcactaaagg    12000
gaagcggccg cttacatttt acttacaatt tggactttcc gcccttcttg gcctttatga    12060
ggatctctct gattttcctt gcgtcgagtt ttccggtaag acctttccggt acttcgtcca    12120 caaacacaac tcctccgcgc aacttttcg cggttgttac ttgactggcg acgtaatcca    12180
cgatctcttt ttccgtcatc gtctttccgt gctccaaaac aacaacgcg gcgggaagtt    12240 caccggcgtc atcgtcggga agacctgcca cgcccgcgtc gaagatgttg gggtgttgta    12300
acaatatcga ttccaattca gcggggggcca cctgatatcc tttgtattta attaaagact    12360
tcaagcggtc aactatgaag aagtgttcgt cttcgtccca gtaagctatg tctccagaat    12420
gtagccatcc atccttgtca atcaaggcgt tggtcgcttc cggattgttt acataaccgg    12480
acataatcat aggtcctctg acacataatt cgcctctctg attaacgccc agcgttttcc    12540
cggtatccag atccacaacc ttcgcttcaa aaaatggaac aactttaccg accgcgcccg    12600
gtttatcatc cccctcgggt gtaatcagaa tagctgatgt agtctcagtg agcccatatc    12660
cttgtcgtat ccctggaaga tggaagcgtt ttgcaaccgc ttccccgact tctttcgaaa    12720
gaggtgcgcc cccagaagca atttcgtgta aattagataa atcgtatttg tcaatcagag    12780
tgcttttggc gaagaatgaa aatagggttg gtactagcaa cgcactttga atttttgtaat    12840 cctgaaggga tcgtaaaaac agctcttctt caaatctata cattaagacg actcgaaatc    12900
cacatatcaa atatccgagt gtagtaaaca ttccaaaacc gtgatggaat ggaacaacac    12960
ttaaaatcgc agtatccgga atgatttgat tgccaaaaat aggatctctg gcatgcgaga    13020
```

```
atctgacgca ggcagttcta tgcggaaggg ccacacccct aggtaaccca gtagatccag   13080
aggaattcat tatcagtgca attgttttgt cacgatcaaa ggactctggt acaaaatcgt   13140
attcattaaa accgggaggt agatgagatg tgacgaacgt gtacatcgac tgaaatccct   13200
ggtaatccgt tttagaatcc atgataataa ttttctggat tattggtaat ttttttttgca  13260 cgttcaaaat ttttttgcaac ccctttttgg aaacaaacac tacggtaggc tgcgaaatgt  13320
tcatactgtt gagcaattca cgttcattat aaatgtcgtt cgcgggcgca actgcaactc   13380
cgataaataa cgcgcccaac accggcataa agaattgaag agagttttca ctgcatacga   13440
cgattctgtg atttgtattc agcccatatc gtttcatagc ttctgccaac cgaacggaca   13500
tttcgaagta ttccgcgtac gtgatgttca cctcgatatg tgcatctgta aaagcaattg   13560
ttccaggaac cagggcgtat ctcttcatag cctta tgcag ttgctctcca gcggttccat   13620
cctctagagg atagaatggc gccgggcctt tctttatgtt tttggcgtct tccagctgct   13680
ctatgccagc atttcctgca aatgagaaat tagaaccaga ggcttgacga attccagtta   13740
aaccatgtcc tctgtggaca ccagttaaac ttgactagag cacttcatat gtcagagtgt   13800
acagtgcagt atgcctaggt tatcccatat cacaataaaa aaagtctgc tggtctgcct   13860 actagtgata taaatggca tcatatccta aagctcttta ttgtgaaagt atgtttcttc    13920
cacacaacca accagttaag tatgagaatt ctagtaggga tgtagattaa ccttttatct   13980
aatagttttg gcatcaaaat tctttaatat tgattgtttt acattaacct ttcaactttc   14040
taacatctga acttttttaaa tgttcaaaaa catttgtttt ccacaaacca taagtttta    14100 caaaagtaag attcactttc ataatgctgg cagacttact ccttagattt aaggaatgtg   14160
agcaccttcc ttctttttga ttttgtctaa aaccctgtaa ggaaaataaa ggaagttaaa   14220
aaaaatagct atatagatat agatagctat atatagatag cttttatatgg atgttaaaaa   14280 gcattttgtt tcacaagaca ttttacttat tttattcaac aaaatatgat cagaaattaa   14340
gttgatagtc ttttaatgta ctttaaaagt tatcccaaag aaaacaatta ttaggctgca   14400
gttaaggttt tcttgcagtg gctcatgcct acaatcccac aactttggga ggcggaggta   14460
gggggatcac ttgagacctg gagcttgaca ccacccctggg caacataatg agaccctgtc   14520
tctacaaaaa atttaaaaat taggccggcg tggtggctca tgctaggcac agtggctcac   14580
gcctgtaatc ccagcacttt gggaggccga gacagttgga tcacctgagc tcaggagttc   14640
gagaacagcc tggccaacat ggcaaaaccc cgtttctact gaaagtacaa aaaattagcc   14700
aggcatggtg gtgggacct ctaatcccag ctacttggga ggttgaggca ggagaatcac   14760
ttgaacccag gaggcggagg ctgcagtgag ctgagattta caccactgca ctccagcctg   14820
ggtgacagag caagactctg tctcaaaaaa aaataaataa ataaaaataa aaattagcca   14880
ggtgcagtgg cattatcact gtagtcccag ctactcggga aactgaggtg agaggactgc   14940
ttgagccctg gaggtcaagg ctgcagtgag ctgtgaatgt gcccttgcac tccagcctga   15000
gcaatagagt gagacctggt ctctaaaaaa taaaatttgg gaggcggagc ttgcagtgag   15060
ccgagactgc gccactgtac tccagcctgg gtgacagagc gagactccgt ctcaaaaaaa   15120
aaaaaaaaat aaaataaaat aaaataattt taaatgttct gactaaaata caatagaaca   15180
tgtccgtagg agactaacgt ataaagtgac aagtttgaag ccatactccc caaggttcaa   15240
tgtggtacac attaccccag atctttgtgc attaaaaaaa tttcatttct cttggaaggc   15300
cgaggcgggt ggatcacggg gtcaggagat tgagaccatc ctggctaaca cagtgaaacc   15360
ctgtctttac aaaaaaatac aaaaaattag acaggcgtgg tggcaggcaa ctgtagtccc   15420
```

```
agctacctct gaggctgagg caggagaatg gcgtgaatcc aggaggcaga gcttgctgtg    15480
agccaagatc acgccattgc actccagcct gggcaacaga gcaagactcc gtctcaaaaa    15540
aaaaaaaaaa aaaaaagaat ttcatttttc atttatgaaa aattatccca tcttttccat    15600
tccctacaat caatttcaaa tcagagatta aaacattatt tagaaaaagt ataatttcaa    15660
ttcaaaagtg tataatcaaa ataatctaac aatagcatga aagcttttta aaattaacta    15720
aaattatact tagggacaat gcaagagtaa tttaagcctc agacagttgt attttttat     15780 ttttattttt tagtaatata aagagagaag caagtagtat tttataaatt tacaaaacaa    15840
agtcacataa ctacaaaaaa attgtcagga aaagatgctg agtgattact taccatataa    15900
tagccagtat gatagccact catgtaccat gaaattaaca tacttcccaa agcatcagca    15960
tcatcaagag aatctggaca tatgggaggt ggtgggggaa ttatctcgag tggtccagaa    16020
ggaaatggag gcagccagca tgatagtaag tggggtggtg gtggtggcgg tggcggtggt    16080
gggccattga attttagacc tggctttcct ggtcccagtc ttggccctgg catgggggt     16140 ggtggaggga gaaaagagtt ccatggagca gatttgggct tgatgttatc tgatttattt    16200
ccaggagacc tggagttctc actttcatct gttgaaactt ggctttcatt ttcattctct    16260
tgagcattct gttctatatt attagctact tcacagattg gggaaagtag atcggacaga    16320
ttttgctcct ctctatttcc atatccagtg taaaccacaa cacaggtttc tctcttaaaa    16380
tcaattgaag caatggtagc tgggtaaatg caaccgtctt ctgaccaaat ggcagaacat    16440
ttgtccccaa ctttccactg ttgtaaggaa gctgcagtat tcttcttttg gctttattc     16500 ttcttagcag gttttctttt aggtgtggtt tttggtttac ccgaagtttc acaaatgtca    16560
ccattcttta gagcatgctt aaatgaagcc acagctttat catatgcttt tatcagtgct    16620
gtatcatccc aaatgtcaga atcatcgctc tggcctgtgc cgcgccggaa cagcacggaa    16680
tcctcctgct ccgggacgcc gccaccactg ccgccgctgc tcatcgccat agcaaacccg    16740
cgggtgcgca gcgtggggcc ccgtcccttc ttaagagtga cgacttccgc cgcccggggc    16800
ttctgggagc ggaacagtac ggtggccggg aggaccgctt gtagtaactt ctcacgcttt    16860
ctacgagtgg ttatcgccct cccacatttg tggcgtgtat attttcatt tctctcaatc     16920 cttttcatttc actgtgttat atttcctttc cttttttttt tgtttgtttg ttttgagaca    16980
gagcctcgcc ctgtcgctca ggctggagtg cagcggcgcg atctcggctc actgcagcct    17040
cgacttcttg ggctcaagcg atcctcccac ctcagcctcc ccagtagcta ggactatagg    17100
cgtgcgccac caagctcagc tattttttgt atttagtaga gacggggttt cggcatgttg    17160
cttaggcctc gtctcgaact ccagtgtgtg tgtgtgtgtg tgtgtgtgtg tgtgtgtgtg    17220
tgtgtgtgta gatatttatt cccctcccc cttggaaaag taaatgtaag ctcctactag     17280
gaatttaaaa cctgcttgat ctatataaag acaaacaagg aaagacaaac atgggggcag    17340
gaaggaaggc agatccttaa acactagaag atatttgatc ccccaacctt atttgttgtt    17400
tgttttgaga cggagtctcg ctctgtcgtc agagtgcagt ggcaccatct cggctcattg    17460
cagcctcgac ctcccgagct caagcgatcc tcccgcctca acctcccaag tagctaggac    17520
cacaggggca cgccaccaca cccggctagt ttctgtatgt tttgtagagg cggcgtttgg    17580
agcatattgt gtaggctggt ctcgaactcc tgagctcaag atattccgcc cgcctctggc    17640
atcccaaaat gctgggatta caggtgtgag ccacctcgcc cagcctccag tattcttttt    17700
tttttttgcg acagagtatt gctctgtcac ccaggctgga atgcagtggc gtgatctcag    17760
ctcactgcaa cctctgcctc ccaggttcaa gcaattctgc ctcagccccc cgagtagctg    17820
```

-continued

```
ggattacagg cgcccaccac cacacccggc taattttgt attttagta aagatggggt    17880
ttcaccatgt tggccaggct ggtcttgaac tcctgacctc gtaatccgac cgcctcggcc    17940
tcccaaagtg ctgggattac aggtgtgagc caccacaccg ggcctccagt attctttatt    18000
aagcatctag ggttgctaaa tggcttatat gtacatagta tatatatt tttaactcca     18060
cgaaaggaac tttgagctct tcccccaaaa taccccttggc ttctatatag tatacaagaa    18120
atatctgtgg aggaagggga gaatgggatg atgttgacca agtgtacaaa aatggtaact    18180
ctgtagaggt aatatgtgga atgtaatcat ttcacaatgt atatctaaac atcaaatggt    18240
acaccttaaa tatatacaat ttttaggggt ctggtacggt ggctcatgcc tataatccca    18300
gcactttggg aggccaaggt gggtggatca cttgaggtca ggacttcaag accagcctgg    18360
ccaacatggt gaaaccctgt ttctcctaaa aatacaaaaa tcagccgggt gtggtggtgc    18420
aggcctgtaa tgacagctgc ttgggaggct gagccaggag aatcacttga actcgggagg    18480
cggaggttgc agtgagccaa gatcacgcca ctgcactcca gcctgagtga cagagtgcga    18540
ctccatctca aacaaataaa tatgtacaat ttttatgtgt caaaaaagtt aaattgtcac    18600
aagataaaaa aaaaaattta aatctcatgt caggaaagta atgtgccaaa ggtacatctc    18660
acagataaac atgaaaacct gcactccagc ctgggcgaca gagtgaggct gtgtctcaga    18720
aaaaaaaaaa aaagtaaaaa aaaagtatg tttttataaa gcttgcttag attttctga     18780
atcataaaaa ttctcacaat tgcatttgat gtcaaaattt aaacaaatta cctggacata    18840
ttacatgatg gttaaaaaaa taaatttaaa caaaatatag aaccaggttt cttttttgttt    18900
ttaattttt ttcttttga gacggagtct cgctctgcca cccagactgg agtgcagtgg    18960
ctcactgcaa cctctgcctc ccgggttcaa gtgattctcc tgtctcagct cccgagtac     19020
ctaggattac aggcgtgtgc caccacaccc agctaatttt tgtatttta gtagagactg    19080
ggttttgcca tgttggtcag gttggtctca aactcctgac cttgtgatcc gcccgcctca    19140
gcctcccaaa gtgctgcgat tacaggcatg agccaccgca cccagccatt tcttttgtt    19200
tttattattt agagatataa ttgatatact atagaattaa tcgttttaga gagtacaatt    19260
gaatggtaga tagagcggaa accttaatat attcacaagg ttgtgcaacc atcactacta    19320
tctaactcca gaacatttta atcacccacc aaagaaactc tgtttccttt agcagtgcgc    19380
tgccatgctc agctattttt tgggagagaa ggggtctccc catgttgtcc acgctggtct    19440
caaactcggt tgcttaagca gtcctcccac ttgagccgct gtgcccaggc ctgagttact    19500
atatttataa aagttatttc atatgataga caaatcattc aaaacataat gaggtaaact    19560
gccaaaagaa accatttac catatttgaa ggcatttaat gtaaatgttg aatttaattt    19620
catgtactgg aatcagtctt tttgcatatg taattttcat accaaaaatc tctcttcagt    19680
tgactcctgg aactctctca tgataaaata aaagtttcaa ataatgtcgg ggtggtggct    19740
aacacctgta atcccagcac tgtgggagtc cgaggcaggt ggatcacatg aggtcaggag    19800
tttgagacca gcctagccaa catggcaaca ctaaagatat gaaagtcagc caggcatggt    19860
ggtgcatgcc tgtaatctca gctactaggg aggctgaggc acaaaaatca cttgaaactg    19920
ggaggtggag gttgcaatga gctgagatcg tgccactgca caccagcctg tgagacagag    19980
caagactctg tctcaaaaaa aaaaaaaaaa aaaaaaaaaa aagggccaag tatggtggct    20040
catgcctgta atcctagcac tttgggaggc tgagtgggag aggatcattt gagcccaagt    20100
```

```
aacatggtca ggccccatct ctacaaaaat aaattagctg ggcatggtgg tatgggcttg    20160
tggtacattt atattggctc atgtccaata tgaccgccat                          20200
```